US009085622B2

(12) United States Patent
Clarke et al.

(10) Patent No.: US 9,085,622 B2
(45) Date of Patent: Jul. 21, 2015

(54) ANTIGEN BINDING PROTEINS

(75) Inventors: Neil James Clarke, Stevenage (GB);
Kyung Oh Johanson, King of Prussia,
PA (US); Zdenka Ludmila Jonak, King
of Prussia, PA (US); **Alexander H.
Taylor**, King of Prussia, PA (US);
Christopher B. Hopson, Collegeville,
PA (US); Stephen H. Trulli, King of
Prussia, PA (US); Zdenka Haskova,
King of Prussia, PA (US); **Judithann M.
Lee, King of Prussia, PA (US); John R.
White, King of Prussia, PA (US); Yu
Xue**, King of Prussia, PA (US)

(73) Assignee: **GLAXOSMITHKLINE
INTELLECTUAL PROPERTY
DEVELOPMENT LIMITED** (GB)

( * ) Notice: Subject to any disclaimer, the term of this patent is extended or adjusted under 35 U.S.C. 154(b) by 0 days.

(21) Appl. No.: 13/639,918

(22) PCT Filed: Sep. 2, 2011

(86) PCT No.: PCT/US2011/050322
§ 371 (c)(1),
(2), (4) Date: Oct. 8, 2012

(87) PCT Pub. No.: WO2012/031198
PCT Pub. Date: Mar. 8, 2012

(65) Prior Publication Data
US 2013/0156779 A1 Jun. 20, 2013

Related U.S. Application Data

(60) Provisional application No. 61/379,840, filed on Sep. 3, 2010, provisional application No. 61/440,460, filed on Feb. 8, 2011.

(51) Int. Cl.
C07K 16/28 (2006.01)
A61K 39/395 (2006.01)
C07K 16/32 (2006.01)
A61K 39/00 (2006.01)

(52) U.S. Cl.
CPC .............. C07K 16/28 (2013.01); C07K 16/32 (2013.01); A61K 2039/505 (2013.01); C07K 2317/24 (2013.01); C07K 2317/33 (2013.01); C07K 2317/565 (2013.01); C07K 2317/72 (2013.01); C07K 2317/732 (2013.01); C07K 2317/734 (2013.01); C07K 2317/77 (2013.01); C07K 2317/92 (2013.01)

(58) Field of Classification Search
CPC .............. C07K 16/32; C07K 16/2863; C07K 2317/14; C07K 2317/24; C07K 2317/34; C07K 16/28; C07K 2317/565; A61K 39/395; A61K 39/39558; A61K 2039/505
See application file for complete search history.

(56) References Cited

U.S. PATENT DOCUMENTS

| 5,183,884 | A | 2/1993 | Kraus et al. |
| 5,480,968 | A | 1/1996 | Kraus et al. |
| 5,804,396 | A | 9/1998 | Plowman et al. |
| 5,820,859 | A | 10/1998 | Kraus et al. |
| 5,916,755 | A | 6/1999 | Kraus et al. |
| 5,968,511 | A | 10/1999 | Akita et al. |
| 6,277,640 | B1 | 8/2001 | Bennett et al. |
| 6,416,168 | B1 | 7/2002 | Silverbrook et al. |
| 6,417,168 | B1 | 7/2002 | Greene et al. |
| 6,627,196 | B1 | 9/2003 | Baughman et al. |
| 6,632,979 | B2 | 10/2003 | Erickson et al. |
| 6,639,060 | B1 | 10/2003 | Kraus et al. |
| 6,639,061 | B1 | 10/2003 | Cook et al. |
| 6,737,056 | B1 | 5/2004 | Presta et al. |
| 6,962,789 | B2 | 11/2005 | Bacus |
| 7,097,840 | B2 | 8/2006 | Erickson et al. |
| 7,097,940 | B2 | 8/2006 | Uetani et al. |
| 7,105,308 | B2 | 9/2006 | Chan-Hui et al. |
| 7,125,680 | B2 | 10/2006 | Singer et al. |
| 7,135,300 | B2 | 11/2006 | Chan-Hui et al. |
| 7,192,582 | B2 | 3/2007 | Hudson et al. |
| 7,235,641 | B2 | 6/2007 | Kufer et al. |
| 7,255,999 | B2 | 8/2007 | Singh et al. |
| 7,285,649 | B2 | 10/2007 | Akita et al. |
| 7,314,916 | B2 | 1/2008 | Singer et al. |

(Continued)

FOREIGN PATENT DOCUMENTS

| AU | 654805 B2 | 11/1997 |
| AU | 727082 | 11/2000 |

(Continued)

OTHER PUBLICATIONS

Paul, Fundamental Immunology, 3rd Edition, 1993, pp. 292-295.*
Rudikoff et al., Proc. Nat'l Acad. Sci. USA 1982; 79:1979-83.*
Dall'Acqua et al., Methods 2005; 36:43-60.*
De Genst et al., Dev Comp Immunol 2006; 30:187-98.*
Naidu et al., Br J Cancer 1998; 78(10):1385-90.*
Brand et al., Anticancer Res. 2006; 26:463-70.*
Chan and Carter, Nature Reviews Immunology, 2010; 10:301-316.*
Rajkumar & Gullick, Br. J. Cancer, 1994; 70:459-65.*
Baselga, et al., Nature Reviews, vol. 9, Jul. 2009, p. 463-475.
Junttila, et al., Clin. Cancer Res., vol. 9, Nov. 1, 2003, p. 5346-5357.
Singer, et al., J. Biol. Chem., 276(47):44266(2001).
Package insert for DuoSet IC, R&D Systems, 2012.
R&D Systems, Human ErbB3/Her3 Antibody, Clone # 66223, Catalog # MAB3481, Oct. 4, 2010.

(Continued)

Primary Examiner — Sheela H Huff
Assistant Examiner — Jessica H Roark
(74) Attorney, Agent, or Firm — William Peter Long; William T. Han

(57) ABSTRACT

The present disclosure relates to antigen binding proteins, such as antibodies, that bind to HER3, polynucleotides encoding such antigen binding proteins, pharmaceutical compositions comprising said antigen binding proteins and methods of manufacture. The present disclosure also concerns the use of such antigen binding proteins in the treatment or prophylaxis of diseases associated with breast cancer, ovarian cancer, prostate cancer, bladder cancer, pancreatic, gastric, melanoma and other cancers that overexpress HER3.

69 Claims, 59 Drawing Sheets

(56) References Cited

U.S. PATENT DOCUMENTS

| | | | |
|---|---|---|---|
| 7,323,553 B2 | 1/2008 | Fahrner et al. |
| 7,332,580 B2 | 2/2008 | Adams et al. |
| 7,332,585 B2 | 2/2008 | Adams et al. |
| 7,390,632 B2 | 6/2008 | Maihle et al. |
| 7,485,704 B2 | 2/2009 | Fahrner et al. |
| 7,498,142 B2 | 3/2009 | Yarden et al. |
| 7,517,670 B2 | 4/2009 | Umaña et al. |
| 7,521,541 B2 | 4/2009 | Eigenbrot et al. |
| 7,534,866 B2 | 5/2009 | Chang et al. |
| 7,560,111 B2 | 7/2009 | Kao et al. |
| 7,575,893 B2 | 8/2009 | Simmons et al. |
| 7,579,170 B2 | 8/2009 | Beliard et al. |
| 7,591,994 B2 | 9/2009 | Govindan et al. |
| 7,625,558 B2 | 12/2009 | Greene et al. |
| 7,651,703 B2 | 1/2010 | Cleland et al. |
| 7,659,368 B2 | 2/2010 | Fitzpatrick et al. |
| 7,705,130 B2 | 4/2010 | Rothe et al. |
| 7,744,882 B2 | 6/2010 | Maihle et al. |
| 7,745,398 B2 | 6/2010 | Maihle et al. |
| 7,754,441 B2 | 7/2010 | Sauvage et al. |
| 7,771,958 B2 | 8/2010 | Bacus et al. |
| 7,807,789 B2 | 10/2010 | Guo et al. |
| 7,846,440 B2 | 12/2010 | Schoeberl et al. |
| 7,855,275 B2 | 12/2010 | Eigenbrot et al. |
| 7,892,549 B2 | 2/2011 | Paton et al. |
| 7,897,723 B2 | 3/2011 | Bock et al. |
| 7,906,624 B2 | 3/2011 | Greene et al. |
| 7,931,895 B2 | 4/2011 | Beliard et al. |
| 7,947,839 B2 | 5/2011 | Gazzard et al. |
| 7,951,918 B2 | 5/2011 | Glaser et al. |
| 7,981,418 B2 | 7/2011 | Amler et al. |
| 7,999,083 B2 | 8/2011 | Govindan et al. |
| 8,017,752 B1 | 9/2011 | Maihle et al. |
| 8,025,879 B2 | 9/2011 | Liu et al. |
| 8,048,888 B2 | 11/2011 | Wosikowski-Buters et al. |
| 8,153,124 B2 | 4/2012 | Beliard et al. |
| 8,349,574 B2 | 1/2013 | Bates et al. |
| 8,362,215 B2 | 1/2013 | Keyt et al. |
| 8,501,417 B2 | 8/2013 | Pohlmann et al. |
| 8,715,665 B2 | 5/2014 | Janne et al. |
| 2001/0023241 A1 | 9/2001 | Sliwkowski et al. |
| 2002/0002276 A1 | 1/2002 | Fitzpatrick et al. |
| 2002/0004587 A1 | 1/2002 | Miller et al. |
| 2002/0042087 A1 | 4/2002 | Sliwkowski et al. |
| 2002/0064805 A1 | 5/2002 | Akita et al. |
| 2002/0165193 A1 | 11/2002 | Greene et al. |
| 2003/0013126 A1 | 1/2003 | Singh et al. |
| 2003/0143568 A1 | 7/2003 | Singer et al. |
| 2003/0190702 A1 | 10/2003 | Maihle et al. |
| 2003/0229212 A1 | 12/2003 | Fahrner et al. |
| 2004/0057950 A1 | 3/2004 | Waksal et al. |
| 2004/0063140 A1 | 4/2004 | Kraus et al. |
| 2004/0071696 A1 | 4/2004 | Adams et al. |
| 2004/0072290 A1 | 4/2004 | Umana et al. |
| 2004/0106161 A1 | 6/2004 | Bossenmaier et al. |
| 2004/0116330 A1 | 6/2004 | Naito et al. |
| 2004/0126818 A1 | 7/2004 | Chan-Hui et al. |
| 2004/0138417 A1 | 7/2004 | Fitzpatrick et al. |
| 2004/0197332 A1* | 10/2004 | Ullrich et al. ............. 424/145.1 |
| 2004/0197835 A1 | 10/2004 | Chan-Hui et al. |
| 2004/0229293 A1 | 11/2004 | Chan-Hui et al. |
| 2004/0229299 A1 | 11/2004 | Badal et al. |
| 2004/0229310 A1 | 11/2004 | Simmons et al. |
| 2004/0229380 A1 | 11/2004 | Chan-Hui et al. |
| 2004/0254108 A1 | 12/2004 | Ma et al. |
| 2005/0001587 A1 | 1/2005 | Bender |
| 2005/0038231 A1 | 2/2005 | Fahrner et al. |
| 2005/0079184 A1 | 4/2005 | Hsing-Chang et al. |
| 2005/0130238 A1 | 6/2005 | Chan-Hui et al. |
| 2005/0136050 A1 | 6/2005 | Kufer et al. |
| 2005/0136494 A1 | 6/2005 | Akita et al. |
| 2005/0147612 A1 | 7/2005 | Yayon et al. |
| 2005/0170438 A1 | 8/2005 | Chan-Hui et al. |
| 2005/0170439 A1 | 8/2005 | Chan-Hui et al. |
| 2005/0208043 A1 | 9/2005 | Adams et al. |
| 2005/0232931 A1 | 10/2005 | Ma et al. |
| 2005/0244409 A1* | 11/2005 | Erickson-Miller et al. ............. 424/143.1 |
| 2005/0272637 A1 | 12/2005 | Clinton et al. |
| 2005/0276812 A1 | 12/2005 | Ebens et al. |
| 2006/0025576 A1 | 2/2006 | Miller et al. |
| 2006/0073140 A1 | 4/2006 | Greene et al. |
| 2006/0099205 A1 | 5/2006 | Adams et al. |
| 2006/0121044 A1 | 6/2006 | Amler et al. |
| 2006/0140960 A1* | 6/2006 | Wang et al. ............. 424/155.1 |
| 2006/0154333 A1 | 7/2006 | Pienkos et al. |
| 2006/0177907 A1 | 8/2006 | Singer et al. |
| 2006/0182719 A1 | 8/2006 | Zhang et al. |
| 2006/0182751 A1 | 8/2006 | Gazzard et al. |
| 2006/0188509 A1 | 8/2006 | Derynck et al. |
| 2006/0233808 A1 | 10/2006 | Deperthes et al. |
| 2006/0269545 A1 | 11/2006 | Umana et al. |
| 2006/0281093 A1 | 12/2006 | Kim et al. |
| 2007/0086942 A1 | 4/2007 | Chang et al. |
| 2007/0092940 A1 | 4/2007 | Eigenbrot et al. |
| 2007/0122407 A1 | 5/2007 | Akita et al. |
| 2007/0178102 A1 | 8/2007 | Yarden et al. |
| 2007/0197430 A1 | 8/2007 | Baell et al. |
| 2007/0269446 A1 | 11/2007 | Sauvage et al. |
| 2008/0038271 A1 | 2/2008 | Amler et al. |
| 2008/0050370 A1 | 2/2008 | Glaser et al. |
| 2008/0057064 A1 | 3/2008 | Zhou et al. |
| 2008/0069820 A1 | 3/2008 | Fuh et al. |
| 2008/0076139 A1 | 3/2008 | Singh et al. |
| 2008/0108795 A1 | 5/2008 | Guo et al. |
| 2008/0112961 A1 | 5/2008 | Stavenhagen et al. |
| 2008/0124334 A1 | 5/2008 | Akita et al. |
| 2008/0124345 A1 | 5/2008 | Rothe et al. |
| 2008/0138349 A1 | 6/2008 | Stavenhagen et al. |
| 2008/0166294 A1 | 7/2008 | de Sauvage et al. |
| 2008/0171040 A1 | 7/2008 | Ebens, et al. |
| 2008/0171067 A1 | 7/2008 | Govindan et al. |
| 2008/0187966 A1 | 8/2008 | Simmons et al. |
| 2008/0206136 A1 | 8/2008 | Greene et al. |
| 2008/0260757 A1 | 10/2008 | Holt et al. |
| 2008/0261829 A1 | 10/2008 | Harvey et al. |
| 2008/0267961 A1 | 10/2008 | Maihle et al. |
| 2008/0269467 A1 | 10/2008 | Allan et al. |
| 2008/0274078 A1 | 11/2008 | Haskova et al. |
| 2008/0274115 A1 | 11/2008 | Maihle et al. |
| 2009/0010840 A1 | 1/2009 | Adams et al. |
| 2009/0035258 A1 | 2/2009 | Haskova et al. |
| 2009/0035792 A1 | 2/2009 | Singh et al. |
| 2009/0036651 A1 | 2/2009 | Moya et al. |
| 2009/0048122 A1 | 2/2009 | Glaser et al. |
| 2009/0053786 A1 | 2/2009 | Kao et al. |
| 2009/0092617 A1 | 4/2009 | Bock et al. |
| 2009/0155259 A1 | 6/2009 | Derynck et al. |
| 2009/0175865 A1 | 7/2009 | Eigenbrot et al. |
| 2009/0175867 A1 | 7/2009 | Thompson et al. |
| 2009/0181022 A1 | 7/2009 | Nielsen et al. |
| 2009/0186019 A1 | 7/2009 | Umana et al. |
| 2009/0191201 A1 | 7/2009 | Heiss et al. |
| 2009/0202536 A1 | 8/2009 | Ebens, et al. |
| 2009/0214576 A1 | 8/2009 | Bacus et al. |
| 2009/0232737 A1 | 9/2009 | Moya et al. |
| 2009/0246206 A1 | 10/2009 | Nielsen et al. |
| 2009/0252681 A1 | 10/2009 | Laeremans et al. |
| 2009/0274693 A1 | 11/2009 | Gilmer et al. |
| 2009/0286737 A1 | 11/2009 | Greene et al. |
| 2009/0291085 A1 | 11/2009 | Schoeberl et al. |
| 2009/0298061 A1 | 12/2009 | Wirtz et al. |
| 2010/0003766 A1 | 1/2010 | Junutula et al. |
| 2010/0008975 A1 | 1/2010 | Amler et al. |
| 2010/0018361 A1 | 1/2010 | Chervenak et al. |
| 2010/0028346 A1 | 2/2010 | Lutz et al. |
| 2010/0033482 A1 | 2/2010 | Zhou et al. |
| 2010/0047829 A1 | 2/2010 | Rothe et al. |
| 2010/0056761 A1 | 3/2010 | Schoeberl et al. |
| 2010/0074900 A1 | 3/2010 | Ghayur et al. |
| 2010/0104589 A1 | 4/2010 | Govindan et al. |
| 2010/0111856 A1 | 5/2010 | Gill et al. |
| 2010/0119457 A1 | 5/2010 | Lenz et al. |
| 2010/0119511 A1 | 5/2010 | Wang et al. |

(56) References Cited

U.S. PATENT DOCUMENTS

| | | | |
|---|---|---|---|
| 2010/0129314 A1 | 5/2010 | Singh et al. |
| 2010/0167945 A1 | 7/2010 | Singh et al. |
| 2010/0169729 A1 | 7/2010 | Datta et al. |
| 2010/0183504 A1 | 7/2010 | Chen et al. |
| 2010/0183631 A1 | 7/2010 | Rothe et al. |
| 2010/0189649 A1 | 7/2010 | Greene et al. |
| 2010/0196310 A1 | 8/2010 | Haskova et al. |
| 2010/0210034 A1 | 8/2010 | Bates et al. |
| 2010/0233080 A1 | 9/2010 | Umaña et al. |
| 2010/0233732 A1 | 9/2010 | Bates et al. |
| 2010/0240035 A1 | 9/2010 | Jablons et al. |
| 2010/0248225 A1 | 9/2010 | Bankaitis-Davis et al. |
| 2010/0249382 A1 | 9/2010 | Desjarlais et al. |
| 2010/0255010 A1 | 10/2010 | Fuh et al. |
| 2010/0266584 A1 | 10/2010 | Schoeberl et al. |
| 2010/0267933 A1 | 10/2010 | Wilson et al. |
| 2010/0279323 A1 | 11/2010 | Bacus et al. |
| 2010/0297076 A1 | 11/2010 | Morrison et al. |
| 2010/0305058 A1 | 12/2010 | Lancaster et al. |
| 2010/0306864 A1 | 12/2010 | Tsuji et al. |
| 2010/0310557 A1 | 12/2010 | Keyt et al. |
| 2010/0316626 A1 | 12/2010 | Buonanno et al. |
| 2011/0027190 A1 | 2/2011 | Hasmann et al. |
| 2011/0027291 A1 | 2/2011 | Schoeberl et al. |
| 2011/0033482 A1 | 2/2011 | Ullrich et al. |
| 2011/0033483 A1 | 2/2011 | Thompson et al. |
| 2011/0039300 A1 | 2/2011 | Bayer et al. |
| 2011/0052570 A1 | 3/2011 | Klagsbrun et al. |
| 2011/0059076 A1 | 3/2011 | Mcdonagh et al. |
| 2011/0059081 A1 | 3/2011 | Bacus |
| 2011/0091461 A1 | 4/2011 | Ledbetter et al. |
| 2011/0091473 A1 | 4/2011 | Golab et al. |
| 2011/0104112 A1 | 5/2011 | Morrison et al. |
| 2011/0105729 A1 | 5/2011 | Ledbetter et al. |
| 2011/0110852 A1 | 5/2011 | Miller et al. |
| 2011/0117096 A1 | 5/2011 | Bossenmaier et al. |
| 2011/0123523 A1 | 5/2011 | Schoeberl et al. |
| 2011/0130547 A1 | 6/2011 | Guo et al. |
| 2011/0136150 A1 | 6/2011 | Reiffen et al. |
| 2011/0137017 A1 | 6/2011 | Eigenbrot et al. |
| 2011/0159513 A1 | 6/2011 | Schoeberl et al. |
| 2011/0165157 A1 | 7/2011 | Derynck et al. |
| 2011/0229406 A1 | 9/2011 | Hettmann et al. |
| 2011/0229478 A1 | 9/2011 | Zhou et al. |
| 2011/0229493 A1 | 9/2011 | Jackson et al. |
| 2011/0245103 A1 | 10/2011 | Amler et al. |
| 2011/0246399 A1 | 10/2011 | Amler et al. |
| 2011/0256154 A1 | 10/2011 | Vincent et al. |
| 2011/0268654 A1 | 11/2011 | Hilderbrand et al. |
| 2011/0281748 A1 | 11/2011 | Singh et al. |
| 2011/0293513 A1 | 12/2011 | Govindan et al. |
| 2012/0195831 A1 | 8/2012 | Zhang et al. |
| 2012/0201813 A1 | 8/2012 | Presta et al. |
| 2012/0202224 A1 | 8/2012 | Presta et al. |
| 2012/0208238 A1 | 8/2012 | Georgiou et al. |
| 2012/0213705 A1 | 8/2012 | Dimasi et al. |
| 2012/0219551 A1 | 8/2012 | Johnson et al. |
| 2012/0225058 A1 | 9/2012 | Lazar et al. |
| 2012/0230980 A1 | 9/2012 | Lazar et al. |

FOREIGN PATENT DOCUMENTS

| | | |
|---|---|---|
| AU | 20000056329 | 10/2002 |
| AU | 2002314495 A1 | 1/2003 |
| AU | 757237 | 2/2003 |
| AU | 2002333384 | 2/2003 |
| AU | 2003273218 A1 | 7/2003 |
| AU | 2003218600 A1 | 10/2003 |
| AU | 2004200705 | 3/2004 |
| AU | 2004265253 | 6/2004 |
| AU | 2004226162 A1 | 10/2004 |
| AU | 2004252465 A1 | 1/2005 |
| AU | 2005216126 A1 | 2/2005 |
| AU | 2005216126 B2 | 2/2005 |
| AU | 2005262459 A1 | 6/2005 |
| AU | 2005262459 B2 | 6/2005 |
| AU | 2004303510 | 7/2005 |
| AU | 2005286607 B2 | 9/2005 |
| AU | 2002326531 A8 | 11/2005 |
| AU | 2005249490 | 12/2005 |
| AU | 2005242195 | 1/2006 |
| AU | 2005256155 A1 | 1/2006 |
| AU | 784157 B2 | 2/2006 |
| AU | 2005286607 | 3/2006 |
| AU | 2005325200 | 7/2006 |
| AU | 2003203831 B2 | 8/2006 |
| AU | 2006211037 | 8/2006 |
| AU | 2006216732 | 8/2006 |
| AU | 2006290433 A1 | 12/2006 |
| AU | 2006332065 B2 | 12/2006 |
| AU | 2007211344 A1 | 1/2007 |
| AU | 2007230822 A1 | 3/2007 |
| AU | 2007257692 A1 | 6/2007 |
| AU | 2007216733 | 9/2007 |
| AU | 2007299774 A1 | 9/2007 |
| AU | 2008200400 A1 | 2/2008 |
| AU | 2008200654 B2 | 4/2008 |
| AU | 2008276251 A1 | 7/2008 |
| AU | 2008231114 | 10/2008 |
| AU | 2008259930 | 12/2008 |
| AU | 2009241589 A1 | 11/2009 |
| AU | 2009243493 A1 | 12/2009 |
| AU | 2009271401 A1 | 1/2010 |
| CA | 2589421 A1 | 10/1997 |
| CA | 2332331 | 11/1999 |
| CA | 2437814 | 8/2002 |
| CA | 2450793 | 12/2002 |
| CA | 2478925 | 12/2003 |
| CA | 2069900 | 7/2004 |
| CA | 2531595 | 2/2005 |
| CA | 2535510 | 3/2005 |
| CA | 2556832 | 9/2005 |
| CA | 2601700 | 6/2006 |
| CA | 2606081 | 11/2006 |
| CA | 2619298 | 3/2007 |
| CA | 2664108 | 3/2007 |
| CA | 2633776 | 6/2007 |
| CA | 2246429 | 7/2007 |
| CA | 2612467 | 7/2007 |
| CA | 2633222 | 7/2007 |
| CA | 2641026 | 8/2007 |
| CA | 2646508 | 9/2007 |
| CA | 2647130 | 10/2007 |
| CA | 2654317 | 12/2007 |
| CA | 2654584 | 12/2007 |
| CA | 2677108 | 9/2008 |
| CA | 2681790 | 10/2008 |
| CA | 2681827 | 10/2008 |
| CA | 2687819 | 12/2008 |
| CA | 2688477 | 12/2008 |
| CA | 2691692 | 1/2009 |
| CA | 2693013 | 1/2009 |
| CA | 2716826 | 9/2009 |
| CA | 2721093 | 10/2009 |
| CA | 2722109 | 11/2009 |
| CA | 2722466 | 11/2009 |
| CA | 2727278 | 1/2010 |
| CA | 2732658 | 2/2010 |
| EP | 0 502 927 A1 | 9/1992 |
| EP | 0 502 927 A4 | 5/1993 |
| EP | 0 896 586 A1 | 2/1999 |
| EP | 0 502 927 B1 | 3/1999 |
| EP | 1 283 053 A1 | 2/2003 |
| EP | 1 053 009 B1 | 9/2004 |
| EP | 1 510 579 A2 | 3/2005 |
| EP | 1 058 562 B1 | 8/2006 |
| EP | 0 896 586 B1 | 10/2006 |
| EP | 1 728 802 A2 | 12/2006 |
| EP | 1 187 634 B1 | 12/2007 |
| EP | 1 889 631 A1 | 2/2008 |
| EP | 1 272 527 B1 | 12/2008 |
| EP | 2 016 951 | 1/2009 |
| EP | 2 016 951 A1 | 1/2009 |

(56) References Cited

FOREIGN PATENT DOCUMENTS

| | | |
|---|---|---|
| EP | 1 414 494 B1 | 3/2009 |
| EP | 1 636 593 B1 | 3/2009 |
| EP | 2 067 792 A2 | 6/2009 |
| EP | 2 138 511 A1 | 12/2009 |
| EP | 1 752 471 A1 | 1/2010 |
| EP | 912 734 B1 | 3/2010 |
| EP | 2 286 844 A2 | 2/2011 |
| EP | 1 335 658 B1 | 3/2011 |
| EP | 1 666 052 B1 | 6/2011 |
| EP | 1 817 340 B1 | 5/2012 |
| EP | 2 380 025 B1 | 9/2013 |
| EP | 2 132 573 B1 | 4/2014 |
| WO | WO 91/08214 A1 | 6/1991 |
| WO | WO 96/14864 A1 | 5/1996 |
| WO | WO 97/35885 | 10/1997 |
| WO | WO 97/35885 A1 | 10/1997 |
| WO | WO 98/02463 A1 | 1/1998 |
| WO | WO 98/02540 A1 | 1/1998 |
| WO | WO 98/53051 A1 | 11/1998 |
| WO | WO 99/39729 A2 | 8/1999 |
| WO | WO 99/39729 A3 | 8/1999 |
| WO | WO 99/44645 A1 | 9/1999 |
| WO | WO 99/60023 A1 | 11/1999 |
| WO | WO 00/27426 A1 | 5/2000 |
| WO | WO 00/78347 A1 | 12/2000 |
| WO | WO 01/00244 A2 | 1/2001 |
| WO | WO 01/00244 A3 | 1/2001 |
| WO | WO 01/77342 | 10/2001 |
| WO | WO 01/77342 A1 | 10/2001 |
| WO | WO 02/060470 A1 | 8/2002 |
| WO | WO 02/010973 A3 | 12/2002 |
| WO | WO 02/102972 A2 | 12/2002 |
| WO | WO 02/102972 A3 | 12/2002 |
| WO | WO 02/102973 A2 | 12/2002 |
| WO | WO 02/102983 | 12/2002 |
| WO | WO 03/001602 A2 | 1/2003 |
| WO | WO 03/001602 A3 | 1/2003 |
| WO | WO 03/011897 A1 | 2/2003 |
| WO | WO 03/012072 A2 | 2/2003 |
| WO | WO 03/012072 A3 | 2/2003 |
| WO | WO 03/012092 A1 | 2/2003 |
| WO | WO 03/013602 A1 | 2/2003 |
| WO | WO 03/080835 A1 | 10/2003 |
| WO | WO 03/102132 A2 | 12/2003 |
| WO | WO 03/102132 A3 | 12/2003 |
| WO | WO 2004/008099 A2 | 1/2004 |
| WO | WO 2004/008099 A3 | 1/2004 |
| WO | WO 2004/008099 A8 | 1/2004 |
| WO | WO 2004/040010 A1 | 5/2004 |
| WO | WO 2004/065417 A2 | 8/2004 |
| WO | WO 2004/087766 A2 | 10/2004 |
| WO | WO 2004/094463 A2 | 11/2004 |
| WO | WO 2004/094463 A3 | 11/2004 |
| WO | WO 2004/087766 A3 | 12/2004 |
| WO | WO 2005/112969 A2 | 1/2005 |
| WO | WO 2005/013804 A2 | 2/2005 |
| WO | WO 2005/013804 A3 | 2/2005 |
| WO | WO 2005/014618 A2 | 2/2005 |
| WO | WO 2005/016968 A2 | 2/2005 |
| WO | WO 2005/016968 A3 | 2/2005 |
| WO | WO 2005/019470 A2 | 3/2005 |
| WO | WO 2005/019470 A3 | 3/2005 |
| WO | WO 2005/037071 A3 | 4/2005 |
| WO | WO 2005/040339 A2 | 5/2005 |
| WO | WO 2005/040339 A3 | 5/2005 |
| WO | WO 2005/044302 A1 | 5/2005 |
| WO | WO 2005/045058 A2 | 5/2005 |
| WO | WO 2005/045058 A3 | 5/2005 |
| WO | WO 2005/001048 A2 | 6/2005 |
| WO | WO 2005/049829 A1 | 6/2005 |
| WO | WO 2005/061547 A2 | 7/2005 |
| WO | WO 2005/079434 A2 | 9/2005 |
| WO | WO 2005/079434 A3 | 9/2005 |
| WO | WO 2005/081898 A2 | 9/2005 |
| WO | WO 2005/061547 A3 | 11/2005 |
| WO | WO 2005/117973 | 12/2005 |
| WO | WO 2005/117973 A2 | 12/2005 |
| WO | WO 2005/117973 A3 | 12/2005 |
| WO | WO 2005/117986 A2 | 12/2005 |
| WO | WO 2006/007398 A1 | 1/2006 |
| WO | WO 2006/007398 A9 | 1/2006 |
| WO | WO 2006/068640 A1 | 1/2006 |
| WO | WO 2006/034488 A2 | 3/2006 |
| WO | WO 2005/112969 A3 | 4/2006 |
| WO | WO 2006/042002 A2 | 4/2006 |
| WO | WO 2006/042002 A3 | 4/2006 |
| WO | WO 2006/000034 A1 | 5/2006 |
| WO | WO 2005/001048 A3 | 6/2006 |
| WO | WO 2005/117986 A3 | 6/2006 |
| WO | WO 2006/058074 | 6/2006 |
| WO | WO 2006/060021 A2 | 6/2006 |
| WO | WO 2006/063042 A2 | 6/2006 |
| WO | WO 2006/063042 A3 | 6/2006 |
| WO | WO 2006060021 A3 | 6/2006 |
| WO | WO 2006/072620 A1 | 7/2006 |
| WO | WO 2006/078307 A1 | 7/2006 |
| WO | WO 2006/082515 A2 | 8/2006 |
| WO | WO 2006/084018 A2 | 8/2006 |
| WO | WO 2006/084018 A3 | 8/2006 |
| WO | WO 2006/091209 A2 | 8/2006 |
| WO | WO 2006/091693 A2 | 8/2006 |
| WO | WO 2006/092693 A3 | 8/2006 |
| WO | WO 2006/034488 A3 | 9/2006 |
| WO | WO 2006/096663 A2 | 9/2006 |
| WO | WO 2006/096663 A3 | 9/2006 |
| WO | WO 2006/096861 A2 | 9/2006 |
| WO | WO 2006/096861 A3 | 9/2006 |
| WO | WO 2006/096861 A9 | 9/2006 |
| WO | WO 2006/107617 A3 | 10/2006 |
| WO | WO 2006/114115 A1 | 11/2006 |
| WO | WO 2007/015935 A2 | 2/2007 |
| WO | WO 2007/015935 A3 | 2/2007 |
| WO | WO 2007/015935 A9 | 2/2007 |
| WO | WO 2007/031875 A2 | 3/2007 |
| WO | WO 2007/031875 A3 | 3/2007 |
| WO | WO 2006/082515 A3 | 6/2007 |
| WO | WO 2007/071777 A2 | 6/2007 |
| WO | WO 2007/071777 A3 | 6/2007 |
| WO | WO 2007/077028 A2 | 7/2007 |
| WO | WO 2007/084181 A2 | 7/2007 |
| WO | WO 2007/084181 A3 | 7/2007 |
| WO | WO 2007/077028 A3 | 9/2007 |
| WO | WO 2007/109254 A2 | 9/2007 |
| WO | WO 2007/109254 A3 | 9/2007 |
| WO | WO 2007/112193 | 10/2007 |
| WO | WO 2007/115571 | 10/2007 |
| WO | WO 2007/115571 A2 | 10/2007 |
| WO | WO 2007/145862 A2 | 12/2007 |
| WO | WO 2007/145862 A3 | 12/2007 |
| WO | WO 2007/146968 A2 | 12/2007 |
| WO | WO 2007/146968 A3 | 12/2007 |
| WO | WO 2007145832 B1 | 12/2007 |
| WO | WO 2008/019394 A2 | 2/2008 |
| WO | WO 2008/019394 A3 | 2/2008 |
| WO | WO 2008/025527 A1 | 3/2008 |
| WO | WO 2008/027236 | 3/2008 |
| WO | WO 2008/027263 A2 | 3/2008 |
| WO | WO 2008/027263 A3 | 3/2008 |
| WO | WO 2008/036802 A2 | 3/2008 |
| WO | WO 2008/036802 A3 | 3/2008 |
| WO | WO 2008/064884 A1 | 6/2008 |
| WO | WO 2008/066498 A1 | 6/2008 |
| WO | WO 2007/115571 A3 | 7/2008 |
| WO | WO 2008/079302 A2 | 7/2008 |
| WO | WO 2008/083949 A2 | 7/2008 |
| WO | WO 2008/083949 A3 | 7/2008 |
| WO | WO 2008/088658 A2 | 7/2008 |
| WO | WO 2008/100624 A2 | 8/2008 |
| WO | WO 2008/100624 A3 | 8/2008 |
| WO | WO 2008/109440 A2 | 9/2008 |
| WO | WO 2008/109440 A3 | 9/2008 |
| WO | WO 2008/109440 A8 | 9/2008 |
| WO | WO 2008/118733 A2 | 10/2008 |
| WO | WO 2008/118733 A3 | 10/2008 |

(56) References Cited

FOREIGN PATENT DOCUMENTS

| | | |
|---|---|---|
| WO | WO 2008/119493 A1 | 10/2008 |
| WO | WO 2008/127710 A2 | 10/2008 |
| WO | WO 2007/115571 A8 | 11/2008 |
| WO | WO 2008/140493 A2 | 11/2008 |
| WO | WO 2008/140603 A2 | 11/2008 |
| WO | WO 2008/145846 A2 | 12/2008 |
| WO | WO 2008/148546 A2 | 12/2008 |
| WO | WO 2008/151072 | 12/2008 |
| WO | WO 2008/151072 A1 | 12/2008 |
| WO | WO 2009/003145 A1 | 12/2008 |
| WO | WO 2009/009523 A2 | 1/2009 |
| WO | WO 2009/012140 A2 | 1/2009 |
| WO | WO 2009/012140 A3 | 1/2009 |
| WO | WO 2009/023266 A1 | 2/2009 |
| WO | WO 2009/045579 A2 | 4/2009 |
| WO | WO 2009/052830 A1 | 4/2009 |
| WO | WO 2005/014618 A3 | 5/2009 |
| WO | WO 2009/082443 A2 | 7/2009 |
| WO | WO 2009/108637 A1 | 9/2009 |
| WO | WO 2009/111707 A1 | 9/2009 |
| WO | WO 2009/121631 A2 | 10/2009 |
| WO | WO 2009/126920 | 10/2009 |
| WO | WO 2009/134776 A2 | 11/2009 |
| WO | WO 2009/134776 A3 | 11/2009 |
| WO | WO 2009/134870 A1 | 11/2009 |
| WO | WO 2009/134976 A1 | 11/2009 |
| WO | WO 2009/137429 A1 | 11/2009 |
| WO | WO 2009/156179 A1 | 12/2009 |
| WO | WO 2010/008726 A1 | 1/2010 |
| WO | WO 2010/009794 A1 | 1/2010 |
| WO | WO 2010/019952 | 2/2010 |
| WO | WO 2009/156179 A8 | 3/2010 |
| WO | WO 2010/051502 A2 | 5/2010 |
| WO | WO 2010/083252 A2 | 7/2010 |
| WO | WO 2010/083470 A1 | 7/2010 |
| WO | WO 2010/097126 A1 | 9/2010 |
| WO | WO 2010/099186 | 9/2010 |
| WO | WO 2010/108127 A1 | 9/2010 |
| WO | WO 2010/127181 A1 | 11/2010 |
| WO | WO 2010/136569 A1 | 12/2010 |
| WO | WO 2011008990 A1 | 1/2011 |
| WO | WO 2011/019620 A1 | 2/2011 |
| WO | WO 2011/022727 A2 | 2/2011 |
| WO | WO 2011/031397 A1 | 3/2011 |
| WO | WO 2011/031840 | 3/2011 |
| WO | WO 2011/044368 | 4/2011 |
| WO | WO 2011/047180 | 4/2011 |
| WO | WO 2011/060206 A3 | 5/2011 |
| WO | WO 20110/60206 A2 | 5/2011 |
| WO | WO 2011/044311 A2 | 6/2011 |
| WO | WO 2011/044311 A3 | 6/2011 |
| WO | WO 2011/103242 | 8/2011 |
| WO | WO 2011/109625 | 9/2011 |
| WO | WO 2011/112953 A2 | 9/2011 |
| WO | WO 2011/136911 A2 | 11/2011 |
| WO | WO 2011/139629 A2 | 11/2011 |
| WO | WO 2011/143414 A1 | 11/2011 |
| WO | WO 2011/144749 | 11/2011 |
| WO | WO 2011/144749 A1 | 11/2011 |
| WO | WO 2011/146568 A1 | 11/2011 |
| WO | WO 2012/103341 A1 | 8/2012 |
| WO | WO 2012/106578 A1 | 8/2012 |
| WO | WO 2012/106587 A1 | 8/2012 |
| WO | WO 2012/120500 A2 | 9/2012 |
| WO | WO 2012/125807 A2 | 9/2012 |

OTHER PUBLICATIONS

R&D Systems, Human ErbB3/Her3 Antibody, Clone # 526922, Catalog # MAB3482, Jun. 28, 2010.

Lee-Hoeflich, et al., 2008, Cancer Research, 68(14); 5878, A central role for HER3 in *HER2*-Amplifired Breast Cancer.

Merrimack Pharmaceuticals Initiates Enrollment in Phase 1 of MM-121, an ErbB3 Antagonist, Biopharm CEDD update—Alert Aug. 11, 2008.

AACR Annual Meeting, San Diego CA, contract No. 3974, Antibodies, Apr. 12-16, 2008.

Edward Htun Van Der Horst, et al., Anti-HER-3 MAbs inhibit HER-3-mediated signaling in breast cancer cell lines resistant to anti-HER-2 antibodies. Internation Journal of Cancer, vol. 115, No. 4, Jul. 1, 2005, pp. 519-527.

Anne W. Hamburger, the Role of ErbB3 and its Binding Partners in Breast Cancer Progression and Resistance to Hormone and Tyrosine Kinase Directed Therapies., Journal of Mammary Gland Biology and Neoplasia, vol. 13, No. 2, Apr. 19, 2008, pp. 225-233.

Yamane-Ohnuki Naoko, et al., Prodiction of therapeutic antibodies with controlled fucosylation, MABS, vol. 1, No. 3, May 1, 2009, pp. 230-236.

Amin DN, Campbell MR, Moasser MM. The role of HER3, the unpretentious member of the HER family, in cancer biology and cancer therapeutics. *Seminars Cell* and *Dev Biol*. 2010;21:944-50.

Beji A, Horst D, Engel J, Kirchner T, Ullrich A. Toward the prognostic significance and therapeutic potential of HER3 receptor tyrosine kinase in human colon cancer. *Clin Cancer Res*. 2012;18:956-68.

Casalini P, Iorio MV, Galmozzi E, Menard S. Role of HER receptors family in development and differentiation. *J Cell Physiol*. 2004;200:343-50.

Dall'Acqua WF, Kiener PA, Wu H. Properties of Human IgG1's engineered for enhanced binding to the neonatal Fc Recptor (FcRn). *J Biol Chem*. 2006;281:23514-24.

Engelman, Jeffrey A., et al., MET Applification Leads to Gefitinib Resistance in Lung Cancer by Activating ERBB3 Signaling, Science 316, 1039-1043, 2007.

Tolmachev, et al., Radionuclide Therapy of HER2-Positive Microxenografts Using a 177Lu-Labeled HER2-Specific Affibody Molecule, Cancer Res 2007; 67: (6). Mar. 15, 2007.

Edward Htun van der Horst, et al., Anti-Her-3 MAbs Inhibit Her-3-Mediated Signaling in Breast Cancer Cell Lines Resistant to Anti-Her-2 Antibodies. Int. J. Cancer: 115, 519-527 (2005).

G Sithanandam1 and LM Anderson2, the ERBB3 receptor in cancer and cancer gene therapy. Cancer Gene Therapy (2008), 1-36.

Wallasch, et al., Heregulin-dependent regulation of HER2/neu oncogenic signaling by heterodimerization with HER3. The EMBO Journal vol. 14 No. 17 pp. 4267-4275, 1995.

Scott, et al., Coordinate Suppression of *ERBB2* and *ERBB3* by Enforced Expression of microRNA *miR-125a* or *miR-125b*. The latest version is at www.jbc.org/cgi/doi/10.1074/jbc.M609383200 JBC Papers in Press. Published on Nov. 16, 2006 as Manuscript M609383200.

Hynes, et al., ErbB receptors and signaling pathways in cancer. Current Opinion in Cell Biology 2009, 21:1-8.

Xue, et al., ErbB3-Dependent Motility and Intravasation in Breast Cancer Metastasis. (Cancer Res 2006; 66(3): 1418-26).

Yokoe, et al., the Asn418-Linked N-Glycan of ErbB3 Plays a Crucial Role in Preventing Spontaneous Heterodimerization and Tumor Promotion. [Cancer Res 2007;67(5):1935-42].

Soltoff, et al., ErbB3 Is Involved in Activation of Phosphatidylinositol 3-Kinase by Epidermal Growth Factor. Molecular and Cellular Biology, Jun. 1994, pp. 3550-3558 vol. 14, No. 6, 0270-7306, 1994.

W J *Gullick*, the Type 1 growth factor receptors and their ligands considered as a complex system, *Endocrine-Related Cancer* (2001) 8 75-82.

Sergina, et al., Escape from HER-family tyrosine kinase inhibitor therapy by the kinase-inactive HER3, Nature. 2007; doi:10.1038/nature05474.

Sheng, et al., An Activated ErbB3/NRG1 Autocrine Loop Supports in Vivo Proliferation in Ovarian Cancer Cells, Cancer Cell Mar. 16, 2010 1 17:298-31.

Mills, et al., The Rebirth of a Phoenix: Ovarian Cancers Are Addicted to ErbB-3. Cancer Cell 17, Mar. 16, 2010.

Weinstein, et al., the oncogene heregulin induces apoptosis in breast epithelial cells and tumors, Oncogene (1998).

Holmes, et al., Identification of Heregulin, Science 1992.

Kraus, et al., Isolation and characterization of ERBB3, a third member of the ERBB/epidermal growth factor receptor family: Evidence

(56) References Cited

OTHER PUBLICATIONS for overexpression in a subset of human mammary tumors, Proc. Natl. Acad. Sci. USA, vol. 86, pp. 9193-9197, Dec. 1989 Biochemistry.

Jin, et al., Cross-Talk Between the ErbB/HER Family and the Type I Insulin-Like Growth Factor Receptor Signaling Pathway in Breast Cancer, J Mammary Gland Biol Neoplasia (2008) 13:485498.

Lee-Hoeflich, et al., A Central Role for HER3 in HER2-Amplified Breast Cancer: Implications for Targeted Therapy, Cancer Res 2008; 68: (14). Jul. 15, 2008.

Lemke, Neuregulin-1 and Myelination, Science STKE 2006.

Lin, et al., Soluble ErbB3 Levels in BoneMarrow and Plasma of Men with Prostate Cancer, Clin Cnacer Res 2008; 14(12) Jul. 15, 2008.

Merrimack Anti Her3 Poster AACR 2008.

Meyer, Letters to Nature, 1995, vol. 378: 386-390.

MM121 2010 Supplementary CAN Mar. 15, 2010 Schoeberl.

Corfas, et al., Nature Neuroscience, vol. 7, No. 6, Jun. 2004.

Sakai, et al. Pertuzumab, a novel HER dimerization inhibitor, inhibits the growth of human lung cancer cells mediated by the HER3 signaling pathway. Cancer Sci. Sep. 2007, vol. 98, No. 9, 1498-1503.

Kim, et al., the Journal of Biological Chemistry, vol. 269, No. 40, Issue of Oct. 7, pp. 24747-24755, 1994.

Boudeau, et al., Emerging roles of pseudokinases Trends in Cell Biology vol. 16 No. 9, Aug. 2006.

Robinson, et al., Targeting ErbB2 and ErbB3 with a bispecific single-chain Fv enhances targeting selectivity and induces a therapeutic effect in vitro, British Journal of Cancer (2008), 1-11.

Wheeler, et al., Mechanisms of acquired resistance to cetuximab: role of HER (ErbB) family members, Oncogene (2008) 27, 3944-3956.

Schoeberl et al., (2009). Therapeutically Targeting ErbB3, Jun. 30, 2009; Sci Signaling.

Schoeberl, et al., Therapeutics, Targets, and Chemical Biology an ErbB3 Antibody, MM-121, Is Active in Cancers with Ligand-Dependent Activation, Cancer Res 2010; 70(6):2485-94.

Sergina, et al., the HER family and cancer: emerging molecular mechanisms and therapeutic targets, 2007 Trends Mol Med 13(12).

Xia, et al., Combining lapatinib (GW572016), a small molecule inhibitor of ErbB1 and ErbB2 tyrosine kinases, with therapeutic anti-ErbB2 antibodies enhances apoptosis of ErbB2- overexpressing breast cancer cells, Oncogene (2005) 24, 6213-6221.

Groner, et al., *Current Molecular*Medicine 2004, 4, 539-547. 2004 Bentham Science Publishers Ltd. Therapeutic Antibodies.

Anti-her3 Competitor Assets Report, Jun. 18, 2008.

* cited by examiner

ANTIGEN BINDING PROTEINS

RELATED APPLICATIONS

This application is a US National Stage Application under 35 USC §371 of International Application No. PCT/US2011/050322 filed Sep. 2, 2011 which claims the benefit of U.S. Provisional Patent Application No. 61/379,840 filed on Sep. 3, 2010 and the benefit of U.S. Provisional Patent Application No. 61/440,460 filed on Feb. 8, 2011. The entire teachings of the above identified applications are incorporated herein by reference.

FIELD OF THE DISCLOSURE

The present disclosure relates to antigen binding proteins, such as antibodies, which bind to the HER3 receptor, polynucleotides encoding such antigen binding proteins, pharmaceutical compositions comprising said antigen binding proteins, and methods of manufacture. The present disclosure also concerns the use of such antigen binding proteins in the treatment or prophylaxis of diseases associated with a variety of cancers.

BACKGROUND OF THE DISCLOSURE

HER3 (also called ErbB3) (SEQ ID NO: 21) is one of four structurally related receptor tyrosine kinases comprising the ErbB/HER protein family or epidermal growth factor receptor (EGFR) family of receptors. These receptors are made up of an extracellular region that contains approximately 620 amino acids, a single transmembrane spanning region, and a cytoplasmic tyrosine kinase domain. The extracellular region of each family member is made up of four subdomains, L1, S1 (CR1), L2 and S2 (CR2), where "L" signifies a leucine-rich repeat domain and "CR" a cysteine-rich region. Activation of these receptors typically requires ligand-induced receptor dimerization. HER3 is unique among this family in that, while it has a ligand (Neuregulin-1, NRG; Heregulin, HRG; see Table 1) binding domain, it has no intrinsic tyrosine kinase activity due to the presence of certain amino acid changes in the kinase domain. Therefore, it can bind ligand, but as a homodimer, does not convey the signal into the cell through protein phosphorylation. However, it does form heterodimers with other EGF receptor family members that have kinase activity (e.g., HER1/HER3; HER2/HER3; HER3/HER4), to form active signaling-competent moieties. Of particular note is the pairing with HER2, since the HER2/HER3 combination appears to have the highest proliferative potential through various intracellular pathways including the PI3K/pAKT pathway. When HER3 forms dimers with HER2, the resulting signaling complex can be disrupted by antibodies, such as pertuzumab, directed to the HER2 component. In addition, the affinity of HER3 for HRG may be increased when coexpressed with HER2. Recently, the interactions of HER3 with other cell surface receptors (including those outside of the HER family, such as c-MET) have emerged as important escape mechanisms for resistance to certain anti-cancer agents. Alternate transcriptional splice variants encoding different isoforms of HER3 have been characterized, though not fully. One isoform lacks the intermembrane region and is secreted outside the cell. This form may act to modulate the activity of the membrane-bound form by sequestering ligand. Heterodimerization of HER3 with other receptors leads to the activation of pathways important in cell growth and survival. Therefore, controlled expression and activation of these pathways is a necessity for normal growth of the organism and any impairment of such can lead to disease.

The four members of the HER protein family are capable of forming homodimers, heterodimers, and higher order oligomers upon activation by a subset of potential growth factor ligands. Table 1 below lists known ligands of the HER family of receptors.

TABLE 1

| ErbB (HER) receptor | Ligand |
| --- | --- |
| EGFR | Epidermal growth factor (EGF) |
|  | Transforming growth factor alpha (TGFa) |
|  | Amphiregulin (AR) |
|  | Epigen |
| EGFR & HER4 | Betacellulin (BTC) |
|  | Heparin-binding growth factor (HB-EGF) |
|  | Epiregulin (EPR) |
| HER2 | None |
| HER3 & HER4 | Neuregulin 1/Heregulin (NRG-1; HRG) |
|  | Neuregulin 2 (NRG-2) |
| HER4 | Neuregulin 3 (NRG-3) |
|  | Neuregulin 4 (NRG-4) |
|  | Tomoregulin |

In mice, loss of signaling by any member of the ErbB family results in embryonic lethality with defects in organs including the lungs, skin, heart and brain. On the other hand, excessive ErbB/HER signaling is associated with the development of a wide variety of solid tumor types. ErbB-1 (EGFR/HER1) and ErbB-2 (HER2) are found in many human cancers and their excessive signaling may be critical factors in the development and malignancy of these tumors. For example, EGFR is overexpressed in many cancers including lung and colon. Drugs such as cetuximab, gefitinib, erlotinib are used to inhibit the activity of this receptor in those settings. The HER2 gene is amplified and the protein overexpressed in breast cancer, which is currently treated with herceptin, tamoxifen and lapatinib, amongst others. Escape from sensitivity to these treatments is an increasing problem in cancer, and is a major reason why more novel and effective treatments are required. Amplification of the HER3 gene and/or overexpression of its protein have been reported in numerous cancers. Recently, it has been shown that acquired resistance to, e.g., gefitinib can be linked to hyperactivity of HER3. This is linked to an acquired overexpression of c-MET that phosphorylates HER3, which, in turn, activates the PI3K/Akt pathway—a key cell growth/survival pathway.

The HER3 receptor (SEQ ID NO: 21) has unique properties and occupies a key node in cell signaling pathways mediated by the HER receptor family. It is also increasingly implicated in mechanisms of resistance to common cancer therapeutic agents. Since it lacks a functionally active kinase domain, it is not 'druggable' with conventional small molecules. However, as a cell surface receptor that relies on interaction with other cell surface receptors for its activity in various key growth, survival and differentiation pathways, it is an attractive target for biopharmaceutical approaches.

Thus, a need exists for therapeutic antibodies that target HER3 receptors and for methods of treating cancers with such antibodies.

SUMMARY OF THE DISCLOSURE

One aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 2, SEQ ID NO: 3, and SEQ ID NO: 4; and/or a light chain variable region having at least one CDR with 75% or greater sequence identity to an amino acid sequence selected from the group consisting of SEQ ID NO: 6, SEQ ID NO: 7, and SEQ ID NO: 8.

Another aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 23, SEQ ID NO: 24, and SEQ ID NO: 25; and/or a light chain variable region having at least one CDR with 75% or greater sequence identity to an amino acid sequence selected from the group consisting of SEQ ID NO: 27, SEQ ID NO: 28, and SEQ ID NO: 29.

Another aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 45, SEQ ID NO: 46, and SEQ ID NO: 47; and/or a light chain variable region having at least one CDR with 75% or greater sequence identity to an amino acid sequence selected from the group consisting of SEQ ID NO: 49, SEQ ID NO: 50, and SEQ ID NO: 51.

Another aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 31, SEQ ID NO: 32, and SEQ ID NO: 33; and/or a light chain variable region having at least one CDR with 75% or greater sequence identity to an amino acid sequence selected from the group consisting of SEQ ID NO: 35, SEQ ID NO: 36, and SEQ ID NO: 37.

Another aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 10, SEQ ID NO: 11, and SEQ ID NO: 12; and/or a light chain variable region having at least one CDR with 75% or greater sequence identity to an amino acid sequence selected from the group consisting of SEQ ID NO: 12, SEQ ID NO: 7, SEQ ID NO: 8, SEQ ID NO: 18, SEQ ID NO: 19, and SEQ ID NO: 20. Another aspect of the disclosure is an antigen binding protein that specifically binds to the HER3 receptor comprising a heavy chain variable region sequence having the amino acid sequence shown in SEQ ID NO: 1 and a light chain variable region sequence having the amino acid sequence shown in SEQ ID NO: 5.

Another aspect of the disclosure is an antigen binding protein that specifically binds to the HER3 receptor comprising a heavy chain variable region sequence having the amino acid sequence shown in SEQ ID NO: 22 and a light chain variable region sequence having the amino acid sequence shown in SEQ ID NO: 26.

Another aspect of the disclosure is an antigen binding protein that specifically binds to the HER3 receptor comprising a heavy chain variable region sequence having the amino acid sequence shown in SEQ ID NO: 44 and a light chain variable region sequence having the amino acid sequence shown in SEQ ID NO: 48.

Another aspect of the disclosure is an antigen binding protein that specifically binds to the HER3 receptor comprising a heavy chain variable region sequence having the amino acid sequence shown in SEQ ID NO: 30 and a light chain variable region sequence having the amino acid sequence shown in SEQ ID NO: 34.

Another aspect of the disclosure is an antigen binding protein that specifically binds to the HER3 receptor comprising a heavy chain variable region sequence having the amino acid sequence shown in SEQ ID NO: 9 and a light chain variable region sequence selected from the group consisting of the amino acid sequence shown in SEQ ID NO: 13 and the amino acid sequence shown in SEQ ID NO: 17.

Another aspect of the disclosure is an antigen binding protein that specifically binds to the HER3 receptor comprising a heavy chain variable region sequence having the amino acid sequence shown in SEQ ID NO: 30 and a light chain variable region sequence having the amino acid sequence shown in SEQ ID NO: 57.

Another aspect of the disclosure is an antigen binding protein that specifically binds to the HER3 receptor which binds which specifically binds to a peptide chain domain comprising amino acid residues 184 to 329 of SEQ ID NO: 21

Another aspect of the disclosure is an antigen binding protein that specifically binds to the HER3 receptor which specifically binds to a peptide chain domain comprising amino acid residues 330 to 495 of SEQ ID NO: 21.

Another aspect of the disclosure is an antigen binding protein which specifically binds a HER3 receptor and comprises CDRH1 having the amino acid sequence shown in SEQ ID NO: 2, CDRH2 having the amino acid sequence shown in SEQ ID NO: 3, CDRH3 having the amino acid sequence shown in SEQ ID NO: 4, CDRL1 having the amino acid sequence shown in SEQ ID NO: 6, CDRL2 having the amino acid sequence shown in SEQ ID NO: 7, and CDRL3 having the amino acid sequence shown in SEQ ID NO: 8.

Another aspect of the disclosure is an antigen binding protein which specifically binds a HER3 receptor and comprises CDRH1 having the amino acid sequence shown in SEQ ID NO: 23, CDRH2 having the amino acid sequence shown in SEQ ID NO: 24, CDRH3 having the amino acid sequence shown in SEQ ID NO: 25, CDRL1 having the amino acid sequence shown in SEQ ID NO: 27, CDRL2 having the amino acid sequence shown in SEQ ID NO: 28, and CDRL3 having the amino acid sequence shown in SEQ ID NO: 29.

Another aspect of the disclosure is an antigen binding protein which specifically binds a HER3 receptor and comprises CDRH1 having the amino acid sequence shown in SEQ ID NO: 31, CDRH2 having the amino acid sequence shown in SEQ ID NO: 32, CDRH3 having the amino acid sequence shown in SEQ ID NO: 33, CDRL1 having the amino acid sequence shown in SEQ ID NO: 35, CDRL2 having the amino acid sequence shown in SEQ ID NO: 36, and CDRL3 having the amino acid sequence shown in SEQ ID NO: 37.

Another aspect of the disclosure is an antigen binding protein which specifically binds a HER3 receptor and comprises CDRH1 having the amino acid sequence shown in SEQ ID NO: 45, CDRH2 having the amino acid sequence shown in SEQ ID NO: 46, CDRH3 having the amino acid sequence shown in SEQ ID NO: 47, CDRL1 having the amino acid sequence shown in SEQ ID NO: 49, CDRL2 having the amino acid sequence shown in SEQ ID NO: 50, and CDRL3 having the amino acid sequence shown in SEQ ID NO: 51.

Another aspect of the disclosure is an antigen binding protein which specifically binds a HER3 receptor and comprises CDRH1 having the amino acid sequence shown in SEQ ID NO: 10, CDRH2 having the amino acid sequence shown in SEQ ID NO: 11, CDRH3 having the amino acid sequence shown in SEQ ID NO: 12, CDRL1 having the amino acid sequence shown in SEQ ID NO: 14, CDRL2 having the amino acid sequence shown in SEQ ID NO: 15, and CDRL3 having the amino acid sequence shown in SEQ ID NO: 16.

Another aspect of the disclosure is an antigen binding protein which specifically binds a HER3 receptor and comprises CDRH1 having the amino acid sequence shown in SEQ ID NO: 10, CDRH2 having the amino acid sequence shown in SEQ ID NO: 11, CDRH3 having the amino acid sequence shown in SEQ ID NO: 12, CDRL1 having the amino acid sequence shown in SEQ ID NO: 18, CDRL2 having the amino acid sequence shown in SEQ ID NO: 19, and CDRL3 having the amino acid sequence shown in SEQ ID NO: 20.

The disclosure also provides isolated nucleic acids, expression vectors, recombinant host cells, methods for the production of antigen binding proteins, pharmaceutical compositions, methods of treating cancer, uses, and methods for the production of antigen binding proteins all of which relate to these aspects of the disclosure.

Another aspect of the disclosure is an antigen binding protein comprising a heavy chain sequence having amino acid residues 20 to 466 of the amino acid sequence shown in SEQ ID NO: 100 and a light chain sequence having amino acid residues 20 to 238 of the amino acid sequence shown in SEQ ID NO: 104.

Another aspect of the disclosure is an antigen binding protein comprising a heavy chain sequence having amino acid residues 20 to 466 of the amino acid sequence shown in SEQ ID NO: 102 and a light chain sequence having amino acid residues 20 to 238 of the amino acid sequence shown in SEQ ID NO: 104.

Another aspect of the disclosure is an isolated nucleic acid encoding amino acid residues 20 to 466 of the amino acid sequence shown in SEQ ID NO: 100.

Another aspect of the disclosure is an isolated nucleic acid encoding amino acid residues 20 to 238 of the amino acid sequence shown in SEQ ID NO: 104.

Another aspect of the disclosure is an isolated nucleic acid encoding amino acid residues 20 to 466 of the amino acid sequence shown in SEQ ID NO: 102.

Figure 28:
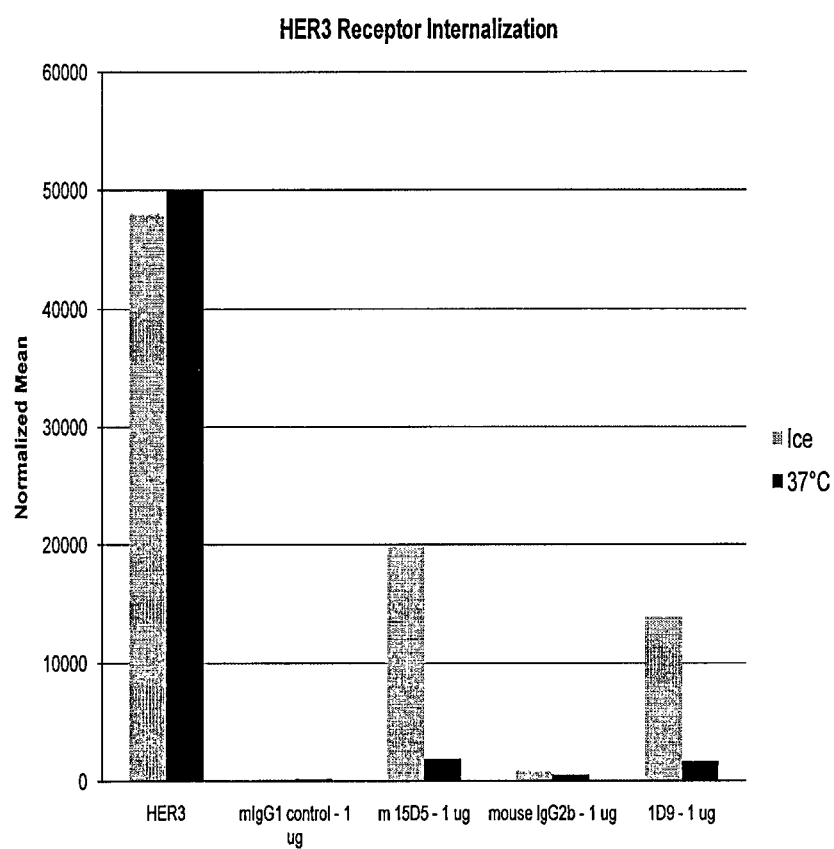

FIG. 28. The murine 15D5 antibody (M5.15D5.2 μl.H10) and humanized 1D9 antibody induced receptor internalization in human CHL-1 melanoma cells.

Figure 29A:
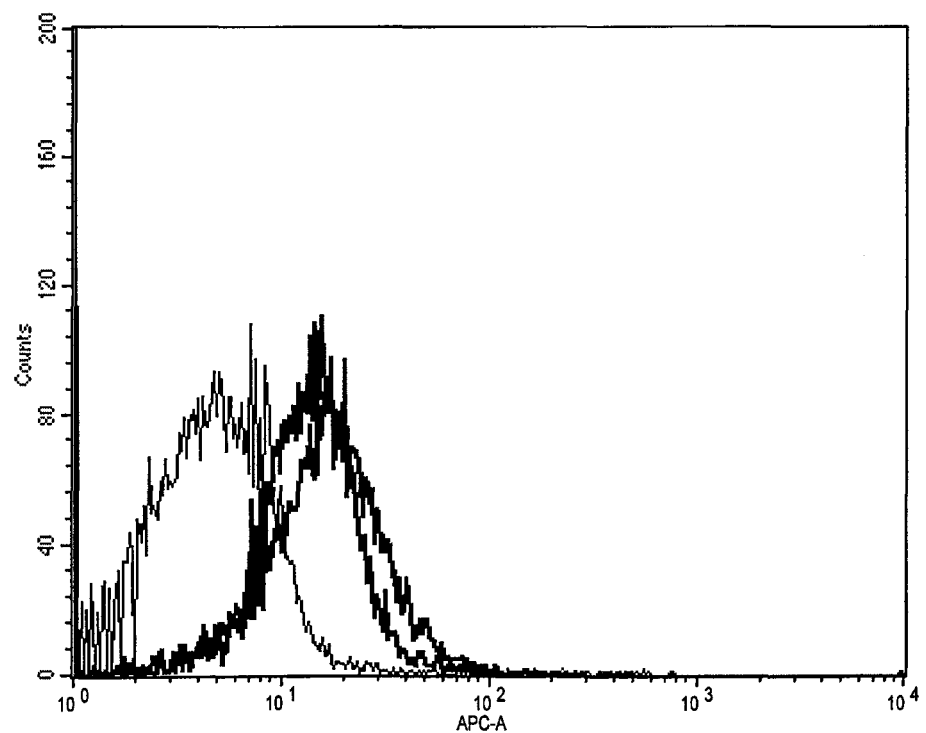
Figure 29B:
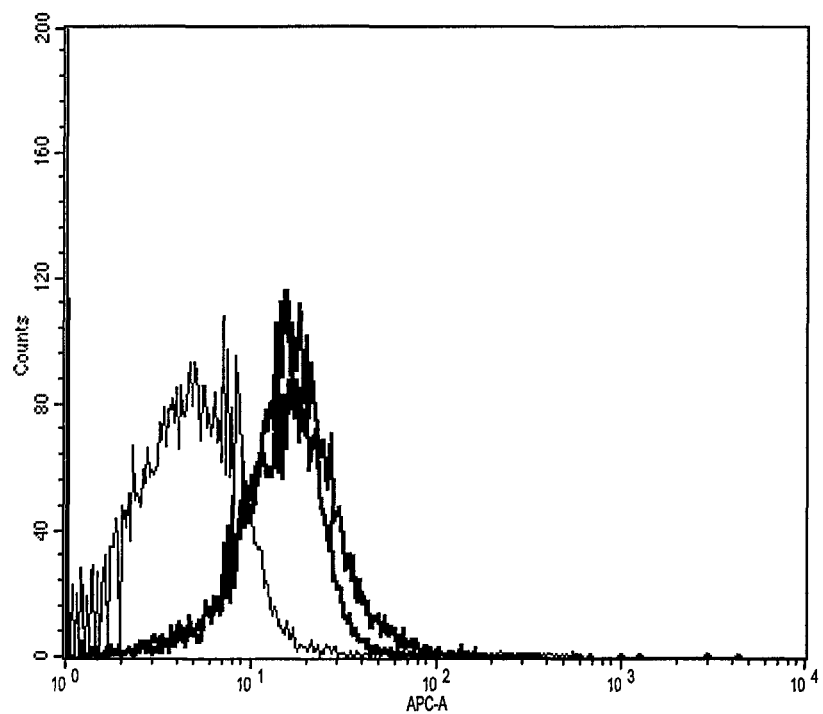
Figure 29C:
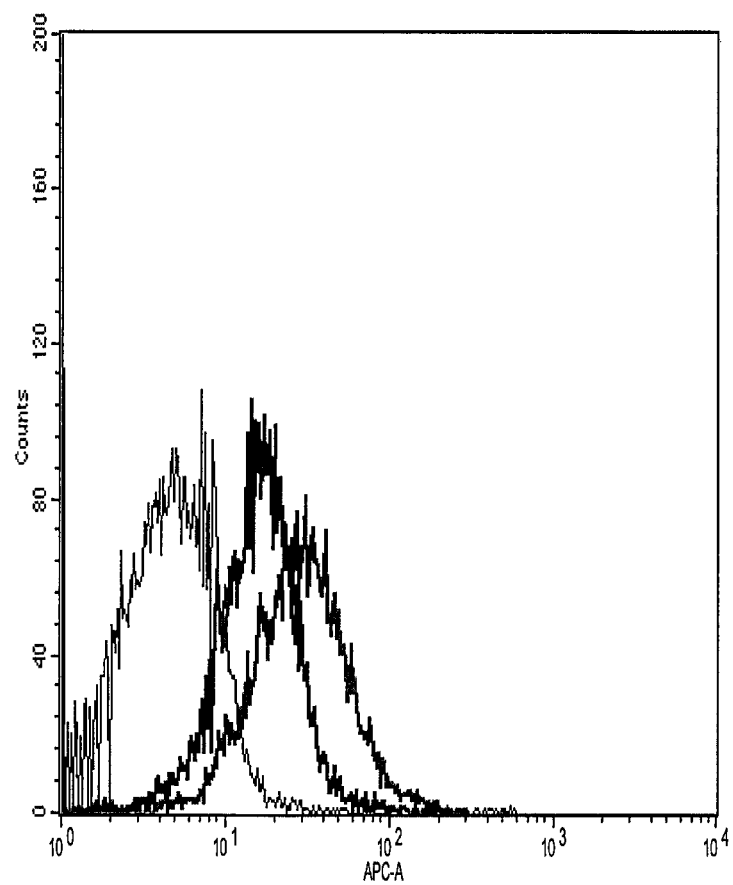

FIG. 29. (a) The murine 1D9 antibody (M5.1D9.1F5) cross-reacts with murine HER3 expressed on B16F10 cells. (b) The murine 24H5 antibody (M5.24H5.C2) cross-reacts with murine HER3 expressed on B16F10 cells. (c) The murine 15D5 antibody (M5.15D5.1C1) cross-reacts with murine HER3 expressed on B16F10 cells.

Figure 30:
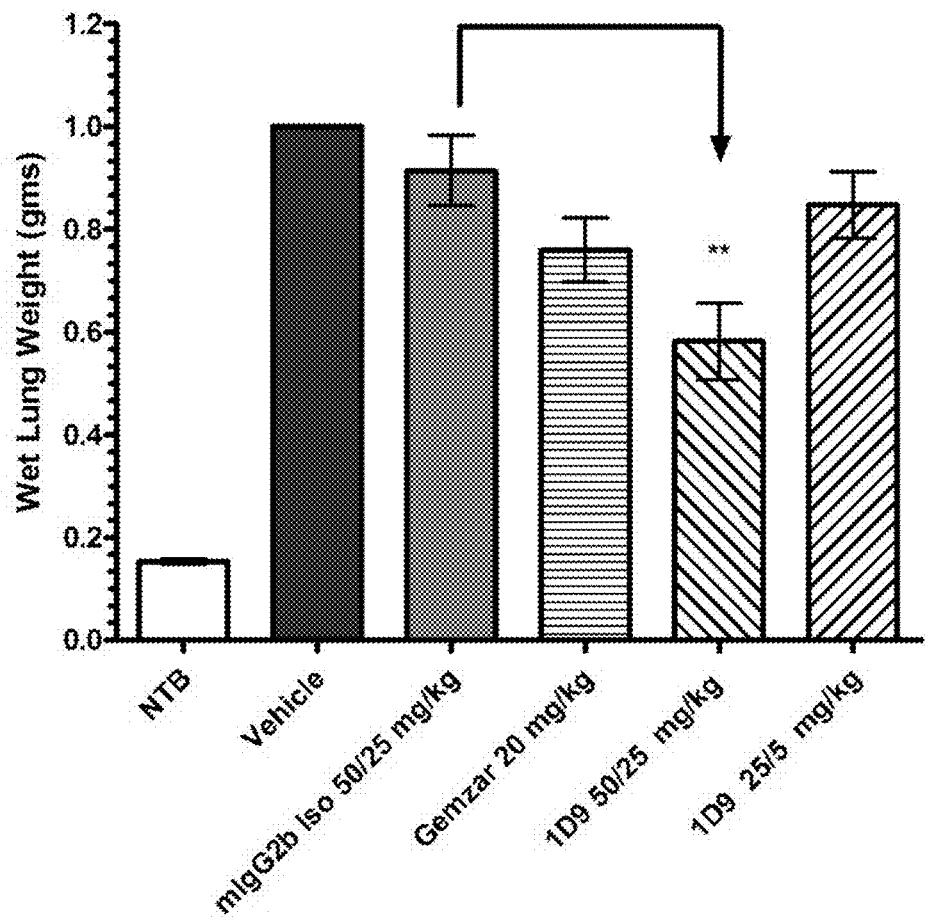

FIG. 30. Efficacy of mouse anti-HER3 mAb, murine 1D9 antibody, in the B16F10 syngeneic tumor model. C57BL/6 mice, administered a bolus i.v. injection of mouse B16F10 melanoma cells, were treated with isotype control, mouse Her3 mAb (m1D9) or GEMZAR™ (gemcitabine) to assess the effect on tumor cell colonization in the lung. Isotype control and m1D9 were administered on Day 3 (25 or 50 mg/kg, i.p.) and on Days 7 and 11 (5 or 25 mg/kg, i.p.) post B16F10 injection. GEMZAR™ was administered on Day 3 only (20 mg/kg, i.v.). Lungs were collected on Day 20 for wet weight measurements. Treatment with m-1D9 resulted in a dose-dependent decrease in lung weight compared to the isotype control ($p<0.01$; One-Way ANOVA with Dunnett's post test). NTB=non tumor bearing mice.

Figure 31:
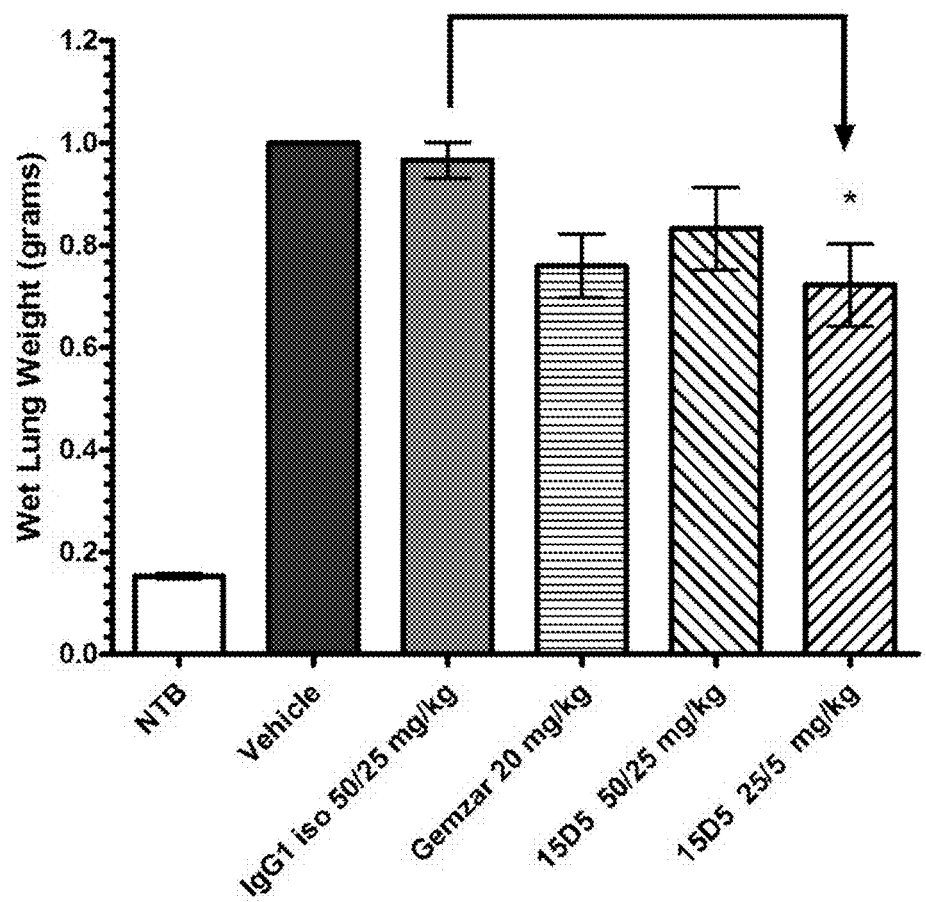

FIG. 31. Efficacy of mouse anti-HER3 mAb, murine 15D5 antibody, in the B16F10 syngeneic tumor model. C57BL/6 mice, administered a bolus i.v. injection of mouse B16F10 melanoma cells, were treated with isotype control, mouse Her3 mAb (m15D5) or GEMZAR™ to assess the effect on tumor cell colonization in the lung. Isotype control and m15D5 were administered on Day 3 (25 or 50 mg/kg, i.p.) and on Days 7 and 11 (5 or 25 mg/kg, i.p.) post B16F10 injection. GEMZAR™ was administered on Day 3 only (20 mg/kg, i.v.). Lungs were collected on Day 20 for wet weight measurements. Treatment with GEMZAR™ and m15D5 resulted in lower lung weights, however, only 25/5 mg/kg m15D5 was statistically significant compared to the isotype control ($p<0.05$; One-Way ANOVA with Dunnett's post test). NTB=non tumor bearing mice.

Figure 32:
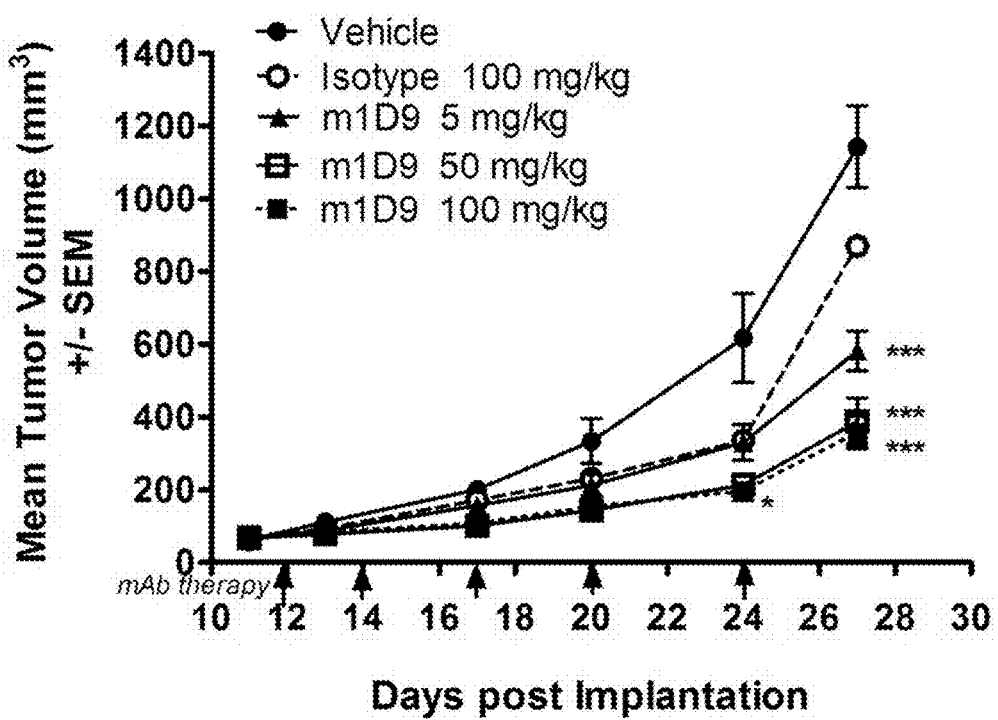

FIG. 32. Efficacy of mouse Anti-HER3 mAb, murine 1D9 antibody, in the CHL-1 xenograft model. Treatment with mouse anti-HER3 mAb, m1D9, twice weekly at 5 to 100 mg/kg i.p. resulted in decreased CHL-1 tumor growth in CB-17 SCID mice. Dose-dependent and statistically significant decreases compared to isotype control were observed on Days 24 and 27 post implantation (*$p<0.05$; ***$p<0.001$; 2-Way ANOVA repeated measures analysis with Bonferroni post test).

Figure 33:
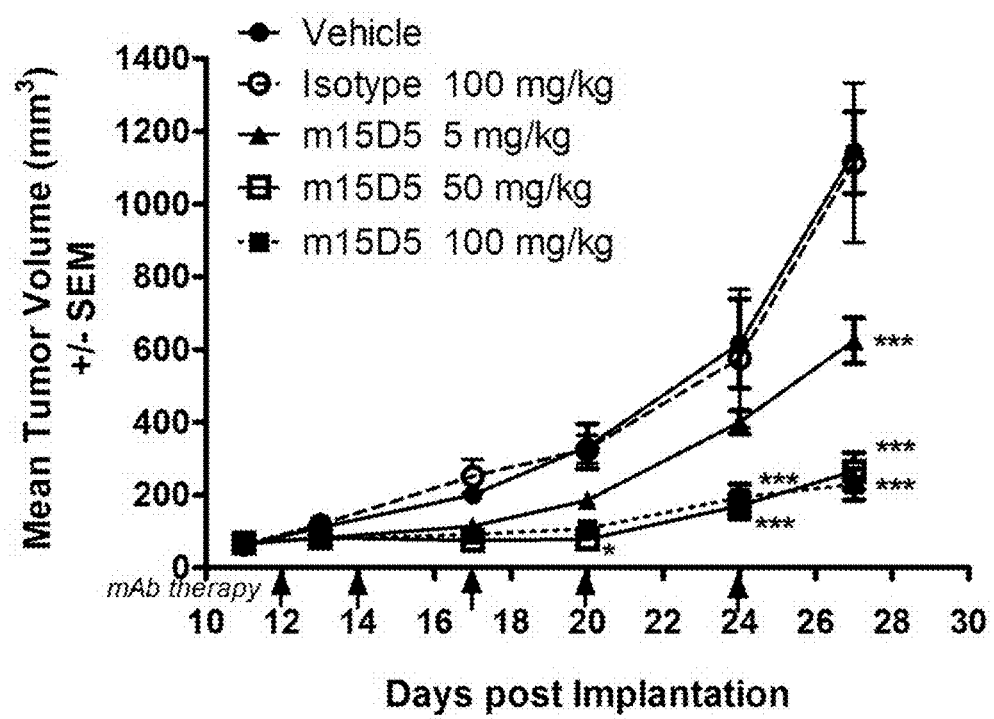

FIG. 33. Efficacy of mouse anti-HER3 mAb, murine 15D5 antibody, in the CHL-1 xenograft model. Treatment with mouse anti-HER3 mAb, m15D5, twice weekly at 5 to 100 mg/kg i.p. resulted in decreased CHL-1 tumor growth in CB-17 SCID mice. Dose-dependent and statistically significant decreases compared to isotype control were observed on Days 20, 24 and 27 post implantation (*$p<0.05$; ***$p<0.001$; 2-Way ANOVA repeated measures analysis with Bonferroni post test).

Figure 34:
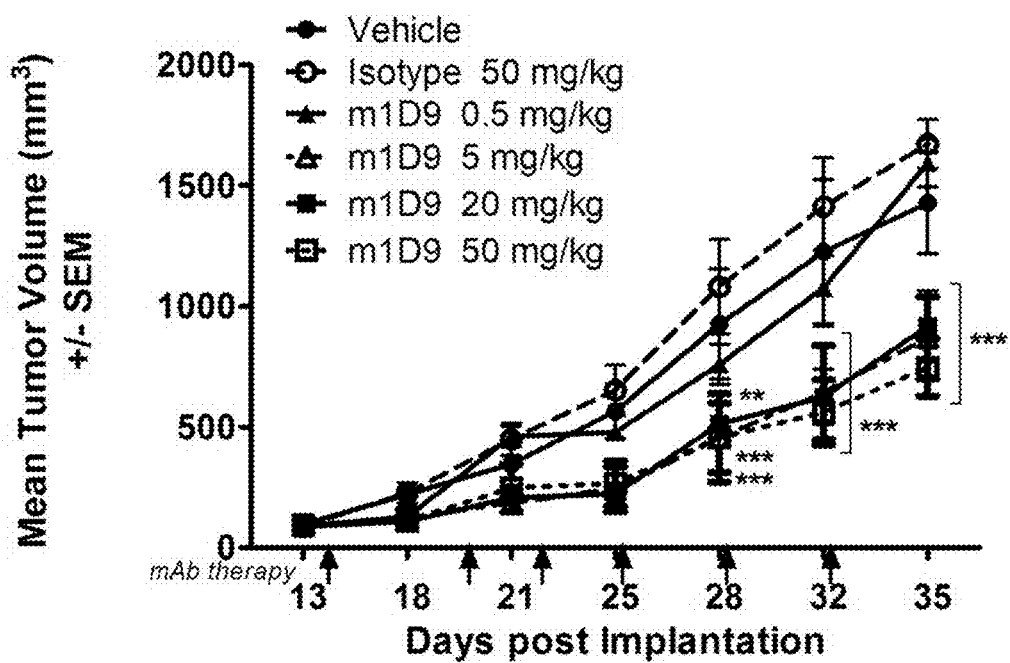

FIG. 34. Efficacy of mouse anti-HER3 mAb, murine 1D9 antibody, in the BxPC3 xenograft model. Treatment with mouse anti-HER3 mAb, m1D9, twice weekly at 0.5 to 50 mg/kg i.p., resulted in dose-dependent and statistically significant decreases in BxPC3 tumor growth in CB-17 SCID mice ($p<0.01$; *$p<0.001$; 2-Way ANOVA repeated measures analysis with Bonferroni post test).

Figure 35:
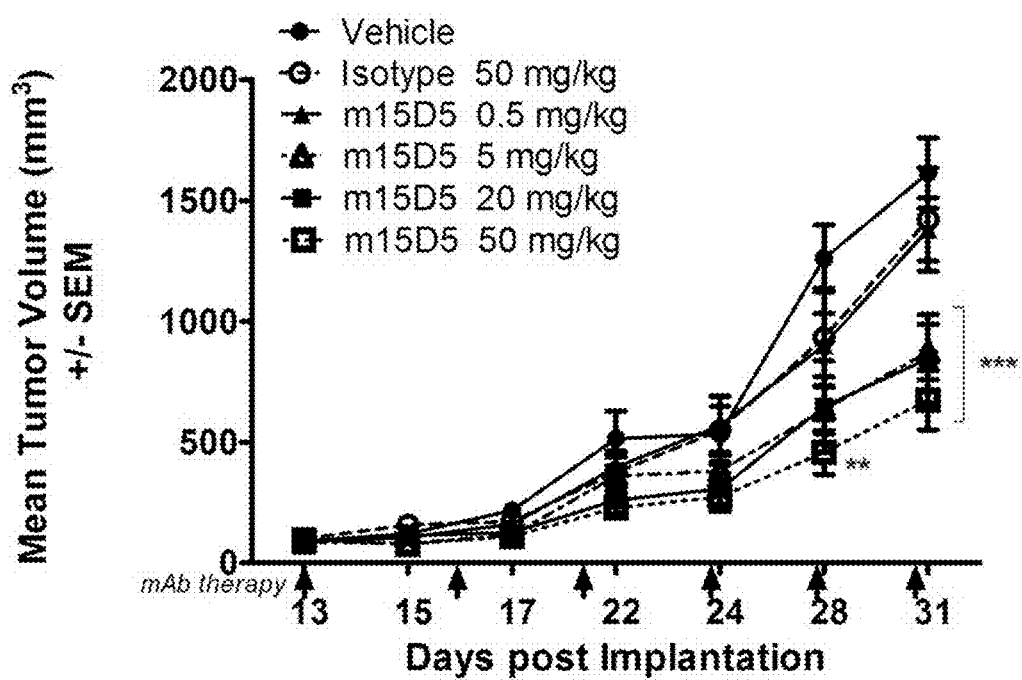

FIG. 35. Efficacy of mouse anti-HER3 mAb, murine 15D5 antibody, in the BxPC3 xenograft model. Treatment with mouse anti-HER3 mAb, m15D5, twice weekly at 0.5 to 50 mg/kg i.p., resulted in dose-dependent and statistically significant decreases in BxPC3 tumor growth in CB-17 SCID mice ($p<0.01$; *$p<0.001$; 2-Way ANOVA repeated measures analysis with Bonferroni post test).

Figure 36:
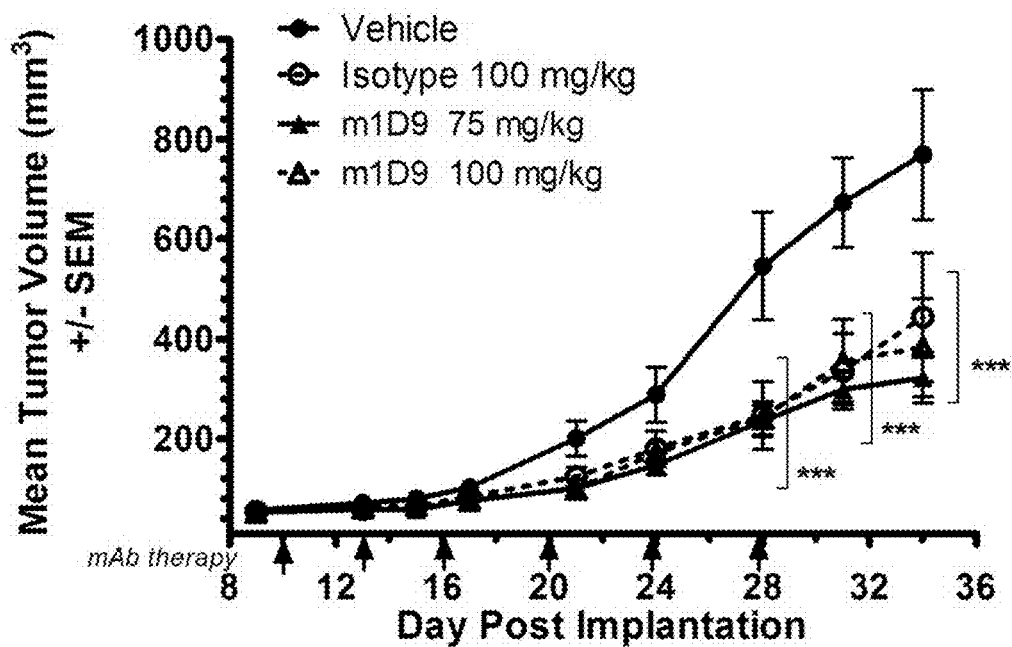

FIG. 36. Efficacy of mouse anti-HER3 mAb, murine 1D9 antibody, in the NCI-N87 xenograft model. Treatment of CB-17 SCID mice with m1D9, twice weekly at 75 or 100 mg/kg i.p., resulted in decreased N87 tumor growth compared to the vehicle control. A similar decrease was observed with the isoype control, mouse IgG2b ($p<0.01$; *$p<0.001$; 2-Way ANOVA repeated measures analysis with Bonferroni post test).

Figure 37:
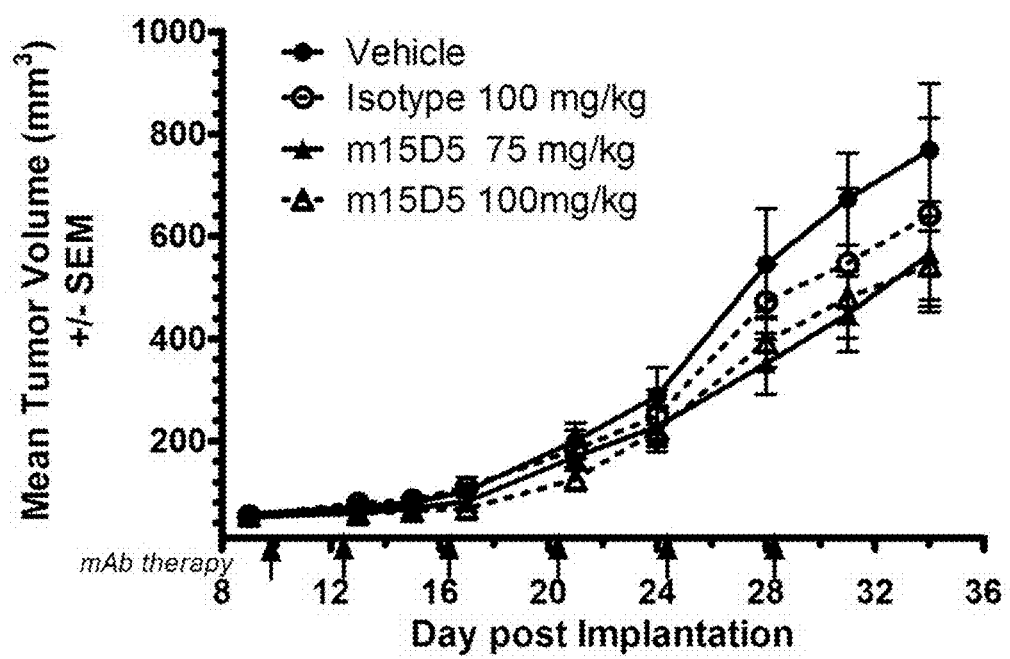

FIG. 37. Efficacy of mouse anti-HER3 mAb, murine 15D5 antibody, in the NCI—N87 xenograft model. Treatment of CB-17 SCID mice with m15D5, twice weekly at 75 or 100 mg/kg i.p., resulted in a lower N87 tumor volume compared to the vehicle or isotype control groups; however differences were not statistically significant.

Figure 38:
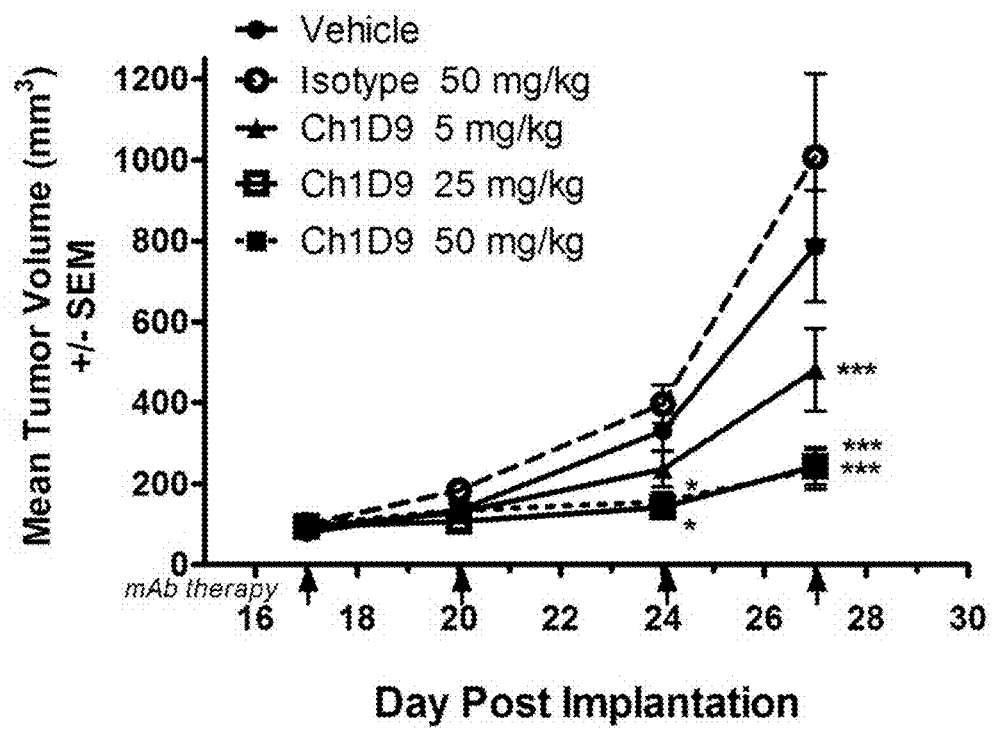

FIG. 38. Efficacy of chimeric anti-HER3 mAb, chimeric 1D9 antibody, in the CHL-1 xenograft model. Treatment with chimeric anti-HER3 mAb, Ch1D9, twice weekly at 5 to 50 mg/kg i.p., resulted in decreased CHL-1 tumor growth in CB-17 SCID mice. Dose-dependent and statistically significant decreases compared to isotype control were observed on Days 24 and 27 post implantation (*$p<0.05$; ***$p<0.001$; 2-Way ANOVA repeated measures analysis with Bonferroni post test).

Figure 39:
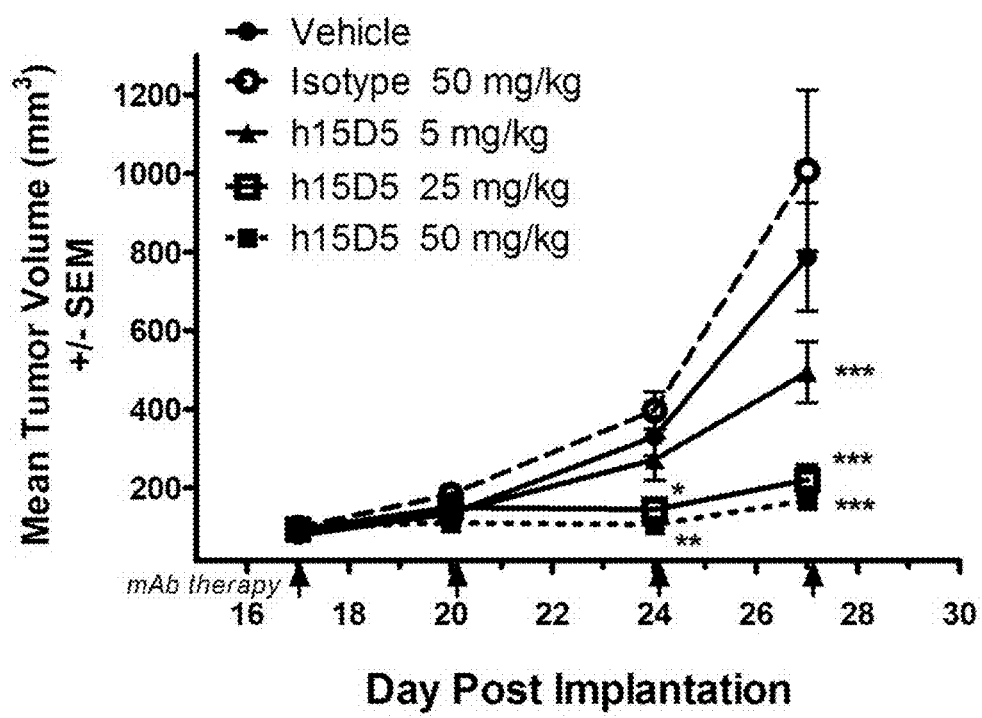

FIG. 39. Efficacy of humanized anti-HER3 mAb, humanized 15D5 antibody, in the CHL-1 xenograft model. Treatment with humanized anti-HER3 mAb, h15D5, twice weekly at 5 to 50 mg/kg i.p., resulted in decreased CHL-1 tumor growth in CB-17 SCID mice. Dose-dependent and statistically significant decreases compared to isotype control were observed on Days 24 and 27 post implantation (*$p<0.05$; $p<0.01$, *$p<0.001$; 2-Way ANOVA repeated measures analysis with Bonferroni post test).

Figure 40:
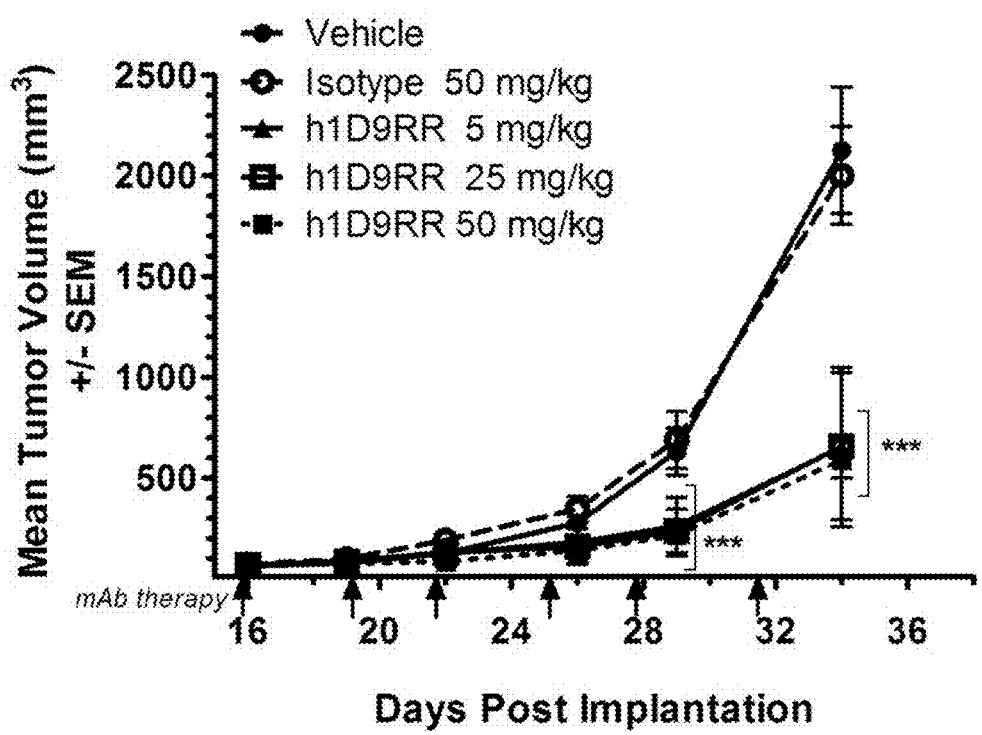

FIG. 40. Efficacy of humanized anti-HER3 mAb, humanized 1D9 RR antibody, in the CHL-1 xenograft model. Treatment with humanized 1D9RR, twice weekly at 5 to 50 mg/kg i.p., resulted in decreased CHL-1 tumor growth in CB-17 SCID mice. The decrease in tumor growth was similar and statistically signifcant at all dose levels compared to the isoptype control on Days 29 and 34 post implantation. (***$p<0.001$; 2-Way ANOVA repeated measures analysis with Bonferroni post test).

Figure 41:
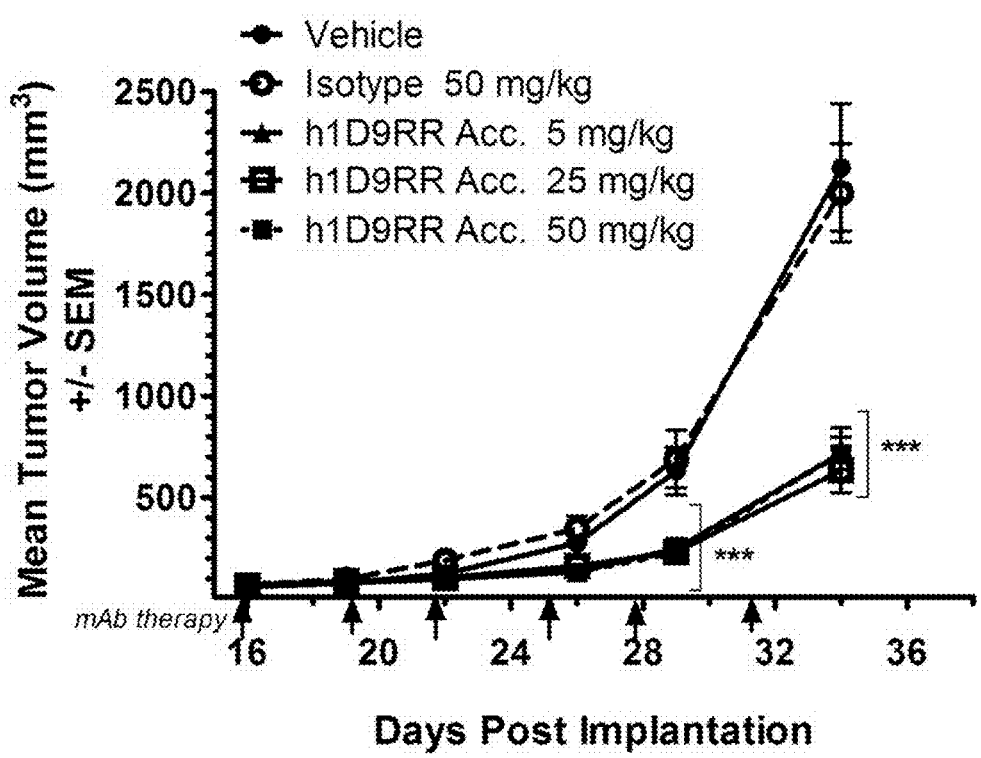

FIG. 41. Efficacy of humanized 1D9 RR ACCRETAMAB™ in the CHL-1 xenograft model. Treatment with humanized 1D9 RR ACCRETAMAB™, twice weekly at 5 to 50 mg/kg i.p., resulted in decreased CHL-1 tumor growth in CB-17 SCID mice. The decrease in tumor growth was similar and statistically signifcant at all dose levels compared to the isoptype control on Days 29 and 34 post implantation. (***$p<0.001$; 2-Way ANOVA repeated measures analysis with Bonferroni post test).

Figure 42:
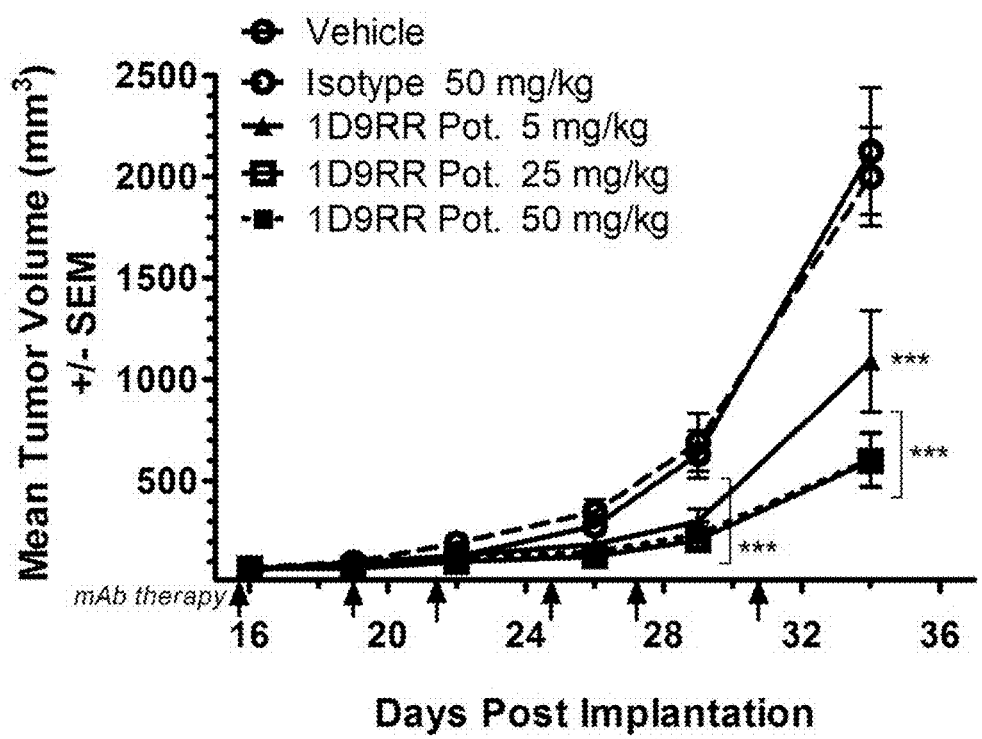

FIG. 42. Efficacy of humanized 1D9 RR POTELLIGENT™ in the CHL-1 xenograft model. Treatment with humanized 1D9 RR POTELLIGENT™, twice weekly at 5 to 50 mg/kg i.p., resulted in decreased CHL-1 tumor growth in CB-17 SCID mice. The decrease in tumor growth was dose-dependent and statistically significant compared to the isoptype control on Days 29 and 34 post implantation. (***$p<0.001$; 2-Way ANOVA repeated measures analysis with Bonferroni post test).

Figure 43:
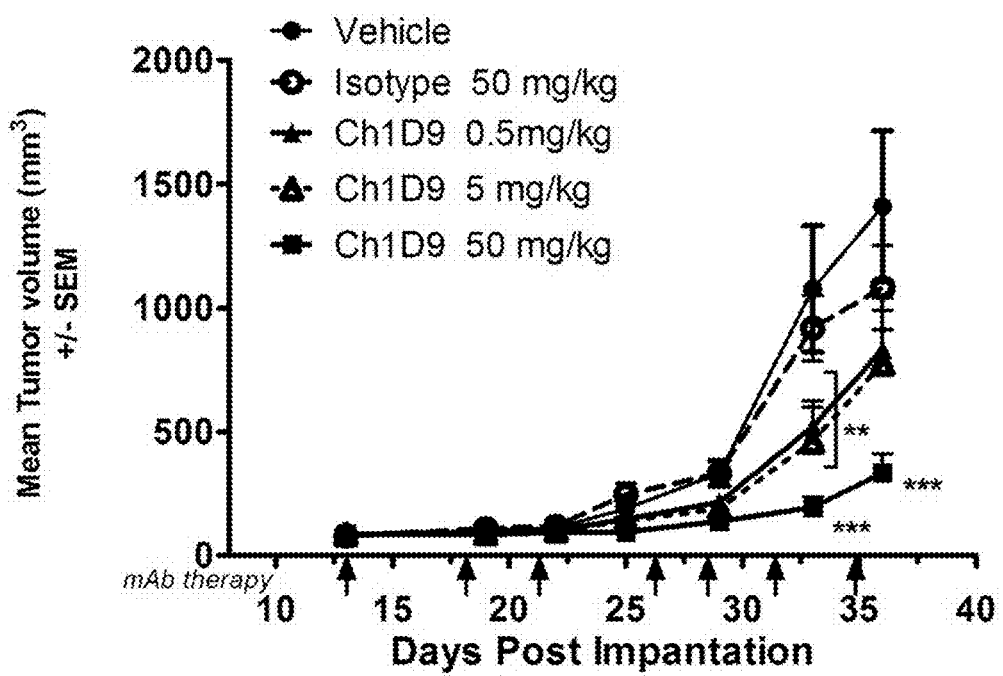

FIG. 43. Efficacy of chimeric Anti-HER3 mAb, chimeric 1D9 antibody, in the BxPC3 xenograft model (subcutaneous implant). CB-17 SCID mice were treated with chimeric anti-HER3 mAb, ch1D9, twice weekly at 0.5 to 50 mg/kg i.p. to assess effect on BxPC3 tumor growth. Dose-dependent and statistically significant decreases in tumor growth were observed in the 0.5, 5 and 50 mg/kg treatment groups compared to the isotype control on Day 33, and in the 50 mg/kg group on Day 36 post implantation ($p<0.01$; *$p<0.001$; 2-Way ANOVA repeated measures analysis with Bonferroni post test).

Figure 44:
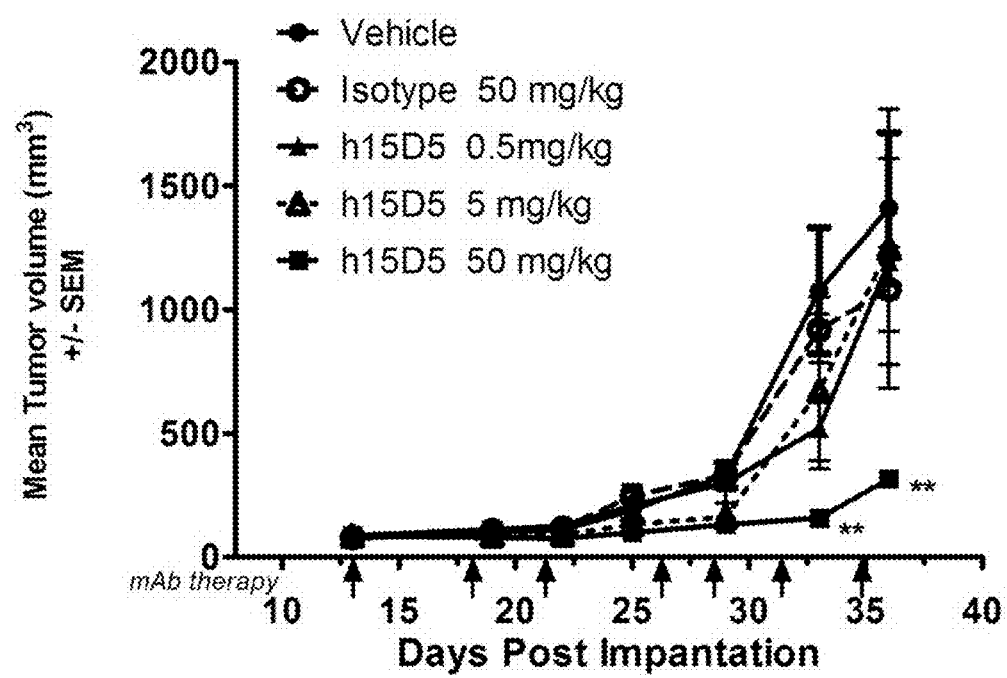

FIG. 44. Efficacy of humanized anti-HER3 mAb, humanized 15D5 antibody, in the BxPC3 xenograft model (subcutaneous implant). CB-17 SCID mice were treated with humanized anti-HER3 mAb, h15D5, twice weekly at 0.5 to 50 mg/kg i.p. to assess effect on BxPC3 tumor growth. Decreased tumor growth was observed in the 50 mg/kg group compared to the isotype control on Days 33 and 36 post implantation (**$p<0.01$; 2-Way ANOVA repeated measures analysis with Bonferroni post test).

Figure 45:
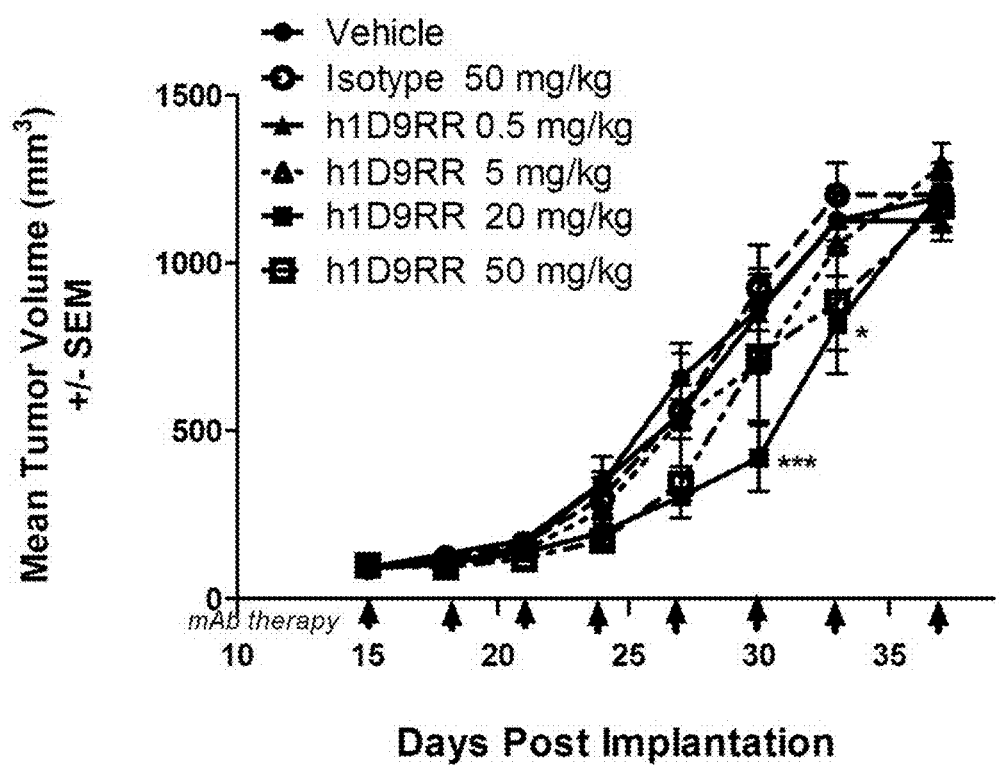

FIG. 45. Efficacy of humanized 1D9 RR antibody in the BxPC3 xenograft model (subcutaneous implant). h1D9RR was administered to BxPC3 tumor bearing CB-17 SCID mice twice weekly i.p. at 0.5 to 50 mg/kg to determine effect on tumor cell growth. The observed decrease in tumor volume in the 20 mg/kg group returned to isotype control level by Day 36. (*$p<0.05$; ***$p<0.001$; 2-Way ANOVA repeated measures analysis with Bonferroni post test comparison).

Figure 46:
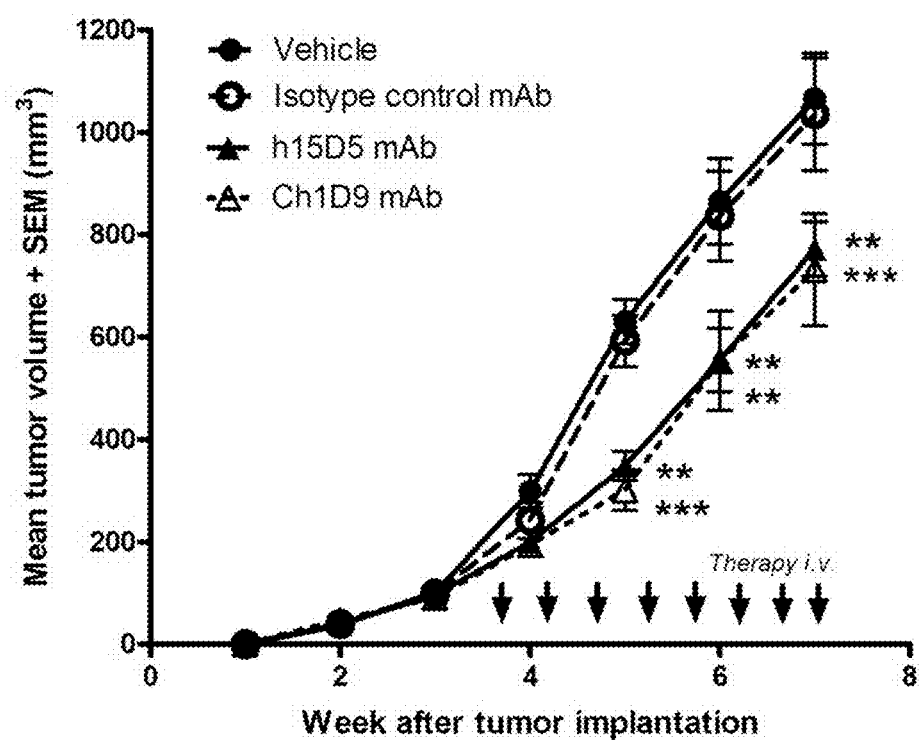

FIG. 46. Efficacy of chimeric 1D9 antibody and humanized 15D5 antibody in the BxPC3 xenograft model (orthotopic implant). BxPC3 pancreatic cancer fragments were implanted orthotopically into the pancreas of female CB-17 SCID mice. The HER3 mAbs, h15D5 and Ch1D9, were administered twice weekly at 50 mg/kg once tumor volumes reached 80-100 mm3. Tumor volumes were determined by ultrasound (Vevo Image Analysis) at weekly intervals. Treatment with anti-HER3 mAbs caused significant decrease in tumor growth compared to the isotype control at weeks 5, 6 and 7 post implantation ( $p<0.01$; *$p<0.001$; 2-Way ANOVA with Bonferroni post test comparison).

Figure 47:
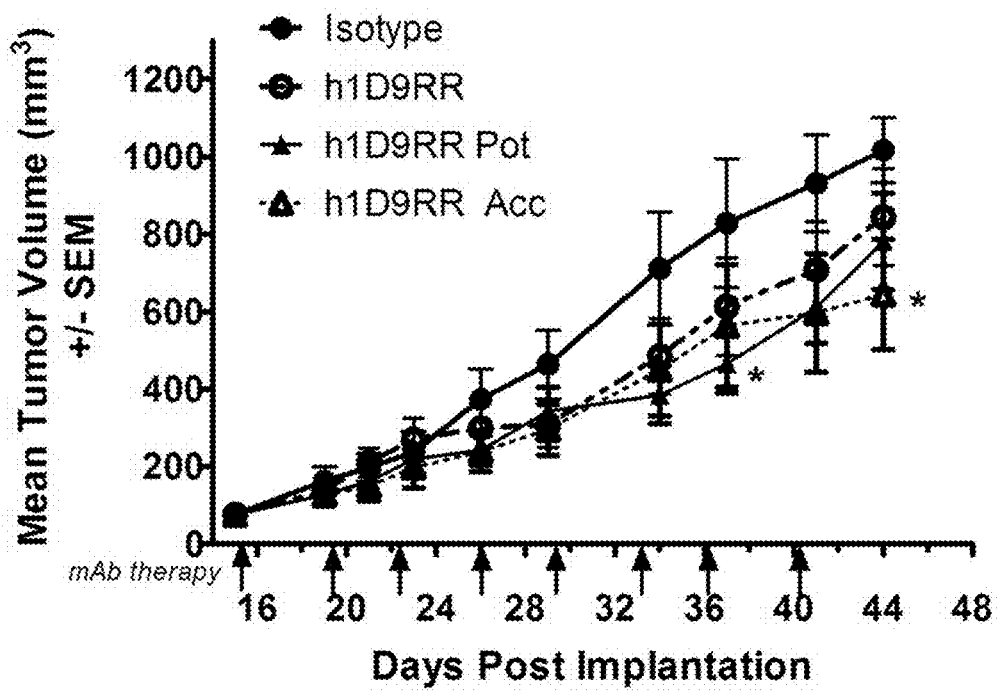

FIG. 47. Efficacy of humanized 1D9 RR antibody and variants in the NCI-N87 xenograft model. CB-17 SCID mice were administered the indicated humanized HER3 mAbs (humanized 1D9 RR antibody, humanized 1D9 RR POTELLIGENT™ antibody and humanized 1D9 RR ACCRETAMAB™ antibody) at 50 mg/kg twice weekly i.p. to determine effect on N87 tumor cell growth. Statistically significant decreases in tumor volume were observed on Day 37 in the h1D9 RR POTELLIGENT™ group and on Day 44 in the h1D9RR ACCRETAMAB™ group compared to the isotype control (*$p<0.05$; 2-Way ANOVA with Bonferroni post test comparison).

Figure 48:
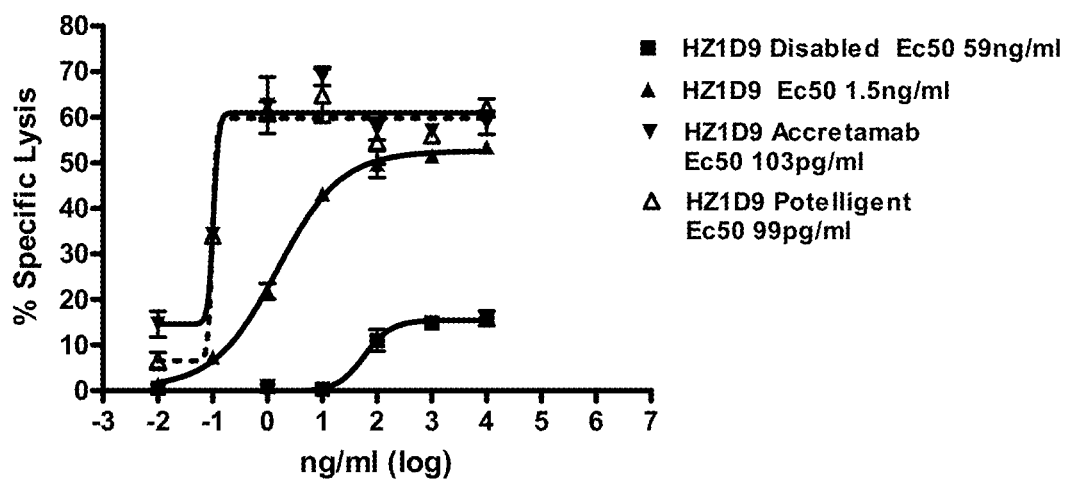

FIG. 48. ADCC assay using HER3 transduced HEK293 as target cells and human PBL as effector cells (donor 2126).

Figure 49:
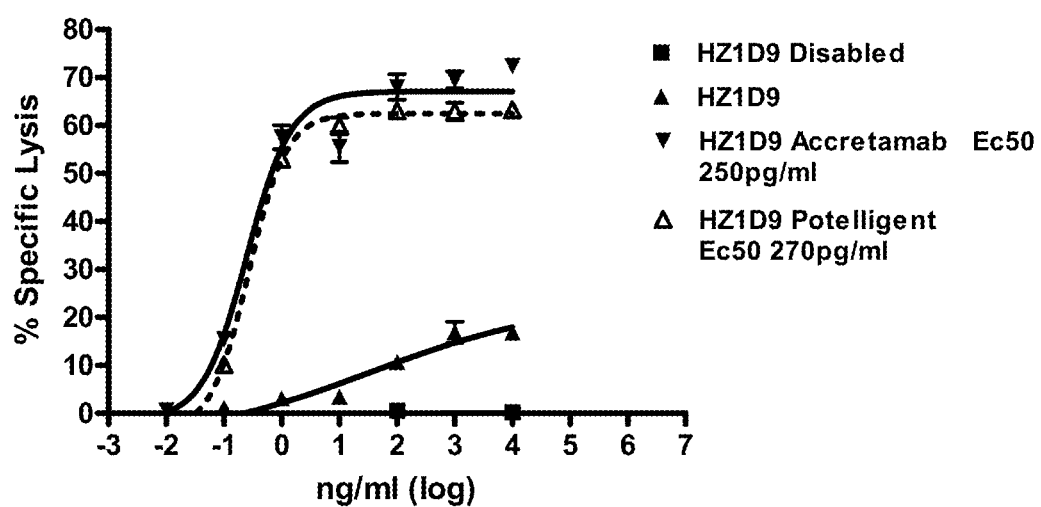

FIG. 49. ADCC assay using CHL-1 cells as target cells and human PBL as effector cells (donor 2126).

Figure 50:
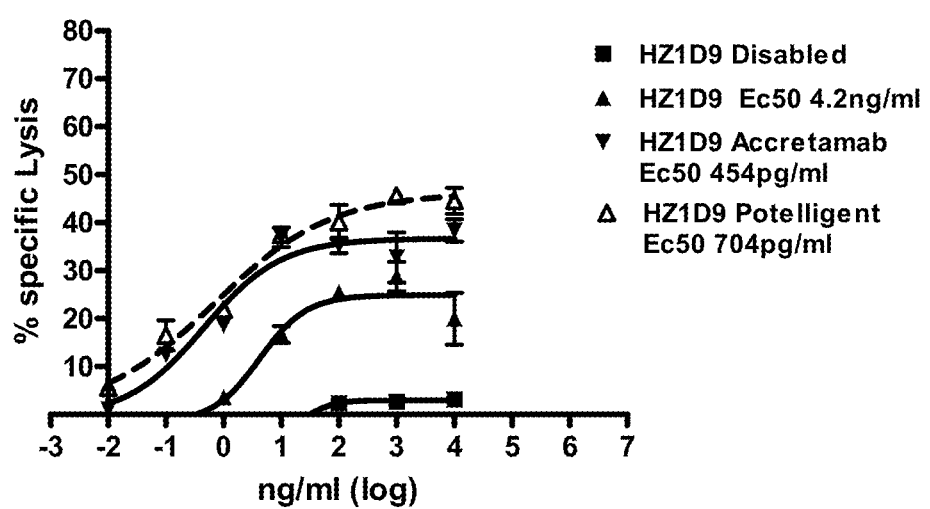

FIG. 50. ADCC assay using HER3 transduced HEK293 cells as target cells and cynomolgus monkey PBL as effector cells (70-105).

Figure 51:
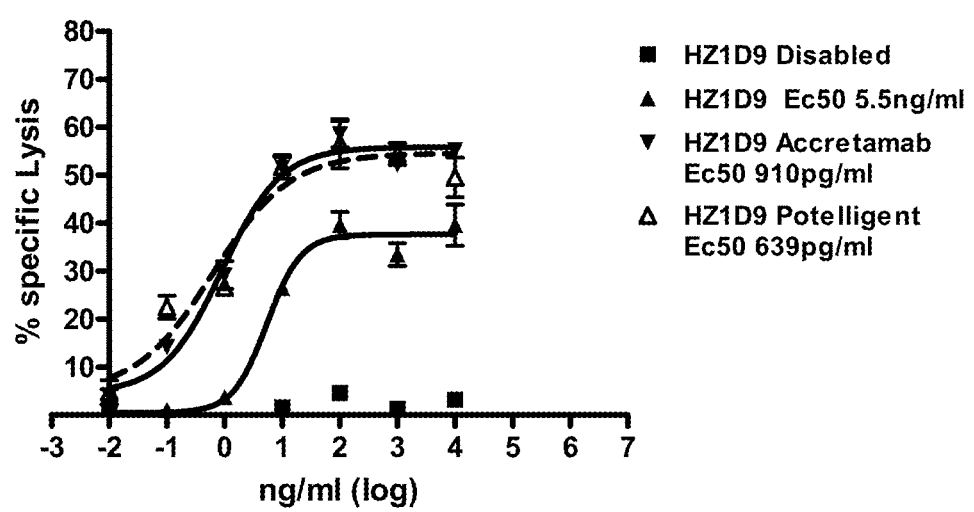

FIG. 51. ADCC assay using HER3 transduced HEK293 cells as target cells and cynomolgus monkey PBL as effector cells (70-113).

Figure 52:
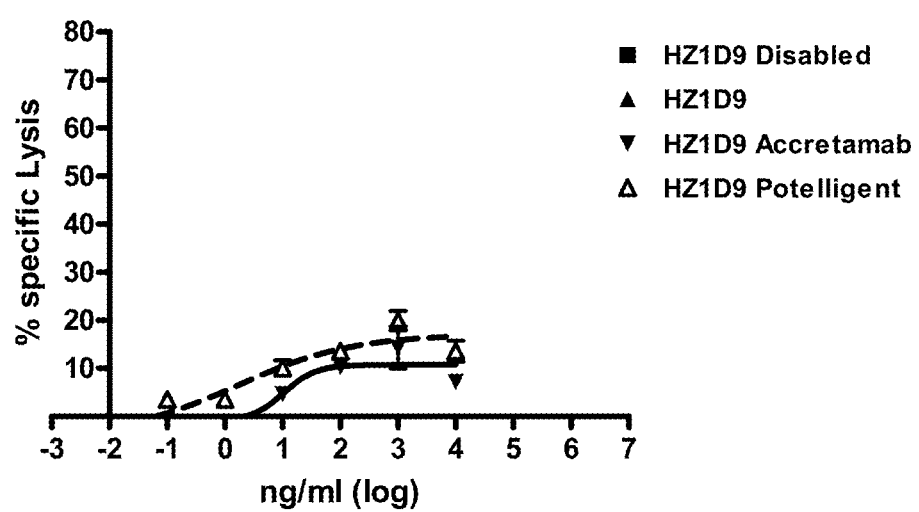

FIG. 52. ADCC assay using CHL-1 cells as target cells and cynomolgus monkey PBL as effector cells (70-105).

Figure 53:
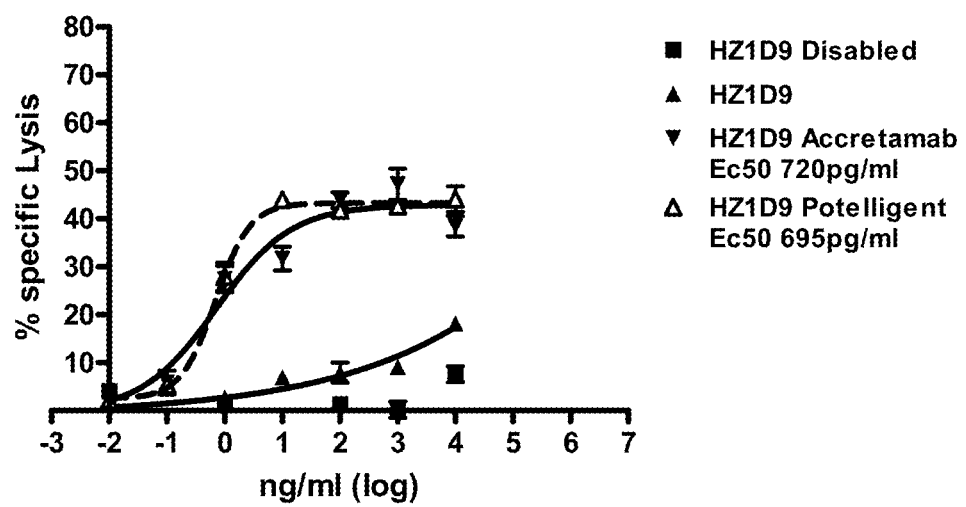

FIG. 53. ADCC assay using CHL-1 cells as target cells and cynomolgus monkey PBL as effector cells (70-113).

Figure 54:
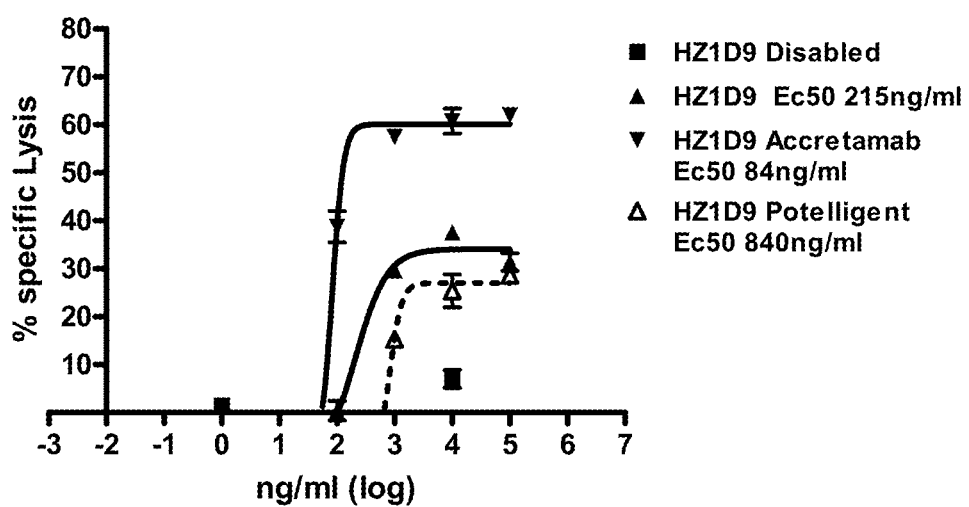

FIG. 54. CDC assay using HER3BACMAM™ transduced HEK293 target cells and CALBIOCHEM™ rabbit complement.

Figure 55:
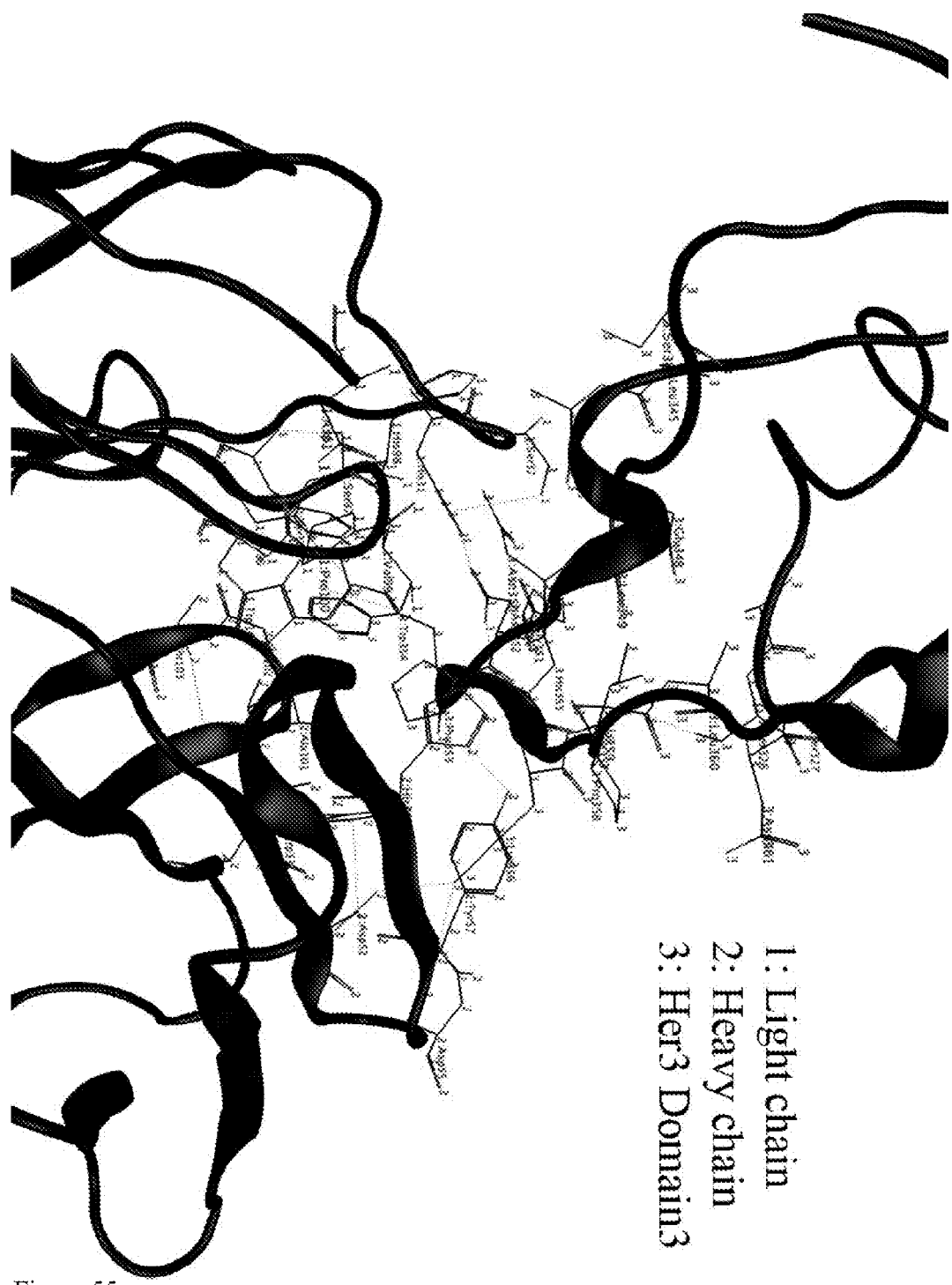

FIG. 55. X-ray crystallographic structure showing amino acid contacts between domain III of the human HER3 ECD (SEQ ID NO: 66; co-crystallized fragment) and the murine 1D9 light chain variable region and murine 1D9 heavy chain variable region (in co-crystallized murine 1D9 antibody derived Fab).

DETAILED DESCRIPTION OF THE DISCLOSURE

The present disclosure provides antigen binding proteins and related subject matter.

The terms, "HER3" and "HER3 receptor", as used herein are interchangeable, and refer to any one of: the full-length unprocessed precursor form of HER3; mature. HER3 that results from post-translational cleavage of the C-terminal domain; in latent and non-latent (active) forms. The terms "HER3" and "HER3 receptor", as used herein, also refer to any fragments and variants of the HER3 receptor that retain one or more biological activities associated with the HER3 receptor.

The full-length unprocessed precursor form of the HER3 receptor comprises pro-peptide and the C-terminal domain that forms the mature protein, with or without a signal sequence. This form is also known as polyprotein. The HER3 receptor precursor may be present as a monomer or homodimer.

Mature HER3 is the protein. that is cleaved from the C-terminus of the HER3 precursor protein, also known as the C-terminal domain. Mature HER3 may be present as a monomer, homodimer, or in a HER3 latent complex. Depending on conditions, mature HER3 may establish equilibrium between a combination of these different forms.

HER3 pro-peptide is the polypeptide that is cleaved from the N-terminal domain of the HER3 precursor protein following cleavage of the signal sequence. Pro-peptide is also known as latency-associated peptide (LAP). HER3 pro-peptide is capable of non-covalently binding to the pro-peptide binding domain on mature HER3.

A HER3 receptor antigen binding protein can bind to any one or any combination of precursor, mature, monomeric, dimeric, latent and active forms of the HER3 receptor. The antigen binding protein may bind mature HER3 receptor in its monomeric and/or dimeric forms. The antigen binding protein may bind the HER3 receptor when it is in a complex with pro-peptide and/or follistatin. Alternatively the antigen binding protein may bind the HER3 receptor when it is in a complex with the HER2 receptor or other HER3 interacting receptors (e.g., heterodimers of HER3).

The term "antigen binding protein", as used herein refers to isolated antibodies, antibody fragments, antigen binding fragments and other protein constructs, such as domains, which are capable of binding to the HER3 receptor (SEQ ID NO: 21), domain II of the HER3 receptor which comprises amino acid residues 184 to 329 of SEQ ID NO: 21, or domain III of the HER3 receptor which comprises amino acid residues 330 to 495 of SEQ ID NO: 21.

The term "antibody", is used herein in the broadest sense refers to molecules with an immunoglobulin-like domain and includes monoclonal, recombinant, polyclonal, chimeric, humanized, bispecific and heteroconjugate antibodies such as monoclonal antibody/domain antibody conjugates; a single variable domain; a domain antibody; antigen binding fragments; immunologically effective fragments; single chain Fv;

diabodies; TANDABS™, etc. (for a summary of alternative "antibody" formats, see Holliger, et al., *Nature Biotechnology*, Vol 23, No. 9: 1126-1136 (2005)).

The phrase "single variable domain", as used herein, refers to an antigen binding protein variable domain (for example, $V_H$, $V_{HH}$, $V_L$) that specifically binds an antigen or epitope independently of a different variable region or domain.

The terms "domain antibody" or "dAb™", as used herein, may be considered the same as a "immunoglobulin single variable domain" that is capable of binding to an antigen. A immunoglobulin single variable domain may be a human antibody variable domain, but also includes single antibody variable domains from other species, such as rodent (for example, as disclosed in WO 00/29004), nurse shark, and Camelid $V_{HH}$ dAb™s. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "domain antibodies". As used herein $V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol 44, 656-665 (2006) and US20050043519A which are incorporated herein by reference.

As used herein, the term "domain", refers to a folded protein structure that has tertiary structure independent of the rest of the protein. Generally, domains are responsible for discrete functional properties of proteins, and, in many cases, may be added, removed or transferred to other proteins without loss of function of the remainder of the protein and/or of the domain. The term "immunoglobulin single variable domain", as used herein, is a folded polypeptide domain comprising sequences characteristic of antibody variable domains. It therefore includes complete antibody variable domains and modified variable domains, for example, in which one or more loops have been replaced by sequences that are not characteristic of antibody variable domains, or antibody variable domains that have been truncated or comprise N- or C-terminal extensions, as well as folded fragments of variable domains that retain at least the binding activity and specificity of the full-length domain. A domain can bind an antigen or epitope independently of a different variable region or domain.

The term "Epitope-binding domain" refers to a domain that specifically binds an antigen or epitope independently of a different V region or domain, this may be a domain antibody (dAb™), for example a human, camelid or shark immunoglobulin single variable domain or it may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEL and GroES; transferrin (trans-body); ankyrin repeat protein (DARPin); peptide aptamer; C-type lectin domain (Tetranectin); human gamma-crystallin and human ubiquitin (affilins); PDZ domains; scorpion toxin, kunitz type domains of human protease inhibitors; and fibronectin (adnectin); which has been subjected to protein engineering in order to obtain binding to a ligand other than the natural ligand.

An antigen binding fragment may be provided by means of arrangement of one or more CDRs on non-antibody protein scaffold, such as a domain. The domain may be a domain antibody, or it may be a domain that is a derivative of a scaffold selected from the group of: CTLA-4 (Evibody); lipocalin; Protein A derived molecules, such as Z-domain of Protein A (Affibody, SpA), A-domain (Avimer/Maxibody); Heat shock proteins such as GroEl and GroES; transferrin (trans-body); ankyrin repeat protein (DARPin); peptide aptamer; C-type lectin domain (Tetranectin); human-crystallin and human ubiquitin (affilins); PDZ domains; scorpion toxin, kunitz type domains of human protease inhibitors; and fibronectin (adnectin); which has been subjected to protein engineering in order to obtain binding to an antigen, such as the HER3 receptor, other than the natural ligands.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633

An affibody is a scaffold derived from Protein A of *Staphylococcus aureus*, which can be engineered to bind to antigen. The domain consists of a three-helical bundle of approximately 58 amino acids. Libraries have been generated by randomisation of surface residues. For further details, see *Protein Eng. Des. Sel.* 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem. 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two-helices and a-turn. They can be engineered to bind different target antigens by randomising residues in the first-helix and a-turn of each repeat. Their binding interface can be increased by increasing the number of modules (a method of affinity maturation). For further details see J. Mol. Biol. 332, 489-503 (2003), PNAS100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present disclosure could be derived from any of these alternative protein domains.

An antigen binding fragment or an immunologically effective fragment may comprise partial heavy or light chain variable sequences. Fragments are at least 5, 6, 8 or 10 amino acids in length. Alternatively, the fragments are at least 15, at least 20, at least 50, at least 75, or at least 100 amino acids in length.

The term "specifically binds", as used herein in relation to antigen binding, proteins means that the antigen binding protein binds to the HER3 receptor as well as a discrete domain, or discrete amino acid sequence, within a HER3 receptor with no or insignificant binding to other (for example, unrelated) proteins. This term, however, does not exclude the fact that the antigen binding proteins may also be cross-reactive with closely related molecules (for example, the HER2 receptor). The antigen binding proteins described herein may bind to the HER3 receptor with at least 2, 5, 10, 50, 100, or 1000-fold greater affinity than they bind to closely related molecules, such as the HER2 receptor.

Ranges provided herein include all values within a particular range described and values about an endpoint for a particular range.

The binding affinity ($K_D$) of the antigen binding protein-HER3 interaction may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 μM and 500 μM; or between 500 μM and 1 nM. The binding affinity of the antigen binding protein is determined by the association constant (Ka) and the dissociation constant (Kd) (KD=Kd/Ka). The binding affinity may be measured by BIACORE™, for example, by capture of the test antibody onto a protein-A coated sensor surface and flowing HER3 receptor over this surface. Alternatively, the binding affinity can be measured by FORTEBIO™, for example, with the test antibody receptor captured onto a protein-A coated needle and flowing HER3 receptor over this surface.

The $K_d$ may be $1\times10^{-3}$ $Ms^{-1}$ or less, $1\times10^{-4}$ $Ms^{-1}$ or less, or $1\times10^{-5}$ $Ms^{-1}$ or less. The $K_d$ may be between $1\times10^{-5}$ $Ms^{-1}$ and $1\times10^{4}$ $Ms^{-1}$; or between $1\times10^{4}$ $Ms^{-1}$ and $1\times10^{-3}$ $Ms^{-1}$. A slow $K_d$ may result in a slow dissociation of the antigen binding protein-ligand complex and improved neutralization of the ligand. Exemplary Binding affinities and related data for the antigen binding proteins described herein are provided in Table 2.

TABLE 2

| HER3 leads and competitors | Murine 15D5 antibody | Chimeric 15D5 antibody | Humanized 15D5 antibody (H4L1) | Murine 1D9 antibody | Chimeric 1D9 antibody | Humanized 1D9 antibody (H6L2) |
|---|---|---|---|---|---|---|
| Binds to HER3 domain | II | II | II | III | III | III |
| Ig class | murine IgG1 | | Hu IgG1 | murine IgG2b | | Hu IgG1 |
| Affinity - ECD (KD) | ~2 nM | ~1 nM | 3.5 nM | ~1 nM | ~1 nM | 4.1 nM |
| Affinity - domain II | 70 pM | 20 pM | 74 pM | | | |
| Affinity - domain III | | | | 390 pM | 198 pM | 18 pM |
| Affinity - domain I | | | | | | |

In Table 2, "murine 15D5 antibody" refers to a monoclonal antibody comprising the variable heavy chain, variable light chain, complementarity determining regions and framework regions shown in SEQ ID NO:s 1-8; "humanized 15D5 antibody" refers to a monoclonal antibody comprising the variable heavy chain, variable light chain, complementarity determining regions and framework regions shown in SEQ ID NO:s 22-29; "murine 1D9 antibody" refers to a monoclonal antibody comprising the variable heavy chain, variable light chain, complementarity determining regions and framework regions shown in SEQ ID NO:s 44-51; "humanized 1D9 antibody" refers to a monoclonal antibody comprising the variable heavy chain, variable light chain, complementarity determining regions and framework regions shown in SEQ ID NO:s 30-37. In particular, the "humanized 1D9" monoclonal antibody in Table 2 comprises the heavy chain variable region amino acid sequence shown in SEQ ID NO: 30 and the variable light chain amino acid sequence shown in SEQ ID NO: 57 as well as the corresponding complementarity determining regions shown in SEQ ID NO:s 30-33 and SEQ ID NO:s 35-37."

The term "ECD" means extracellular domain and, with regard to HER3 may refer to a peptide chain comprising domains I, II, III and IV of a HER3 isoform such as one having the amino acid sequence shown in SEQ ID NO: 21.

The term "neutralizes", as used herein, means that the biological activity of HER3 is reduced in the presence of an antigen binding protein as described herein in comparison to the activity of HER3 in the absence of the antigen binding protein, in vitro or in vivo. Neutralization may be due, but not limited to one or more of, blocking HER3 binding to its ligand, preventing HER3 from being activated by its ligand, down-regulating the HER3 receptor or its ligands, interfering with the ability of the receptor to adopt an 'active' (e.g., signaling-competent) conformation, blocking the ability of the receptor to homo-, hetero or oligomerize or otherwise affecting receptor activity or effector function.

Measurement of HER3 receptor activity includes, but is not limited to, methods that determine levels of phosphorylated receptor (pHER3), phosphorylated AKT (pAKT), complex formation between HER3 and members of the HER (or other) families of receptors, reduction in PI3Kinase, ERK2, c-Jun or PYK2 activity, proliferation of HER3 expressing tumor cell lines, ability of said lines to grow in soft agar (clonal growth), migration of such lines across a membrane in response to ligand etc.

The reduction or inhibition in biological activity may be partial or total. A neutralizing antigen binding protein may neutralize the activity of the HER3 receptor by at least 20%, 30% 40%, 50%, 55%, 60%, 65%, 70%, 75%, 80%, 82%, 84%, 86%, 88%, 90%, 92%, 94%, 95%, 96%, 97%, 98%, 99% or 100% relative to HER3 activity in the absence of the antigen binding protein. In functional assays, IC50 is the concentration that reduces a biological response by 50% of its maximum.

Neutralization may be determined or measured using one or more assays known to the skilled person, or as described herein. For example, antigen binding protein binding to HER3 can be assessed in a sandwich ELISA, by BIA-CORE™, FMAT, FORTEBIO™, or similar in vitro assays.

An ELISA-based receptor binding assay can be used to determine the neutralising activity of the antigen binding protein by measuring HER3 receptor binding to its ligands, neuregulin 1 and neuregulin 2 immobilised on a plate in the presence of the antigen binding protein.

Alternatively, a cell-based receptor binding assay can be used to determine the neutralizing activity of the antigen binding protein by measuring inhibition of receptor binding, downstream signaling, and gene activation.

In vivo neutralization may be determined using a number of different assays in animals that demonstrate changes in, for example, any one or a combination of HER3 mediated function and/or signal transduction for example, reduction in phosphorylated HER3 (pHER3), phosphorylated AKT (pAKT), complex formation between HER3 and members of the HER (or other) families of receptors, reduction in PI3Kinase, ERK2, c-Jun or PYK2 activity and also by measuring the ability of the antigen binding protein to prevent, reduce or otherwise diminish tumor cell growth in e.g. tumor xenograft models.

The term "Effector Function" as used herein is meant to refer to one or more of Antibody dependant cell mediated cytotoxic activity (ADCC) and complement—dependant cytotoxic activity (CDC) mediated responses, Fc-mediated phagocytosis and antibody recycling via the FcRn receptor. The interaction between the constant region of an antibody and various Fc receptors (FcR) is believed to mediate the effector functions of the antibody. Significant biological effects can be a consequence of effector functionality, in particular, antibody-dependent cellular cytotoxicity (ADCC), fixation of complement (complement dependent cytotoxicity or CDC), phagocytosis (antibody-dependent cell-mediated phagocytosis or ADCP) and half-life/clearance of the antibody. Usually, the ability to mediate effector function requires binding of the antibody to an antigen and not all antibodies will mediate every effector function.

Effector function can be measured in a number of ways including for example via binding of the FcγRIII to Natural Killer cells or via FcγRI to monocytes/macrophages to measure for ADCC effector function. For example the antibody or antigen binding fragment of the present invention has an increased ADCC effector function when measured against the equivalent wild type antibody or antigen binding fragment thereof in a Natural Killer cell assay. Examples of such assays can be found in Shields et al, 2001 The Journal of Biological Chemistry, Vol. 276, p6591-6604; Chappel et al, 1993 The Journal of Biological Chemistry, Vol 268, p25124-25131; Lazar et al, 2006 PNAS, 103; 4005-4010. Examples of assays to determine CDC function include that described in 1995 Jl mm Meth 184:29-38.

Various modifications to the heavy chain constant region of antibodies may be carried out depending on the desired effector property. Human constant regions which essentially lack the functions of a) activation of complement by the classical pathway; and b) mediating antibody-dependent cellular cytotoxicity include the IgG4 constant region and the IgG2 constant region. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168). Human IgG1 constant regions containing specific mutations or altered glycosylation on residue Asn297 have also been described to enhance binding to Fc receptors. These have also been shown to enhance ADCC and CDC, in some cases (Lazar et al. PNAS 2006, 103; 4005-4010; Shields et al. J Biol Chem 2001, 276; 6591-6604; Nechansky et al. Mol Immunol, 2007, 44; 1815-1817).

For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antibody bound to antigen and the formation of the Fc/Fcγ complex induces a range of effects including cytotoxicity, immune cell activation, phagocytosis and release of inflammatory cytokines. Specific substitutions in the constant region (including S239D/1332E) are known to increase the affinity of the heavy chain constant region for certain Fc receptors, thus enhancing the effector functionality of the antibody (Lazar et al. PNAS 2006). It will be apparent to those skilled in the art that the term "derived", as used herein, is intended to define not only the source in the sense of it being the physical origin for the material, but also to define material which is structurally identical to the material but which does not originate from the reference source. Thus "residues found in the donor antibody" need not necessarily have been purified from the donor antibody.

By "isolated", it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass.

The term "expression vector" as used herein means an isolated nucleic acid which can be used to introduce a nucleic acid of interest into a cell, such as a eukaryotic cell or prokaryotic cell, or a cell free expression system where the nucleic acid sequence of interest is expressed as a peptide chain such as a protein. Such expression vectors may be, for example, cosmids, plasmids, viral sequences, transposons, and linear nucleic acids comprising a nucleic acid of interest. Once the expression vector is introduced into a cell or cell free expression system (e.g., reticulocyte lysate) the protein encoded by the nucleic acid of interest is produced by the transcription/translation machinery. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, Drosophila expression vectors, and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors. Those of ordinary skill in the art will recognize many other suitable expression vectors and expression systems.

The term "recombinant host cell" as used herein means a cell that comprises a nucleic acid sequence of interest that was isolated prior to its introduction into the cell. For example, the nucleic acid sequence of interest may be in an expression vector while the cell may be prokaryotic or eukaryotic. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells or any derivative thereof. Most preferably, the eukaryotic cell is a HEK293, NS0, SP2/0, or CHO cell. E. coli is an exemplary prokaryotic cell. A recombinant cell according to the disclosure may be generated by transfection, cell fusion, immortalization, or other procedures well known in the art. A nucleic acid sequence of interest, such as an expression vector, transfected into a cell may be extrachromasomal or stably integrated into the chromosome of the cell.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulin(s). In addition, framework support residues may be altered to preserve binding affinity (see, e.g., Queen et al. Proc. Natl. Acad Sci USA, 86:10029-10032 (1989), Hodgson, et al., Bio/Technology, 9:421 (1991)). A suitable human acceptor antibody may be one selected from a conventional database, e.g., the KABAT™ database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies—see, for example, EP-A-0239400 and EP-A-054951.

The term "donor antibody" refers to an antibody that contributes the amino acid sequences of its variable regions, CDRs, or other functional fragments or analogs thereof to a first immunoglobulin partner. The donor, therefore, provides the altered immunoglobulin coding region and resulting expressed altered antibody with the antigenic specificity and neutralising activity characteristic of the donor antibody.

The term "acceptor antibody" refers to an antibody that is heterologous to the donor antibody, which contributes all (or any portion) of the amino acid sequences encoding its heavy and/or light chain framework regions and/or its heavy and/or light chain constant regions to the first immunoglobulin partner. A human antibody may be the acceptor antibody.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat, et al., SEQUENCES OF PROTEINS OF IMMUNOLOGICAL INTEREST, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia, et al. (1989) Nature 342: 877-883. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 3 below represents one definition using each numbering convention for each CDR or binding unit. The Kabat numbering scheme is used in Table 3 to number the variable domain amino acid sequence. It should be noted that some of the CDR definitions may vary depending on the individual publication used.

TABLE 3

|    | Kabat CDR        | Chothia CDR     | AbM CDR         | Contact CDR     | Minimum binding unit |
|----|------------------|-----------------|-----------------|-----------------|----------------------|
| H1 | 31-35/ 35A/35B   | 26-32/ 33/34    | 26-35/ 35A/35B  | 30-35/ 35A/35B  | 31-32                |
| H2 | 50-65            | 52-56           | 50-58           | 47-58           | 52-56                |
| H3 | 95-102           | 95-102          | 95-102          | 93-101          | 95-101               |
| L1 | 24-34            | 24-34           | 24-34           | 30-36           | 30-34                |
| L2 | 50-56            | 50-56           | 50-56           | 46-55           | 50-55                |
| L3 | 89-97            | 89-97           | 89-97           | 89-96           | 89-96                |

As used herein, the term "antigen binding site" refers to a site on an antigen binding protein that is capable of specifically binding to an antigen. This may be a single domain (for example, an epitope-binding domain), or single-chain Fv (ScFv) domains or it may be paired $V_H/V_L$ domains as can be found on a standard antibody.

The term "epitope", as used herein, refers to that portion of the antigen that makes contact with a particular binding domain of the antigen binding protein. An epitope may be linear, comprising an essentially linear amino acid sequence from the antigen. Alternatively, an epitope may be conformational or discontinuous. For example, a conformational epitope comprises amino acid residues which require an element of structural constraint. A discontinuous epitope comprises amino acid residues that are separated by other sequences, i.e. not in a continuous sequence in the antigen's primary sequence. In the context of the antigen's tertiary and quaternary structure, the residues of a discontinuous epitope are near enough to each other to be bound by an antigen binding protein.

For nucleotide and amino acid sequences, the term "identical" or "sequence identity" indicates the degree of identity between two nucleic acid or two amino acid sequences when optimally aligned and compared with appropriate insertions or deletions.

The percent identity between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers, et al., *Comput. Appi. Biosci.*, 4:11-17 (1988), which has been incorporated into the ALIGN program (version 2.0), using a PAM120 weight residue table, a gap length penalty of 12 and a gap penalty of 4. In addition, the percent identity between two amino acid sequences can be determined using the Needleman, et al., *J. Mol. Biol.* 48:444-453 (1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence may be identical to a reference polynucleotide sequence that is 100% identical to the reference sequence, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein by the numerical percent of the respective percent identity (divided by 100) and subtracting that product from said total number of nucleotides in the reference polynucleotide sequence, or:

$$n_n \leq x_n - (x_n \cdot y),$$

wherein $n_n$ is the number of nucleotide alterations, $x_n$ is the total number of nucleotides in the reference polynucleotide sequence as described herein (see the nucleic acid sequences in the "Sequence Listing" for exemplary reference polynucleotides sequences), and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, · is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein (see the amino acid sequences in the "Sequence Listing" for exemplary reference polypeptide sequences), that is 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence by the numerical percent of the respective percent identity (divided by 100) and then subtracting that product from said total number of amino acids in the polypeptide reference sequence as described herein (see, for example SEQ ID NOs:1-21), or:

$$n_a \leq x_a - (x_a \cdot y),$$

wherein $n_a$ is the number of amino acid alterations, $x_a$ is the total number of amino acids in the reference polypeptide sequence, and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, · is the symbol for the multiplication operator, and wherein any non-integer product of $x_a$ and y is rounded down to the nearest integer prior to subtracting it from $x_a$.

The % identity may be determined across the length of the sequence. As defined herein the term "over 75% identical" includes over 75%, 80%, 85%, 95% and 99% identity as well as all discrete values, and discrete subranges, with in this range.

The terms "peptide", "polypeptide", and "protein" each refer to a molecule comprising two or more amino acid residues. A peptide may be monomeric or polymeric.

It is well recognized in the art that certain amino acid substitutions are regarded as being "conservative" Amino acids are divided into groups based on common side-chain properties and substitutions within groups that maintain all or substantially all of the binding affinity of the antigen binding protein are regarded as conservative substitutions. See Table 4. The antigen binding proteins disclosed herein can comprise such "conservative" amino acid substitutions.

TABLE 4

| Side chain | Members |
|---|---|
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

One aspect of the disclosure is an antigen binding protein that specifically binds HER3 comprising a heavy chain variable region having at least one CDR with greater than 75% sequence identity to an amino acid sequence selected from the group consisting of SEQ ID NO: 2, SEQ ID NO: 3, and SEQ ID NO: 4; and/or a light chain variable region having at least one CDR with 75% or greater sequence identity to an amino acid sequence selected from the group consisting of SEQ ID NO: 6, SEQ ID NO: 7, and SEQ ID NO: 8. It is preferred that the antigen binding proteins of the disclosure comprise at least one CDRH3 such as CDRH3 from the murine or humanized 1D9, 15D5, 22A5 monoclonal antibodies disclosed herein.

The disclosure also provides an antigen binding protein that specifically binds HER3 wherein the antigen binding protein is selected from the group consisting of a chimeric antibody and a humanized antibody.

The disclosure also provides an antigen binding protein that specifically binds HER3 comprising a heavy chain variable region having the CDR amino acid sequence shown in SEQ ID NO: 2, the CDR amino acid sequence shown in SEQ ID NO: 3, and the CDR amino acid sequence shown in SEQ ID NO: 4; and a light chain variable region having the CDR amino acid sequence shown in SEQ ID NO: 6, the CDR amino acid sequence shown in SEQ ID NO: 7, and the CDR amino acid sequence shown in SEQ ID NO: 8.

The disclosure also provides an antigen binding protein which specifically binds to a peptide chain domain comprising amino acid residues 184 to 329 of SEQ ID NO: 21. Amino acid residues 184 to 329 of SEQ ID NO: 21 comprise domain II of HER3. Domain II of HER3 is involved in dimer formation, such as heterodimerization.

Another aspect of the disclosure is an antigen binding protein that specifically binds HER3 comprising a heavy chain variable region having at least one CDR with greater than 75% sequence identity to an amino acid sequence selected from the group consisting of SEQ ID NO: 23, SEQ ID NO: 24, and SEQ ID NO: 25; and/or a light chain variable region having at least one CDR with 75% or greater sequence identity to an amino acid sequence selected from the group consisting of SEQ ID NO: 27, SEQ ID NO: 28, and SEQ ID NO: 29.

The disclosure also provides an antigen binding protein that specifically binds HER3 comprising a heavy chain variable region having the CDR amino acid sequence shown in SEQ ID NO: 23, the CDR amino acid sequence shown in SEQ ID NO: 24, and the CDR amino acid sequence shown in SEQ ID NO: 25; and a light chain variable region having the CDR amino acid sequence shown in SEQ ID NO: 27, the CDR amino acid sequence shown in SEQ ID NO: 28, and the CDR amino acid sequence shown in SEQ ID NO: 29.

Another aspect of the disclosure is an antigen binding protein that specifically binds HER3 comprising a heavy chain variable region having at least one CDR with greater than 75% sequence identity to an amino acid sequence selected from the group consisting of SEQ ID NO: 45, SEQ ID NO: 46, and SEQ ID NO: 47; and/or a light chain variable region having at least one CDR with 75% or greater sequence identity to an amino acid sequence selected from the group consisting of SEQ ID NO: 49, SEQ ID NO: 50, and SEQ ID NO: 51.

The disclosure also provides an antigen binding protein that specifically binds HER3 comprising a heavy chain variable region having the CDR amino acid sequence shown in SEQ ID NO: 45, the CDR amino acid sequence shown in SEQ ID NO: 46, and the CDR amino acid sequence shown in SEQ ID NO: 47; and/or a light chain variable region having the CDR amino acid sequence shown in SEQ ID NO: 49, the CDR amino acid sequence shown in SEQ ID NO: 50, and the CDR amino acid sequence shown in SEQ ID NO: 51.

The disclosure also provides an antigen binding protein which specifically binds to a peptide chain domain comprising amino acid residues 330 to 495 of SEQ ID NO: 21. Amino acid residues 330 to 495 of SEQ ID NO: 21 comprise domain III of HER3. Domain III of HER3 is involved in ligand binding by the HER3 receptor.

Another aspect of the disclosure is an antigen binding protein that specifically binds HER3 comprising a heavy chain variable region having at least one CDR with greater than 75% sequence identity to an amino acid sequence selected from the group consisting of SEQ ID NO: 31, SEQ ID NO: 32, and SEQ ID NO: 33; and/or a light chain variable region having at least one CDR with 75% or greater sequence identity to an amino acid sequence selected from the group consisting of SEQ ID NO: 35, SEQ ID NO: 36, and SEQ ID NO: 37.

Another aspect of the disclosure is an antigen binding protein that specifically binds HER3 comprising a heavy chain variable region having the CDR amino acid sequence shown in SEQ ID NO: 31, the CDR amino acid sequence shown in SEQ ID NO: 32, and the CDR amino acid sequence shown in SEQ ID NO: 33; and/or a light chain variable region having the CDR amino acid sequence shown in SEQ ID NO: 35, the CDR amino acid sequence shown in SEQ ID NO: 36, and the CDR amino acid sequence shown in SEQ ID NO: 37.

Another aspect of the disclosure is an antigen binding protein that specifically binds to the HER3 receptor comprising a heavy chain variable region having at least one CDR with greater than 75% sequence identity to an amino acid sequence selected from the group consisting of SEQ ID NO: 10, SEQ ID NO: 11, and SEQ ID NO: 12; and/or a light chain variable region having at least one CDR with 75% or greater sequence identity to an amino acid sequence selected from the group consisting of SEQ ID NO: 12, SEQ ID NO: 7, SEQ ID NO: 8, SEQ ID NO: 18, SEQ ID NO: 19, and SEQ ID NO: 20.

The disclosure also provides an antigen binding protein that specifically binds to the HER3 receptor comprising a heavy chain variable region having the CDR amino acid sequence shown in SEQ ID NO: 10, the CDR amino acid sequence shown in SEQ ID NO: 11, and the CDR amino acid sequence shown in SEQ ID NO: 12; and either a light chain variable region having the CDR amino acid sequence shown in SEQ ID NO: 12, the CDR amino acid sequence shown in SEQ ID NO: 7, and the CDR amino acid sequence shown in SEQ ID NO: 8 or a light chain variable region having the CDR amino acid sequence shown in SEQ ID NO: 18, the CDR amino acid sequence shown in SEQ ID NO: 19, and the CDR amino acid sequence shown in SEQ ID NO: 20.

The disclosure also provides an antigen binding protein that specifically binds HER 3 and which inhibits formation of a dimer comprising the amino acid sequence shown in SEQ ID NO: 21. As those of ordinary skill in the art will recognize inhibition of dimer formation may be determined by assaying dimer quantities both in the presence and absence of an antigen binding protein of the disclosure. Such dimer formation assays are well known in the art and include, for example, co-precipitation based assays or two-hybrid assays.

Another aspect of the disclosure is an antigen binding protein that specifically binds HER3 comprising a heavy chain variable region sequence having the amino acid sequence shown in SEQ ID NO: 1 and a light chain variable region sequence having the amino acid sequence shown in SEQ ID NO: 5.

Another aspect of the disclosure is an antigen binding protein that specifically binds HER3 comprising a heavy chain variable region sequence having the amino acid sequence shown in SEQ ID NO: 22 and a light chain variable region sequence having the amino acid sequence shown in SEQ ID NO: 26.

Another aspect of the disclosure is an antigen binding protein that specifically binds HER3 comprising a heavy chain variable region sequence having the amino acid sequence shown in SEQ ID NO: 44 and a light chain variable region sequence having the amino acid sequence shown in SEQ ID NO: 48.

Another aspect of the disclosure is an antigen binding protein that specifically binds HER3 comprising a heavy chain variable region sequence having the amino acid sequence shown in SEQ ID NO: 30 and a light chain variable region sequence having the amino acid sequence shown in SEQ ID NO: 34.

Another aspect of the disclosure is an antigen binding protein that specifically binds HER3 comprising a heavy chain variable region sequence having the amino acid sequence shown in SEQ ID NO: 9 and a light chain variable region sequence selected from the group consisting of the amino acid sequence shown in SEQ ID NO: 13 and the amino acid sequence shown in SEQ ID NO: 17.

Another aspect of the disclosure is an antigen binding protein that specifically binds to the HER3 receptor comprising a heavy chain variable region sequence having the amino acid sequence shown in SEQ ID NO: 30 and a light chain variable region sequence having the amino acid sequence shown in SEQ ID NO: 57.

The disclosure also provides isolated nucleic acids encoding the antigen binding proteins described herein.

The disclosure also provides an isolated nucleic acid comprising at least one nucleic acid selected from the group consisting of the nucleic acid sequence shown in SEQ ID NO: 38 and the nucleic acid sequence shown in SEQ ID NO: 39.

The disclosure also provides an isolated nucleic acid comprising at least one nucleic acid selected from the group consisting of the nucleic acid sequence shown in SEQ ID NO: 59 and the nucleic acid sequence shown in SEQ ID NO: 60.

The disclosure also provides an isolated nucleic acid comprising at least one nucleic acid selected from the group consisting of the nucleic acid sequence shown in SEQ ID NO: 40 and the nucleic acid sequence shown in SEQ ID NO: 41.

The disclosure also provides an isolated nucleic acid comprising at least one nucleic acid selected from the group consisting of the nucleic acid sequence shown in SEQ ID NO: 52 and the nucleic acid sequence shown in SEQ ID NO: 53.

The disclosure also provides an isolated nucleic acid comprising at least one nucleic acid selected from the group consisting of the nucleic acid sequence shown in SEQ ID NO: 42 and the nucleic acid sequence shown in SEQ ID NO: 43.

The disclosure also provides an isolated nucleic acid comprising at least one nucleic acid selected from the group consisting of the nucleic acid sequence shown in SEQ ID NO: 42 and the nucleic acid sequence shown in SEQ ID NO: 58.

The disclosure also provides an isolated nucleic acid comprising at least one nucleic acid selected from the group consisting of the nucleic acid sequence shown in SEQ ID NO: 54, the nucleic acid sequence shown in SEQ ID NO: 55 and the nucleic acid sequence shown in SEQ ID NO: 56.

The disclosure also provides an isolated nucleic acid comprising at least one nucleic acid selected from the group consisting of the nucleic acid sequence shown in SEQ ID NO: 63, the nucleic acid sequence shown in SEQ ID NO: 64 and the nucleic acid sequence shown in SEQ ID NO: 65.

The disclosure also provides an expression vector comprising the isolated nucleic acids described herein.

The disclosure also provides a recombinant host cell comprising an expression vector comprising the isolated nucleic acids described herein.

The disclosure also provides a method for the production of an antigen binding protein that specifically binds HER3 comprising the step of culturing a recombinant host cell comprising an expression vector comprising the isolated nucleic acids described herein; and recovering the antigen binding protein.

The disclosure also provides a pharmaceutical composition comprising an antigen binding protein described herein; and a pharmaceutically acceptable carrier.

The disclosure also provides a method of treating cancer in a subject comprising the step of administering a therapeutically effective amount of an antigen binding protein described herein to the subject, whereby the cancer in the subject is treated.

The disclosure also provides a method of treating cancer in a mammal comprising administering a therapeutically effective amount of an antigen binding protein as described herein.

In another aspect of the methods of the disclosure the mammal is a human.

In another aspect of the methods of the disclosure the cancer is selected from breast cancer, ovarian cancer, prostate cancer, bladder cancer, pancreatic cancer, skin cancer, gastric cancer and melanoma.

In one embodiment there is also provided an antigen binding protein as described herein for use in use in the treatment of breast cancer, ovarian cancer, prostate cancer, bladder cancer, pancreatic cancer, skin cancer, gastric cancer and melanoma.

The disclosure also provides a method of treating cancer in a subject comprising the steps of a) identifying a subject with a cancer selected from the group consisting of breast cancer, ovarian cancer, prostate cancer, bladder cancer, pancreatic cancer, skin cancer, gastric cancer and melanoma; and b) administering a therapeutically effective amount of an antigen binding protein described herein to the subject, whereby the cancer in the subject is treated.

The disclosure also provides a method of treatment further comprising the step of c) determining the cancer expresses a protein comprising amino acid residues 184 to 329 of SEQ ID NO: 21. Such determinations can be made by assays of intact cancer cells, or preparations of such cells, such as lysates or immunohistochemical (IHC) preparations by a variety of different techniques and reagents such as antigen binding proteins that specifically bind a peptide chain domain comprising amino acid residues 184 to 329 of SEQ ID NO: 21 or nucleic acid primers or probes specific for a nucleic acid sequence encoding amino acid residues 184 to 329 of SEQ ID NO: 21. Such determinations may be made, for example, by the use of flow cytometry including fluorescence activated cell sorting (FACS), ELISA, Southern blotting, Northern blotting or nucleic acid microarray analyses. Such determinations may be made relative to appropriate positive and negative controls or based on previously collected data sets (e.g., the average expression of amino acid residues 184 to 329 of SEQ ID NO: 21 in a particular cell or tissue type).

The disclosure also provides a method of treatment wherein the protein comprises the amino acid sequence shown in SEQ ID NO: 21. The methods of treatment of the disclosure may further comprise determining if at least one tumor cell from said subject has an amplification of a gene encoding SEQ ID NO: 21 or a portion thereof, such as domain II or domain III of HER3, or amplification of RNA transcripts encoding SEQ ID NO: 21 or a portion thereof.

The disclosure also provides a method of treatment further comprising the step of c) determining the cancer expresses a protein comprising amino acid residues 330 to 495 of SEQ ID NO: 21. Such determinations can be made by assays of intact cancer cells, or preparations of such cells, such as lysates or immunohistochemical (IHC) preparations by a variety of different techniques and reagents such as antigen binding proteins that specifically bind amino acid residues 330 to 495 of SEQ ID NO: 21 or nucleic acid primers or probes specific for a nucleic acid sequence encoding amino acid residues 330 to 495 of SEQ ID NO: 21. Such determinations may be made, for example, by the use of flow cytometry including fluorescence activated cell sorting (FACS), ELISA, Southern blotting, Northern blotting or nucleic acid microarray analyses. Such determinations may be made relative to appropriate positive and negative controls or based on previously collected data sets (e.g., the average expression of amino acid residues 330 to 495 of SEQ ID NO: 21 in a particular cell or tissue type).

The disclosure also provides the use of a substance described herein, such as an antigen binding protein, in the manufacture of a medicament for the treatment of condition selected from the group consisting of breast cancer, ovarian cancer, prostate cancer, bladder cancer, pancreatic cancer, skin cancer, gastric cancer and melanoma.

The present disclosure also relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Another aspect of the disclosure is an antigen binding protein which specifically binds to a peptide chain domain comprising amino acid residues 184 to 329 of SEQ ID NO: 21.

Another aspect of the disclosure is an antigen binding protein which specifically binds to a peptide chain domain comprising amino acid residues 330 to 495 of SEQ ID NO: 21.

The disclosure also provides a method for the production of an antigen binding protein that specifically binds HER3 comprising the steps of a) culturing a recombinant host cell comprising an expression vector comprising the isolated nucleic acid as described herein, wherein the FUT8 gene encoding alpha-1,6-fucosyltransferase has been inactivated in the recombinant host cell; and b) recovering the antigen binding protein; whereby the antigen binding protein is produced. Such methods for the production of antigen binding proteins can be performed, for example, using the POTELLIGENT™ technology system available from BioWa, Inc. (Princeton, N.J.) in which CHOK1 SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. No. 7,214,775, U.S. Pat. No. 6,946,292, WO0061739 and WO0231240 all of which are incorporated herein by reference. Those of ordinary skill in the art will also recognize other appropriate systems. Additionally, methods for the recovery of an antigen binding protein expressed by a recombinant host cell are well known in the art and include affinity based chromatography, ion exchange chromatography, and size exclusion based chromatography.

An antigen binding protein of the disclosure may also be provided as an antibody-drug conjugate (ADC). The antigen binding protein may be conjugated via a protease cleavable, peptide linker to a chemotherapeutic drug. Auristatins are one example of such chemotherapeutic agents. Examples of suitable auristatins include monomethyl auristatin E (MMAE) and monomethyl auristatin F (MMAF). Other suitable chemotherapeutic agents are described herein. Those skilled in the art will recognize other suitable chemotherapeutic agents. Conjugates may also be prepared by linking a chemotherapeutic drug to an antigen binding protein via a chemical bond formed from a reactive group.

The disclosure also provides a method for the production of an antigen binding protein that specifically binds HER3 wherein the recombinant host cell is a CHOK1 SV cell.

The disclosure also provides an antigen binding protein that specifically binds HER3 produced by the disclosed methods for production of an antigen binding protein.

The disclosure also provides a method for the production of an antigen binding protein that specifically binds HER3 comprising the steps of a) culturing a recombinant host cell comprising an expression vector comprising an isolated nucleic acid as described herein wherein the expression vector comprises a Fc nucleic acid sequence encoding a chimeric Fc domain having both IgG1 and IgG3 Fc domain amino acid residues; and b) recovering the antigen binding protein; whereby the antigen binding protein is produced. Such methods for the production of antigen binding proteins can be performed, for example, using the COMPLEGENT™ technology system available from BioWa, Inc. (Princeton, N.J.) and Kyowa Hakko Kogyo (now, Kyowa Hakko Kirin Co., Ltd.) Co., Ltd. in which a recombinant host cell comprising an expression vector in which a Fc nucleic acid sequence encoding a chimeric Fc domain having both IgG1 and IgG3 Fc domain amino acid residues is fused to an antibody heavy chain is expressed to produce an antigen binding protein having enhanced complement dependent cytotoxicity (CDC)

activity that is increased relative to an otherwise identical monoclonal antibody lacking such a chimeric Fc domain. Aspects of the COMPLEGENT™ technology system are described in WO2007011041 and US20070148165 each of which are incorporated herein by reference. In the methods of the disclosure CDC activity may also be increased by introducing sequence specific mutations into the Fc region of an IgG chain. Those of ordinary skill in the art will also recognize other appropriate systems.

The disclosure also provides a method for the production of an antigen binding protein that specifically binds HER3 wherein the Fc nucleic acid sequence is fused in frame to a nucleic acid selected from the group consisting of the nucleic acid sequence shown in SEQ ID NO: 40 and the nucleic acid sequence shown in SEQ ID NO: 42. Such methods for the production of antigen binding proteins can be performed, for example, using the ACCRETAMAB™ technology system available from BioWa, Inc. (Princeton, N.J.) which combines the POTELLIGENT™ and COMPLEGENT™ technology systems to produce an antigen binding protein having both ADCC and CDC enhanced activity that is increased relative to an otherwise identical monoclonal antibody lacking a chimeric Fc domain.

The disclosure also provides a method for the production of an antigen binding protein that specifically binds HER3 comprising the steps of a) culturing a recombinant host cell containing an expression vector containing an isolated nucleic acid as described herein, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and b) recovering the antigen binding protein; whereby the antigen binding protein is produced in a cell with a functional FUT8 gene.

The disclosure also provides a method for the production of an antigen binding protein that specifically binds HER3 wherein the Fc nucleic acid sequence is fused in frame to a nucleic acid selected from the group consisting of the nucleic acid sequence shown in SEQ ID NO: 40 and the nucleic acid sequence shown in SEQ ID NO: 42.

The disclosure also provides a method of treating a pre-cancerous condition in a subject comprising the step of administering a therapeutically effective amount of an antigen binding protein described herein to the subject, whereby the pre-cancerous condition in the subject is treated.

The disclosure also provides a method of treating a pre-cancerous condition in a subject comprising the steps of a) identifying a subject with a pre-cancerous condition; and b) administering a therapeutically effective amount of an antigen binding protein of the disclosure to the subject, whereby the pre-cancerous condition in a subject is treated.

The disclosure also provides a method of treating a pre-cancerous condition in a subject further comprising the step of c) determining the cancer expresses a protein comprising amino acid residues 184 to 329 of SEQ ID NO: 21.

The disclosure also provides a method of treating a pre-cancerous condition in a subject wherein the protein comprises the amino acid sequence shown in SEQ ID NO: 21.

The disclosure also provides a method of treating a pre-cancerous condition in a subject further comprising the step of c) determining the cancer expresses a protein comprising amino acid residues 330 to 495 of SEQ ID NO: 21.

Another aspect of the disclosure is an antigen binding protein which specifically binds a HER3 receptor and comprises CDRH1 having the amino acid sequence shown in SEQ ID NO: 2, CDRH2 having the amino acid sequence shown in SEQ ID NO: 3, CDRH3 having the amino acid sequence shown in SEQ ID NO: 4, CDRL1 having the amino acid sequence shown in SEQ ID NO: 6, CDRL2 having the amino acid sequence shown in SEQ ID NO: 7, and CDRL3 having the amino acid sequence shown in SEQ ID NO: 8.

Another aspect of the disclosure is an antigen binding protein which specifically binds a HER3 receptor and comprises CDRH1 having the amino acid sequence shown in SEQ ID NO: 23, CDRH2 having the amino acid sequence shown in SEQ ID NO: 24, CDRH3 having the amino acid sequence shown in SEQ ID NO: 25, CDRL1 having the amino acid sequence shown in SEQ ID NO: 27, CDRL2 having the amino acid sequence shown in SEQ ID NO: 28, and CDRL3 having the amino acid sequence shown in SEQ ID NO: 29.

Another aspect of the disclosure is an antigen binding protein which specifically binds a HER3 receptor and comprises CDRH1 having the amino acid sequence shown in SEQ ID NO: 31, CDRH2 having the amino acid sequence shown in SEQ ID NO: 32, CDRH3 having the amino acid sequence shown in SEQ ID NO: 33, CDRL1 having the amino acid sequence shown in SEQ ID NO: 35, CDRL2 having the amino acid sequence shown in SEQ ID NO: 36, and CDRL3 having the amino acid sequence shown in SEQ ID NO: 37.

Another aspect of the disclosure is an antigen binding protein which specifically binds a HER3 receptor and comprises CDRH1 having the amino acid sequence shown in SEQ ID NO: 45, CDRH2 having the amino acid sequence shown in SEQ ID NO: 46, CDRH3 having the amino acid sequence shown in SEQ ID NO: 47, CDRL1 having the amino acid sequence shown in SEQ ID NO: 49, CDRL2 having the amino acid sequence shown in SEQ ID NO: 50, and CDRL3 having the amino acid sequence shown in SEQ ID NO: 51.

Another aspect of the disclosure is an antigen binding protein which specifically binds a HER3 receptor and comprises CDRH1 having the amino acid sequence shown in SEQ ID NO: 10, CDRH2 having the amino acid sequence shown in SEQ ID NO: 11, CDRH3 having the amino acid sequence shown in SEQ ID NO: 12, CDRL1 having the amino acid sequence shown in SEQ ID NO: 14, CDRL2 having the amino acid sequence shown in SEQ ID NO: 15, and CDRL3 having the amino acid sequence shown in SEQ ID NO: 16.

Another aspect of the disclosure is an antigen binding protein which specifically binds a HER3 receptor and comprises CDRH1 having the amino acid sequence shown in SEQ ID NO: 10, CDRH2 having the amino acid sequence shown in SEQ ID NO: 11, CDRH3 having the amino acid sequence shown in SEQ ID NO: 12, CDRL1 having the amino acid sequence shown in SEQ ID NO: 18, CDRL2 having the amino acid sequence shown in SEQ ID NO: 19, and CDRL3 having the amino acid sequence shown in SEQ ID NO: 20.

The disclosure also provides a pharmaceutical composition as described herein for use in medicine.

The disclosure also provides a pharmaceutical composition as described herein for use in the treatment of breast cancer, ovarian cancer, prostate cancer, bladder cancer, pancreatic cancer, skin cancer, gastric cancer and melanoma.

The disclosed antigen binding proteins that specifically binds HER3 may be an antibody, for example, a monoclonal antibody. Several such exemplary antibodies are described herein including murine versions of the 15D5, 1D9 and 22A5 monoclonal antibodies as well as humanized versions of the 15D5 and 1D9 monoclonal antibodies. Epitope mapping approaches indicate 15D5 monoclonal antibody binds to domain II of HER3 and are able to inhibit or interfere with ligand—induced receptor dimerization between HER3 and other receptors such as, for example, those in Table 1. These include, but are not limited to: HER2 and other HER family receptors, c-MET and other tyrosine kinase or cell surface receptors. The result of inhibiting or interfering with the ability of HER3 to interact with these receptors is to inhibit or diminish receptor-mediated cell signaling processes or pathways that are HER3 dependent.

Epitope mapping also indicates the 1D9 monoclonal antibodies bind to domain III of HER3 to inhibit HER3 ligand binding and heterodimer formation.

The disclosed antigen binding proteins that specifically binds HER3 may bind to and neutralize the HER3 receptor (also known as ErbB3) (SEQ ID NO: 21) and compete for binding to the HER3 receptor with a reference antibody that comprises a heavy chain variable region sequence of SEQ ID NO: 1 or 9, and a light chain variable region sequence of SEQ ID NO: 5, 13, or 17). The antigen binding proteins that specifically binds HER3, such as the murine and humanized 15D5 monoclonal antibodies, may bind domain II of the HER3 receptor (residues 184-329 of SEQ ID NO: 21), but does not bind domains I (residues 20-183 of SEQ ID NO: 21), III (amino acid residues 330-495 of SEQ ID NO: 21), or IV (amino acid residues 496-643 of SEQ ID NO: 21 of the HER3 receptor (SEQ ID NO: 21). Domain II of the HER3 receptor is an important interface for the formation of receptor dimers such that the two antigen binding proteins described herein are candidate dimerization inhibitors. The antigen binding proteins that specifically bind HER3, such as murine and humanized 1D9 antibodies, may also bind domain III to prevent binding of ligand to the HER3 receptor. The disclosed antigen binding proteins that specifically bind HER3 may also compete with the murine or humanized 15D5, 1D9 or 22A5 monoclonal antibodies described herein.

The antigen binding proteins of the disclosure, or pharmaceutical compositions comprising these, may also be used in methods of treating a subject afflicted with hyperproliferative or HER3 associated disorders, such as cancers that are based on number of factors such as HER3 expression. Such tumors or cancers may be selected from, but not limited to, the group of: breast cancer, ovarian cancer, gastrointestinal cancer, prostate cancer, bladder cancer, pancreatic cancer, stomach cancer, endometrial cancer, lung cancer, kidney cancer, head and neck cancers, glioma, melanoma and non melanoma skin cancers, as well as other skin cancers and other HER3 expressing or overexpressing cancers. The antigen binding proteins may also be used to detect HER3 positive cancers that are responsive to EGFR targeted therapies such as AG1478-trastuzumab combinations or pertuzumab which inhibit HER2/HER3 heterodimerization. See e.g., Lee-Hoeflich et al., 68 Cancer. Res. 5875 (2008) and Emlet et al., 94 Br. J. Cancer 1144 (2006). In addition, benefit from this disclosure will be derived by persons from groups including: 1) anti-HER2 mAb-resistant patients, 2) anti-HER2 mAb-ineligible patients, 3) anti HER1 (EGFR) mAb-resistant or ineligible patients, and 4) patients with tyrosine kinase (small molecule)-resistant tumors. Antigen binding proteins of the disclosure could be used alone in monotherapy, or in combination therapy approaches, wherein the agent is administered in conjunction with other agents specified elsewhere in this document. The disclosure provides methods that may lead to inhibition or regression of a cancerous tumor in a subject, extended patient survival, time to tumor progression or quality of patient life wherein such methods comprise the step of administering a therapeutically effective amount of an antigen binding protein alone, or in combination with other specific agents as defined herein.

Trastuzumab emtansine, also called trastuzumab-DM1 or trastuzumab-MCC-DM1 (abbreviated T-DM1) is an antibody-drug conjugate consisting of the antibody trastuzumab (HERCEPTINT™) linked to the cytotoxin mertansine (DM1). It has the structure:

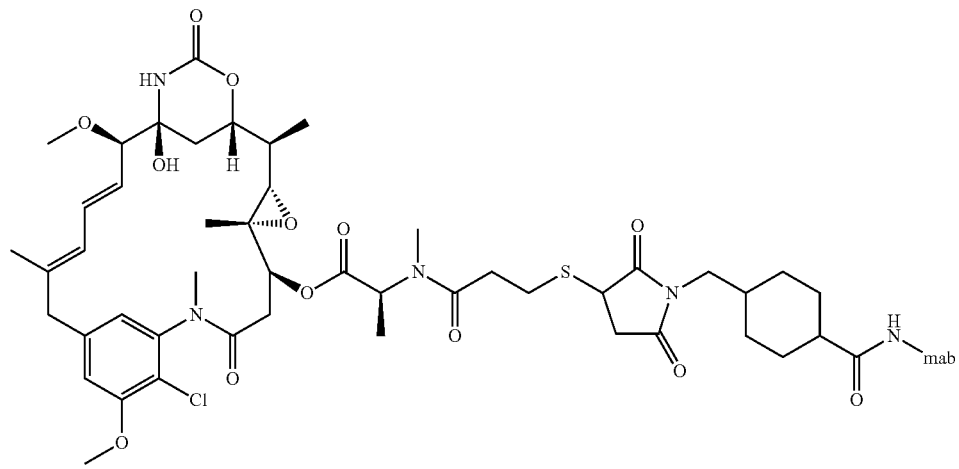

Another embodiment of the disclosure is a method of treating cancer in a mammal comprising administering a therapeutically effective amount of an antigen binding protein of the disclosure with at least one other agent as described herein. Such agents are described, at for example, pages 59-78 of the disclosure.

In another embodiment the at least one other agent is selected from the group consisting of trastuzumab, pertuzumab and T-DM1.

The antigen binding proteins of the disclosure may also be used for the treatment of a subject afflicted with tumors selected from but not limited to the group of: breast cancer, ovarian cancer, gastrointestinal cancer, prostate cancer, bladder cancer, pancreatic cancer, stomach cancer, endometrial cancer, lung cancer, kidney cancer, head and neck cancers, glioma, melanoma and non melanoma skin cancers and other HER3 expressing or overexpressing cancers.

The antigen binding proteins of the disclosure may also be for use in the treatment of breast cancer, ovarian cancer, gastrointestinal cancer, prostate cancer, bladder cancer, pancreatic cancer, stomach cancer, endometrial cancer, lung cancer, kidney cancer, head and neck cancers, glioma, melanoma and non melanoma skin cancers and other HER3 expressing or overexpressing cancers.

The antigen binding protein may bind to and neutralize the HER3 receptor and compete for binding to the HER3 receptor with a reference antibody comprising a heavy chain variable region sequence of SEQ ID NO: 1 or 9, and a light chain variable region sequence of SEQ ID NO: 5, 13, or 17.

Alternatively, the antigen binding protein may bind to and neutralize the HER3 receptor and compete for binding to the HER3 receptor with a reference antibody comprising a heavy chain variable region sequence of SEQ ID NO: 1 or 9, and a light chain variable region sequence of SEQ ID NO: 5, 13, or 17. In some embodiments the antigen binding protein does not bind to the HER2 receptor.

The reference antibody may comprise the following heavy chain and light chain combinations: (1) murine 15D5 antibody (M5.15D5.2A1.1H10; murine monoclonal antibody; comprising SEQ ID NOs: 1 and 5); (2) murine 22A5 antibody (M5.22A5.1G6.1 C10; murine monoclonal antibody; comprising SEQ ID NOs: 9, 13, and 17); (3) humanized 15D5 antibody (humanized monoclonal antibody; comprising SEQ ID NO:s 22 and 26); (4) humanized 1D9 antibody (humanized monoclonal antibody; comprising SEQ ID NO:s 30 and 34); (5) murine 1D9 antibody (murine monoclonal antibody; comprising SEQ ID NO:s 44 and 48); (6) humanized 1D9 RR (also referred to as humanized 1D9_E antibody a humanized monoclonal antibody; comprising SEQ ID NO:s 30 and 57). The second antibody, the murine 22A5 antibody, has 2 light chain variable domains (SEQ ID NOs; 13 and 17) so that different heavy and light chain combinations are formed. The reference antibody may also comprise an antibody described in Table 17 below.

Competition between the antigen binding protein and the reference antibody may be determined by competition ELISA. Competition for neutralization of HER3 may be determined by any one or a combination of: competition for binding to HER3, for example as determined by ELISA, FMAT or BIACORE™; competition for inhibition of HER3 to the neuregulin 1 and neuregulin 2 ligands; and competition for inhibition of cell signaling resulting in luciferase expression in an A204 cell based assay. A competing antigen binding protein may bind to the same epitope, an overlapping epitope, or an epitope in close proximity of the epitope to which the reference antibody binds.

The antigen binding protein may not bind significantly to the HER3 peptide fragment or artificial peptide sequence. The antigen binding protein may not bind to the HER3 peptide fragment or artificial peptide sequence at a ratio range of 1:1 to 1:10, of antigen binding protein to peptide, respectively.

Binding or lack of binding between the antigen binding protein and the HER3 receptor peptide fragment or artificial peptide sequence may be determined by ELISA or by SDS PAGE using reducing conditions. For example, binding or lack of binding of the antigen binding protein to the linear full-length HER3 receptor sequence may be determined by reducing SDS PAGE.

The present disclosure also provides an antigen binding protein that binds to and neutralizes the HER3 receptor and comprises CDRH3 of SEQ ID NOs:4, 15, or 20 or a variant CDR thereof.

The antigen binding protein may further comprise one or more CDRs, or all CDRs, in any combination, selected from: CDRH1 (SEQ ID NOs:2, 10, or 31), CDRH2 (SEQ ID NOs: 3, 11, or 32), CDRH3 (SEQ ID NO: 4, 12 or 33), CDRL1 (SEQ ID NO: 6, 14, 18, or 35), CDRL2 (SEQ ID NO: 7, 15, 19, or 36), and CDRL3 (SEQ ID NO: 8, 16, 20, or 37); or a variant thereof.

For example, the antigen binding protein may comprise CDRH3 (SEQ ID NO: 4, 12 or 33) and CDRH1 (SEQ ID NOs: 2, 10, or 31), or variants thereof. The antigen binding protein may comprise CDRH3 (SEQ ID NO: 4, 12 or 33) and CDRH2 (SEQ ID NOs: 3, 11, or 32), or variants thereof. The antigen binding protein may comprise CDRH1 (SEQ ID NOs:2, 10, or 31), CDRH2 (SEQ ID NOs: 3, 11, or 32), and CDRH3 (SEQ ID NO: 4, 12 or 33), or variants thereof.

The antigen binding protein may comprise CDRL1 (SEQ ID NO: 6, 14, 18, or 35) and CDRL2 (SEQ ID NO: 7, 15, 19, or 36), or variants thereof. The antigen binding protein may comprise CDRL2 (SEQ ID NO: 7, 15, 19, or 36) and CDRL3 (SEQ ID NO: 8, 16, 20, or 37), or variants thereof. The antigen binding protein may comprise CDRL1 (SEQ ID NO: 6, 14, 18, or 35), CDRL2 (SEQ ID NO: 7, 15, 19, or 36), and CDRL3 (SEQ ID NO: 8, 16, 20, or 37), or variants thereof.

The antigen binding protein may comprise CDRH3 (SEQ ID NO: 4, 12 or 33) and CDRL3 (SEQ ID NO: 8, 16, 20, or 37), or variants thereof. The antigen binding protein may comprise CDRH3 (SEQ ID NO: 4, 12 or 33), CDRH2 (SEQ ID NOs: 3, 11, or 32), and CDRL3 (SEQ ID NO: 8, 16, 20, or 37), or variants thereof. The antigen binding protein may comprise CDRH3 (SEQ ID NO: 4, 12 or 33), CDRH2 (SEQ ID NOs: 3, 11, or 32), CDRL2 (SEQ ID NO: 7, 15, 19, or 36), and CDRL3 (SEQ ID NO: 8, 16, 20, or 37), or variants thereof.

The antigen binding protein may comprise CDRH1 (SEQ ID NOs: 2, 10, or 31), CDRH2 (SEQ ID NOs: 3, 11, or 32), CDRH3 (SEQ ID NO: 4, 12 or 33), CDRL1 (SEQ ID NO: 6, 14, 18, or 35), CDRL2 (SEQ ID NO: 7, 15, 19, or 36) and CDRL3 (SEQ ID NO: 8, 16, 20, or 37), or variants thereof.

The present disclosure also provides an antigen binding protein which binds to and neutralizes the HER3 receptor, wherein the antigen binding protein is a chimeric or a humanized antibody comprising the corresponding CDRH3 of the variable domain sequence of SEQ ID NO: 1, 9 or 30 or a variant CDRH3.

The chimeric or humanized antigen binding protein may further comprise one or more, or all of the corresponding CDRs selected from the variable domain sequence of SEQ ID NO: 1, SEQ ID NO: 9, SEQ ID NO: 30, or a variant CDR thereof.

For example, the antigen binding protein may comprise corresponding CDRH3 and corresponding CDRH1, or variants thereof. The antigen binding protein may comprise corresponding CDRH3 and corresponding CDRH2, or variants thereof. Alternative, the antigen binding protein may comprise corresponding CDRH1, corresponding CDRH2, and corresponding CDRH3; or variants thereof.

The antigen binding protein may comprise corresponding CDRL1 and corresponding CDRL2, or variants thereof. In addition antigen binding protein may comprise corresponding CDRL2 and corresponding CDRL3, or variants thereof. The antigen binding protein also may comprise corresponding CDRL1, corresponding CDRL2 and corresponding CDRL3, or variants thereof.

The antigen binding protein may comprise corresponding CDRH3 and corresponding CDRL3, or variants thereof. The antigen binding protein may comprise corresponding CDRH3, corresponding CDRH2 and corresponding CDRL3, or variants thereof. Alternatively, the antigen binding protein may comprise corresponding CDRH3, corresponding CDRH2, corresponding CDRL2 and corresponding CDRL3, or variants thereof.

The antigen binding protein may comprise corresponding CDRH1, corresponding CDRH2, corresponding CDRH3, corresponding CDRL1, corresponding CDRL2 and corresponding CDRL3, or variants thereof.

The corresponding CDRs can be defined by reference to Kabat (1987), Chothia (1989), AbM or contact methods. One definition of each of the methods can be found at Table 3 and can be applied to the reference heavy chain variable domain of SEQ ID NO: 1, 9 or 30 and the reference light chain variable domain of SEQ ID NO: 5, 13, 17 or 35 to determine the corresponding CDR.

For example, the antigen binding protein may comprise a binding unit CDR H3 and a binding unit CDR H1, or variants thereof. The antigen binding protein may comprise a binding unit CDR H3 and a binding unit CDR H2, or variants thereof. The antigen binding protein may comprise a binding unit CDR H1, a binding unit CDR H2, and a binding unit CDR H3; or variants thereof.

The antigen binding protein may comprise a binding unit CDR L1 and a binding unit CDR L2, or variants thereof. The antigen binding protein may comprise a binding unit CDR L2 and a binding unit CDR L3, or variants thereof. The antigen binding protein may comprise a binding unit CDR L1, a binding unit CDR L2, and a binding unit CDR L3; or variants thereof.

The antigen binding protein may comprise a binding unit CDR H3 and a binding unit CDR L3, or variants thereof. Alternatively, the antigen binding protein may comprise a binding unit CDR H3, a binding unit CDR H2, and a binding unit CDR L3; or variants thereof. The antigen binding protein may comprise a binding unit CDR H3, a binding unit CDR H2, a binding unit CDR L2, and a binding unit CDR L3; or variants thereof.

The antigen binding protein may comprise a binding unit CDR H1, a binding unit CDR H2, a binding unit CDR H3, a binding unit CDR L1, a binding unit CDR L2, and a binding unit CDR L3; or variants thereof.

A CDR variant or variant binding unit includes an amino acid sequence modified by at least one amino acid, wherein said modification can be chemical or a partial alteration of the amino acid sequence (for example by no more than 10 amino acids), which modification permits the variant to retain the biological characteristics of the unmodified sequence. For example, the variant is a functional variant which binds to and neutralizes HER3. A partial alteration of the CDR amino acid sequence may be by deletion or substitution of one to several amino acids, or by addition or insertion of one to several amino acids, or by a combination thereof (for example by no more than 10 amino acids). The CDR variant or binding unit variant may contain 1, 2, 3, 4, 5 or 6 amino acid substitutions, additions or deletions, in any combination, in the amino acid sequence. The CDR variant or binding unit variant may contain 1, 2 or 3 amino acid substitutions, insertions or deletions, in any combination, in the amino acid sequence. The substitutions in amino acid residues may be conservative substitutions, for example, substituting one hydrophobic amino acid for an alternative hydrophobic amino acid. For example, leucine may be substituted with valine, or isoleucine.

The antigen binding protein comprising the CDRs, corresponding CDRs, variant CDRs, binding units or variant binding units described, may display a potency for binding to HER3, as demonstrated by ED50, of within 10-fold, or within 5-fold of the potency demonstrated by a reference antibody described herein. Potency for binding to HER3, as demonstrated by ED50, may be carried out by an ELISA assay.

The antigen binding protein may or may not have a substitution at amino acid position 54 from asparagine (N) to aspartate (D) or glutamine (Q). The antigen binding protein variant may or may not have a substitution at amino acid position 91 from cysteine (C) to serine (S).

One or more of the CDRs, corresponding CDRs, variant CDRs or binding units described herein may be present in the context of a human framework, for example as a humanized or chimeric variable domain.

The humanized heavy chain variable domain may comprise the CDRs described in the sequence listing, corresponding CDRs, binding units, or variants thereof, within an acceptor antibody framework having 75% or greater, 80% or greater, 85% or greater, 90% or greater, 95% or greater, 98% or greater, 99% or greater or 100% identity in the framework regions to the human variable domain sequence in SEQ ID NOs:1 and 9. The humanized light chain variable domain may comprise the CDRs listed in SEQ ID NOs:6, 7, 8, 14, 15, 16, 18, 19, or 20, corresponding CDRs, binding units, or variants thereof, within an acceptor antibody framework having 75% or greater, 80% or greater, 85% or greater, 90% or greater, 95% or greater, 98% or greater, 99% or greater or 100% identity.

The antigen binding protein variable heavy chain may have a serine (S) amino acid residue at position 28 and/or a threonine (T) amino acid residue at position 105. The antigen binding protein variable light chain may have an arginine (R) amino acid residue at position 16 and/or a tyrosine (Y) amino acid residue at position 71 and/or an alanine (A) amino acid residue at position 100. For example, the antigen binding protein may comprise serine (S) at position 28 of the variable heavy chain and tyrosine (Y) at position 71 of the variable light chain.

The disclosure also provides an antigen binding protein that binds to and neutralizes HER3 and comprises any one of the following heavy chain and light chain variable region combinations: (1) murine 15D5 antibody (M5.15D5.2A1.1H10; murine monoclonal antibody; comprising SEQ ID NOs: 1 and 5); (2) murine 22A5 antibody (M5.22A5.1G6.1 C10; murine monoclonal antibody; comprising SEQ ID NOs: 9, 13, and 17); (3) humanized 15D5 antibody (humanized monoclonal antibody; comprising SEQ ID NO:s 22 and 26); (4) humanized 1D9 antibody (humanized monoclonal antibody; comprising SEQ ID NO:s 30 and 34); (5) murine 1D9 antibody (murine monoclonal antibody; comprising SEQ ID NO:s 44 and 48); (6) humanized 1D9 RR (also referred to as humanized 1D9_E antibody a humanized monoclonal antibody; comprising SEQ ID NO:s 30 and 57).

Any of the heavy chain variable regions may be combined with a suitable human constant region. Any of the light chain variable regions may be combined with a suitable constant region.

Antigen binding proteins as described above, for example variants with a partial alteration of the sequence by chemical modification and/or insertion, deletion or substitution of one or more amino acid residues, or those with 75% or greater, 80% or greater, 85% or greater, 90% or greater, 95% or greater, 98% or greater, or 99% or greater identity to any of the sequences described above, may display a potency for binding to HER3, as demonstrated by ED50, of within 10-fold, or within 5-fold of the potency demonstrated by (1) M5 15D5 2A1 1H10 (murine monoclonal antibody; comprising SEQ ID NOs: 1 and 5); (2) M5_22A5 1G6 1 C10 (murine monoclonal antibody; comprising SEQ ID NOs: 9, 13, and 17); (3) humanized 15D5 (humanized monoclonal antibody; comprising SEQ ID NO:s 22 and 26); (4) humanized 1D9 (humanized monoclonal antibody; comprising SEQ ID NO:s 30 and 34); (5) murine 1D9 (murine monoclonal antibody; comprising SEQ ID NO:s 44 and 48); (6) humanized 1D9_E (humanized monoclonal antibody; comprising SEQ ID NO:s 30 and 57). Potency for binding to HER3, as demonstrated by ED50, may be carried out by an ELISA assay.

The antigen binding proteins described herein may not bind to a peptide fragment of the HER3 receptor. The peptide fragment of the HER3 receptor may be any fragment consisting of up to 14 amino acids of the HER3 sequence. The peptide fragment of HER3 may be linear. The peptide fragment of HER3 may be any fragment of the HER3 receptor sequence, including the full length sequence, wherein the sequence is linear.

Binding or lack of binding between the antigen binding protein and the HER3 peptide fragment or artificial peptide sequence may be determined by ELISA or by SDS PAGE using reducing conditions. For example, binding or lack of binding of the antigen binding protein to the linear full length HER3 sequence may be determined by reducing (i.e., denaturing) SDS PAGE.

The epitope of the HER3 receptor to which the antigen binding proteins described herein bind may be a conformational or discontinuous epitope. The antigen binding proteins described herein may not bind to a linear epitope on the HER3 receptor. For example, the antigen binding protein may not bind to a reduced or denatured sample of the HER3 receptor. The conformational or discontinuous epitope may be identical to, similar to, or overlap with the HER3 receptor binding site. The epitope may be accessible when the HER3 receptor is in its mature form and as part of a dimer with another receptor molecule. The epitope may also be accessible when the HER3 receptor is in its mature form and as part of a tetramer with other HER3 receptor binding molecules as described. The epitope may be distributed across two HER3 receptor polypeptides. This type of discontinuous epitope may comprise sequences from each HER3 receptor molecule. The sequences may, in the context of the dimer's tertiary and quaternary structure, be near enough to each other to form an epitope and be bound by an antigen binding protein. Conformational and/or discontinuous epitopes may be identified by known methods, for example CLIPS™ (Pepscan Systems).

The antigen binding protein may have a half life of at least 6 hours, at least 1 day, at least 2 days, at least 3 days, at least 4 days, at least 5 days, at least 7 days, or at least 9 days in vivo in humans, or in a murine animal model.

Mutational changes to the Fc effector portion of the antibody can be used to change the affinity of the interaction between the FcRn and antibody to modulate antibody turnover. The half life of the antibody can be extended in vivo. This would be beneficial to patient populations as maximal dose amounts and maximal dosing frequencies could be achieved as a result of maintaining in vivo IC50 for longer periods of time.

The HER3 receptor polypeptide to which the antigen binding protein binds may be a recombinant polypeptide. The HER3 receptor may be in solution, or may be attached to a solid surface. For example, the HER3 receptor may be attached to beads, such as magnetic beads. In addition, the HER3 receptor may be biotinylated. The biotin molecule conjugated to the HER3 receptor may be used to immobilize HER3 on a solid surface by coupling biotinstreptavidin on the solid surface.

The antigen binding protein may be derived from rat, mouse, primate (e.g., cynomolgus, Old World monkey or Great Ape), or human. The antigen binding protein may be a humanized or chimeric antibody.

The antigen binding protein may comprise a constant region, which may be of any isotype or subclass. The constant region may be of the IgG isotype, for example, IgG1, IgG2, IgG3, IgG4 or variants thereof. The antigen binding protein constant region may be IgG1.

The antigen binding protein may comprise one or more modifications selected from a mutated constant domain such that the antibody has enhanced effector functions/ADCC and/or complement activation. Examples of suitable modifications are described in Shields, et al., *J. Biol. Chem.* (2001) 276:6591-6604, Lazar, et al., *PNAS* (2006) 103:4005-4010 and U.S. Pat. No. 6,737,056, WO2004063351 and WO2004029207.

The antigen binding protein may comprise a constant domain with an altered glycosylation profile such that the antigen binding protein has enhanced effector functions/ADCC and/or complement activation. Examples of suitable methodologies to produce an antigen binding protein with an altered glycosylation profile are described in WO2003/011878, WO2006/014679, and EP1229125.

The present disclosure also provides a nucleic acid molecule that encodes an antigen binding protein as described herein. The nucleic acid molecule may comprise sequences encoding both the heavy chain variable or full length sequence; and the light chain variable or full length sequence. Alternatively, the nucleic acid molecule that encodes an antigen binding protein described herein may comprise sequences encoding the heavy chain variable or full length sequence; or light chain variable or full length sequence.

The present disclosure also provides an expression vector comprising a nucleic acid molecule as described herein. Also provided is a recombinant host cell comprising an expression vector as described herein.

The antigen binding protein described herein may be produced in a suitable host cell. A method for the production of the antigen binding protein as described herein may comprise the step of culturing a host cell as described herein and recovering the antigen binding protein. A recombinant transformed, transfected, or transduced host cell may comprise at least one expression cassette, whereby said expression cassette comprises a polynucleotide encoding a heavy chain of the antigen binding protein described herein and further comprises a polynucleotide encoding a light chain of the antigen binding protein described herein. Alternatively, a recombinant transformed, transfected or transduced host cell may comprise at least one expression cassette, whereby a first expression cassette comprises a polynucleotide encoding a heavy chain of the antigen binding protein described herein and further comprise a second cassette comprising a polynucleotide encoding a light chain of the antigen binding protein described herein. A stably transformed host cell may comprise a vector comprising one or more expression cassettes encoding a heavy chain and/or a light chain of the antigen binding protein described herein. For example such host cells may comprise a first vector encoding the light chain and a second vector encoding the heavy chain.

The host cell may be eukaryotic, for example, mammalian. Examples of such cell lines include CHO or NS0. The host cell may be cultured in a culture media, for example, serum-free culture media. The antigen binding protein may be secreted by the host cell into the culture media. The antigen binding protein can be purified to at least 95% or greater (e.g., 98% or greater) with respect to said culture media containing the antigen binding protein. Methods for culturing cells in different media compositions and ambient conditions are well known to those skilled in the art.

A pharmaceutical composition comprising the antigen binding protein and a pharmaceutically acceptable carrier may be provided. A kit-of-parts comprising the pharmaceutical composition together with instructions for use may be provided. For convenience, the kit may comprise the reagents in predetermined amounts with instructions for use.

Antibody Structures

Intact Antibodies

The light chains of antibodies from most vertebrate species can be assigned to one of two types called Kappa and Lambda based upon the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b.

The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies.

The constant regions are not directly involved in the binding of the antibody to the antigen, but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

The human IgG2 constant region has been reported to essentially lack the ability to activate complement by the classical pathway or to mediate antibody-dependent cellular cytotoxicity. The IgG4 constant region has been reported to lack the ability to activate complement by the classical pathway and mediates antibody-dependent cellular cytotoxicity only weakly. Antibodies essentially lacking these effector functions may be termed 'non-lytic' antibodies.

Human Antibodies

Human antibodies may be produced by a number of methods known to those of skill in the art. Human antibodies can be made by the hybridoma method using human myeloma or mouse-human heteromyeloma cells lines. See Kozbor (1984) *J. Immunol* 133, 3001, and Brodeur, MONOCLONAL ANTIBODY PRODUCTION TECHNIQUES AND APPLICATIONS, 51-63 (Marcel Dekker Inc, 1987). Alternative methods include the use of phage libraries or transgenic mice both of which utilize human variable region repertoires (see Winter (1994) *Annu. Rev. Immunol* 12: 433-455; Green (1999) *J. Immunol. Methods* 231: 11-23).

Several strains of transgenic mice are now available wherein their mouse immunoglobulin loci has been replaced with human immunoglobulin gene segments (see Tomizuka (2000) PNAS 97: 722-727; Fishwild (1996) *Nature Biotechnol.* 14: 845-851; Mendez (1997) *Nature Genetics*, 15: 146-156). Upon antigen challenge, such mice are capable of producing a repertoire of human antibodies from which antibodies of interest can be selected.

Phage display technology can be used to produce human antigen binding proteins (and fragments thereof), see McCafferty (1990) *Nature* 348: 552-553 and Griffiths, et al., *EMBO* 13: 3245-3260 (1994).

The technique of affinity maturation (*Marks Bio/technol* (1992) 10: 779-783) may be used to improve binding affinity wherein the affinity of the primary human antibody is improved by sequentially replacing the H and L chain variable regions with naturally occurring variants and selecting on the basis of improved binding affinities. Variants of this technique such as "epitope imprinting" are now also available. See, for example, WO 93/06213; Waterhouse (1993) *Nuci. Acids Res.* 21: 2265-2266.

Chimeric and Humanized Antibodies

Chimeric antibodies are typically produced using recombinant DNA methods. DNA encoding the antibodies (e.g., cDNA) are isolated and sequenced using conventional procedures (e.g., by using oligonucleotide probes that are capable of binding specifically to genes encoding the H and L chains of the antibody. Hybridoma cells serve as a typical source of such DNA. Once isolated, the DNA is placed into expression vectors which are then transfected into host cells such as *E. coli*, COS cells, CHO cells or myeloma cells that do not otherwise produce immunoglobulin protein to obtain synthesis of the antibody. The DNA may be modified by substituting the coding sequence for human L and H chains for the corresponding non-human (e.g., murine) H and L constant regions. See, for example, Morrison (1984) *PNAS* 81: 6851.

A large decrease in immunogenicity can be achieved by grafting only the CDRs of a non-human (e.g., murine) antibodies ("donor" antibodies) onto human framework ("acceptor framework") and constant regions to generate humanized antibodies (see Jones, et al. (1986) *Nature* 321: 522-525; and Verhoeyen, et al. (1988) *Science* 239: 1534-1536). However, CDR grafting per se may not result in the complete retention of antigen-binding properties and it is frequently found that some framework residues (sometimes referred to as "back mutations") of the donor antibody need to be preserved in the humanized molecule, if significant antigen-binding affinity is to be recovered (see Queen, et al. (1989) *PNAS* 86: 10,029-10,033: Co, et al. (1991) *Nature* 351: 501-502). In this case, human variable regions showing the greatest sequence homology to the non-human donor antibody are chosen from a database in order to provide the human framework (FR). The selection of human FRs can be made either from human consensus or individual human antibodies. Where necessary, key residues from the donor antibody can be substituted into the human acceptor framework to preserve CDR conformations. Computer modelling of the antibody may be used to help identify such structurally important residues. See WO 99/48523.

Alternatively, humanization may be achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan, et al. (1991) *Mol. Immunol.* 28: 489-498; and Pedersen, et al. (1994) *J. Mol. Biol.* 235: 959-973). Therefore, it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark, et al. (1994) in *Handbook of Experimental Pharmacology* Vol. 113: The pharmacology of Monoclonal Antibodies, Springer-Verlag, 105-134). This procedure of humanization is referred to as "veneering" because only the surface of the antibody is altered, the supporting residues remain undisturbed. Further alternative approaches include that set out in WO04/006955 and the procedure of HUMANEERING™ (Kalobios) which makes use of bacterial expression systems and produces antibodies that are close to human germline in sequence (Alfenito-M Advancing Protein Therapeutics January 2007, San Diego, Calif.).

Bispecific Antigen Binding Proteins

A bispecific antigen binding protein is an antigen binding protein having binding specificities for at least two different epitopes. Methods of making such antigen binding proteins are known in the art. Traditionally, the recombinant production of bispecific antigen binding proteins is based on the co-expression of two immunoglobulin H chain-L chain pairs, where the two H chains have different binding specificities. See Millstein, et al. (1983) *Nature* 305: 537-539; WO 93/08829; and Traunecker, et al. (1991) *EMBO* 10: 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, $CH_2$ and CH3 regions. The CH1 region containing the site necessary for light chain binding may be present in at least one of the fusions. DNA encoding these fusions, and if desired the L chain are inserted into separate expression vectors and are then co-transfected into a suitable host organism. It is possible, though, to insert the coding sequences for two or all three chains into one expression vector. In one approach, the bispecific antibody is composed of a H chain with a first binding specificity in one arm and a H-L chain pair, providing a second binding specificity in the other arm. See WO 94/04690; see also Suresh, et al. (1986) *Methods in Enzymology* 121: 210.

Antigen Binding Fragments

Fragments lacking the constant region lack the ability to activate complement by the classical pathway or to mediate antibody-dependent cellular cytotoxicity. Traditionally, such fragments are produced by the proteolytic digestion of intact antibodies by, e.g., papain digestion (see, for example, WO 94/29348), but may be produced directly from recombinantly transformed host cells. For the production of ScFv, see Bird, et al. (1988) *Science* 242: 423-426. In addition, antigen binding fragments may be produced using a variety of engineering techniques as described below.

Fv fragments appear to have lower interaction energy of their two chains than Fab fragments. To stabilize the association of the $V_H$ and $V_L$ domains, they have been linked with peptides (Bird, et al. (1988) *Science* 242: 423-426; Huston, et al. (1988) *PNAS* 85(16): 5879-5883), disulphide bridges (Glockshuber, et al. (1990) *Biochemistry* 29: 1362-1367) and "knob in hole" mutations (Zhu, et al. (1997) *Protein Sci.,* 6: 781-788). ScFv fragments can be produced by methods well known to those skilled in the art, see Whitlow, et al. (1991) *Methods Companion Methods Enzymol,* 2: 97-105 and Huston, et al. (1993) *Int. Rev. Immunol* 10: 195-217. ScFv may be produced in bacterial cells such as *E. coli* or in eukaryotic cells. One disadvantage of ScFv is the monovalency of the product, which precludes an increased avidity due to polyvalent binding, and their short half-life. Attempts to overcome these problems include bivalent $(ScFv')_2$ produced from ScFv containing an additional C-terminal cysteine by chemical coupling (Adams, et al. (1993) *Can. Res* 53: 4026-4034; and McCartney, et al. (1995) *Protein Eng.* 8: 301-314) or by spontaneous site-specific dimerisation of ScFv containing an unpaired C-terminal cysteine residue (see Kipriyanov, et al. (1995) *Cell. Biophys* 26: 187-204). Alternatively, ScFv can be forced to form multimers by shortening the peptide linker to 3 to 12 residues to form "diabodies", see Holliger, et al. (1993) *PNAS* 90: 6444-6448. Reducing the linker still further can result in ScFv trimers ("triabodies", see Kortt, et al. (1997) *Protein Eng* 10: 423-433) and tetramers ("tetrabodies", see Le Gall, et al. (1999) *FEBS Lett,* 453: 164-168). Construction of bivalent ScFv molecules can also be achieved by genetic fusion with protein dimerising motifs to form "miniantibodies" (see Pack, et al. (1992) *Biochemistry* 31: 1579-1584) and "minibodies" (see Hu, et al. (1996) *Cancer Res.* 56: 3055-3061). ScFv-Sc-Fv tandems $((ScFV)_2)$ may also be produced by linking two ScFv units by a third peptide linker, see Kurucz, et al. (1995) *J. Immol.* 154: 4576-4582. Bispecific diabodies can be produced through the noncovalent association of two single chain fusion products consisting of $V_H$ domain from one antibody connected by a short linker to the $V_L$ domain of another antibody, see Kipriyanov, et al. (1998) *Int. J. Can* 77: 763-772. The stability of such bispecific diabodies can be enhanced by the introduction of disulphide bridges or "knob in hole" mutations as described supra, or by the formation of single chain diabodies (ScDb), wherein two hybrid ScFv fragments are connected through a peptide linker see Kontermann, et al. (1999) *J. Immunol. Methods* 226:179-188. Tetravalent bispecific molecules are available by, e.g., fusing a ScFv fragment to the CH3 domain of an IgG molecule or to a Fab fragment through the hinge region. See Coloma, et al. (1997) *Nature Biotechnol.* 15: 159-163. Alternatively, tetravalent bispecific molecules have been created by the fusion of bispecific single chain diabodies (see Alt, et al. (1999) *FEBS Lett* 454: 90-94. Smaller tetravalent bispecific molecules can also be formed by the dimerization of either ScFv-ScFv tandems with a linker containing a helix-loop-helix motif (DiBi miniantibodies, see Muller, et al. (1998) *FEBS Lett* 432: 45-49) or a single chain molecule comprising four antibody variable domains ($V_H$ and $V_L$) in an orientation preventing intramolecular pairing (tandem diabody, see Kipriyanov, et al. (1999) *J. Mol. Biol.* 293: 41-56). Bispecific $F(ab')_2$ fragments can be created by chemical coupling of Fab' fragments or by heterodimerization through leucine zippers (see Shalaby, et al. (1992) *J. Exp. Med.* 175: 217-225; and Kostelny, et al. (1992), *J. Immunol.* 148: 1547-1553). Also available are isolated $V_H$ and $V_L$ domains (Domantis plc). See U.S. Pat. No. 6,248,516; U.S. Pat. No. 6,291,158; and U.S. Pat. No. 6,172,197.

Heteroconjugate Antibodies

Heteroconjugate antibodies are composed of two covalently joined antibodies formed using any convenient cross-linking methods. See, for example, U.S. Pat. No. 4,676, 980.

Other Modifications

The antigen binding proteins of the present disclosure may comprise other modifications to enhance or change their effector functions. The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies may be carried out depending on the desired property. For example, specific mutations in the Fc region to render an otherwise lytic antibody, non-lytic is detailed in EP 0629 240 and EP 0307 434, or one may incorporate a salvage receptor binding epitope into the antibody to increase serum half life. See U.S. Pat. No. 5,739,277. Human Fcγ receptors include FcγR (I), FcγRIIa, FcγRIIb, FcγRIIIa and neonatal FcRn. Shields, et al. (2001) *J. Biol. Chem.* 276: 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining $CH_1$ and $CH_2$. While FcγRI utilizes only the common set of IgG1 residues for binding, FcγRII and FcγRIII interact with distinct residues in addition to the common set. Alteration of some residues reduced binding only to FcγRII (e.g., Arg-292) or FcγRIII (e.g., Glu-293). Some variants showed improved binding to FcγRII or FcγRIII but did not affect binding to the other receptor (e.g., Ser-267Ala improved binding to FcγRII but binding to FcγRIII was unaffected). Other variants exhibited improved binding to FcγRII or FcγRIII with reduction in binding to the other receptor (e.g., Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans (1997) *Immunol. Res* 16: 29-57; and Ghetie, et al. (2000) *Annu. Rev. Immunol.* 18: 739-766). Human IgG1 residues determined to interact directly with human FcRn includes 11e253, Ser254, Lys288, Thr307, Gln311, Asn434 and His435. Substitutions at any of the positions described in this section may enable increased serum half-life and/or altered effector properties of the antibodies.

Other modifications include glycosylation variants of the antibodies. Glycosylation of antibodies at conserved positions in their constant regions is known to have a profound effect on antibody function, particularly effector functioning such as those described above. See, for example, Boyd, et al. (1996) *Mol. Immunol.* 32: 1311-1318. Glycosylation variants of the antibodies or antigen binding fragments thereof wherein one or more carbohydrate moiety is added, substituted, deleted or modified are contemplated. Introduction of an asparagine-X-serine or asparagine-X-threonine motif creates a potential site for enzymatic attachment of carbohydrate moieties and may, therefore, be used to manipulate the glycosylation of an antibody. In Raju, et al. (2001) *Biochemistry* 40: 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced as a mixture of glycoforms. This mixture is particularly apparent when antibodies are produced in eukaryotic, particularly mammalian cells. A variety of methods have been developed to manufacture defined glycoforms. See Zhang, et al. (2004) *Science* 303: 371: Sears, et al. (2001) *Science* 291: 2344; Wacker, et al. (2002) *Science* 298: 1790; Davis, et al. (2002) *Chem. Rev.* 102: 579; Hang, et al. (2001) *Acc. Chem. Res* 34: 727. The antibodies (for example, of the IgG isotype, e.g. IgG1) as herein described may comprise a defined number (e.g., 7 or less, for example 5 or less, such as two or a single) of glycoform(s).

The antibodies may be coupled to a non-proteinaeous polymer such as polyethylene glycol (PEG), polypropylene glycol or polyoxyalkylene. Conjugation of proteins to PEG is an established technique for increasing the half-life of proteins, as well as reducing antigenicity and immunogenicity of proteins. The use of PEGylation with different molecular weights and styles (linear or branched) has been investigated with intact antibodies, as well as with Fab' fragments. See Koumenis et al., (2000) *Int. J. Pharmaceut.* 198: 83-95.

Production Methods

Antigen binding proteins may be produced in transgenic organisms, such as goats (see Pollock, et al. (1999) *J. Immunol. Methods* 231: 147-157), chickens (see Morrow (2000) *Genet. Eng. News* 20:1-55, mice (see Pollock, et al.) or plants (see Doran (2000) *Curr. Opinion Biotechnol.* 11: 199-204; Ma (1998) *Nat. Med.* 4: 601-606; Baez, et al. (2000) *BioPharm* 13: 50-54; Stoger, et al. (2000) *Plant Mol. Biol.* 42: 583-590).

Antigen binding proteins may also be produced by chemical synthesis. However, antigen binding proteins are typically produced using recombinant cell culturing technology well known to those skilled in the art. A polynucleotide encoding the antigen binding protein is isolated and inserted into a replicable vector such as a plasmid for further cloning (amplification) or expression. One expression system is a glutamate synthetase system (such as sold by Lonza Biologics), particularly where the host cell is CHO or NS0. Polynucleotide encoding the antigen binding protein is readily isolated and sequenced using conventional procedures (e.g., oligonucleotide probes). Vectors that may be used include plasmid, virus, phage, transposons, minichromosomes of which plasmids are typically used. Generally, such vectors further include a signal sequence, origin of replication, one or more marker genes, an enhancer element, a promoter and transcription termination sequences operably linked to the antigen binding protein polynucleotide so as to facilitate expression. Polynucleotide encoding the light and heavy chains may be inserted into separate vectors and introduced, for example, by transformation, transfection, electroporation or transduction, into the same host cell concurrently or sequentially or, if desired, both the heavy chain and light chain can be inserted into the same vector prior to said introduction.

Codon optimisation may be used with the intent that the total level of protein produced by the host cell is greater when transfected with the codon-optimised gene in comparison with the level when transfected with the wild-type sequence. Several methods have been published (Nakamura, et al. (1996) *Nucleic Acids Research* 24: 214-215; WO98/34640; WO97/11086). Due to the redundancy of the genetic code, alternative polynucleotides to those disclosed herein (particularly those codon optimised for expression in a given host cell) may also encode the antigen binding proteins described herein. The codon usage of the antigen binding protein of this disclosure thereof can be modified to accommodate codon bias of the host cell such to augment transcript and/or product yield (e.g., Hoekema, et al., (1987), *Mol Cell Biol* 7(8): 2914-24). The choice of codons may be based upon suitable compatibility with the host cell used for expression.

Signal Sequences

Antigen binding proteins may be produced as a fusion protein with a heterologous signal sequence having a specific cleavage site at the N-terminus of the mature protein. The signal sequence should be recognized and processed by the host cell. For prokaryotic host cells, the signal sequence may be, for example, an alkaline phosphatase, penicillinase, or heat stable enterotoxin II leaders. For yeast secretion, the signal sequences may be, for example, a yeast invertase leader, a factor leader or acid phosphatase leaders. See, e.g., WO90/13646. In mammalian cell systems, viral secretory leaders, such as herpes simplex gD signal, and a native immunoglobulin signal sequence may be suitable. Typically, the signal sequence is ligated in reading frame to DNA encoding the antigen binding protein.

Origin of Replication

Origin of replications are well known in the art with pBR322 suitable for most gram-negative bacteria, 2μ plasmid for most yeast and various viral origins, such as SV40, polyoma, adenovirus, VSV or BPV for most mammalian cells. Generally the origin of replication component is not needed for mammalian expression vectors, but the SV40 may be used, because it contains the early promoter.

Selection Marker

Typical selection genes encode proteins that (a) confer resistance to antibiotics or other toxins, e.g., ampicillin, neomycin, methotrexate or tetracycline or (b) complement auxiotrophic deficiencies or supply nutrients not available in the complex media or (c) combinations of both. The selection scheme may involve arresting growth of the host cell. Cells which have been successfully transformed with the genes encoding the antigen binding protein, survive due to, e.g., drug resistance conferred by the co-delivered selection marker. One example is the DHFR selection marker, wherein transformants are cultured in the presence of methotrexate. Cells can be cultured in the presence of increasing amounts of methotrexate to amplify the copy number of the exogenous gene of interest. CHO cells are a particularly useful cell line for the DHFR selection. A further example is the glutamate synthetase expression system (Lonza Biologics). An example of a selection gene for use in yeast is the trp1 gene. See Stinchcomb, et al. (1979) *Nature* 282: 38.

Promoters

Suitable promoters for expressing antigen binding proteins are operably linked to DNA/polynucleotide encoding the antigen binding protein. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes, e.g., enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, rous sarcoma virus (RSV) promoter, and the early or late Simian virus 40. Of course the choice of promoter is based upon suitable compatibility with the host cell used for expression. A first plasmid may comprise a RSV and/or SV40 and/or CMV promoter, DNA encoding light chain variable region ($V_L$), κC region together with neomycin and ampicillin resistance selection markers and a second plasmid comprising a RSV or SV40 promoter, DNA encoding the heavy chain variable region ($V_H$), DNA encoding the γ1 constant region, DHFR and ampicillin resistance markers.

Enhancer Element

Where appropriate, e.g., for expression in higher eukaryotes, an enhancer element operably linked to the promoter element in a vector may be used. Mammalian enhancer sequences include enhancer elements from globin, elastase, albumin, fetoprotein, and insulin. Alternatively, one may use an enhancer element from a eukaroytic cell virus, such as SV40 enhancer (at bp 100-270), cytomegalovirus early promoter enhancer, polyma enhancer, baculoviral enhancer or murine IgG2a locus (see WO04/009823). The enhancer may be located on the vector at a site upstream to the promoter. Alternatively, the enhancer may be located elsewhere, for example, within the untranslated region or downstream of the polyadenylation signal. The choice and positioning of enhancer may be based upon suitable compatibility with the host cell used for expression.

Polyadenylation/Termination

In eukaryotic systems, polyadenylation signals are operably linked to DNA/polynucleotide encoding the antigen binding protein. Such signals are typically placed 3' of the open reading frame. In mammalian systems, non-limiting examples include signals derived from growth hormones, elongation factor-1 alpha and viral (e.g., SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic systems, polyadenylation signals are typically not required, and it is, instead, usual to employ shorter and more defined terminator sequences. The choice of polyadenylation/termination sequences may be based upon suitable compatibility with the host cell used for expression.

Other Methods/Elements for Enhanced Yields

In addition to the above, other features that can be employed to enhance yields include chromatin remodelling elements, introns and host-cell specific codon modification.

Host Cells

Suitable host cells for cloning or expressing vectors encoding antigen binding proteins are prokaroytic, yeast or higher eukaryotic cells. Suitable prokaryotic cells include eubacteria, e.g., enterobacteriaceae such as *Escherichia*, e.g., *E. coli* (for example, ATCC 31,446; 31,537; 27,325), *Enterobacter, Erwinia, Klebsiella Proteus, Salmonella*, e.g., *Salmonella typhimurium, Serratia* e.g. *Serratia marcescans* and *Shigella* as well as Bacilli such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g., ATCC 16,045; 12,424; 24178; 56,500), *yarrowia* (EP402, 226), *Pichia pastoris* (EP 183 070, see also Peng, et al. (2004) *J Biotechnol.* 108: 185-192), *Candida, Trichoderma reesia* (EP 244 234), Penicillin, *Tolypocladium* and *Aspergillus* hosts, such as *A. nidulans* and *A. niger*, are also contemplated.

Higher eukaryotic host cells include mammalian cells, such as COS-1 (ATCC No. CRL 1650), COS-7 (ATCC CRL 1651), human embryonic kidney line 293, baby hamster kidney cells (BHK) (ATCC CRL.1632), BHK570 (ATCC NO: CRL 10314), 293 (ATCC NO.CRL 1573), Chinese hamster ovary cells CHO (e.g., CHO-K1, ATCC NO: CCL 61, DHFR-CHO cell line, such as DG44 (see Urlaub, et al. (1986) *Somatic Cell Mol. Genet.* 12: 555-556), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2, and myeloma or lymphoma cells, e.g., NS0 (see U.S. Pat. No. 5,807,715), Sp2/0, Y0.

Such host cells may also be further engineered or adapted to modify quality, function and/or yield of the antigen binding protein. Non-limiting examples include expression of specific modifying (e.g., glycosylation) enzymes and protein folding chaperones.

Cell Culturing Methods

Host cells transformed with vectors encoding antigen binding proteins may be cultured by any method known to those skilled in the art. Host cells may be cultured in spinner flasks, roller bottles or hollow fibre systems but for large scale production that stirred tank reactors are used particularly for suspension cultures. The stirred tankers may be adapted for aeration using, e.g., spargers, baffles or low shear impellers. For bubble columns and airlift reactors direct aeration with air or oxygen bubbles maybe used. Where the host cells are cultured in a serum free culture media, the media is supplemented with a cell protective agent, such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes, such as fed-batch, repeated batch processing (see Drapeau, et al. (1994) *Cytotechnology* 15: 103-109), extended batch process or perfusion culture. Although recombinantly transformed mammalian host cells may be cultured in serum-containing media such as fetal calf serum (FCS), for example, such host cells are cultured in synthetic serum-free media such as disclosed in Keen, et al. (1995) *Cytotechnology* 17: 153-163, or commercially available media such as ProCHO-CDM or UltraCHO™ (Cambrex N.J., USA), supplemented, where necessary, with an energy source such as glucose and synthetic growth factors, such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see, e.g., Scharfenberg, et al. (1995) in ANIMAL CELL TECHNOLOGY: DEVELOPMENTS TOWARDS THE 21ST CENTURY (Beuvery, et al., eds, 619-623, Kluwer Academic publishers).

Antigen binding proteins secreted into the media may be recovered and purified using a variety of techniques to provide a degree of purification suitable for the intended use. For example the use of antigen binding proteins for the treatment of human patients typically mandates at least 95% purity, more typically 98% or 99% or greater purity (compared to the crude culture medium). Cell debris from the culture media is typically removed using centrifugation followed by a clarification step of the supernatant using, e.g., microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. The antibodies, following various clarification steps, can be captured using Protein A or G affinity chromatography. Further chromatography steps can follow, such as ion exchange and/or HA chromatography, anion or cation exchange, size exclusion chromatography, and ammonium sulphate precipitation. Various virus removal steps may also be employed (e.g., nanofiltration using, e.g., a DV-20 filter). Following these various steps, a purified (for example a monoclonal) preparation comprising at least 75 mg/ml or greater, or 100 mg/ml or greater, of the antigen binding protein is provided. Such preparations are substantially free of aggregated forms of antigen binding proteins.

Bacterial systems may be used for the expression of antigen binding fragments. Such fragments can be localized intracellularly within the periplasm, or secreted extracellularly. Insoluble proteins can be extracted and refolded to form active proteins according to methods known to those skilled in the art, see Sanchez, et al. (1999) *J. Biotechnol.* 72: 13-20; and Cupit, et al. (1999) *Lett Appl Microbiol* 29: 273-277.

Deamidation is a chemical reaction in which an amide functional group is removed. In biochemistry, the reaction is important in the degradation of proteins because it damages the amide-containing side chains of the amino acids asparagine and glutamine. Deamidation reactions are believed to be one of the factors that can limit the useful lifetime of a protein, they are also one of the most common post-translational modifications occurring during the manufacture of therapeutic proteins. For example, a reduction or loss of in vitro or in vivo biological activity has been reported for recombinant human DNAse and recombinant soluble CD4, whereas other recombinant proteins appear to be unaffected. The ability of the antigen binding proteins described herein to bind to HER3 seems to be unaffected under stress conditions that induce deamidation. Thus, the biological activity of the antigen binding proteins described herein, and their useful lifetime is unlikely to be affected by deamidation.

Pharmaceutical Compositions

Purified preparations of an antigen binding protein as described herein may be incorporated into pharmaceutical compositions for use in the treatment of the human diseases, disorders and conditions described herein. The terms "diseases", "disorders", and "conditions" are herein used interchangeably. The pharmaceutical composition can be used in the treatment of diseases where the HER3 receptor contributes to the disease, or where neutralizing the activity of the HER3 receptor will be beneficial. The pharmaceutical composition comprising a therapeutically effective amount of the antigen binding protein described herein can be used in the treatment of diseases responsive to neutralization of the HER3 receptor.

The pharmaceutical preparation may comprise an antigen binding protein in combination with a pharmaceutically acceptable carrier. The antigen binding protein may be administered alone, or as part of a pharmaceutical composition.

Typically, such compositions comprise a pharmaceutically acceptable carrier as known and called for by acceptable pharmaceutical practice. See, e.g., REMINGTONS PHARMACEUTICAL SCIENCES, 16th edition (1980) Mack Publishing Co. Examples of such carriers include sterilised carriers, such as saline, Ringers solution, or dextrose solution, optionally buffered with suitable buffers to a pH within a range of 5 to 8.

Pharmaceutical compositions may be administered by injection or continuous infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an IgG1 isotype, a chelator of copper, such as citrate (e.g., sodium citrate) or EDTA or histidine, may be added to the pharmaceutical composition to reduce the degree of copper-mediated degradation of antibodies of this isotype. See EP0612251. Pharmaceutical compositions may also comprise a solubilizer, such as arginine base, a detergent/anti-aggregation agent such as polysorbate 80, and an inert gas such as nitrogen to replace vial headspace oxygen.

Effective doses and treatment regimes for administering the antigen binding protein are generally determined empirically and may be dependent on factors, such as the age, weight, and health status of the patient and disease or disorder to be treated. Such factors are within the purview of the attending physician. Guidance in selecting appropriate doses may be found in, e.g., Smith, et al. (1977) ANTIBODIES1N HUMAN DIAGNOSIS AND THERAPY, Raven Press, New York.

The dosage of antigen binding protein administered to a subject is generally between 1 μg/kg to 150 mg/kg, between 0.1 mg/kg and 100 mg/kg, between 0.5 mg/kg and 50 mg/kg, between 1 and 25 mg/kg or between 1 and 10 mg/kg of the subject's body weight. For example, the dose may be 10 mg/kg, 30 mg/kg, or 60 mg/kg. The dose may also be from 10 mg/kg to 110 mg/mg 15 mg/kg to 25 mg/kg or 15 mg/kg to 100 mg/kg. The antigen binding protein may be administered, for example, parenterally, subcutaneously, intravenously, or intramuscularly. The dose may be any discrete subrange with these dosage ranges.

If desired, the effective daily dose of a therapeutic composition may be administered as two, three, four, five, six or more sub-doses administered separately at appropriate intervals throughout the day, optionally, in unit dosage forms.

The administration of a dose may be by slow continuous infusion over a period of from 2 to 24 hours, such as of from 2 to 12 hours, or from 2 to 6 hours. Such an administration may result in reduced toxic side effects.

The administration of a dose may be repeated one or more times as necessary, for example, three times daily, once every day, once every 2 days, once a week, once a fortnight, once a month, once every 3 months, once every 6 months, or once every 12 months. The antigen binding proteins may be administered by maintenance therapy, for example once a week for a period of 6 months or more. The antigen binding proteins may be administered by intermittent therapy, for example, for a period of 3 to 6 months and then no dose for 3 to 6 months, followed by administration of antigen binding proteins again for 3 to 6 months, and so on, in a cycle.

For example, the dose may be administered subcutaneously, once every 14 or 28 days, in the form of multiple sub-doses on each day of administration.

The dosage can be determined or adjusted by measuring the amount of circulating anti-HER3 antigen binding proteins after administration in a biological sample by using anti-idiotypic antibodies that target the anti-HER3 antigen binding proteins. The antigen binding protein can be administered in an amount and for a duration effective to down-regulate HER3 activity in the subject.

The antigen binding protein may be administered to the subject in such a way as to target therapy to a particular site. For example, the antigen binding protein may be injected locally into muscle, for example skeletal muscle.

The antigen binding protein may be used in combination with one or more other therapeutically active agents, such as antibodies or small molecule inhibitors of other receptor tyrosine kinases such as, but not limited to, other HER family members, c-Met, IGF-1R, receptor ligands such as Vascular Endothelial Growth Factor (VEGF), cytotoxic agents such as doxorubicin, cis-platin or carboplatin, cytokines or antineoplastic agents. Examples of the latter include, but are not limited to, antibodies or immunomodulatory proteins, small molecule inhibitors or chemotherapeutic agents from the group of mitotic inhibitors, kinase inhibitors, alkylating agents, anti metabolites, intercalating antibiotics, growth factor inhibitors, cell cycle inhibitors, enzymes, topoisomerase inhibitors, histone deacetylase inhibitors, anti-survival agents, biological response modifiers, anti-hormones, eg anti androgens and anti angiogenesis agents. When the anti neoplastic agent is radiation, treatment can be achieved either with an internal (brachytherapy BT) or external (external beam radiation therapy: EBRT) source. The antibodies of the disclosure may be conjugated, by any type of mechanism including chemical bonds, hydrophobic interactions, electrostatic interactions and the like, to chemotherapeutic agents or radioisotopes as described herein or in WO2007/077028 the entire disclosure of which is incorporated herein by reference.

The antibodies of the disclosure may be used combination with other therapeutically active agents in the treatment of the diseases described herein. Such combinations can be used in the treatment of diseases where the HER3 receptor contributes to the disease, or where neutralizing the HER3 receptor will be beneficial.

When the antigen binding protein is used in combination with other therapeutically active agents, the individual components may be administered either together or separately, sequentially or simultaneously, in separate or combined pharmaceutical formulations, by any convenient route. If administered separately or sequentially, the antigen binding protein and the therapeutically active agent(s) can be administered in any order.

The combinations referred to above may be presented for use in the form of a single pharmaceutical formulation comprising a combination as defined above, optionally together with a pharmaceutically acceptable carrier or excipient. Such pharmaceutically acceptable carriers or excipients are well known in the art and include those disclosed in WO2007//077028 the entire disclosure of which is incorporated herein by reference. Additionally, the entire disclosure of any other references identified herein is incorporated by reference into the present disclosure.

When combined in the same formulation, it will be appreciated that the components must be stable and compatible with each other and the other components of the formulation and may be formulated for administration. When formulated separately, they may be provided in any convenient formulation, for example, in such a manner as known for antigen binding proteins in the art.

When in combination with a second therapeutic agent active against the same disease, the dose of each component may differ from that when the antigen binding protein is used alone. Appropriate doses will be readily appreciated by those skilled in the art.

The antigen binding protein and the therapeutically active agent(s) can act synergistically. In other words, administering the antigen binding protein and the therapeutically active agent(s) in combination has a greater effect on the disease, disorder, or condition described herein than the sum of the effect of each alone.

As used herein, the term "effective amount" means that amount of a drug or pharmaceutical agent that will elicit the biological or medical response of a tissue, system, animal or human that is being sought, for instance, by a researcher or clinician. A pharmaceutical agent may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. Tumors may be hematopoietic tumor, for example, tumors of blood cells or the like, meaning liquid tumors. Specific examples of clinical conditions based on such a tumor include leukemia such as chronic myelocytic leukemia or acute myelocytic leukemia; myeloma such as multiple myeloma; lymphoma and the like.

By the term "treating" and grammatical variations thereof as used herein, is meant therapeutic therapy. In reference to a particular condition, treating means: (1) to ameliorate the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, (4) to slow the progression of the condition or one or more of the biological manifestations of the condition or (5) to prevent the onset of one or more of the biological manifistations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Prophylactic therapy is appropriate, for example, when a subject is considered at high risk for developing cancer, such as when a subject has a strong family history of cancer or when a subject has been exposed to a carcinogen.

In the methods of the disclosure an antigen binding protein can be "co-administered" which means either the simultaneous administration or any manner of separate sequential administration of an antigen binding protein, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present disclosure. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present disclsoure include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the antigen binding proteins of the disclosure are chemotherapeutic agents. Examples of such chemotherapeutic agents and other categories of therapeutic agents that may be combined with the antigen binding proteins of the disclosure in compositions, or by co-administration in a method of treatment, are described below.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL™. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE™. Docetaxel is indicated for the treatment of breast cancer. Docetaxel is a semisynthetic derivative of paclitaxel q. v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN™ as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN™ as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE™), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL™ as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATINT™ as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN™. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN™. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN™ tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN™ TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU™. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome™. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN™. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOMET™ or as an injectable as CERUBIDINE™. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX™ or ADRIAMYCIN RDF™. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE™. Bleomycin is indicated as a palliative treatment, as a single agent or in combination with other agents, of squamous cell carcinoma, lymphomas, and testicular carcinomas Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID™ and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON™ and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U™ and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOLT™. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID™. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR™. Gemcitabine exhibits cell phase specificity at 5-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino [1,2-b]quinoline-3,14(4H,12H)-dione hydrochloride, is commercially available as the injectable solution CAMPTOSART™.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes.

Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN™. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

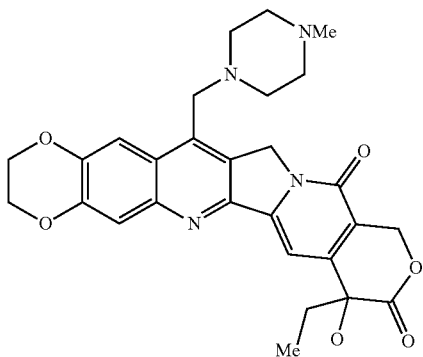

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases include MAP kinase cascade blockers which also include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present disclosure are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

Antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin™ erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also be useful in the present invention Inhibitors of angiogenesis related VEGFR and TIE2 are discussed above in regard to signal transduction inhibitors (both receptors are receptor tyrosine kinases). Angiogenesis is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present disclosure. For example, anti-VEGF antibodies, which do not recognize VEGFR (the receptor tyrosine kinase), but bind to the ligand; small molecule inhibitors of integrin (alpha-beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the antigen binding proteins of the disclosure. There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al (2000), Cancer Res. 60: 3569-3576; and Chen Y, Hu D, Eling D J, Robbins J, and Kipps TJ. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat. Acad. Sci. U.S.A.* 97(18): 10014-10019 (2000)), and are included as cell cycle signaling inhibitors. Histone deacetylase (HDAC) inhibitors are implicated in the transcriptional activation of p21WAF1/CIP1 (Vigushin et al., *Anticancer Drugs*, 13(1): 1-13 (January 2002)), and are suitable cell cycle signaling inhibitors for use herein.

Examples of such HDAC inhibitors include:

1. Vorinostat, including pharmaceutically acceptable salts thereof. Marks et al., *Nature Biotechnology* 25, 84 to 90 (2007); Stenger, *Community Oncology* 4, 384-386 (2007). Vorinostat has the following chemical structure and name:

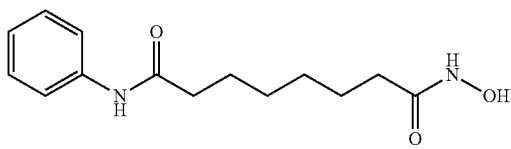 [SMILES: O=C(CCCCCCC(=O)Nc1ccccc1)NO]

N-hydroxy-N-phenyl-octanediamide.

2. Romidepsin, including pharmaceutically acceptable salts thereof. Vinodhkumar et al., *Biomedicine & Pharmacotherapy* 62 (2008) 85-93. Romidepsin, has the following chemical structure and name:

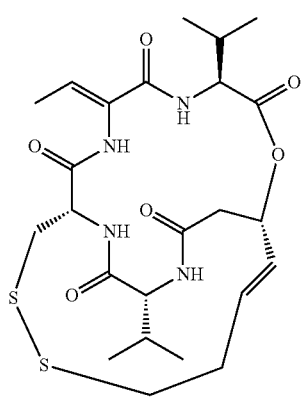 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone.

3. Panobinostat, including pharmaceutically acceptable salts thereof. *Drugs of the Future* 32(4): 315-322 (2007).
Panobinostat, has the following chemical structure and name:

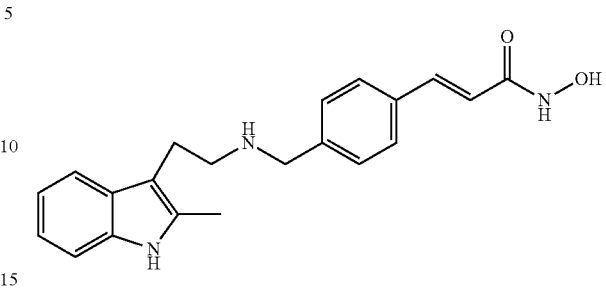

(2E)-N-hydroxy-3-[4-({[2-(2-methyl-1H-indol-3-yl)ethyl]amino}methyl)phenyl]acrylamide.

4. Valproic acid, including pharmaceutically acceptable salts thereof. Gottlicher, et al., EMBO J. 20(24): 6969-6978 (2001).
Valproic acid, has the following chemical structure and name:

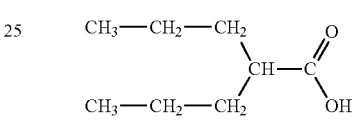

2-propylpentanoic acid.

5. Mocetinostat (MGCD0103), including pharmaceutically acceptable salts thereof. Balasubramanian et al., Cancer Letters 280: 211-221 (2009).
Mocetinostat, has the following chemical structure and name:

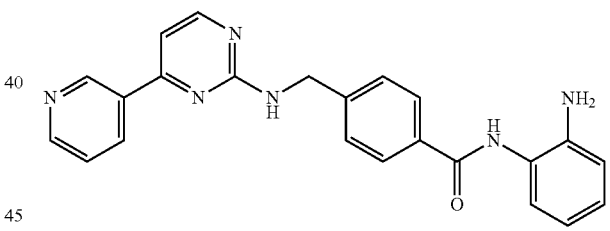

N-(2-Aminophenyl)-4-[[(4-pyridin-3-ylpyrimidin-2-yl)amino]methyl]benzamide.

Further examples of such HDAC inhibitors are included in Bertrand European Journal of Medicinal Chemistry 45, (2010) 2095-2116, particularly the compounds of Table 3 therein as indicated below.

Hydroxamic acids

1

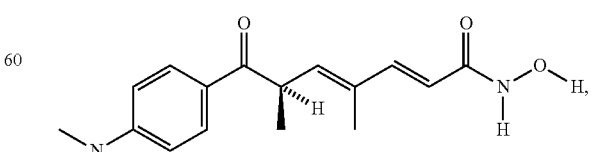

Trichostatine A (TSA)

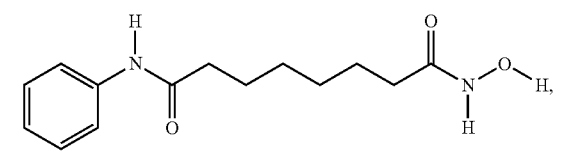
SAHA
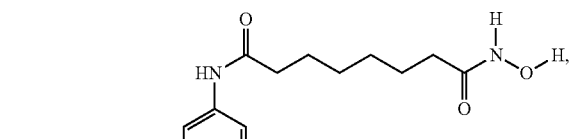
Tubacin
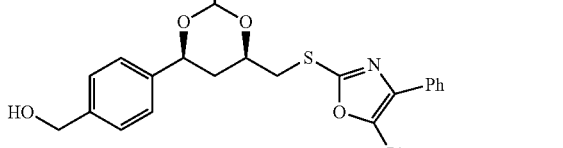
LAQ824
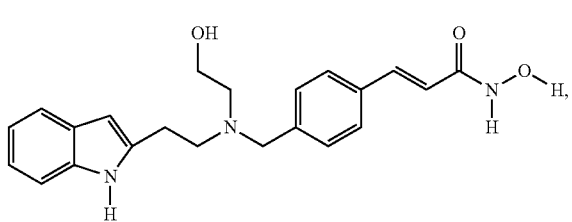
Sulfonamide
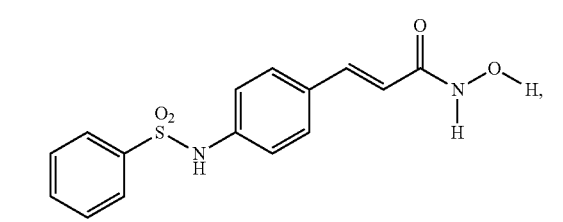
Scriptaid
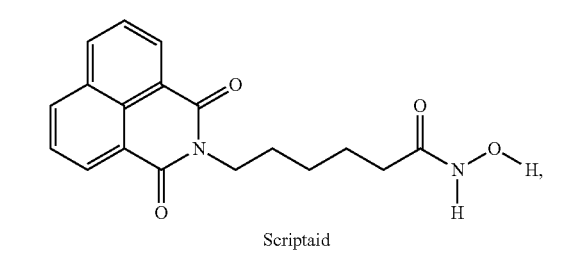
CBHA
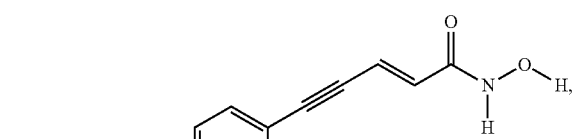
Oxamflatin
Cyclic tetrapeptides
FK228
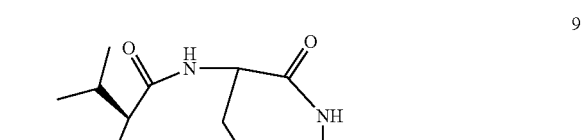
Apicidin
Short chain carboxylic acids
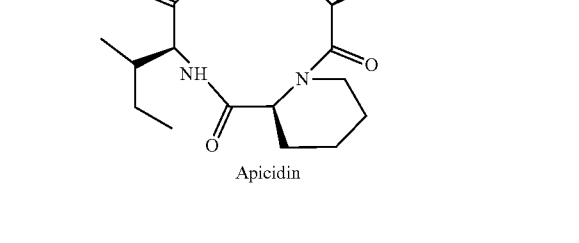
Valproic acid

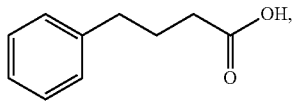

Phenylbutyric acid

Benzamides

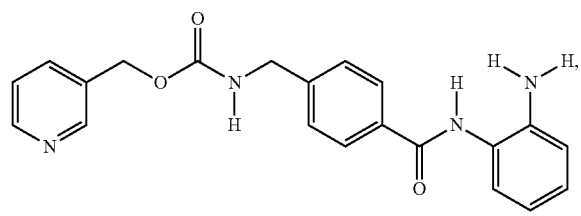

MS-275

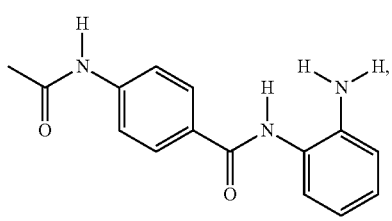

Cl-994

Keto derivatives

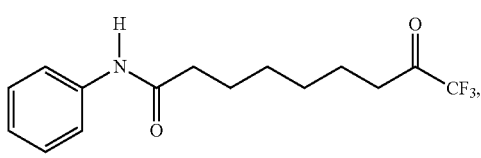

Trifluorométhyl cétone

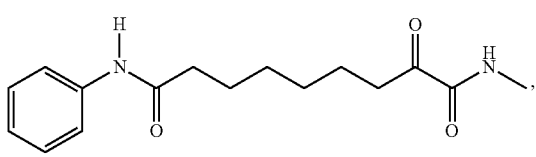

alpha-cétoamide

The cancer treatment methods of the disclosure also includes the co-administration of an antigen binding protein of the disclosure and/or a pharmaceutically acceptable salt, hydrate, solvate or pro-drug thereof and at least one antineoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors. The antigen binding proteins of the disclosure may be used in combination with a MEK inhibitor such as, for example, N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, including the dimethyl sulfoxide solvate, thereof, which is disclosed and claimed in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, can be prepared as described in United States Patent Publication No. US 2006/0014768, Published Jan. 19, 2006, the entire disclosure of which is hereby incorporated by reference. The antigen binding proteins of the disclosure may be used in combination with a B-Raf inhibitor such as, for example, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682. The antigen binding proteins of the disclosure may be used in combination with an Akt inhibitor such as, for example, N-{(1S)-2-amino-1-[(3,4-difluorophenyl)methyl]ethyl}-5-chloro-4-(4-chloro-1-methyl-1H-pyrazol-5-yl)-2-furancarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3,4-difluorophenyl)methyl]ethyl}-5-chloro-4-(4-chloro-1-methyl-1H-pyrazol-5-yl)-2-furancarboxamide can be prepared as described in International Application No. PCT/US2008/053269. The antigen binding proteins of the disclosure may also be used in combination with an Akt inhibitor such as, for example, N-{(1S)-2-amino-1-[(3-fluorophenyl)methyl]ethyl}-5-chloro-4-(4-chloro-1-methyl-1H-pyrazol-5-yl)-2-thiophenecarboxamide or a pharmaceutically acceptable salt thereof, which is disclosed and claimed in International Application No. PCT/US2008/053269, having an International filing date of Feb. 7, 2008; International Publication Number WO 2008/098104 and an International Publication date of Aug. 14, 2008, the entire disclosure of which is hereby incorporated by reference. N-{(1S)-2-amino-1-[(3-fluorophenyl)methyl]ethyl}-5-chloro-4-(4-chloro-1-methyl-1H-pyrazol-5-yl)-2-thiophenecarboxamide is the compound of example 96 and can be prepared as described in International Application No. PCT/US2008/053269. N-{(1S)-2-amino-1-[(3-fluorophenyl)methyl]ethyl}-5-chloro-4-(4-chloro-1-methyl-1H-pyrazol-5-yl)-2-thiophenecarboxamide is in the form of a hydrochloride salt. The salt form can be prepared by one of skill in the art from the description in International Application No. PCT/US2010/022323, having an International filing date of Jan. 28, 2010.

Pazopanib is another composition that may be co-administered with an antigen binding protein of the disclosure. Pazopanib, which commercially available as VOTRIENT™, is a tyrosine kinase inhibitor (TKI). Pazopanib is presented as the hydrochloride salt, with the chemical name 5-[[4-[(2,3-dimethyl-2H-indazol-6-yl)methylamino]-2-pyrimidinyl]amino]-2-methylbenzenesulfonamide monohydrochloride. Pazoponib is approved for treatment of patients with advanced renal cell carcinoma.

Rituximab is another composition that may be co-administered with an antigen binding protein of the disclosure. Rituximab is a chimeric monoclonal antibody which is sold as RITUXAN™ and MABTHERA™. Rituximab binds to $CD_2O$ on B cells and causes cell apopotosis. Rituximab is administered intravenously and is approved for treatment of rheumatoid arthritis and B-cell non-Hodgkin's lymphoma.

Ofatumumab is another composition that may be co-administered with an antigen binding protein of the disclosure. Ofatumumab is a fully human monoclonal antibody which is sold as ARZERRA™. Ofatumumab binds to $CD_2O$ on B cells and is used to treat chronic lymphocytic leukemia (CLL; a type of cancer of the white blood cells) in adults who are refractory to treatment with fludarabine (Fludara) and alemtuzumab (Campath).

mTOR inhibitors may be co-administered with an antigen binding protein of the disclosure. mTOR inhibitors include but are not limited to rapamycin and rapalogs, RAD001 or everolimus (Afinitor), CCl-779 or temsirolimus, AP23573, AZD8055, WYE-354, WYE-600, WYE-687 and Pp121.

Bexarotene is another composition that may be co-administered with an antigen binding protein of the disclosure. Bexarotene is sold as Targretin™ and is a member of a subclass of retinoids that selectively activate retinoid X receptors (RXRs). These retinoid receptors have biologic activity distinct from that of retinoic acid receptors (RARs). The chemical name is 4-[1-(5,6,7,8-tetrahydro-3,5,5,8,8-pentamethyl-2-naphthalenyl)ethenyl] benzoic acid. Bexarotene is used to treat cutaneous T-cell lymphoma (CTCL, a type of skin cancer) in people whose disease could not be treated successfully with at least one other medication.

Sorafenib is another composition that may be co-administered with an antigen binding protein of the disclosure. Sorafenib is marketed as Nexavar™ and is in a class of medications called multikinase inhibitors. Its chemical name is 4-[4-[[4-chloro-3-(trifluoromethyl)phenyl]carbamoylamino] phenoxy]-N-methyl-pyridine-2-carboxamide. Sorafenib is used to treat advanced renal cell carcinoma (a type of cancer that begins in the kidneys). Sorafenib is also used to treat unresectable hepatocellular carcinoma (a type of liver cancer that cannot be treated with surgery).

The disclosure provides methods of treating cancer. The cancer treated in the disclosed methods may be selected from: brain (gliomas), glioblastomas, astrocytomas, glioblastoma multiforme, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Megakaryoblastic leukemia, multiple myeloma, acute megakaryocytic leukemia, promyelocytic leukemia, and Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

The pre-cancerous condition in the methods of the disclosure may be cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

The pharmaceutical composition may comprise a kit of parts of the antigen binding protein together with other medicaments, optionally with instructions for use. For convenience, the kit may comprise the reagents in predetermined amounts with instructions for use.

The terms "individual", "subject" and "patient" are used herein interchangeably. The subject is typically a human. The subject may also be a mammal, such as a mouse, rat, or primate (e.g., a marmoset or monkey). The subject can be a non-human animal. The antigen binding proteins also have veterinary use. The subject to be treated may be a farm animal, for example, a cow or bull, sheep, pig, ox, goat or horse, or may be a domestic animal such as a dog or cat. The animal may be any age, or a mature adult animal. Where the subject is a laboratory animal, such as a mouse, rat or primate, the animal can be treated to induce a disease or condition associated with breast, ovarian, prostate or bladder cancer.

Treatment can be therapeutic, prophylactic or preventative. The subject will be one who is in need thereof. Those in need of treatment may include individuals already suffering from a particular medical disease, in addition to those who may develop the disease in the future.

Thus, the antigen binding protein described herein can be used for prophylactic or preventative treatment. In this case, the antigen binding protein described herein is administered to an individual in order to prevent or delay the onset of one or more aspects or symptoms of the disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The antigen binding protein described herein may also be used in methods of therapy. The term "therapy", as used herein, encompasses alleviation, reduction, or prevention of at least one aspect or symptom of a disease. For example, the antigen binding protein described herein may be used to ameliorate or reduce one or more aspects or symptoms of a disease described herein.

The antigen binding protein described herein is used in an effective amount for therapeutic, prophylactic or preventative treatment. A therapeutically effective amount of the antigen binding protein described herein is an amount effective to ameliorate or reduce one or more aspects or symptoms of the disease. The antigen binding protein described herein may also be used to treat, prevent, or cure the disease described herein.

The antigen binding protein described herein can have a generally beneficial effect on the subject's health, for example it can increase the subject's expected longevity.

The antigen binding protein described herein need not affect a complete cure, or eradicate every symptom or manifestation of the disease to constitute a viable therapeutic treatment. As is recognised in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

The disorder, disease, or condition includes breast cancer, ovarian cancer, prostate cancer, and bladder cancer. The disease may be associated with high levels of HER3. The antigen binding proteins described herein can be used to modulate the level of HER3 and/or the activity of HER3.

Diagnostic Methods of Use

The antigen binding proteins described herein may be used to detect HER3 in a biological sample in vitro or in vivo for diagnostic purposes. For example, the anti-HER3 antigen binding proteins, such as the murine or humanized 15D5 monoclonal antibodies, can be used to detect HER3 in cultured cells, in a tissue or in serum. The tissue may have been first removed (for example, a biopsy) from a human or animal body. Conventional immunoassays may be employed, including ELISA, Western blot, immunohistochemistry, or immunoprecipitation.

By correlating the presence or level of HER3 with a disease, one of skill in the art can diagnose the associated disease. Furthermore, detection of increased levels of HER3 in a subject may be indicative of a patient population that would be responsive to treatment with the antigen binding proteins described herein. Detection of a reduction in HER3 level, function or signal transducing capabilities may be indicative of the biological effect of decreased tumor size in subjects treated with the antigen binding proteins described herein.

The antigen binding proteins may be provided in a diagnostic kit comprising one or more antigen binding proteins, a detectable label, and instructions for use of the kit. For convenience, the kit may comprise the reagents in predetermined amounts with instructions for use.

Gene Therapy

Nucleic acid molecules encoding the antigen binding proteins described herein can be administered to a subject in need thereof. The nucleic acid molecule may express the CDRs in an appropriate scaffold or domain, the variable domain, or the full length antibody. The nucleic acid molecule may be comprised in a vector which allows for expression in a human or animal cell. The nucleic acid molecule or vector may be formulated for administration with a pharmaceutically acceptable excipient and/or one or more therapeutically active agents as discussed above.

Another aspect of the disclosure is an antigen binding protein comprising a heavy chain sequence having amino acid residues 20 to 466 of the amino acid sequence shown in SEQ ID NO: 100 and a light chain sequence having amino acid residues 20 to 238 of the amino acid sequence shown in SEQ ID NO: 104.

The disclosure also provides an antigen binding protein as described herein comprising fucosylated glycans.

The disclosure also provides an antigen binding protein as described herein wherein the fucosylated glycans are selected from the group consisting of G0, G2, G0F, G2F, G1, Man5, G1F and G1F'.

The disclosure also provides an antigen binding protein as described herein comprising non-fucosylated glycans.

The disclosure also provides an antigen binding protein as described herein wherein the non-fucosylated glycans are selected from the group consisting of G0, G2, G1 and Man5.

Another aspect of the disclosure is an antigen binding protein comprising a heavy chain sequence having amino acid residues 20 to 466 of the amino acid sequence shown in SEQ ID NO: 102 and a light chain sequence having amino acid residues 20 to 238 of the amino acid sequence shown in SEQ ID NO: 104.

Another aspect of the disclosure is an isolated nucleic acid encoding amino acid residues 20 to 466 of the amino acid sequence shown in SEQ ID NO: 100.

The disclosure also provides an isolated nucleic comprising the nucleic acid sequence shown in SEQ ID NO: 101.

Another aspect of the disclosure is an isolated nucleic acid encoding amino acid residues 20 to 238 of the amino acid sequence shown in SEQ ID NO: 104.

The disclosure also provides an isolated nucleic acid comprising the nucleic acid sequence shown in SEQ ID NO: 105.

Another aspect of the disclosure is an isolated nucleic acid encoding amino acid residues 20 to 466 of the amino acid sequence shown in SEQ ID NO: 102.

The disclosure also provides an isolated nucleic acid comprising the nucleic acid sequence shown in SEQ ID NO: 103.

The disclosure also provides a recombinant host cell as described herein wherein the FUT8 gene encoding alpha-1,6-fucosyltransferase is present.

The disclosure also provides a recombinant host cell as described herein that is a CHOK1 cell. The term CHOK1 includes a parental CHOK1 cell and cells of any cell lines derived from this parental cell line (e.g., by genetic engineering, clonal selection etc.).

The disclosure also provides a recombinant host cell as described herein wherein the FUT8 gene encoding alpha-1,6-fucosyltransferase has been inactivated.

The disclosure also provides a method for the production of an antigen binding protein comprising the steps of: a) culturing a recombinant host cell comprising an expression vector comprising an isolated nucleic acid encoding an antibody heavy chain as described herein and comprising an isolated nucleic acid encoding an antibody light chain as described herein, wherein the FUT8 gene encoding alpha-1,6-fucosyltransferase is active in the recombinant host cell; and b) recovering the antigen binding protein; whereby the antigen binding protein is produced.

The disclosure also provides a method for the production of an antigen binding protein comprising the steps of: a) culturing a recombinant host cell comprising an expression vector comprising an isolated nucleic acid encoding an antibody heavy chain as described herein and comprising an isolated nucleic acid encoding an antibody light chain as described herein, wherein the FUT8 gene encoding alpha-1,6-fucosyltransferase has been inactivated in the recombinant host cell; and b) recovering the antigen binding protein; whereby the antigen binding protein is produced.

The disclosure also provides an antigen binding protein as described herein for use in treatment of a condition selected from the group consisting of breast cancer, ovarian cancer, prostate cancer, bladder cancer, pancreatic cancer, skin cancer, gastric cancer and melanoma.

EXAMPLES

Example 1

1. Summary

The murine 1D9 antibody (M5.1D9.1F5), the murine 15D5 antibody (M5.15D5.2A1.1H10), the chimeric 1D9 antibody and the chimeric 15D5 antibody, were subjected to BIACORE™ analysis for binding to the full-length human HER3 extracellular domain (ECD) or sub-domains thereof.

2. Introduction

The objective of this example was to determine the affinities of the murine 1D9 antibody, the murine 15D5 antibody, the chimeric 1D9 antibody and the chimeric 15D5 antibody.

3. Methods

3.1. Experimental Protocol(s)

Analyses were performed on a BIACORE™ 2000 instrument (SN#33-0901-2420 GE Healthcare) which was tested with a system check and passed prior to preparation of each new chip. All runs were done at 25° C. using HBS-EP (GE Healthcare BR-1006-69/5 mM HEPES, 150 mM NaCl, 3.4 mM EDTA, 0.005% surfactant P20, pH 7.4) as run buffer. Mouse monoclonal antibodies were analysed using rabbit anti-mouse (RAM) IgG (GE Healthcare BR-1008-38) covalently coupled to a BIACORE™ CM5 chip (GE HEalthcare BR-1000-14) by primary amine chemistry (NHS/EDC activated) (GE Healthcare amine coupling kit BR-1000-50). Chimeric and humanized competitor monoclonal antibodies were analyzed using anti-human, Fc specific monoclonal (GE Healthcare BR-1008-39) similarly coupled. Each chip was also prepared with a reference surface to which no capture reagent antibody is coupled. Sensorgrams for cycles run with differing analyte concentrations are acquired for kinetic analysis. A cycle consists of capturing the monoclonal on the surface, a short stabilization period with flowing run buffer followed by binding of a defined concentration of analyte (ECD or sub-domain protein). Injection of analyte for surface binding (3-4 minutes) yields the association part of curve. This is followed by buffer only flow (3-4 minutes) which allows recording of dissociation data. The cycle is then finished and injection of capture kit supplied regeneration solution (a mild acidic solution for RAM and 3M $MgCl_2$ for anti-human captures) removes the captured antibody/analyte, but does not significantly affect the capability of the capture antibody to perform another capture of monoclonal for subsequent cycles.

The general method for affinity analysis is as follows. First, chips were prepared and tested for resonance units (RU) captured for several monoclonal antibody concentrations. Kinetic cycles were then run in which monoclonal antibody was captured to a level of approximately 100RU, analyte protein was allowed to bind then dissociate and the surface was regenerated to remove all but covalently coupled protein. RAM chips were regenerated with capture kit supplied 100 mM glycine pH1.7 and anti-human chips with capture kit supplied 3M $MgCl_2$. A series of these cycles are run at 6 different concentrations of analyte protein (usually 256 nM, 128 nM, 64 nM, 32 nM, 16 nM and 8 nM). Several buffer cycles were run prior to analyte protein to ensure cycle consistency and in some experiments a buffer cycle is used a "double reference[.]" Analytes used were human full length HER3 extra cellular domain (ECD), separate sub-domains of the extracellular portion of human HER3 (D1, D2, D3, D4), or combination HER3 domain proteins (D1-2 and D2-3). All were human HER3 ECD analytes were expressed and prepared using standard techniques.

During kinetic experiment cycles a mock coupled surface provides a reference which is subtracted from the specific antibody-analyte RU data in run to eliminate buffer artifacts. Double referencing was performed for some runs by subtracting a buffer only cycle from analyte containing cycle data for each concentration in the set of kinetic curves. Resulting curve data are globally fitted to the 1:1 Langmuir model using BIAEVALUATION™ Software (v.3.2).

3.2. Drugs and Materials

A partial list of reagents used in this example follows:

Murine 1D9 aantibody (4.77 mg/ml)

Murine 15D5 antibody (4.23 mg/ml)

Chimeric 1D9 antibody

Chimera 15D5 antibody

All antibodies were formulated and prepared in phosphate buffered saline, pH 7.0.

4. Results

Sensorgrams were generated for each interaction. These were used to evaluate kinetics using BIAEVALUATION™ software. The run and kinetic parameters, including overall KD are presented in Table 5 and Table 6 below.

TABLE 5

Affinities of the murine 1D9 antibody (m1D9) and the chimeric 1D9 antibody (Ch1D9).

| Antibody | Analyte | ka (1/M) | kd (1/Ms) | KD (nM) |
|---|---|---|---|---|
| m1D9 | ECD | $3.55 \times 10^5$ | $2.90 \times 10^{-4}$ | 0.82 |
| m1D9 | Domain 3 | $2.54 \times 10^6$ | $9.70 \times 10^{-4}$ | 0.38 |
| m1D9 | Domain 2-3 | $8.93 \times 10^5$ | $4.21 \times 10^{-4}$ | 0.47 |
| ch1D9 | ECD | $7.40 \times 10^5$ | $8.11 \times 10^{-4}$ | 1.10 |
| ch1D9 | Domain 3 | $4.58 \times 10^6$ | $9.06 \times 10^{-4}$ | 0.20 |

ECD = Full-length human HER3 extracellular domain

Domain # = Human HER3 extracellular domain(s)

TABLE 6

Affinities of the murine 15D5 antibody (m15D5) and the chimeric 15D5 antibody (Ch15D5).

| Antibody | Analyte | ka (1/M) | kd (1/Ms) | KD (nM) |
|---|---|---|---|---|
| m15D5 | ECD | $4.12 \times 10^4$E+04 | $9.57 \times 10^{-5}$ | 2.32 |
| m15D5 | Domain 2 | $1.76 \times 10^6$ | $1.30 \times 10^{-4}$ | 0.07 |
| m15D5 | Domain 1-2 | $3.45 \times 10^5$ | $5.85 \times 10^{-5}$ | 0.17 |
| m15D5 | Domain 2-3 | $1.40 \times 10^6$ | $8.16 \times 10^{-5}$ | 0.06 |
| ch15D5 | ECD | $6.79 \times 10^4$ | $5.89 \times 10^{-5}$ | 0.87 |
| ch15D5 | Domain 2 | $3.82 \times 10^6$ | $6.78 \times 10^{-5}$ | 0.02 |

ECD = Full-length human HER3 extracellular domain

Domain # = Human HER3 extracellular domain(s)

5. Discussion

The monoclonal murine 1D9 antibody and murine 15D5 antibody were generated against the human HER3 extracellular domain. The murine 1D9 antibody antibody binds to the full-length, human HER3 ECD and sub-domain 3 of the human HER3 ECD. The murine 15D5 antibody binds to the full-length, human HER3 ECD and sub-domain 2 of the human HER3 ECD.

Nanomolar and subnanomolar affinities of all antibodies were determined for interaction with the full-length, human HER3 ECD and select human HER3 ECD sub-domains. Similar overall affinities (KD) are seen for both the murine 1D9 antibody and the murine 15D5 antibodies with the murine 1D9 antibody antibody having a faster on (ka) and off rate (kd). The murine 15D5 antibody has been demonstrated to bind to sub-domains 2, 1-2 and 2-3 of the human HER3 ECD, but not to sub-domains 1, 3 or 4 by immunoassay and competitive immunocytochemisry. BIACORE™ analysis shows an augmented affinity for these portions of the HER3 ECD (i.e., sub-domains 2, 1-2 and 2-3 of the human HER3 ECD) relative to the full-length, human HER3 ECD (sub-domains 1-4). This effect is seen with all three sub-domain 2 containing human HER3 ECD protein constructs (D2, D1-2 and D2-3) and, without wishing to be bound by theory, it is believed this may be due to a greater accessibility of the epitope within domain 2 in the smaller sub-domain proteins. Furthermore, without wishing to be bound by theory, it is believed structural considerations make it likely the murine 15D5 antibody has greater affinity for an open conformation of the HER3 receptor. This open conformation has been shown to be the state when the receptor is engaging heregulin ligand. The chimeric 15D5 antibody and the chimeric 1D9 antibody retain similar affinity to the parent murine 1D9 antibody and murine 15D5 antibodies.

Example 2

X-ray crystallographic analysis was coupled with in silico modelling to predict the binding interfaces for the murine 1D9 antibody and its variants. These analyses also provided mechanistic insight into the functional neutralization observed with the murine 1D9 antibody, and facilitated rational antibody maturation. A high resolution (3.0 Å) structure of a complex comprising a murine 1D9 antibody derived Fab bound to domain III of the human HER3 ECD was established. To do this, domain III of the human HER3 ECD and the murine 1D9 antibody were expressed in CHO cells and purified by affinity chromatography as well as size exclusion chromatography. The Fab fragment of the murine 1D9 antibody was generated by papain cleavage using standard methods. The complex comprising a murine 1D9 antibody derived Fab bound to domain III of the human HER3 ECD was generated by mixing 1:1.2 molar ratio of the murine 1D9 antibody derived Fab with domain III of the human HER3 ECD. This protein mixture was then concentrated and crystallized using the hanging drop vapor diffusion method. X-ray diffraction data were collected at the Advanced Photon Source in the Argonne National Laboratory. Diffraction data were indexed and scaled using HKL2000 software (HKL Research, Inc.). The structure was determined by molecular replacement in the program X-PLOR. The initial molecular replacement solution produced was then subjected to multiple rounds of molecular dynamics refinement in CNS and rebuilding with the program WINCOOT. An atomic coordinate file for the complex comprising the murine 1D9 derived Fab bound to domain III of the human HER3 ECD was then produced and the resulting structure was analyzed.

It was determined from this analysis that the epitope on domain III of the human HER3 ECD domain III comprises Ile346, Asn350, Gly351, Asp352, Pro353, Trp354, His355, Lys356, Ile357, Pro358 and Ala359 of SEQ ID NO: 66 which can be found in a fragment comprising amino acid residues 20 to 643 of SEQ ID NO: 21. See Table 7. The contacts between interacting residues are described in Table 7 and FIG. 55.

TABLE 7

Amino acid contacts between domain III of the human HER3 ECD and the murine 1D9 light chain variable region and murine 1D9 heavy chain variable region.

EPITOPE
Amino acid contacts in domain III of the human HER3 ECD (SEQ ID NO: 66; co-crystallized fragment) (paratope residues contacted in brackets)

Ile346 (VL CDR3 His98 (93))
Asn350 [VL Framework1 Asp1 (1); VL CDR3 Val99 (94); VL CDR3 Pro100 (95); VH CDR2 His59 (58)]
Gly351 [VL CDR3 Val99 (94); VH CDR2 His59 (58)]
Asp352 [VL CDR1 His31 (27D); VL CDR3 Ser97 (92); VL CDR3 Val99 (94); VH CDR2 Tyr57 (56); VH CDR2 His59 (58)]
Pro353 [VL CDR3 Val99 (94); VL CDR3 Trp101 (96); VH CDR1 Trp33 (33); VH CDR2 Val50 (50); VH CDR2 Try57 (56); VH CDR2 His59 (58); VH CDR3 Ala101 (97)]
Trp354 [VL CDR1 His31 (27D); VL CDR1 Tyr37 (32); VL CDR3 Gly96 (91); VL CDR3 Trp101 (96); VH CDR3 Leu100 (96); VH CDR3 Ala101 (97); VH CDR3 Gly102 (98); VH CDR3 Thr103 (99)]
His355 [VL CDR1 His31 (27D), VH CDR1 Ser32 (27E)]
Lys356 [VH CDR1 Tryp33 (33); VH CDR2 Asp52 (52); VH CDR2 Asp55 (54); VH CDR2 Tyr57 (56)]
Ile357 [VH CDR2 Tyr57 (56); VH CDR2 His59 (58)]
Pro358 [VH CDR2 Tyr57 (56); VH CDR2 His59 (58)]
Ala359 [VH CDR2 His59 (58)]

PARATOPE
Amino acid contacts in murine 1D9 (1D9.1F5) antibody VH domain (SEQ ID NO: 44) and VL domain (SEQ ID NO: 48) (Kabat definition numbering in parentheses)

VL Framework 1: Asp1 (1)
VL CDR1: His31 (27D), Ser32 (27E), Tyr37 (32)
VL CDR3: Gly96 (91), Ser97 (92), His98 (93), Val99 (94), Pro100 (95), Trp101 (96)
VH CDR1: Trp33 (33)
VH CDR2: Val50 (50), Asp52 (52), Asp55 (54), Tyr57 (56), His59 (58)
VH CDR3: Leu100 (96), Ala101 (97), Gly102 (98), Thr103 (99)

Without wishing to be limited by theory it is believed, based on this high resolution crystal structure, that the murine 1D9 antibody Fab fragment binds exclusively to domain III of the human HER3 ECD and covers an epitope that partially overlaps with the heregulin binding site present in the open conformation of the HER3 ECD. Without wishing to be limited by theory it is also believed, the murine 1D9 antibody Fab can bind the HER3 ECD when it is in the closed conformation to sterically preventing the receptor from adopting the extended conformation required for dimerization. The murine 1D9 antibody Fab is believed to produce its effects, in part, by preventing domain 1 of the human HER3 ECD from adopting the conformation required for dimerization. It is further believed, without wishing to be limited by theory, that the structural effects described here contribute to the potent inhibition of HER3 activity produced by the murine 1D9 antibody, and its variants.

Example 3

Computational structural modeling of the interaction of the murine 15D5 antibody bound with the HER3 ECD in the open conformation was performed with Rosetta Dock software (RosettaCommons.org). The first stage of the algorithm employed by the software, performs a rigid-body Monte Carlo search as well as translating and rotating the antigen around the surface of the antibody using residue-scale interaction potentials. An alignment score the directs the antigen toward the antibody CDR loops. After this low-resolution search, explicit side chains are added to the protein backbones using a backbone-dependent rotamer packing algorithm. A Monte Carlo-plus-minimization scheme then efficiently samples a set of local minima in a small region of docking conformation space by simultaneously optimizing the side-chain conformations and the rigid-body position. The search procedure is repeated from different random starting orientations to create $10^5$ structures, which are then ranked using an energy function dominated by van der Waals interactions, an implicit solvation model and an orientation-dependent hydrogen bonding potential. The top 1000 decoys passing a score cutoff were retained. To improve the resolution of the side-chain predictions, unbound rotamer conformations were included in the rotamer library and gradient-based minimization on the side-chain torsion angles were used. The 200 best-scoring decoys at the end of this high-resolution search are clustered on the basis of pair-wise root mean square deviation (rmsd) using a hierarchical clustering algorithm. Structures within a 2.5 Å clustering threshold are designated as a set, and the lowest-scoring decoy within the set represents the cluster.

The resulting model of the murine 15D5 antibody bound to the human HER3 ECD predicts this antibody binds the HER3 ECD in the open conformation and creates steric hindrance near the dimerization arm. Without wishing to be limited by theory, this suggests the murine 15D5 antibody blocks HER3 dimerization.

Example 4

1. Summary

A series of humanized RR variants of the murine 1D9 antibody and murine 15D5 antibody were generated and expressed using molecular biology techniques. These antibodies were then subjected to BIACORE™ analysis for binding to the full-length human HER3 extracellular domain (ECD).

2. Introduction

The objective of this example was to determine the affinities of the humanized variants of the murine 1D9 and 15D5 antibodies.

3. Methods 3.1. Experimental Protocol(s)
3.2. BIACORE™ Analysis

BIACORE™ analysis was used to determine the binding affinity of the humanized variants of the murine 1D9 antibody and murine 15D5 antibody generated and expressed using standard molecular biology techniques. The humanized variants were the 1D9 H6L2 RR antibody (comprising SEQ ID NO: 30 and SEQ ID NO: 57), 1D9 H0L7 RR antibody (comprising SEQ ID NO: 67 and SEQ ID NO: 85), 1D9 H2L2. RR antibody (comprising SEQ ID NO: 71 and SEQ ID NO: 57), 1D9 H6L6 RR antibody (comprising SEQ ID NO: 38 and SEQ ID NO: 83), 1D9 H6L3 RR antibody (comprising SEQ ID NO: 30 and SEQ ID NO: 77), 1D9 H3L6 RR antibody (comprising SEQ ID NO: 73 and SEQ ID NO: 83), 1D9 H0L9 RR antibody (comprising SEQ ID NO: 67 and SEQ ID NO: 87), 1D9 H2L6 RR antibody (comprising SEQ ID NO: 71 and SEQ ID NO: 83), 1D9 H6L4 RR antibody (comprising SEQ ID NO: 30 and SEQ ID NO: 79), 1D9 116L5 RR antibody (comprising SEQ ID NO: 30 and SEQ ID NO: 81), 1D9 H6L0 RR antibody (comprising SEQ ID NO: 30 and SEQ ID NO: 75), 1D9 H3L2 RR antibody (comprising SEQ ID NO: 73 and SEQ ID NO: 57), 1D9 H6L9 RR antibody (comprising SEQ ID NO: 30 and SEQ ID NO: 87), 15D5 HIL3 antibody (comprising SEQ ID NO: 90 and SEQ ID NO: 98), 15D5 H2L2 antibody (comprising SEQ ID NO: 92 and SEQ ID NO: 96), 15D5 D5 antibody (comprising SEQ ID NO: 90 and SEQ ID NO: 26), 15D5 H3L1 antibody (comprising SEQ ID NO: 94 and SEQ ID NO: 26), 15D5 H2L1 antibody (comprising SEQ ID NO: 92 and SEQ ID NO: 26) and the 15D5 H31.3 antibody (comprising SEQ ID NO: 94 and SEQ ID NO: 98). The chimeric 151)$_5$ antibody (ch15D5) was also analyzed.

The binding kinetics of these antibodies for was assessed using a BIACORE™ 3000. Antibodies were captured on a CM5 biosensor chip to which an immobilized anti-human IgG (Fc specific) BIACORE™ (GE Healthcare cat# BR-1008-39) monoclonal antibody had been conjugated using supplied coupling buffer (9000 RU). Full-length human HER3 ECD concentrations were injected for 120 s at a flow rate of 30 ul/min. Biosensor chips were regenerated as described in Example 1. Kinetics were determined by global fitting of data to the 1:1 Langmuir model using BIACORE™ Evaluation software. Analytical runs were carried out at 25° C. using FIBS-EP as the running buffer.

The basic steps of the BIACORE™ analytical methods are outlined below:

1) Immobilization with anti-human Fc antibody (9000-1000RU; 25 ug/ml, using sodium acetate buffer, pH 5.0);

2) Capture of the antibody of interest (400 ng/ml);

3) Association of analyte to captured antibody (e.g., HER ECD from 512 nM to 16 nM);

4) Dissociation of analyte (e.g., with buffer);

5) BIAcore Kinetic run cycle steps: buffer, 512 nM HER3 ECD, 256 nM HER3 ECD, 128 nM HER3 ECD, 64 nM HER3 ECD, 32 nM HER3 ECD and 16 nM HER3 ECD. Buffer cycle and double referencing were performed as described in Example 1; and 5) Regenerate biosensor chips with BIACORE™ optimized buffers.

4. Results and Discussion

Table 8 and Table 9 below show the data obtained and show that the humanized 1D9 RR antibody (H6L2) and the humanized 15D5 antibody (H4L1) appeared to have the best affinities for the full-length, human HER3 ECD of all the humanized antibodies generated relative to the parental molecules.

TABLE 8

Affinities of the humanized 1D9 RR variant antibodies.

| Antibody | Analyte | ka (1/Ms) | kd (1/s) | KD (M) |
|---|---|---|---|---|
| Humanized 1D9 RR antibody (H6L2) | Human HER3 ECD | $4.3 \times 10^5$ | $1.7 \times 10^{-3}e-3$ | $3.96 \times 10^{-9}$ |
| 1D9 H0L7 RR | Human HER3 ECD | $3.27 \times 10^4$ | $1.95 \times 10^{-3}$ | $5.95 \times 10^{-8}$ |
| 1D9 H2L2 RR | Human HER3 ECD | $3.31 \times 10^5$ | $4.44 \times 10^{-3}$ | $1.34 \times 10^{-8}e-8$ |
| 1D9 H6L6 RR | Human HER3 ECD | $6.94 \times 10^5$ | $4.87 \times 10^{-3}$ | $7.02 \times 10^{-9}$ |
| 1D9 H6L3 RR | Human HER3 ECD | $7.73 \times 10^5$ | $3.02 \times 10^{-3}$ | $3.91 \times 10^{-9}$ |
| 1D9 H3L6 RR | Human HER3 ECD | $3.04 \times 10^4$ | $2.92 \times 10^{-3}$ | $9.58 \times 10^{-8}$ |
| 1D9 H0L9 RR | Human HER3 ECD | $3.77 \times 10^5$ | 0.0144 | $3.81 \times 10^{-8}$ |
| 1D9 H10L6 RR | Human HER3 ECD | $3.77 \times 10^5$ | $7.93 \times 10^{-3}$ | $2.1 \times 10^{-8}$ |
| 1D9 H2 L6 RR | Human HER3 ECD | $4.96 \times 10^5$ | $2.25 \times 10^{-3}$ | $4.54 \times 10^{-9}$ |
| 1D9 H6 L4 RR | Human HER3 ECD | $5.19 \times 10^5$ | $4.1 \times 10^{-3}$ | $7.89 \times 10^{-9}$ |
| 1D9 H 6L5 RR | Human HER3 ECD | $5.4 \times 10^5$ | $3.71 \times 10^{-3}$ | $6.87 \times 10^{-9}$ |
| 1D9 H 6L0 RR | Human HER3 ECD | $4.87 \times 10^5$ | $3.66 \times 10^{-3}$ | $7.51 \times 10^{-9}$ |
| 1D9 H3L2 RR | Human HER3 ECD | $5.33 \times 10^4$ | $3.16 \times 10^{-3}$ | $5.94 \times 10^{-8}$ |
| 1D9 H6 L9 RR | Human HER3 ECD | $6.65 \times 10^5$ | $2.23 \times 10^{-3}$ | $3.35 \times 10^{-9}$ |

TABLE 9

Affinities of the humanized 15D5 variant antibodies.

| Antibody | Analyte | ka (1/Ms) | kd (1/s) | KD (M) |
|---|---|---|---|---|
| Chimeric 15D5 antibody (ch15D5) | Human HER3 ECD | $4.4 \times 10^4$ | $1.4 \times 10^{-4}$ | $3.19 \times 10^{-9}$ |
| Humanized 15D5 antibody (H4L1) | Human HER3 ECD | $7.49 \times 10^4$ | $1.96 \times 10^{-4}$ | $2.62 \times 10^{-9}$ |
| 15D5 H1L3 | Human HER3 ECD | $3.44 \times 10^4$ | $3.45 \times 10^{-4}$ | $1 \times 10^{-8}$ |
| 15D5 H 2L2 | Human HER3 ECD | $3.17 \times 10^5$ | $4.07 \times 10^{-3}$ | $1.28 \times 10^{-8}$ |
| 15D5 H1 L1 | Human HER3 ECD | $3.71 \times 10^4$ | $2.67 \times 10^{-4}$ | $7.19 \times 10^{-9}$ |
| 15D5 H 3L1 | Human HER3 ECD | $4.05 \times 10^4$ | $1.71 \times 10^{-4}$ | $4.21 \times 10^{-9}$ |
| 15D5 H 2L1 | Human HER3 ECD | $4.19 \times 10^4$ | $3.65 \times 10^{-4}$ | $8.7 \times 10^{-9}$ |
| 15D5 H 3L3 | Human HER3 ECD | $4.21 \times 10^4$ | $3.67 \times 10^{-4}$ | $8.72 \times 10^{-9}$ |
| 15D5 H 4L3 | Human HER3 ECD | $3.79 \times 10^4$ | $9.35 \times 10^{-4}$ | $2.47 \times 10^{-8}$ |

Example 5

1. Summary

The humanized 1D9 antibody, the humanized 1D9 Fc disabled antibody, the humanized 1D9 ACCRETAMAB™ antibody and the humanized 1D9 POTELLIGENT™ antibody were generated and expressed using molecular biology techniques. These antibodies were then subjected to BIACORE™ analysis for binding to the full-length human HER3 extracellular domain (ECD), the full-length rat HER3 extracellular domain (ECD) and full-length cynomolgus monkey HER3 extracellular domain (ECD) as indicated below.

2. Introduction

The objective of this example was to determine the affinities of the humanized 1D9 antibody, the humanized 1D9 Fc disabled antibody, the humanized 1D9 ACCRETAMAB™ antibody and the humanized 1D9 POTELLIGENT™ antibody.

3. Methods 3.1. Experimental Protocol(s)
3.2. BIACORE™ Analysis

BIACORE™ analysis was used to determine the binding affinity of the humanized 1D9 antibody, the humanized 1D9 Fc disabled antibody, the humanized 1D9 ACCRETAMAB™ antibody and the humanized 1D9 POTELLIGENT™ antibody.

Protein A was immobilised on a CM5 chip by primary amine coupling to a level of ~1300 resonance units (RU's), humanized antibodies were then captured on this chip. All antibodies were captured to a similar level (100-200 RU's). The full-length, human HER3 ECDs was then passed over the chip at 50 nM, 25 nM, 12.5 nM, 6.25 nM, 3.125 nM and 1.5625 nM for as indicated below. Alternatively, the full-length, rat HER3 ECD or the full-length cynomolgus monkey ECD were passed over the chip at 10 nM, 5 nM, 2.5 nM, 1:25nM, 0.625 nM and 0.3125nM. An injection of buffer alone was used to double reference the binding curves as indicated in Example 1. Regeneration of this surface was achieved using 10 mM Glycine buffer pH 1.5. The binding data was fitted to the 1:1 model using BIACORE™ Evaluation software. Runs were carried out at 25° C. on a BIACORE™ T3000 using HBS-EP as running buffer.

4. Results and Discussion

Table 10 and Table 11 below show the data obtained for binding of the humanized 1D9 antibody, the humanized 1D9

Fc disabled antibody, the humanized 1D9 ACCRETAMAB™ antibody and the humanized 1D9 POTELLIGENT™ antibody to the full-length human HER3 extracellular domain (ECD), the full-length rat HER3 extracellular domain (ECD) and full-length cynomolgus monkey HER3 extracellular domain (ECD) as indicated below.

TABLE 10

Affinities of the humanized 1D9 antibody, the humanized 1D9 Fc disabled antibody, the humanized 1D9 ACCRETAMAB ™ antibody and the humanized 1D9 POTELLIGENT ™ antibody.

| Antibody | Analyte | ka (1/Ms) | kd (1/s) | KD (M) |
| --- | --- | --- | --- | --- |
| Humanized 1D9 antibody | Human HER3 ECD | $4.1 \times 10^5$ | $1.84 \times 10^{-3}$ | $4.5 \times 10^{-9}$ |
| Humanized 1D9 Fc disabled antibody | Human HER3 ECD | $2.71 \times 10^5$ | $1.22 \times 10^{-3}$ | $4.49 \times 10^{-9}$ |
| Humanized 1D9 ACCRETAMAB ™ antibody | Human HER3 ECD | $1.13 \times 10^6$ | $2.33 \times 10^{-3}$ | $2.06 \times 10^{-9}$ |
| Humanized 1D9 POTELLIGENT ™ antibody | Human HER3 ECD | $1.11 \times 10^6$ | $2.23 \times 10^{-3}$ | $2.01 \times 10^{-9}$ |
| Humanized 1D9 POTELLIGENT ™ antibody | Rat HER3 ECD | $3.26 \times 10^5$ | $1.1 \times 10^{-3}$ | $3.37 \times 10^{-9}$ |

TABLE 11

Affinities of the humanized 1D9 H6L2 Fc disabled antibody for the full-length human HER3 ECD, the full-length rat HER3 ECD and full-length cynomolgus monkey HER3 ECD.

| Antibody | Analyte | ka (1/Ms) | kd (1/s) | RD (M) |
| --- | --- | --- | --- | --- |
| Humanized 1D9 Fc disabled antibody | Human HER3 ECD | $2.71 \times 10^5$ | $1.22 \times 10^{-3}$ | $4.49 \times 10^{-9}$ |
| Humanized 1D9 Fc disabled antibody | Cynomolgus monkey HER3 ECD | $1.09 \times 10^6$ | $1.89 \times 10^{-3}$ | $1.73 \times 10^{-9}$ |
| Humanized 1D9 Fc disabled antibody | Rat HER3 ECD | $3.26 \times 10^5$ | $1.1 \times 10^{-3}$ | $3.37 \times 10^{-9}$ |

Characterization of the humanized 1D9 antibody, the humanized 1D9 Fc disabled antibody, the humanized 1D9 ACCRETAMAB™ antibody and the humanized 1D9 POTELLIGENT™ demonstrates specific binding to full-length, human HER3 ECD. Based on cross species homology predictions domain III of the rat HER3 ECD and domain III of the cynomolgus monkey HER3 ECD are about 95% homologous to the domain III human HER3 ECD epitope bound by the humanized 1D9 antibody and its variants. This indicates a strong likelihood for functional cross reactivity. Consistent with this the humanized 1D9 Fc disabled antibody was observed to cross-react with the full-length cynomolgus monkey HER3 ECD and the full-length rat HER3 ECD at a comparable level as assessed by BIACORE™ analysis. See Table 10 and Table 11 above.

Example 6

1. Summary

This example demonstrates the ability of the 1D9 antibodies (e.g., the murine 1D9 antibody and its humanized variants) and 15D5 antibodies (e.g., the murine 15D5 antibody and its humanized variants) to inhibit heregulin induced HER3 phosphorylation, decrease downstream AKT signalling, act as heterodimerization inhibitors to prevent activated EGFR from heterodimerizing with HER3, to prevent heregulin induced EGFR-HER3, HER2-HER3 as well as HER4-HER3 heterodimer formation and to prevent subsequent HER3 phosphorylation.

2. Introduction

The ability of the 1D9 antibodies (e.g., the murine 1D9 antibody and its humanized variants) and 15D5 antibodies (e.g., the murine 15D5 antibody and its humanized variants) to inhibit heregulin induced HER3 phosphorylation, decrease downstream AKT signalling, act as heterodimerization inhibitors to prevent activated EGFR from heterodimerizing with HER3, to prevent heregulin induced EGFR-HER3, HER2-HER3 as well as HER4-HER3 heterodimer formation and to prevent subsequent HER3 phosphorylation were examined 3. Methods 3.1. Experimental Preparation(s)

The models used in these studies conform to UK standards of animal care, as laid down by the Home Office.

3.2. Experimental Protocol(s)

3.2.1 Inhibition of Heregulin induced HER3Receptor Phosphorylation with anti-HER3 mAbs in Cancer Cell Lines BxPC3, CHL-1, N87, SK-BR-3, BT-474, or MCF-7 cells at approximately 80% confluency were harvested with trypsin, washed in 10% FBS/media, and resuspended at 3–5× $10^5$ cells/ml in 10% FBS/media. 100 ul/well was plated into 96 well tissue culture treated flat bottom plates and incubated overnight at 37° C. in a 5% $CO_2$ atmosphere. The next day media was aspirated and replaced with serum free media, and incubated overnight for a serum starve. mAb stocks were then prepped in serum free media, and half log serial dilutions were made. 10 ul of the mAb stocks were added in duplicate to the 96 well cell plates for 8 point concentration curves and incubated for 1 hour at 37° C. 10 ul of HRGβ1 was added next to a final concentration of 30 or 100 ng/ml and incubated for 15 minutes. Media was aspirated and cells were lysed in cold lysis buffer containing phosphatase and protease inhibitors, and rocked on ice for 30 minutes. Lysates were used immediately or frozen at −80° C. and thawed later on ice for use in the Human Phospho-ErbB3 ELISA (R&D Systems catalog number DYC 1769). The ELISA was conducted per the manufacturer's protocol. Data analysis was performed using GRAPHPAD™ PRISM™ software.

3.2.2 Inhibition of Heregulin Induced Akt Phosphorylation with anti-HER3 mAbs in Cancer Cell Lines BxPC3, CHL-1, N87, SK-BR-3, or BT-474 cells at approximately 80% confluency were harvested with trypsin, washed in 10% FBS/media, and resuspended at $3-5 \times 10^5$ cells/ml in 10% FBS/media. 100 ul/well was plated into 96 well tissue culture treated flat bottom plates and incubated overnight at 37° C. in a 5% $CO_2$ atmosphere. The next day media was aspirated and replaced with serum free media, and incubated overnight for a serum starve. The next day mAb stocks were prepped in serum free media, and half 10 g serial dilutions were made. 10 ul of the mAb stocks were added in duplicate to the 96 well cell plates for 8 point concentration curves and incubated for 1 hour at 37° C. 10 ul of HRGB1 was added next to a final concentration of 30 or 100 ng/ml and incubated for 15 minutes. Media was aspirated and cells were lysed in cold lysis buffer containing phosphatase and protease inhibitors, and rocked on ice for 30 minutes. Lysates were used immediately or frozen at −80° C. and thawed later on ice for use in the Human/Mouse/Rat Phospho-Akt (S473) Pan Specific ELISA (R&D Systems catalog number DYC887B). The ELISA was conducted per the manufacturer's protocol. Data analysis was performed using GRAPHPAD™ PRISMT™.

3.2.3 Inhibition of Epidermal Growth Factor or Betacellulin induced HER3Receptor Phosphorylation with anti-HER3 mAbs in SK-BR-3 Breast Cancer Cells SK-BR-3 cells were assayed as described in section 3.2.1 of this example (above) for use in the Human Phospho-ErbB3 ELISA R&D Systems catalog number DYC 1769, with the exception that either epidermal growth factor (EGF) or betacellulin was the activating ligand instead of heregulin.

3.2.4 Inhibition of Heregulin Induced Heterodimer Formation and HER3Receptor Phosphorylation in HER Family Receptor BACMAM™ Transduced CHO Cells A heterodimerization assay was developed using PerkinElmer ALPHALISA™ assay technology to examine anti-HER3 mAb mediated inhibition of HER3 receptor phosphorylation by EGFR, HER2 and HER4 after heregulin-beta1 stimulation. Reagents were prepared according to the PerkinElmer protocol. Briefly, a phospho-tyrosine specific mouse mAb (P-Tyr-100 Cell Signaling Technology catalog #9411 PBS only formulation) was conjugated to ALPHALISA™ acceptor beads (PerkinElmer catalog #6772002). A 10:1 coupling weight ratio was used by conjugating 1 mg of acceptor beads to 100 ug of antibody for 48 hours. A commercially available anti-human HER3 antibody (R&D Systems MAB3481) was biotinylated using a 30:1 molar ratio of biotin to antibody by utilizing 7.6 ul of a 2 mg/ml CHROMA-LINKT™ Biotin 354 (Sulfo NHS, SoluLinK catalog #B-1007-105) per 100 ug of antibody. Anti-HER3 mAbs were then assessed by transducing Chinese hamster ovary cells at $3 \times 10^5$ cells/ml overnight with specific BACMAM™ pairings of EGFR+HER3, HER2+ HER3 and HER4+ HER3 in 96 well plates. The next day anti-HER3 mAbs were added and incubated for 1 hour at 37° C. Heregulin-β1 was then added to a final concentration of 100 ng/ml and plates were incubated for 30 minutes. Media was then aspirated and cells were lysed in cold lysis buffer containing phosphatase and protease inhibitors. Lysates were rocked on ice for 30 minutes and either used immediately or frozen at −80° C. and thawed on ice to perform the ALPHALISA™ assay. 2.5 ul of lysate was then added to 10 ul of 2.5 nM biotinylated anti-human ErbB3 antibody (R&D Systems MAB3481) in 384 well plates and incubated for 1 hour at room temperature. 5 ul/well of a 50 ug/ml phospho-tyrosine specific mouse mAb (P-Tyr-100 Cell Signaling Technology catalog #9411) was then added and incubated for 1 hour with shaking in the dark. 12.5 ul/well of an 80 ug/ml preparation of streptavidin-coated donor beads (PerkinElmer catalog#6760002) was then added and incubated for an additional 30 minutes. Plates were read on the ENVISION™ 2103 multilabel plate reader and data analysis was performed using GRAPHPAD™ PRISMT™.

3.3. Drugs and Materials

Humanized 1D9 POTELLIGENT™ antibody (12.68 mg/ml)
Humanized 1D9 ACCRETAMAB™ antibody (7.45 mg/ml)
Humanized 1D9 antibody (1.88 mg/ml)
Humanized 1D9 Fc disabled antibody (3.713 mg/ml)
Murine 1D9 antibody (M5.1D9.1F5; 4.77 mg/ml)
Murine 15D5 antibody (3.19 mg/ml)
Murine IgG1 isotype control antibody (R&D Systems 500 ug/ml cat# MAB002)
Murine IgG2b isotype control (R&D Systems 500 ug/ml cat# MAB004)
Human anti-malaria mAb (Human isotype control; 5.74 mg/ml)
Heregulin-P1 (HRG(31; 1.88 mg/ml)

3.4. Data Analysis

All data shown in this example represents the average from a minimum of two experiments. Antibody values were divided by the positive control heregulin treated cell values and multiplied by 100 to calculate "% of Heregulin Control Phospho HER3" or "% of Heregulin Control Phospho AKT [.]" The epidermal growth factor or betacellulin positive control treated cell values were used for comparison in the case of epidermal growth factor or betacellulin treated SK-BR-3 cells. Data from individual experiments was averaged, and GRAPHPAD™ PRISM™ analysis software was used to calculate IC50 values.

4. Results

Figure 1:
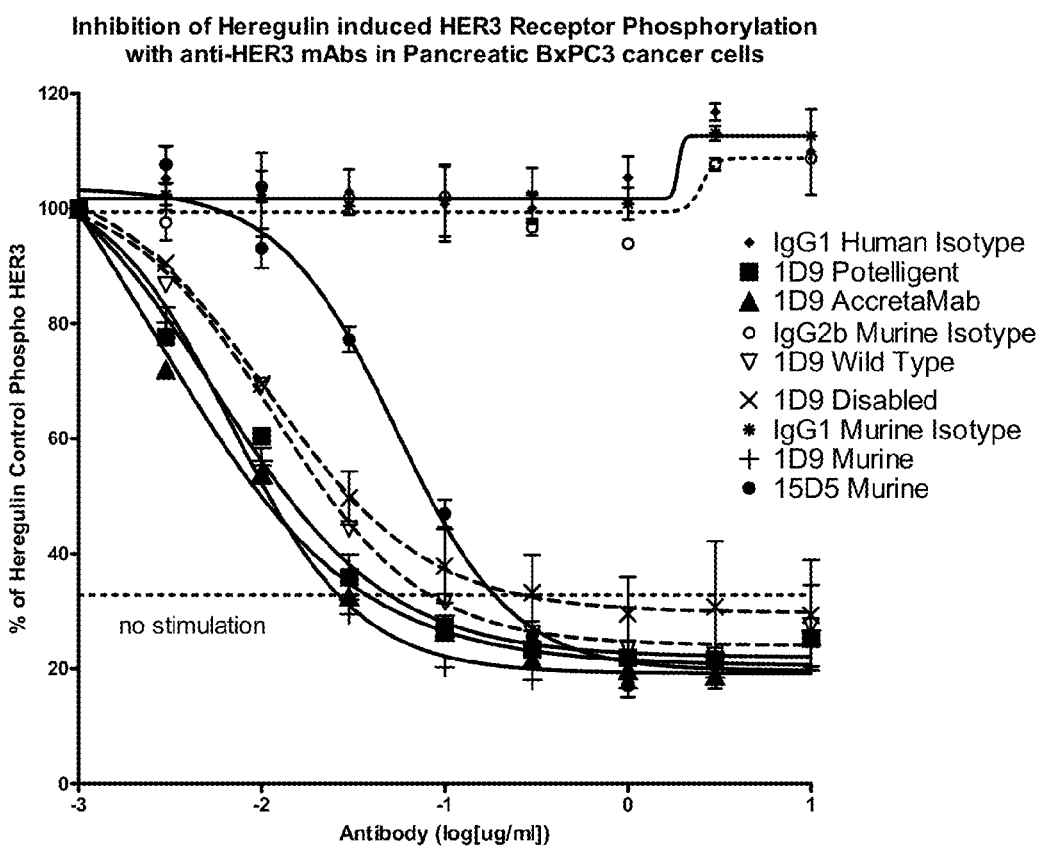
FIG. 1. Inhibition of heregulin induced human HER3 receptor phosphorylation with anti-HER3 antibodies in BxPC3 pancreatic cancer cells.
Figure 2:
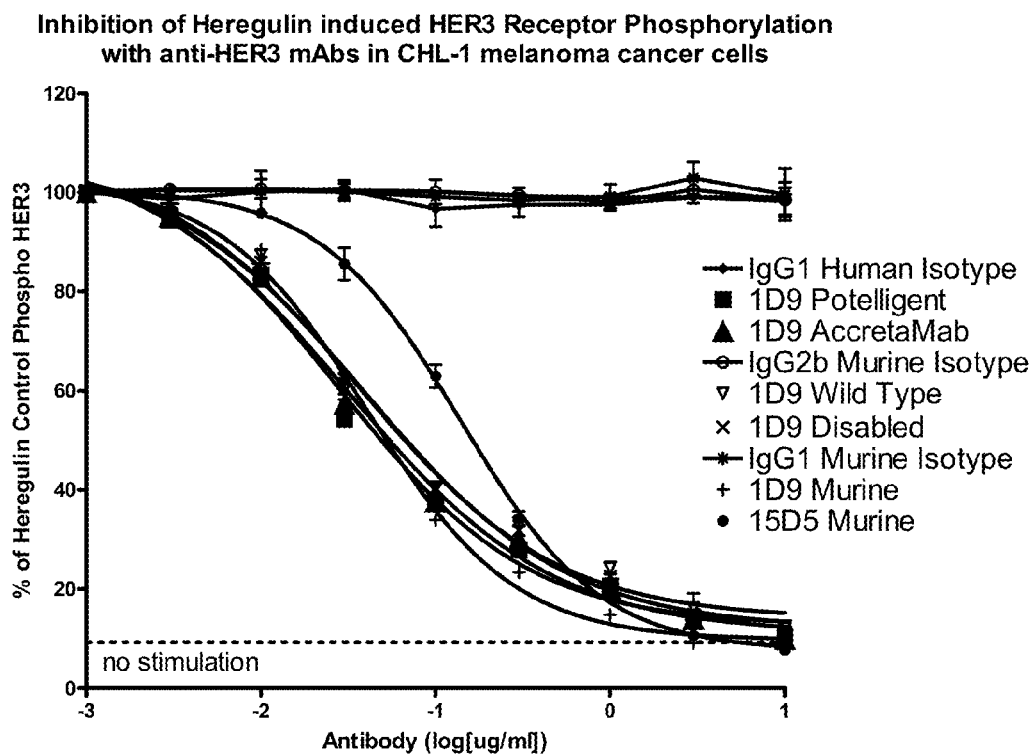
FIG. 2. Inhibition of heregulin induced human HER3 receptor phosphorylation with anti-HER3 antibodies in CHL-1 melanoma cells.
Figure 3:
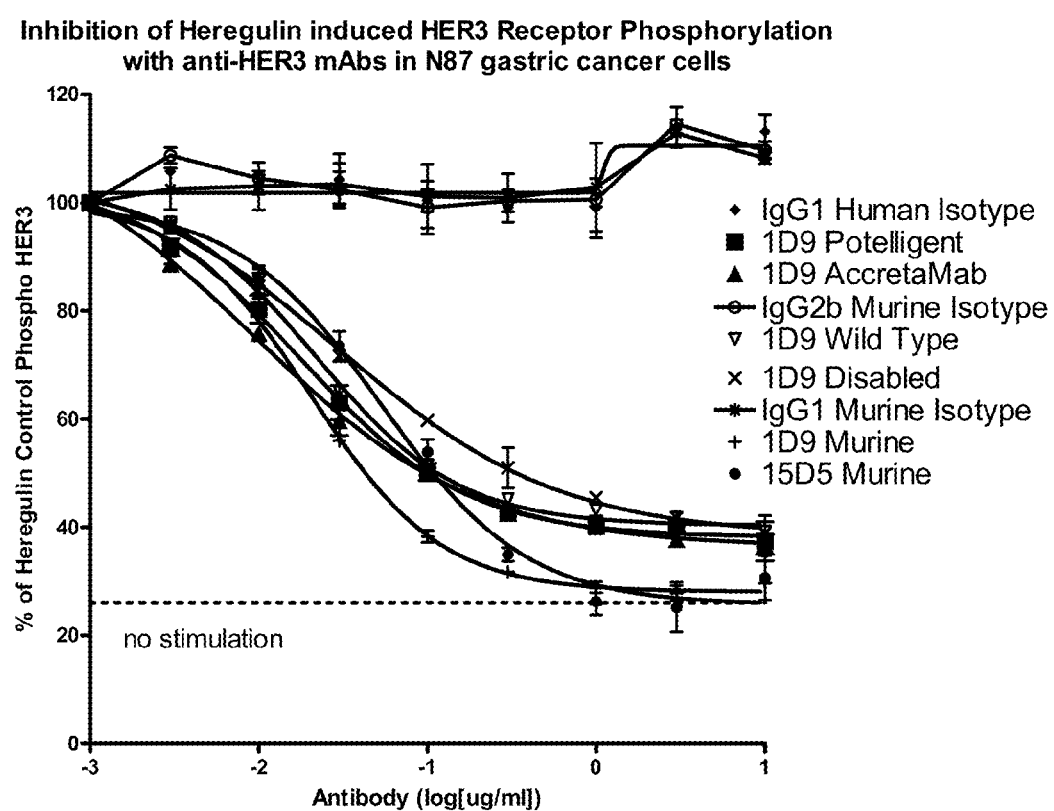
FIG. 3. Inhibition of heregulin induced human HER3 receptor phosphorylation with anti-HER3 antibodies in N87 gastric cancer cells.
Figure 4:
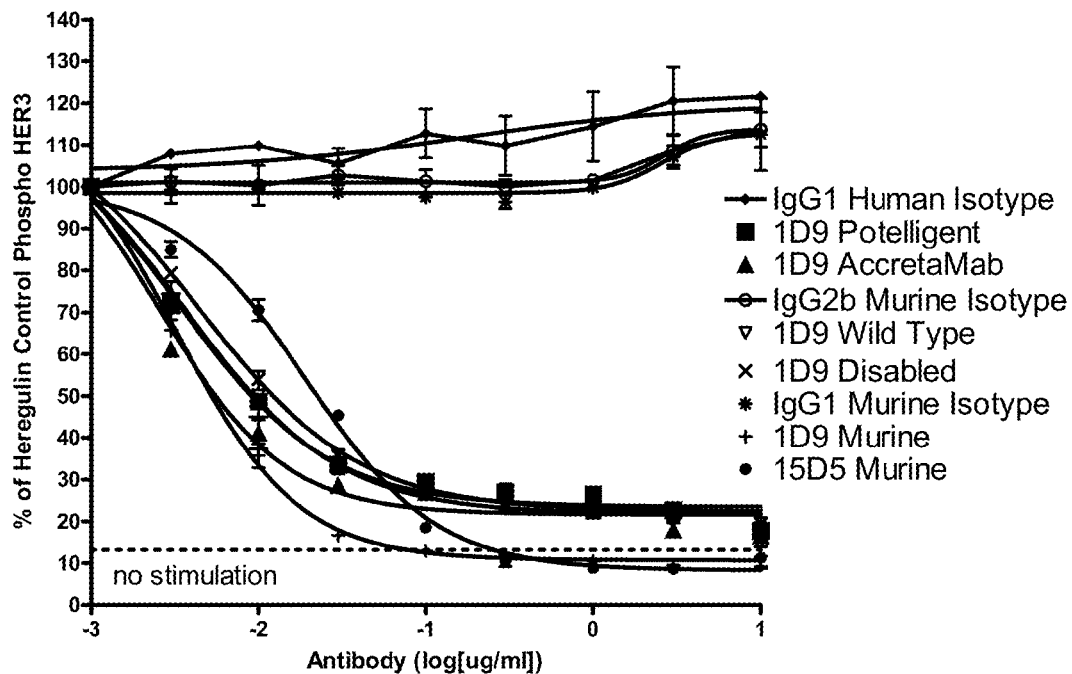
FIG. 4. Inhibition of heregulin induced human HER3 receptor phosphorylation with anti-HER3 antibodies in SK-BR-3 breast cancer cells.
Figure 5:
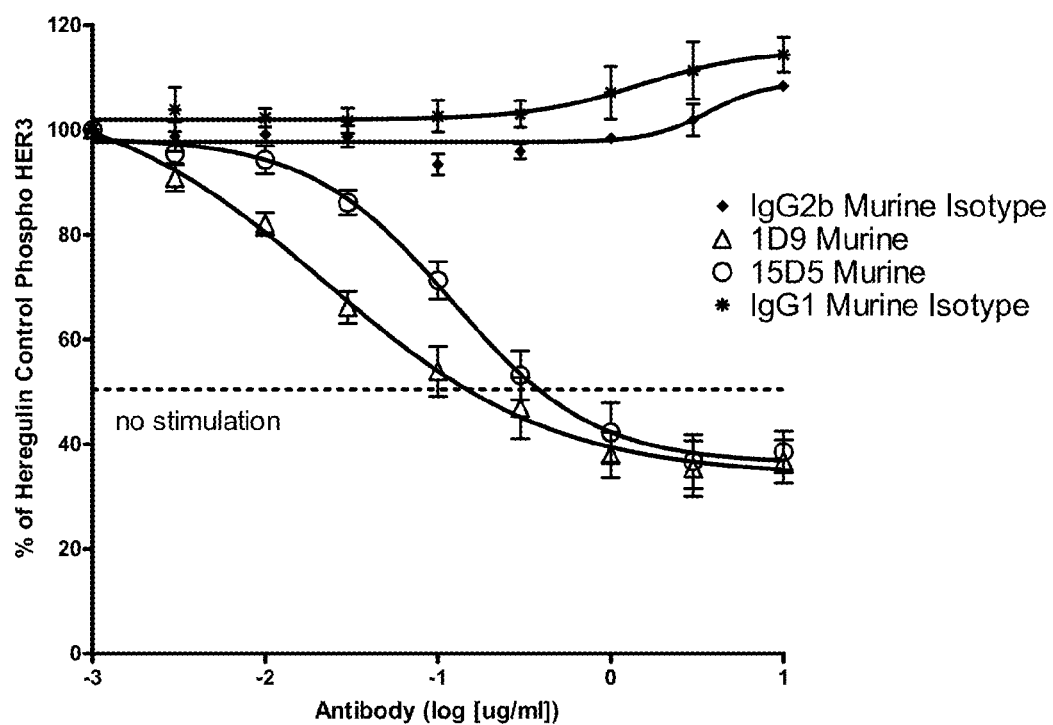
FIG. 5. Inhibition of heregulin induced human HER3 receptor phosphorylation with anti-HER3 antibodies in BT-474 breast cancer cells.

4.2.1 Inhibition of Heregulin Induced HER3Receptor Phosphorylation with anti-HER3 Antibodies in Cancer Cells The anti-HER31D9 and 15D5 antibodies inhibited heregulin induced HER3 phosphorylation in the BxPC3 (FIG. 1), CHL-1 (FIG. 2), N87 (FIG. 3), SK-BR-3 (FIG. 4), BT-474 (FIG. 5), and MCF-7 (FIG. 6) cancer cells. All 1D9 antibody constructs, including the humanized 1D9 POTELLIGENT™ antibody and the humanized ACCRETAMAB™ antibody, showed potent inhibition with IC50 values ranging from 2.5 to 40.6 ng/ml IC50 values, as shown in Table 12.

TABLE 12

Inhibition of heregulin induced human HER3 receptor phosphorylation with anti-HER3 antibodies.
Phospho-HER3 ALPHALISA ™ ELISA IC50 Values (ng/ml)

| Antibody | Cells | | | | | |
| --- | --- | --- | --- | --- | --- | --- |
| | BxPC3 | CHL-1 | N87 | SK-BR-3 | BT-474 | MCF7 |
| Humanized 1D9 POTELLIGENT ™ antibody | 5.6 | 28.2 | 17.5 | 3.4 | n/a | n/a |

TABLE 12-continued

Inhibition of heregulin induced human HER3 receptor phosphorylation with anti-HER3 antibodies.
Phospho-HER3 ALPHALISA ™ ELISA IC50 Values (ng/ml)

| Antibody | Cells | | | | | |
|---|---|---|---|---|---|---|
| | BxPC3 | CHL-1 | N87 | SK-BR-3 | BT-474 | MCF7 |
| Humanized 1D9 ACCRETAMAB ™ antibody | 2.6 | 31.1 | 9.4 | 2.5 | n/a | n/a |
| Humanized 1D9 antibody | 11.6 | 36.5 | 21.8 | 3.6 | n/a | n/a |
| Humanized 1D9 Fc disabled antibody | 10.7 | 39.9 | 29.7 | 4.4 | n/a | n/a |
| Murine 1D9 antibody | 6.8 | 40.6 | 20.4 | 3.2 | 22.3 | 10.4 |
| Murine 15D5 antibody | 54.1 | 138.2 | 53.3 | 19.1 | 119.8 | 59.26 |

4.2.2 Inhibition of Heregulin induced Akt phosphorylation with anti-HER3 mAbs in cancer cells.

Figure 7:
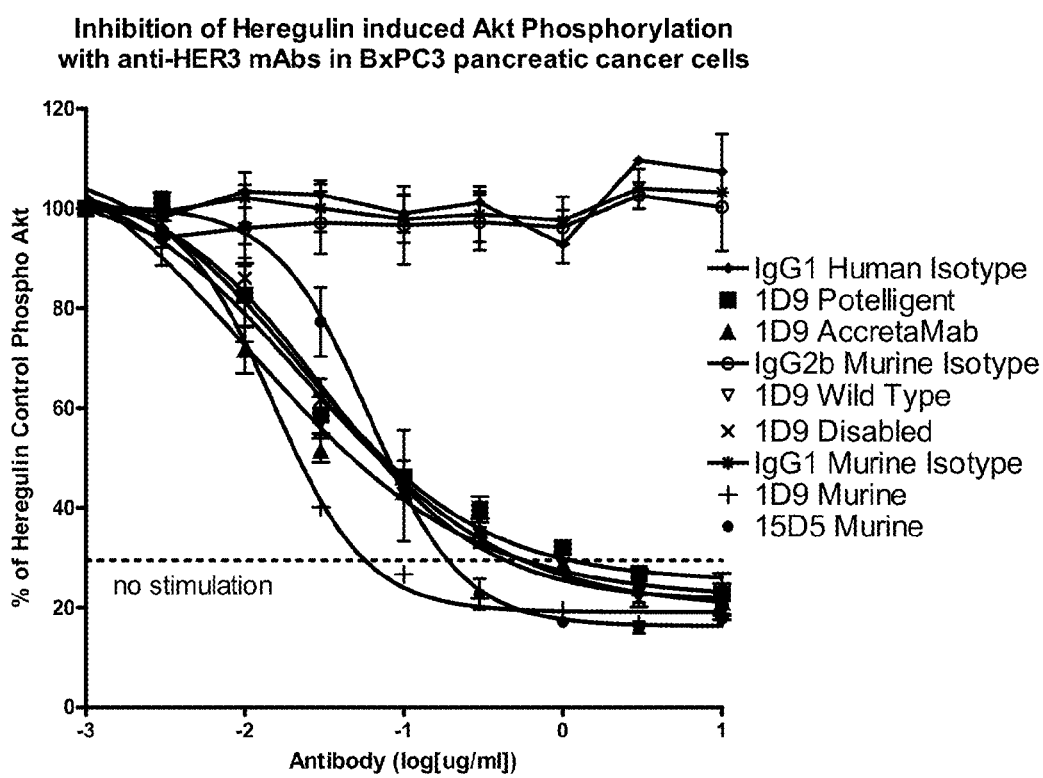
FIG. 7. Inhibition of heregulin induced human Akt phosphorylation with anti-HER3 antibodies in BxPC3 pancreatic cancer cells.
Figure 8:
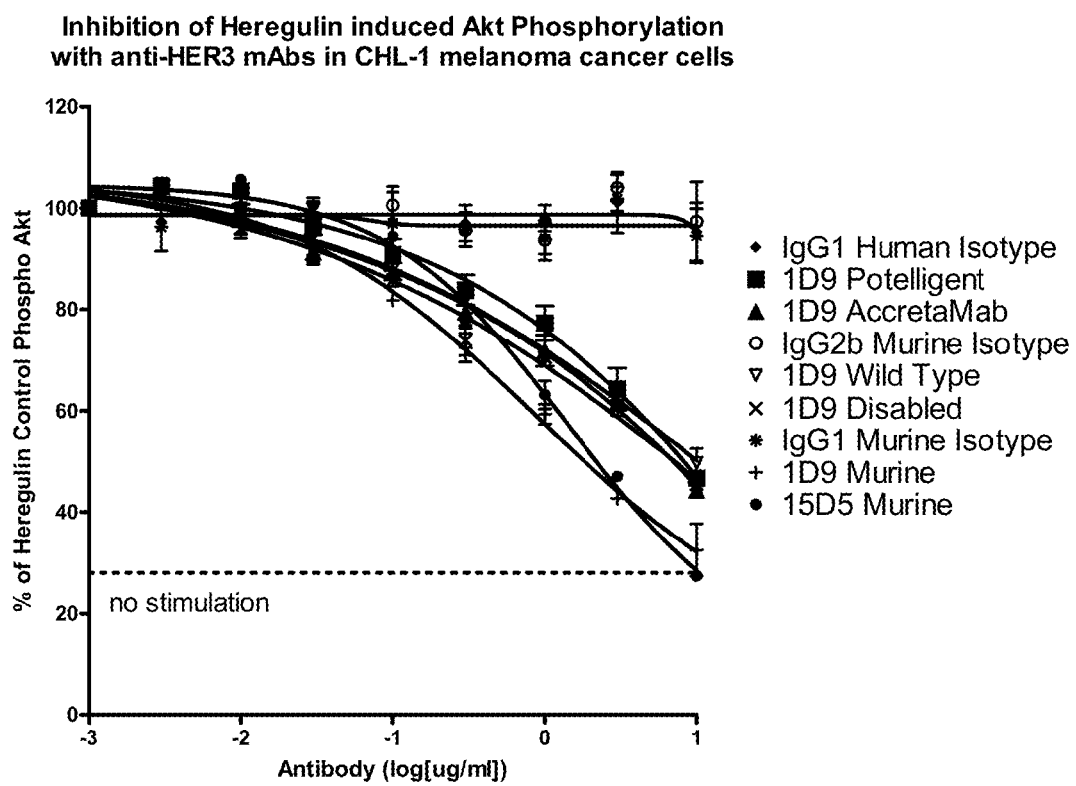
FIG. 8. Inhibition of heregulin induced human Akt phosphorylation with anti-HER3 antibodies in CHL-1 melanoma cells.
Figure 9:
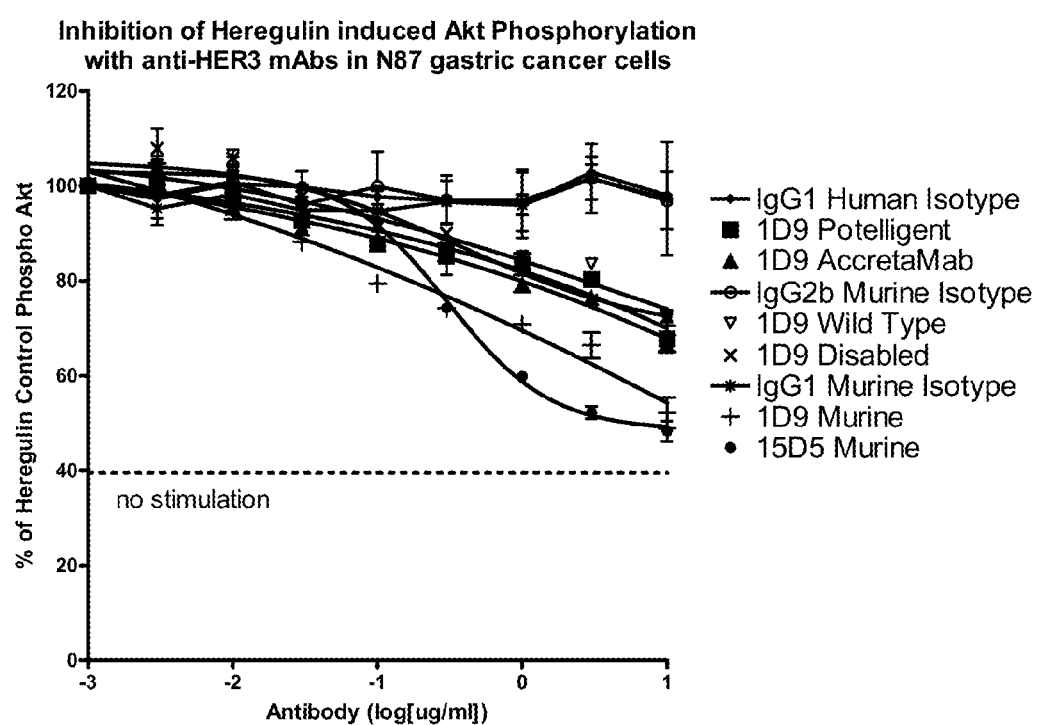
FIG. 9. Inhibition of heregulin induced human Akt phosphorylation with anti-HER3 antibodies in N87 gastric cancer cells.
Figure 10:
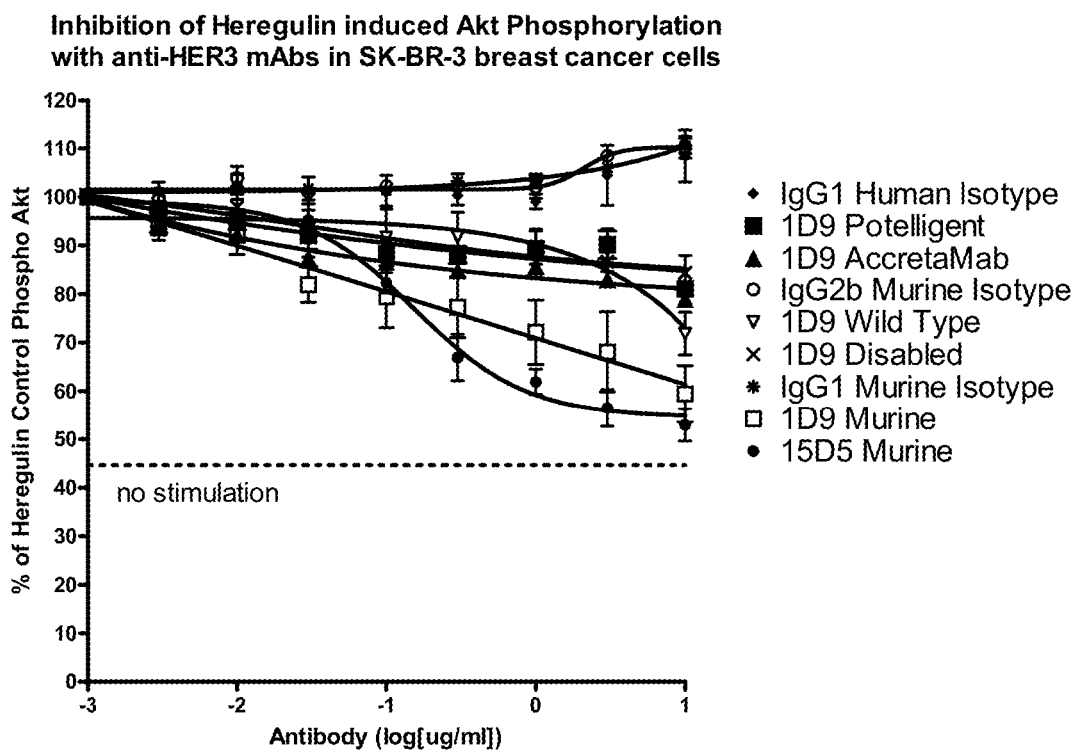
FIG. 10. Inhibition of heregulin induced human Akt phosphorylation with anti-HER3 antibodies in SK-BR-3 breast cancer cells.

The anti-HER31D9 antibodies and 15D5 antibodies decreased heregulin induced AKT phosphorylation in BxPC3 (FIG. 7), CHL-1 (FIG. 8), N87 (FIG. 9), and SK-BR-3 (FIG. 10) cancer cells. The most potent inhibition of AKT phosphorylation was seen in the BxPC3 cells, where the humanized 1D9 ACCRETAMAB™ antibody inhibited heregulin induced phospho-AKT formation with an IC50 value of 2.6 ng/ml (Table 13).

TABLE 13

Inhibition of heregulin induced AKT phosphorylation in BxPC3 breast cancer cells with anti-HER3 antibodies.
Inhibition of Heregulin Induced AKT phosphorylation with anti-HER3 Antibodies Phosopho-AKT ELISA IC50 Values (ng/ml)

| Antibody | Cells BxPC3 |
|---|---|
| Humanized 1D9 POTELLIGENT ™ antibody | 22.8 |
| Humanized 1D9 ACCRETAMAB ™ antibody | 10.8 |
| Humanized 1D9 antibody | 24.4 |
| Humanized 1D9 Fc disabled antibody | 31.6 |
| Murine 1D9 antibody | 15.1 |
| Murine 15D5 antibody | 60.5 |

4.2.3 Inhibition of Epidermal Growth Factor and Betacellulin induced HER3Receptor Phosphorylation with anti-HER3 mAbs in SK-BR-3 Breast Cancer Cells The anti-HER31D9 antibodies and 15D5 antibodies inhibited both epidermal growth factor and betacellulin induced HER3 phosphorylation in SK-BR-3 breast cancer cells. The 1D9 murine construct inhibited ligand induced HER3 receptor phosphorylation with an IC50 value of approximately 3 ng/ml, regardless of the activating ligand used (Table 14). Table 14). Inhibition of epidermal growth factor (EGF), betacellulin (BTC) and heregulin induced human HER3 receptor phosphorylation with anti-HER3 antibodies in SK-BR-3 breast cancer cells.

| | Phospho-HER3 ALPHALISA ™ ELISA IC50 Values (ng/ml) | | |
|---|---|---|---|
| Antibody | Epidermal Growth Factor | Betacellulin | Heregulin |
| Murine 1D9 antibody | 3.0 | 3.6 | 3.2 |
| Murine 15D5 antibody | 23.3 | 36.8 | 19.1 |

4.2.4 Inhibition of Heregulin Induced Heterodimer Formation and HER3Receptor Phosphorylation in combinations of EGFR, HER2 or HER4 with HER3BACMAM™ Transduced CHO Cells The anti-HER31D9 antibodies and 15D5 antibodies inhibited heregulin induced HER3 phosphorylation in CHO cells co-transduced with the human HER3 receptor and the EGFR, HER2, or HER4 receptor as indicated. These antibodies were capable of inhibiting heregulin induced formation of EGFR-HER3, HER2-HER3, or HER4-HER3 heterodimers. IC50 values are listed in Table 15.

TABLE 15

Inhibition of heregulin induced human HER3 receptor phosphorylation with anti-HER3 antibodies.

| | Phospho-HER3 ALPHALISA ™ ELISA IC50 Values (ng/ml) | | |
|---|---|---|---|
| Antibody | CHO EGFR + HER3 | CHO HER2 + HER3 | CHO HER4 + HER3 |
| Murine 1D9 antibody | 43.5 | 141.7 | 129.6 |
| Murine 15D5 antibody | 102.8 | 342.9 | 140.7 |

5. Discussion

The HER3 receptor tyrosine kinase belongs to the human epidermal growth factor receptor family that also includes EGFR (HER1), HER2, and HER4. HER3 binds heregulin ligand, but is intrinsically kinase dead. It must dimerize with other family members to allow transphosphorylation of tyrosine residues in its intracellular C-terminal domain. Subsequent downstream signalling resulting from activated, phosphorylated HER3 receptor includes the PI3K/AKT survival pathway.

Figure 16:
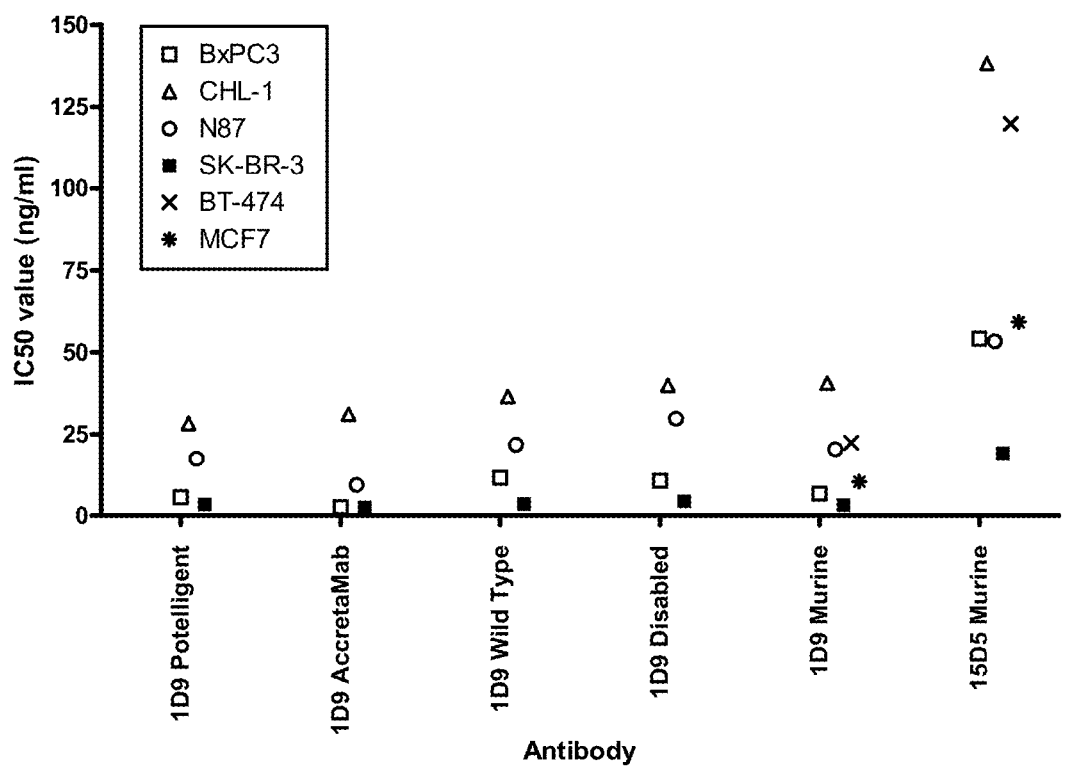
FIG. 16. Inhibition of heregulin induced human HER3 receptor phosphorylation with anti-HER3 antibodies in cancer cells lines (Phospho-HER3ELISA IC50 values).

The data in this example demonstrates the anti-HER31D9 antibodies and 15D5 antibodies can inhibit heregulin induced HER3 receptor phosphorylation. Treatment of cancer cell lines with the 1D9 antibodies prior to heregulin stimulation resulted in complete inhibition of heregulin-induced HER3 phosphorylation. FIG. 16 shows the IC50 values of the different 1D9 antibodies for inhibiting HER3 phosphorylation across different cancer cell lines. Downstream AKT phosphorylation was also decreased with 1D9 antibody and 15D5 antibody treatments. Thus, the 1D9 antibodies and 15D5 antibodies inhibit heregulin-induced HER3 phosphorylation and decrease downstream AKT signalling.

Figure 11:
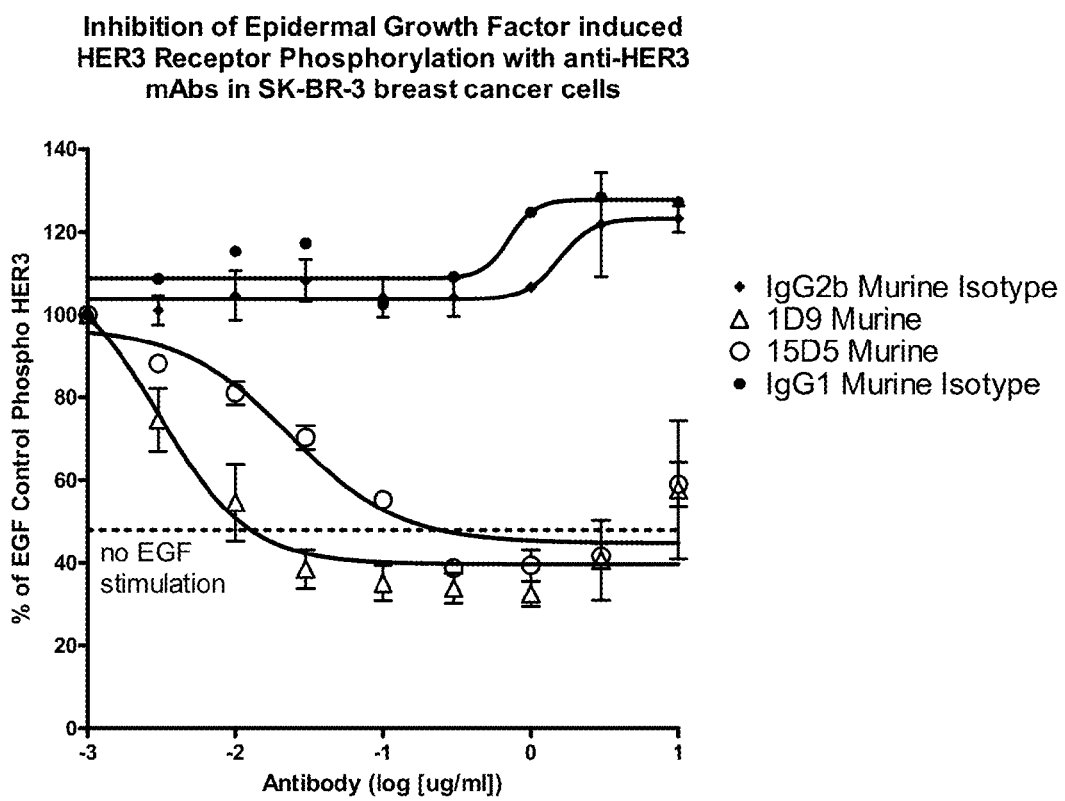
FIG. 11. Inhibition of epidermal growth factor (EGF) induced human HER3 receptor phosphorylation with anti-HER3 antibodies in SK-BR-3 breast cancer cells.
Figure 12:
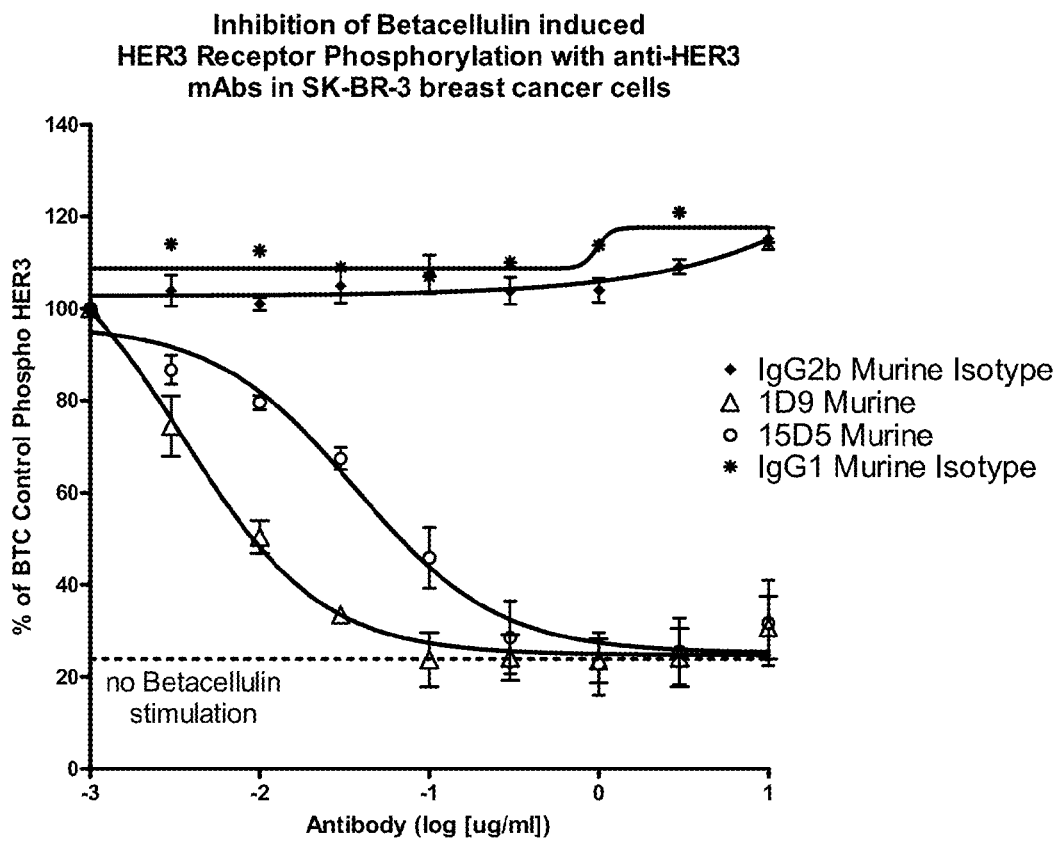
FIG. 12. Inhibition of betacellulin induced human HER3 receptor phosphorylation with anti-HER3 antibodies in SK-BR-3 breast cancer cells.

Epidermal growth factor and betacellulin are ligands for EGFR, and can induce EGFR-HER3 heterodimer formation. SK-BR-3 breast cancer cells showed an induction of HER3 phosphorylation when treated with either of these EGFR ligands. Treatment of SK-BR-3 cells with 1D9 antibodies or 15D5 antbodies inhibited epidermal growth factor or betacellulin induced HER3 phosphorylation (FIG. 11 and FIG. 12). This indicates these antibodies act as heterodimerization inhibitors and can prevent activated EGFR from dimerizing with HER3.

Figure 13:
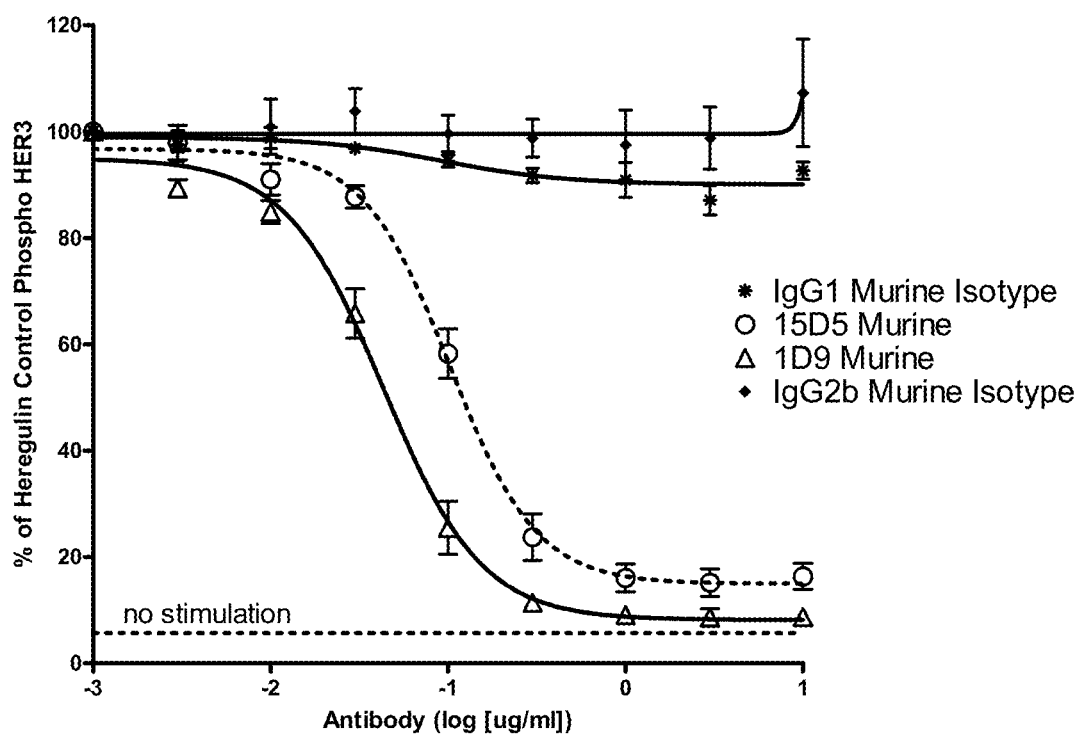
FIG. 13. Inhibition of heregulin induced heterodimer formation and human HER3 receptor phosphorylation with anti-HER3 antibodies in CHO cells transduced with epidermal growth factor receptor (EGFR) and HER3.
Figure 14:
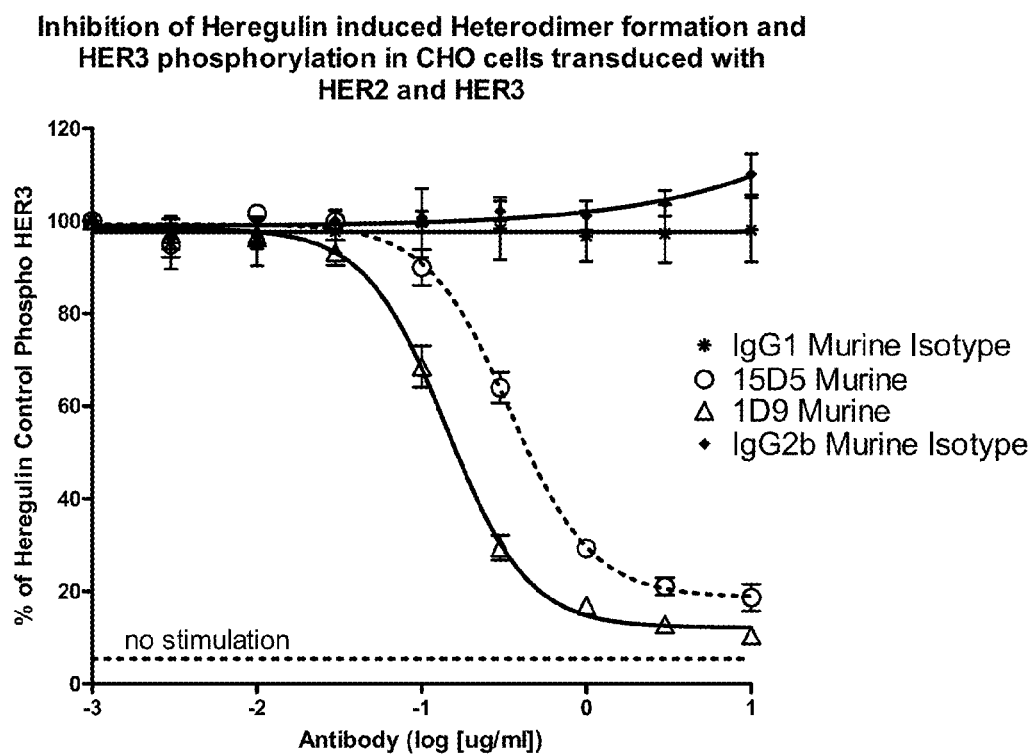
FIG. 14. Inhibition of heregulin induced heterodimer formation and human HER3 receptor phosphorylation with anti-HER3 antibodies in CHO cells transduced with HER2 and HER3.
Figure 15:
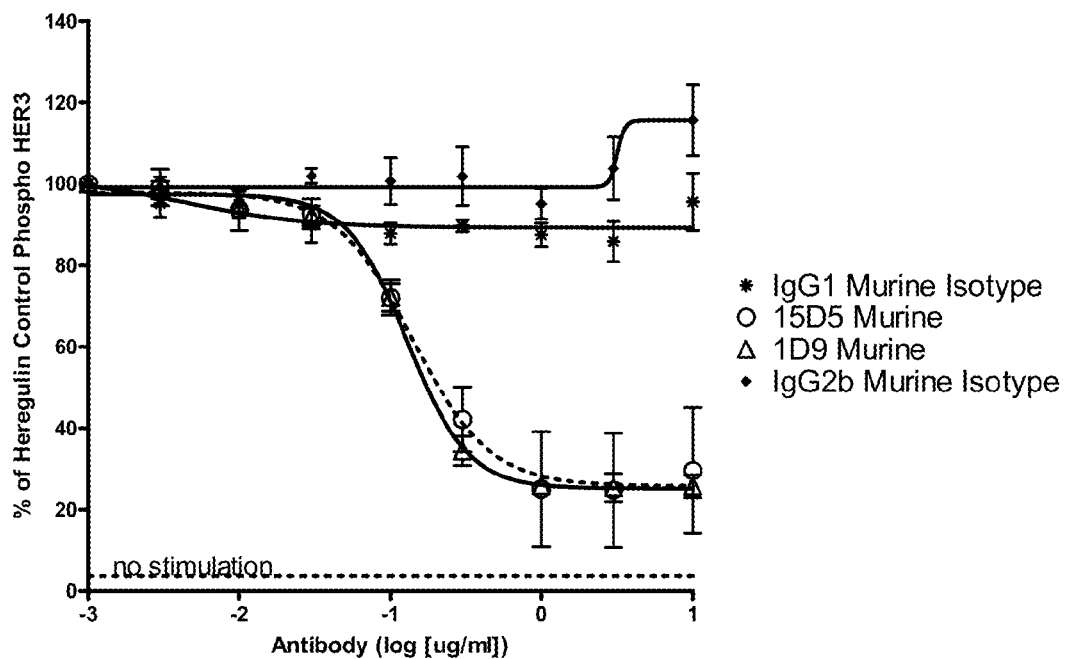
FIG. 15. Inhibition of heregulin induced heterodimer formation and human HER3 receptor phosphorylation with anti-HER3 antibodies in CHO cells transduced with HER4 and HER3.

The 1D9 antibodies and 15D5 antibodies specifically inhibited EGFR-HER3, or HER2-HER3, or HER4-HER3 heregulin-induced heterodimer formation. CHO cells were transduced with HER3 plus only one other family member capable of transphosphorylating HER3 upon heterodimer formation. Regardless of whether EGFR, or HER2, or HER4 was used as the dimerizing partner, the 1D9 antibodies and 15D5 antibodies inhibited heregulin induced HER3 phosphorylation (FIG. 13, FIG. 14 and FIG. 15). This indicates the 1D9 antibodies and 15D5 antibodies prevent heregulin induced heterodimer formation with these other family members and prevent HER3 phosphorylation.

Example 7

1. Summary

The anti-human HER3 antibodies were profiled in several in vitro assays. These included assays for binding of these mAbs to the full length HER3 ECD and specific HER3 domains, assays for binding of these mAbs to tumor cells, proliferation assays, invasion assays, internalization assays, and assays for the cross-species specificity (murine and cynomologus monkey) of these mAbs. The murine 1D9 antibody, the humanized 1D9 antibody, the humanized 1D9 POTELLIGENT™ antibody and the humanized ACCRETAMAB™ antibody were evaluated. The results showed that both the murine and humanized constructs of the anti-human HER31D9 antibodies recognize human HER3 ECD full-length, and bind specifically to Domain 3 of the HER3 ECD. These mAbs inhibit heregulin induced tumor cell proliferation in a dose dependent manner. These mAbs also inhibit heregulin induced tumor cell invasion. The 1D9 antibodies induce HER3 receptor internalization into tumor cells. These mAbs also cross-react with murine HER3.

2. Introduction

This example summarizes the in vitro profiling which was conducted for the anti-human HER3 antibodies. It includes data for both the murine 1D9 antibody, the humanized 1D9 POTELLIGENT™ antibody and the humanized ACCRETAMAB™ antibody. Results from the following assays are described in detail: Full length human HER3 ECD and domain binding, binding on tumor cells, proliferation, invasion, internalization, and cross-specificity (murine).

3. Methods 3.1 HER3Full-length ECD and Domain Binding Assays

Objective: The objective of these assays was to confirm the humanized 1D9 POTELLIGENT™ antibody and the humanized 1D9 ACCRETAMAB™ antibody bind full length HER3 extracellular domain. Another object of these assays was to confirm the mAbs also bind specifically to HER3Domain III.

Dissociation Enhanced Lanthanide Fluorescence Immunoassay (DELFIA) for detection of the anti-HER3 antibodies to HER3 extracellular domain (ECD) was used. The DELFIA procedures were as follows: white Maxisorp 96-well plates (Nunc #437796) were coated with 100 ul/well of 1 ug/ml HER-3 ECD full length or HER3Domain I, II, III and IV in 0.1M carbonate buffer pH 9.5 overnight at 4° C. These plates were blocked with casein in TBS (Thermo Scientific #37532 lot#JD121074). The neat hybridoma supernatant, or the purified anti-HER3 antibodies diluted in Perkin Elmer #4002-0010 Assay Buffer from 10 ug/ml (or 100 ug/ml) to 0.01 ug/ml, or the PK serum samples with a minimum of 3 dilutions (100 ul/well) were added to the plate. These samples were incubated for 2 hours at room temperature while on a plate shaker or overnight at 4° C. 100 ul/well of anti-mouse Eu antibody (PE DELFIA #AD-0124 lot 326-949-A, use at 1:1000=50 ng/ml) or Eu-Labeled anti-human IgG 2nd antibody (Wallac #1244-330 50 ug/ml, use at 1:4,000 dilution for purified antibodies or 1:2,000 for PK test) were used and incubated for 1 hour at room temperature. The plate was washed 4 times with tris-buffer plus 0.05% tween-20 (Perkin Elmer #4010-0010) on a BIOTEK™ plate washer following each antibody incubation step. 100 ul/well of DELFIA enhancement solution (Perkin Elmer 1244-105) was added for 5 minutes at room temperature. The plate was then read on the VICTOR™ 1420 plate reader using the europium time-resolved fluorometry (TRF) protocol. Antibody binding was recorded as europium counts per well.

Figure 17:
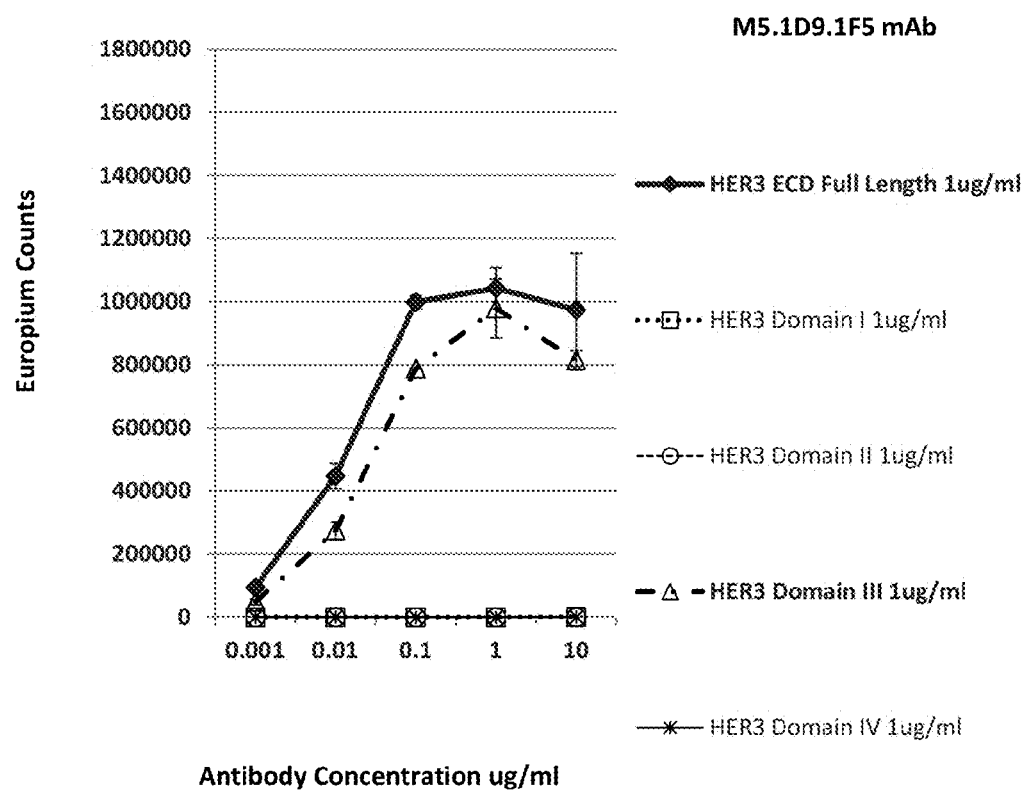
FIG. 17. The murine 1D9 antibody (M5.1D9.1F5) binds the full length human HER3 ECD and human HER3 domain III.
Figure 18:
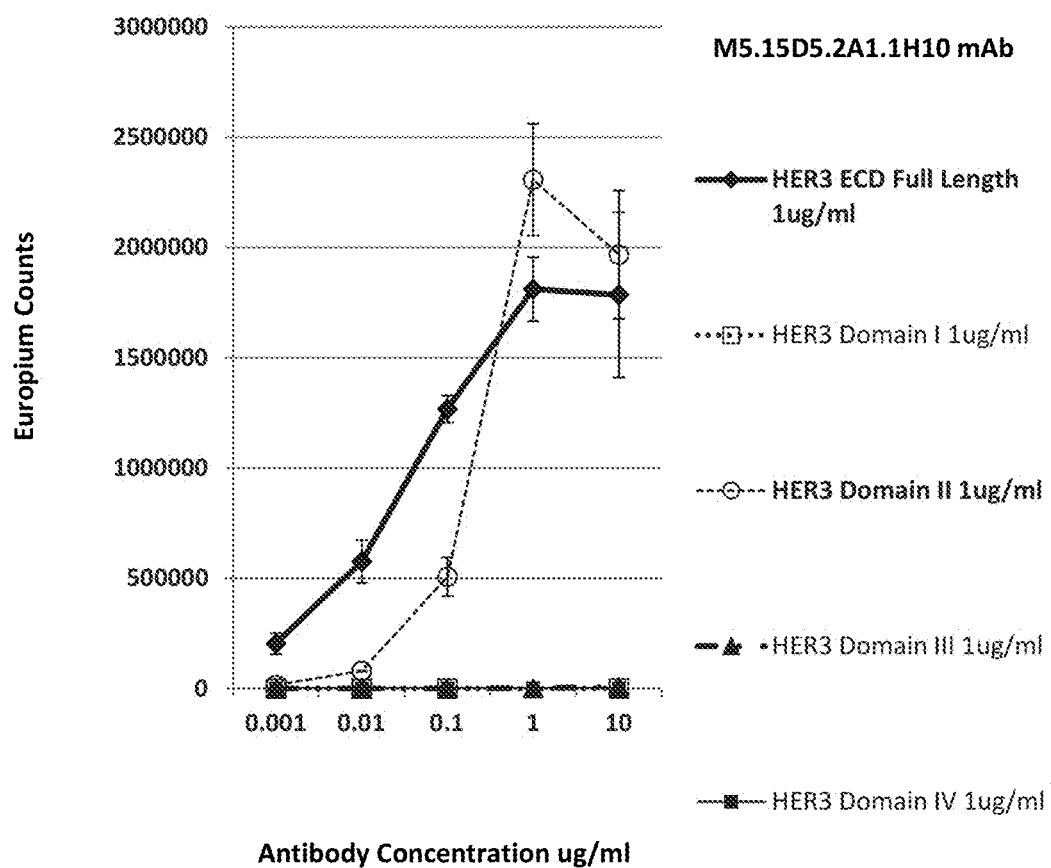
FIG. 18. The murine 15D5 antibody (M5.15D5.2A1.1H10) binds the full length human HER3 ECD and human HER3Domain II.
Figure 19:
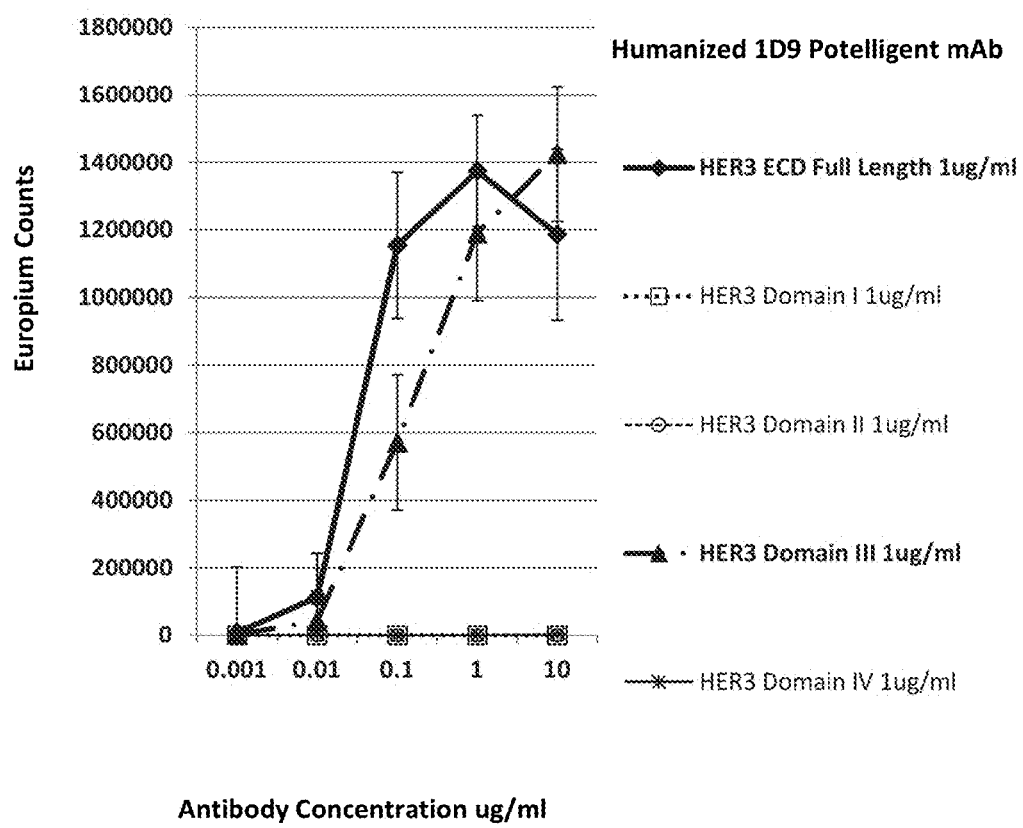
FIG. 19. The humanized 1D9 POTELLIGENT™ antibody binds the full length human HER3 ECD and human HER3Domain III.
Figure 20:
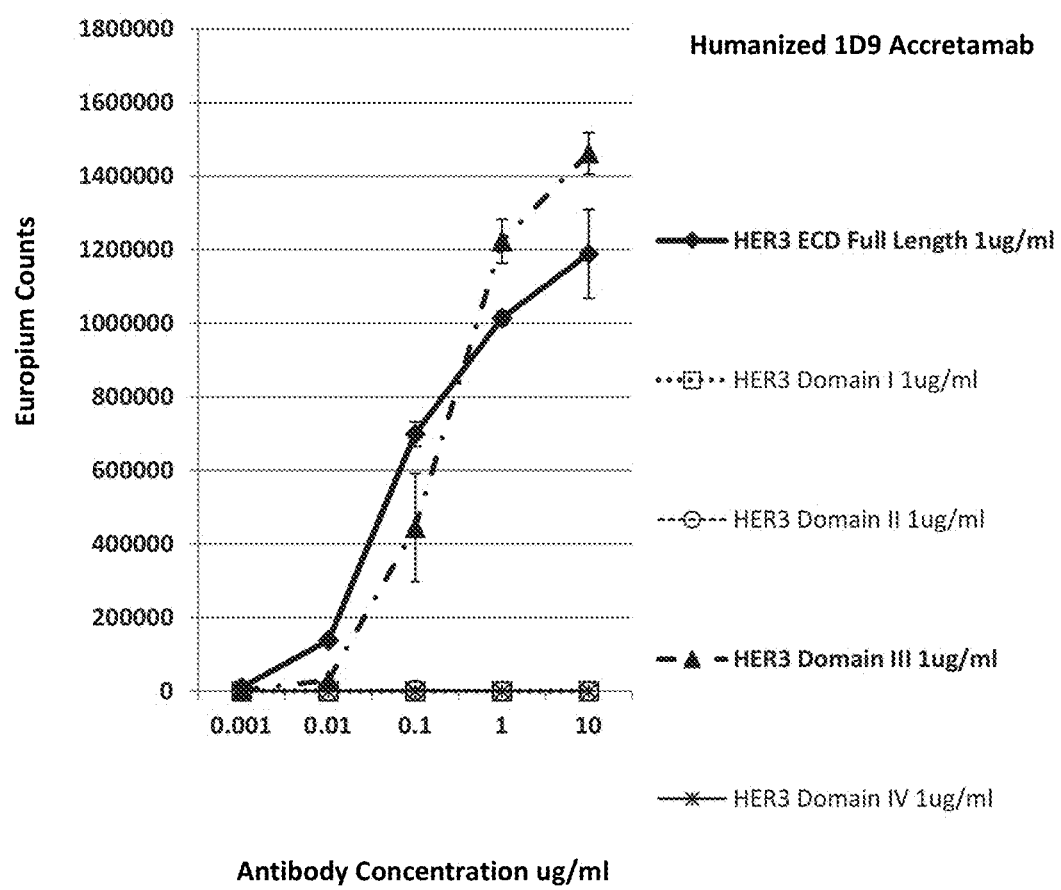
FIG. 20. The humanized 1D9 ACCRETAMAB™ antibody binds the full length human HER3 ECD and human HER3Domain III.
Figure 21:
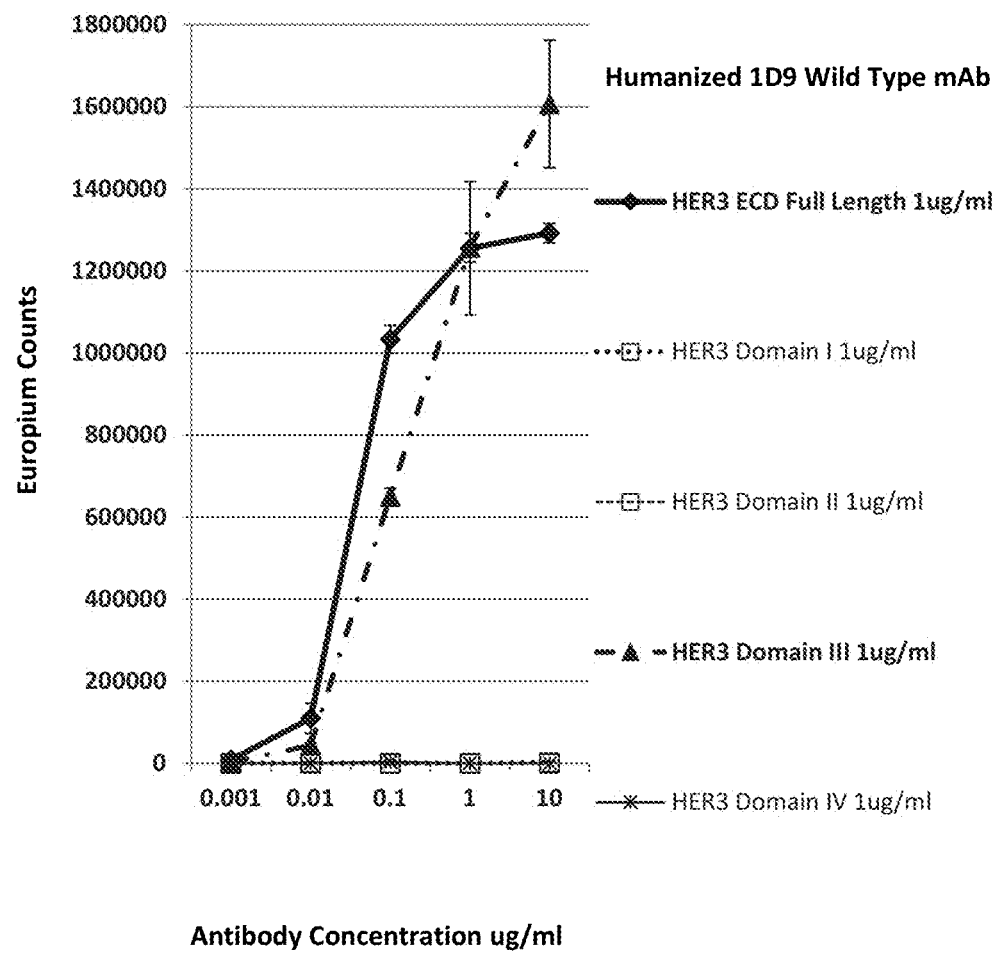
FIG. 21. The humanized 1D9 antibody binds the full length human HER3 ECD and human HER3Domain III.

Results:

FIG. 17 demonstrates specific binding of the murine 1D9 antibody (M5.1D9.1F5) to both the full length HER3 ECD and to HER3Domain III. FIG. 18 demonstrates specific binding of the murine 15D5 antibody (M5.15D5.2A1.1H10) to both the full length HER3 ECD and to HER3Domain II. FIG. 19 demonstrates specific binding of the humanized 1D9 POTELLIGENT™ antibody to the full length HER3 ECD and HER3 Domain III. FIG. 20 demonstrates specific binding of the humanized 1D9 ACCRETAMAB™ antibody to the full length HER3 ECD and HER3Domain III. FIG. 21 demonstrates the specific binding of the humanized 1D9 antibody to the full length HER3 ECD and HER3Domain III. See FIG. 17, FIG. 18, FIG. 19, FIG. 20 and FIG. 21.

Conclusions:

The murine 1D9 antibody (M5.1D9.1F5) specifically binds to both the full length HER3 ECD and to HER3Domain III. The murine 15D5 antibody (M5.15D5.2A1.1H10) specifically binds to both the full length HER3 ECD and to HER3 Domain II. The humanized 1D9 POTELLIGENT™ antibody specifically binds to the full length HER3 ECD and HER3Domain III. The humanized 1D9 ACCRETAMAB™ antibody specifically binds to the full length HER3 ECD and HER3Domain III. The humanized 1D9 antibody specifically binds to the full length HER3 ECD and HER3Domain III. See FIG. 17, FIG. 18, FIG. 19, FIG. 20 and FIG. 21.

3.2 Anti-Human HER3Antibodies Bind to Human Cancer Cell Lines in Flow Cytometry Assays Objective:

To determine the binding profile of the anti-human HER3 antibodies on human cancer cell lines that are known to be HER3 positive cell lines.

Reagents:

FACS Buffer: PBS, 0.2% BSA, 0.1% sodium azide

Antibodies:

Murine 1D9 antibody (M5.1D9.1F5)

Humanized 1D9 antibody

Humanized 1D9 ACCRETAMAB™ antibody

Humanized 1D9 POTELLIGENT™ antibody

PE goat anti-mouse IgG (H+ L)—Caltag Laboratories (M30004-4)

Goat anti-human IgG ALEXAFLUOR647™—Invitrogen (A21445)

Cell Lines: CHL1, BxPC3

Methods:

$5 \times 10^6$ cells, from cell lines that have been previously screened for the HER3 receptor, were added to flow cytometry tubes. Dose response concentrations of each antibody to be tested were added to the appropriate tubes. The cells and antibodies were incubated for 30 minutes on ice. The cells were washed one time with 1 ml of staining buffer and the appropriate secondary antibody was then added to the appropriates tubes. The cells were again incubated for 30 minutes on ice in the dark and then washed and resuspended in FACS buffer. Cells were analyzed on a FACSCANTO™ flow cytometer.

Data Analysis:

Analysis was performed using the FACSDIVA™ software developed by BD Biosciences. Cell populations were gated using forward vs side scatter and histograms of fluorescent intensities were generated.

Figure 22A:
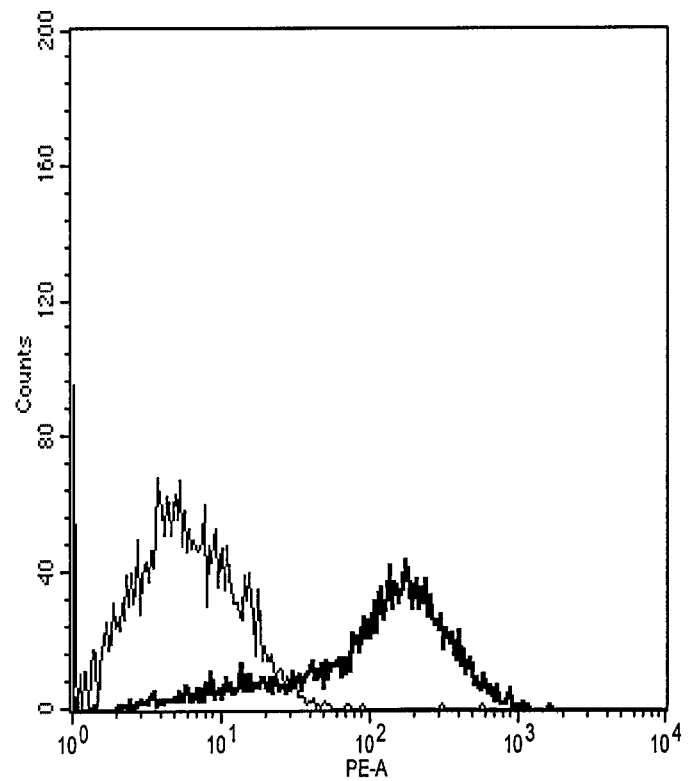
FIG. 22. (a) The murine 1D9 antibody (M5.1D9.1F5) recognizes HER3 on human MCF-7 breast cancer cells as assessed by flow cytometric analyses. (b) The murine 1D9 antibody (M5.1D9.1F5) antibody recognizes HER3 on human BxPC3 pancreatic cancer cells as assessed by flow cytometric analyses.
Figure 22B:
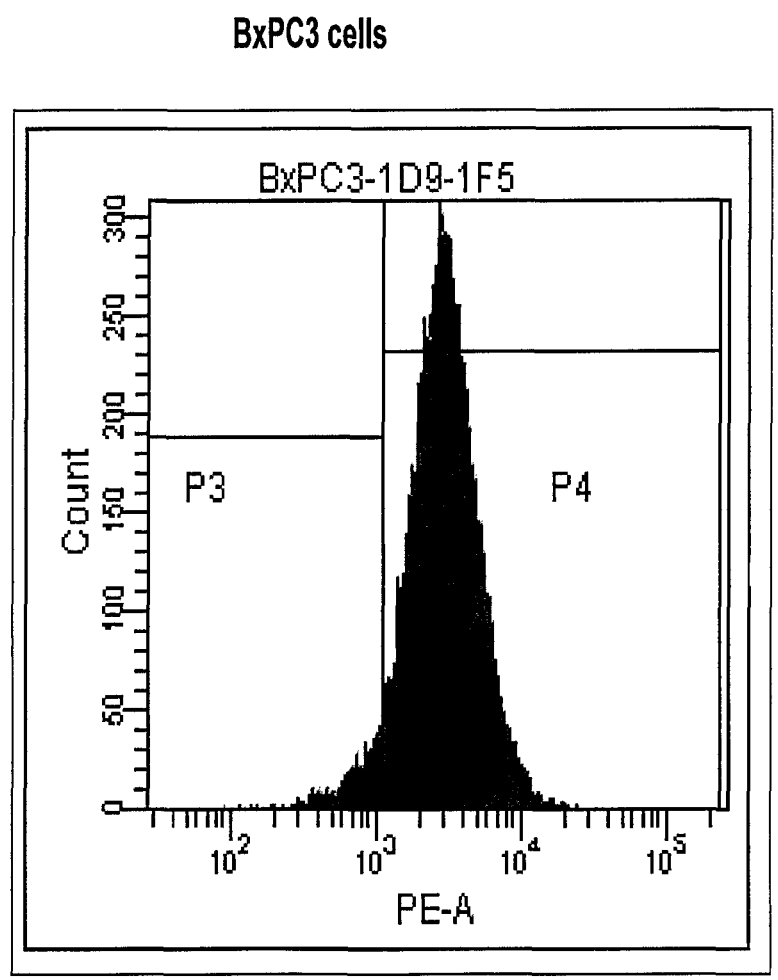
Figure 23A:
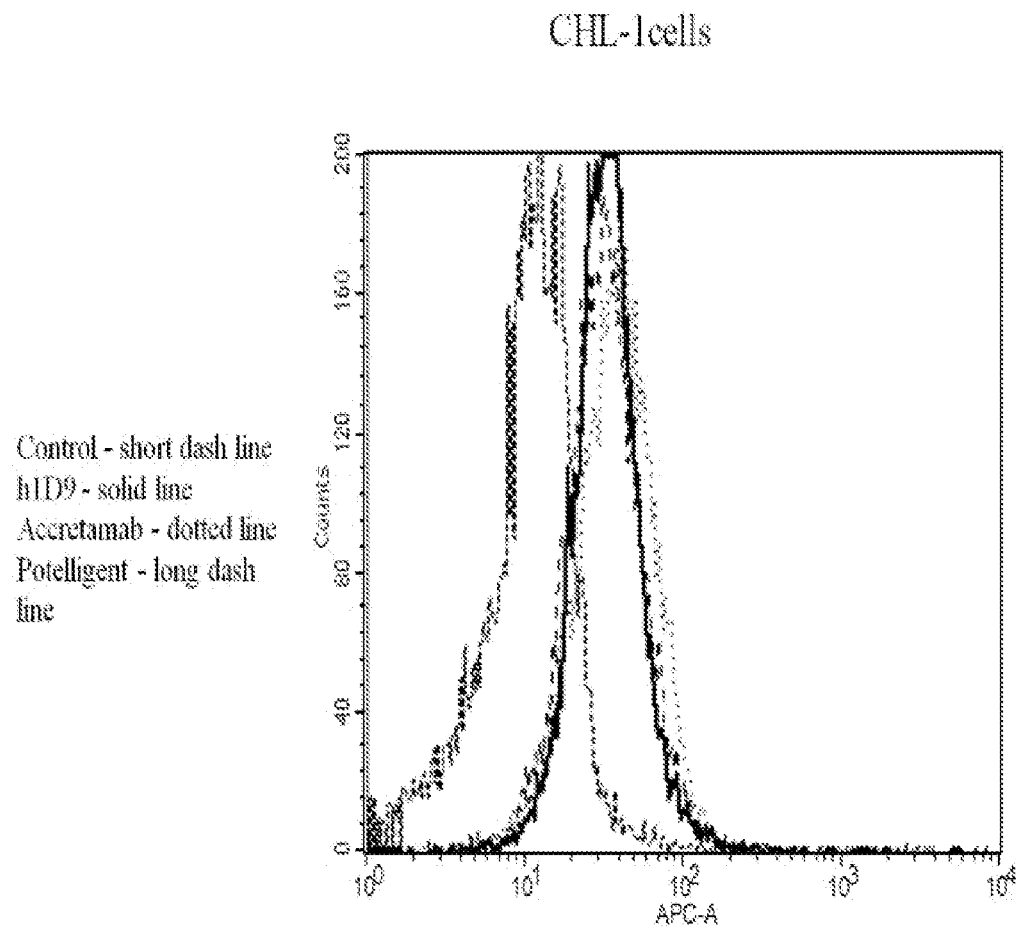
FIG. 23. (a) The humanized 1D9 antibody, the humanized ACCRETAMAB™ 1D9 antibody, and humanized POTELLIGENT™ antibody recognize HER3 on human CHL-1 melanoma cells as assessed by flow cytometric analyses. (b) The humanized 1D9 antibody, the humanized ACCRETAMAB™ 1D9 antibody, and humanized POTELLIGENT™ antibody recognize HER3 on human BxPC3 pancreatic cancer cells as assessed by flow cytometric analyses.
Figure 23B:
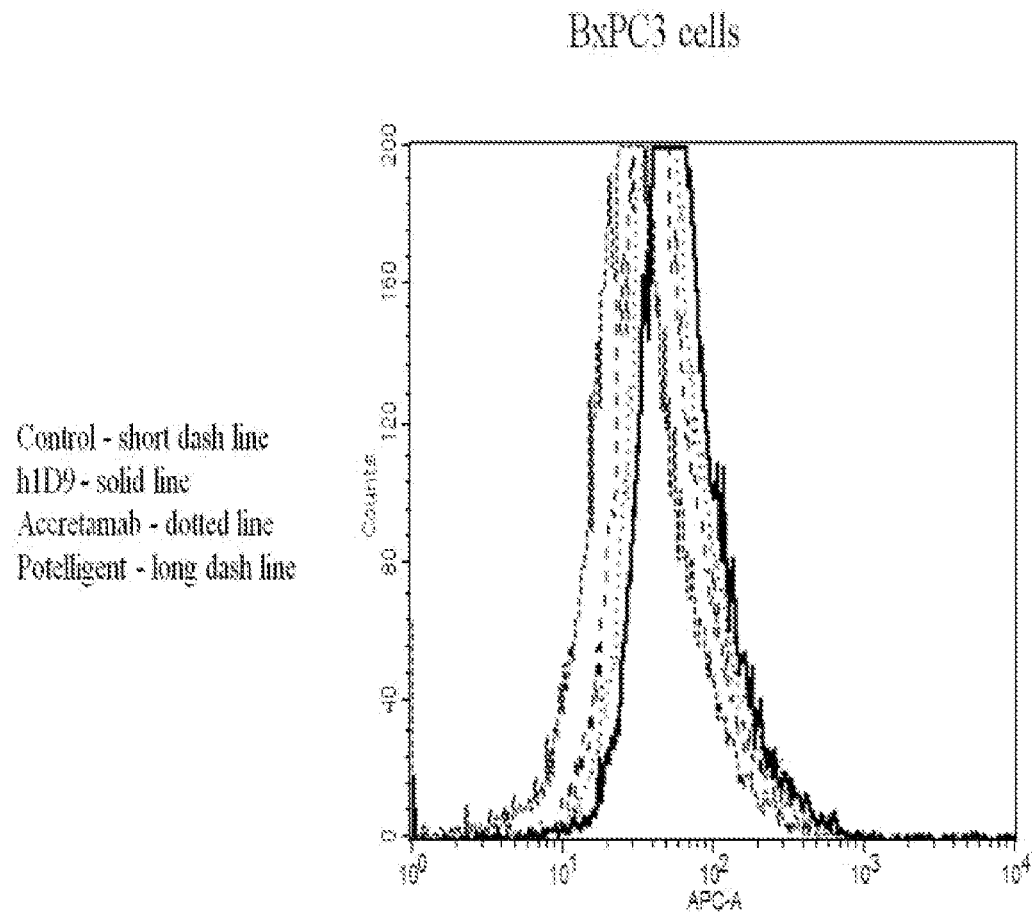

Results:

The histograms for antibody binding to each cell line demonstrate specific binding of the humanized anti-HER3 mAbs by the shift to the right from the isotype control antibody histogram. The murine 1D9 antibody (M5.1D9.1F5) bound human HER3 expressed by MCF7 human breast cancer cells and BxPC3 human pancreatic tumor cells. See FIG. 22. The humanized 1D9 antibody, the humanized 1D9 ACCRETAMAB™ antibody and the humanized 1D9 POTELLIGENT™ antibody all bound human HER3 expressed on CHL-1 human melanoma cells and BxPC3 human pancreatic tumor cells. See FIG. 23.

Conclusions:

The murine 1D9 antibody (M5.1D9.1F5) antibody recognized human HER3 expressed by MCF7 human breast cancer cells and BxPC3 human pancreatic tumor cells. See FIG. 22. The humanized 1D9 antibody, the humanized 1D9 ACCRETAMAB™ antibody and the humanized 1D9 POTELLIGENT™ antibody all recognize human HER3 expressed on the CHL-1 (melanoma) and BxPC3 (pancreatic) human cancer cell lines. See FIG. 23.

3.3 Inhibition of Heregulin Induced Tumor Cell Proliferation with M5.1D9 Inhibition of Heregulin Induced Cell Proliferation Objective:

To determine if any of the anti-human HER3 antibodies can inhibit heregulin-1β induced cell proliferation in either the MCF7 or BxPC3 cell lines.

Reagents:

Complete Media: RPMI, 10% FBS, glutamine

Cell lines:
  MCF7
  BxPC3—ATCC

Antibodies:
  Murine 15D5 antibody (M5.15D5.2A1.1H10)
  Murine 1D9 antibody (M5.1D9.1F5)
  Murine 24H5 antibody (M5.24H5.C2)
  Humanized 1D9 antibody
  Humanized 1D9 ACCRETAMAB™ antibody
  Humanized 1D9 POTELLIGENT™ antibody Cell Titer 96 Non-Radioactive Cell Proliferation Assay (MTT)—Promega G4000.

Method:

$1 \times 10^3$ or $1 \times 10^4$ cells/well of either the MCF7 or the BxPC3 cell lines, respectively, were added to each well of a flat-bottomed 96-well plate in complete media containing 10% serum and incubated overnight at 37° C. The media was removed and replaced with serum-free RPMI. 10 µl of each antibody to be screened was added in quadruplicate to the appropriate wells. The antibodies and cells were incubated for one hour at 37° C. 30 ng/ml of heregulin-1β was added to each well. For the humanized antibody experiments, 100 ng/ml heregulin was used for comparability to the conditions used in p-HER3 and pAkt assays. The plates were incubated for 72 hours at 37° C. Proliferation was determined using a MTT kit by Promega and the plates were analyzed on the ENVISION™ 2103 Multilabel Reader and the data analyzed in Microsoft EXCEL™. The data was graphed as the percentage of heregulin induced growth versus antibody concentration.

Figure 24:
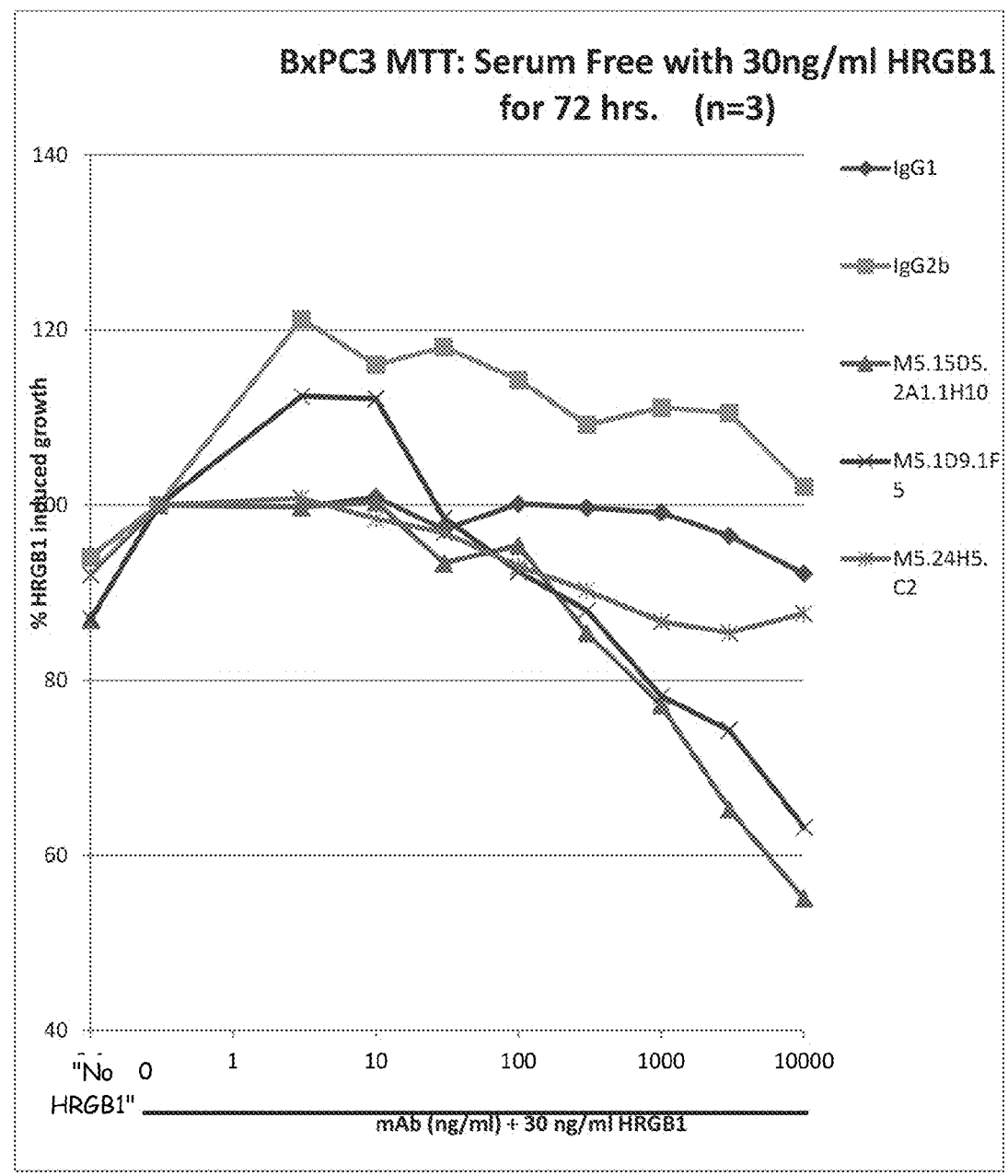
FIG. 24. The murine 1D9 antibody (M5.1D9.1F5) and murine 15D5 antibody (M5.15D5.2A1.1H10) inhibit heregulin induced BxPC3 pancreatic cancer cell proliferation.
Figure 25:
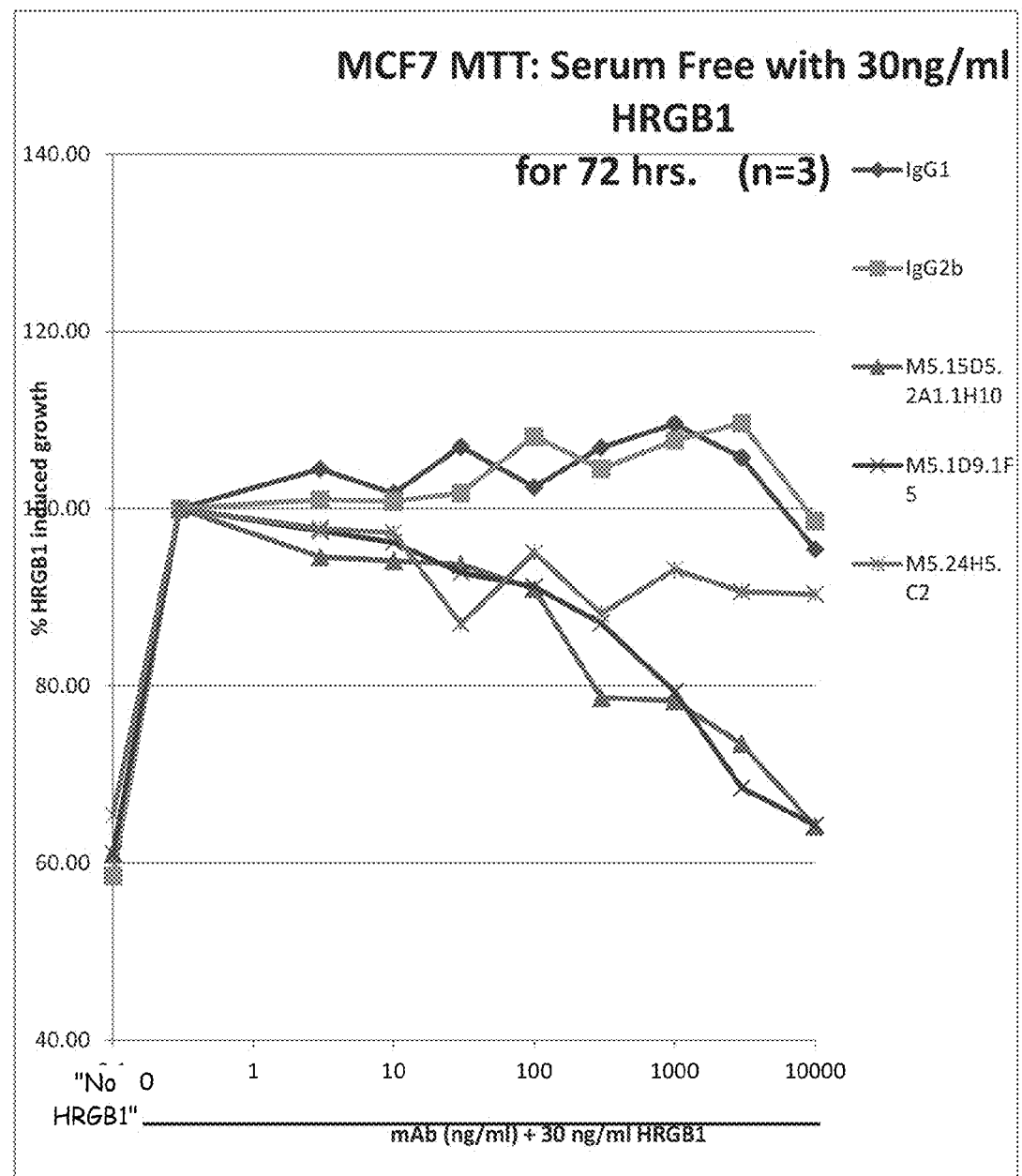
FIG. 25. Themurine 1D9 antibody (M5.1D9.1F5) and murine 15D5 antibody (M5.15D5.2A1.1H10) antibody inhibit heregulin induced MCF-7 breast cancer cell proliferation.
Figure 26:
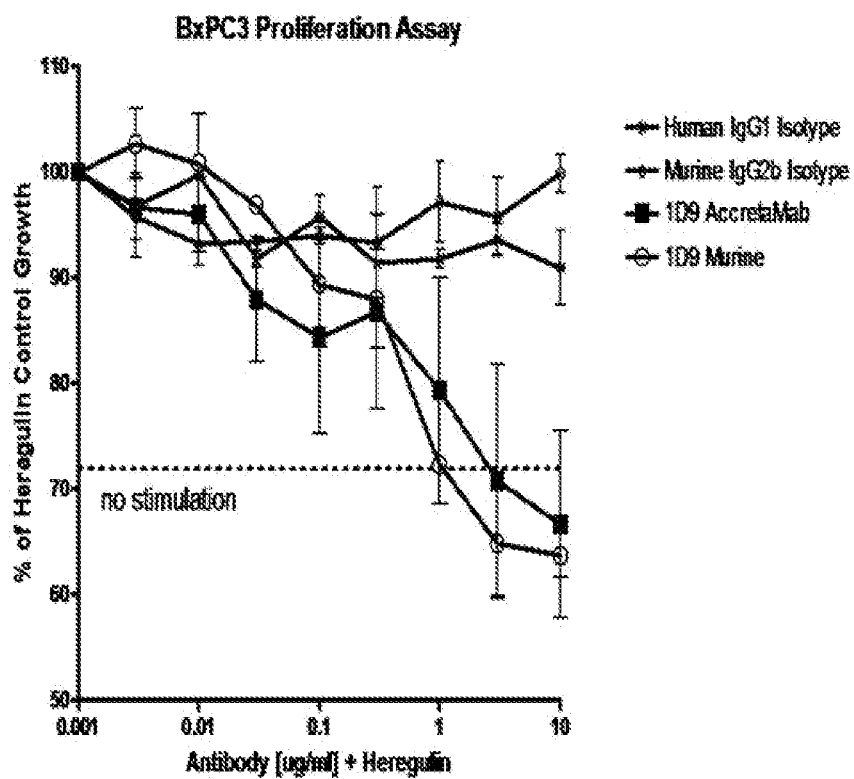
FIG. 26. The humanized 1D9 ACCRETAMAB™ antibody and murine 1D9 antibody inhibit heregulin induced BxPC3 pancreatic cancer cell proliferation.

Results:

There was a good induction of proliferation in response to heregulin-1β with the MCF7 cells (approximately 40%). However, there was a limited response in the BxPC3 cells (approximately 10%). The murine 15D5 antibody (M5.15D5.2A1.1H10) and murine 1D9 antibody (M5.1D9.1F5), both inhibited the heregulin-1β induced MCF7 cell proliferation. The murine 15D5 antibody (M5.15D5.2A1.1H10) and murine 1D9 antibody (M5.1D9.1F5) actually inhibited BxPC3 proliferation below the level of cells alone. The humanized 1D9 ACCRETAMAB™ antibody demonstrated similar inhibition protency as the murine 1D9 antibody (M5.1D9.1F5) in BxPC3 cells. See FIG. 24, FIG. 25 and FIG. 26.

Conclusions:

The murine 15D5 antibody (M5.15D5.2A1.1H10) and murine 1D9 antibody (M5.1D9.1F5) were comparable in their ability to inhibit MCF7 and BxPC3 cell proliferation. See FIG. 24 and FIG. 25. The humanized 1D9 ACCRETAMAB™ antibody inhibits BxPC3 tumor cell proliferation. See FIG. 26.

3.4 Inhibition of Tumor Cell Invasion

Objective:

The purpose of this study was to determine if any of the anti-human HER3 antibodies could inhibit tumor cell invasion after heregulin stimulation.

Method:

Human tumor cell lines previously profiled for HER family expression were used in the invasion assay. BXPC3 cells were shown to express both HER-2 and, to a lesser extent, HER3. The effect of HER3 antibodies on BXPC3 cell invasion was determined using the Trevigen CULTREX™ cell invasion assay (catalogue number 3455-096-K). Briefly, BXPC3 cells were grown to 60% confluence, serum starved overnight, then removed from the culture flask with VERSENE™ chelating agent (EDTA) and trypsin. Cells were washed with quench buffer (RPMI+2% BSA), viability was determined using trypan blue dye exclusion, and cells were suspended in RPMI medium containing no FBS or BSA at 1 million cells/ml for use in the assay. Antibodies were incubated with cells for 1 hour at 37° C. prior to addition to the upper wells of the invasion plate. The bottom wells contained RPMI medium+ 10% non-heat inactivated FBS. One column of bottom wells did, however, receive RPMI without FBS to account for random migration. Cells that migrated were labeled with calcein-am and the bottom chamber read on a VICTOR™ IV plate reader. The fluorescence (RFU) represents the amount of cells that migrated. The RFU for each antibody was divided by the RFU for the isotype control antibody and multiplied by 100 to obtain the "% Control invasion" value.

Figure 27:
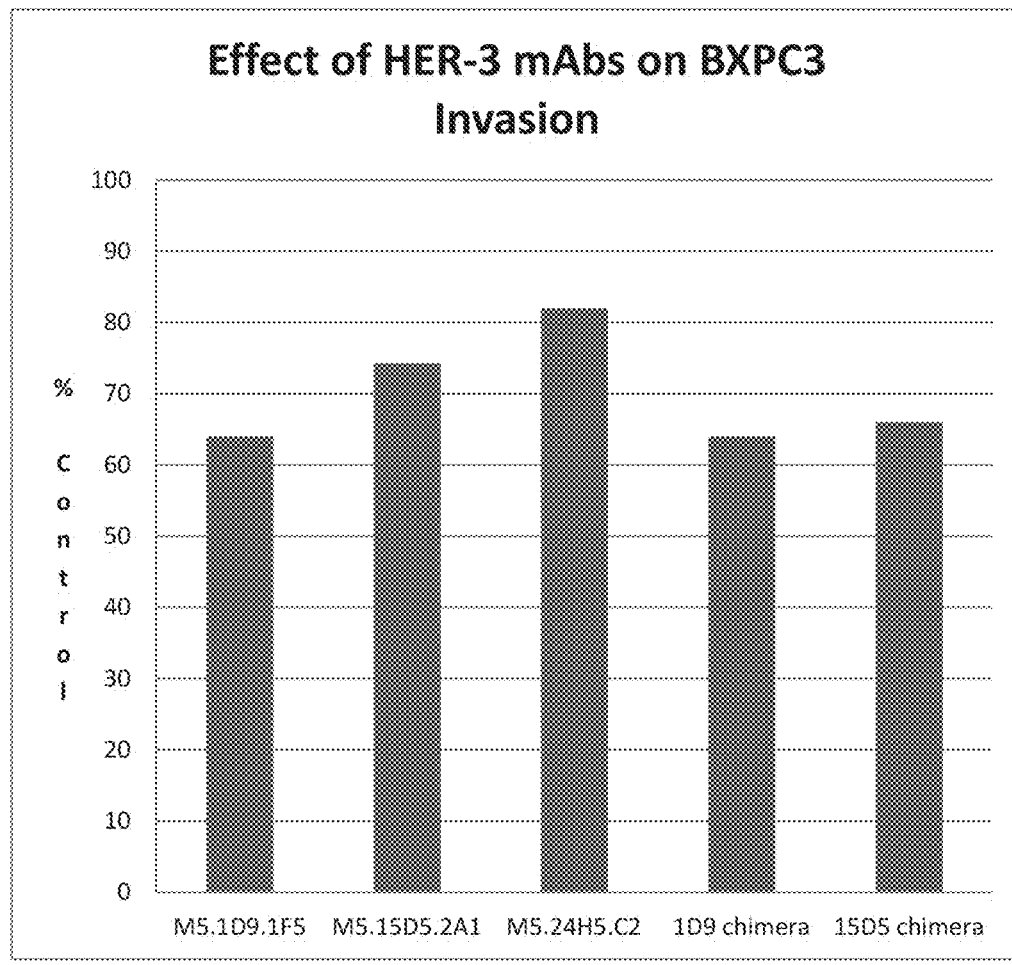
FIG. 27. The murine 1D9 antibody (M5.1D9.1F5), the murine 15D5 antibody (M5.15D5.2A1), the murine-24H5 antibody (M5.24H5.C2), the chimeric 1D9 antibody and the chimeric 15D5 antibody inhibit heregulin induced BxPC3 pancreatic cancer cell invasion.

Results:

The murine 1D9 antibody (M5.1D9.1F5), the chimeric 1D9 antibody and the chimeric 15D5 antibody all inhibited BXPC3 cell invasion by 40%. The murine 15D5 antibody (M5.15D5.2A1.1H10) antibody inhibited cell invasion by 30%. The murine 1D9 antibody (M5.1D9.1F5) inhibited tumor cell invasion by 20%. See FIG. 27.

Conclusions:

The murine 1D9 antibody (M5.1D9.1F5), the chimeric 1D9 antibody and the chimeric 15D5 antibody inhibited tumor cell invasion. See FIG. 27.

3.5 Binding of the Murine 1D9 antibody Antibody to Human Tumor Cells Caused HER3 Receptor Internalization Objective:

To determine if any of the anti-human HER3 antibodies cause internalization of the HER3 receptor upon binding.

Reagents:

Staining buffer: PBS, 0.2% BSA, 0.1% sodium azide

Antibodies:
  IgG1 control—R&D Systems MAB002
  IgG2b control—R&D Systems MAB004
  Murine 15D5 antibody (M5.15D5.2A1.1H10)—(3.19 mg/ml)
  Hz10—(9.82 mg/ml)
  Humanized 1D9 antibody—(1.88 mg/ml)

Secondary Antibodies:
  PE goat anti-mouse IgG (H+ L)—Caltag Laboratories M30004-4
  Goat anti-human IgG ALEXAFLUOR647™—Invitrogen A21445

Method:

100 µl of $5 \times 10^6$ cells/ml were added to flow cytometry tubes containing 10 µg of anti-HER3 antibodies. Each antibody was added in duplicate. One tube of each antibody was incubated on ice, while the other tube was at 37° C. After 2 hours, the cells were washed with 1 ml of staining buffer and counter stained with PE-labelled goat anti-mouse secondary antibody for 30 minutes. Following an additional wash with 1 ml of staining buffer, the cells were analyzed on a FACS-CANTO™ cytometer. Data analysis was performed using FACSDIVA™ software, developed by BD Biosciences. Cell populations were gated using forward versus side scatter and histograms of fluorescent intensities were generated.

Results:

The murine 15D5 antibody (M5.15D5.2A1.1H10) and humanized 1D9 antibody were screened for the internalization of the HER3 receptor on CHL-1 cells. After incubation at 37° C., the antibodies was not detected which indicated the receptor was not on the cell surface. See FIG. 28.

Conclusions:

The murine 15D5 antibody (M5.15D5.2A1.1H10) and humanized 1D9 antibody caused internalization of the HER3 receptor on binding to the receptor. See FIG. 28.

3.6 The Murine 1D9 antibody Cross-Reacts with Murine HER3 on Murine Tumor Cells

Objective:

To determine if any of the anti-human HER3 antibodies cross react with a murine HER3 positive cell line.

Reagents:

FACS Buffer: PBS, 0.2% BSA, 0.1% sodium azide

Antibodies:
  EGFR—Bioscience 44783M
  HER2—Bioscience AH01011
  HER3—Upstate 05-471
  Murine 15D5 antibody
  Murine 1D9 antibody (M5.1D9.1F5)
  Murine 24H5 antibody (M5.24H5.C2)

Cell Lines:
  B16
  B16F10

ZENON™ Labeling Kits:
  Mouse IgG1 PE—Invitrogen Z25021
  Mouse IgG1 APC—Invitrogen Z25051
  Mouse IgG2b APC—Invitrogen Z25151

Method:

Commercially available anti-human EGFR and HER2 antibodies were provided. A commercially available HER3 antibody represented by the provider to recognizes human HER3 was provided. The murine 15D5 antibody, murine 1D9 antibody (M5.1D9.1F5), murine 24H5 antibody (M5.24H5.C2) antibodies were also provided. These antibodies were labeled with either PE or APC using the ZENON™ labeling kits (Invitrogen). $5 \times 10^6$ B16, or B16F10, murine melanoma cells were added to flow cytometry tubes containing the labeled anti-HER3 antibodies. Cells and antibodies were incubated for 30 minutes on ice in the dark, washed and resuspended in FACS buffer. Cells were then analyzed on a FACSCANTO™ flow cytometer. Data analysis was performed using FACSDIVA™ software, developed by BD Biosciences. Cell populations were gated using forward vs. side scatter and histograms of fluorescent intensities were generated.

Results:

The commercially available EGFR, HER2 and HER3 antibodies did not recognize these receptors on the murine cells surface (data not shown). The murine 15D5 antibody, the murine 1D9 antibody (M5.1D9.1F5), and the murine 24H5 antibody (M5.24H5.C2) all recognized HER3 on the surface of B16 and B16F10 cells. See FIG. 29.

Conclusions:

The murine 15D5 antibody, the murine 1D9 antibody (M5.1D9.1F5), and the murine 24H5 antibody (M5.24H5.C2) cross react with murine HER3. See FIG. 29.

Example 8

1. Summary

Mouse models of human cancer have been extensively utilized in the preclinical setting to demonstrate the in vivo activity of new anti-cancer drugs. In the present study, mouse anti-HER3 monoclonal antibodies (mAbs) were evaluated in a mouse syngeneic pulmonary colonization model and in several human xenograft models to establish activity and prioritize lead candidates for further development applicable to human clinical trials.

C57BL/6 mice were given a single i.v. injection of B16F10 melanoma cells to assess pulmonary colonization in the lung with or without anti-HER3 mAb treatment. Murine 1D9 antibody, administered at 50 mg/kg i.p. on Day 3 and 25 mg/kg i.p. on Days 7 and 11 post B16F10 injection, caused a significant reduction ($p<0.001$) in lung weights at study termination, i.e. Day 20 post B16F10 injection. Murine 15D5 antibody also inhibited tumor cell colonization into the lung ($p<0.05$), however the lower dose regimen of 25 and 5 mg/kg, i.p. had greater activity compared to the 50/25 mg/kg dose regimen. Both mouse 1D9 and 15D5 mAbs were subsequently evaluated in xenograft models to assess activity against human tumors.

Mouse anti-HER3 mAbs delayed growth of advanced HER3+ human xenografts implanted into CB-17 SCID mice. Twice weekly treatment with murine 1D9 antibody or murine 15D5 antibody at 0.5 to 100 mg/kg, i.p., resulted in dose-dependent and statistically significant decreases ($p<0.001$ at >5 mg/kg) in CHL-1 melanoma tumor growth. Similar activity was observed against BxPC3 pancreatic tumor growth post subcutaneous implantation in CB-17 SCID mice (p<0.001 at >5 mg/kg).

The 1D9 antibodies and 15D5 antibodies, retained significant and dose-dependent anti-tumor activity in the CHL-1 melanoma xenograft model at doses ranging from 5 to 50 mg/kg (p<0.001). Moreover, humanized 1D9 RR antibody and the humanized 1D9 RR ACCRETAMAB™ antibody had significant and equally potent activity at doses of 5, 25 and 50 mg/kg (p<0.001).

In the subcutaneous and orthotopic BxPC3 xenograft models, 50 mg/kg of chimeric 1D9 antibody or humanized 15D5 antibody caused significant inhibition of tumor growth up until study termination (p<0.001), while 50 mg/kg humanized 1D9 RR antibody showed a significant (p<0.001) but transient effect on tumor growth in the subcutaneous BxPC3 model. Differences in the duration of growth inhibition is likely due to study-to-study variation (i.e., characteristics of implanted BxPC3 fragment), nevertheless efficacy of the genetically engineered mAbs against tumor growth was demonstrated.

Finally, evaluation of humanized 1D9 RR antibody, the humanized 1D9 ACCRETAMAB™ antibody, and the humanized 1D9 POTELLIGENT™ antibody in the NCI-N87 gastric model indicated activity of the enhanced mAbs against CHL-1 melanoma xenografts.

2. Introduction

In this study, murine parental or humanized HER3 monoclonal antibodies were evaluated for anti-tumor activity against advanced HER3+ human xenografts, i.e., CHL-1 melanoma, BxPC3 pancreatic, and NCI-N87 gastric tumors. A syngeneic pulmonary colonization model using mouse B16F10 melanoma cells was included in preliminary evaluations to assess activity of the murine parental anti-HER3 mAbs.

3. Methods 3.1. Experimental Preparation(s)

The models used in these studies conform to UK standards of animal care, as laid down by the Home Office.

The human xenograft tumor model studies were performed in 6-8 week old female CB-17 SCID mice weighing approximately 15-20 grams (Taconic, Indiana, Ind.). Mice were 10-12 weeks old at the time of study initiation. The syngeneic lung colonization model study was performed in 6-8 week old C57B1 female mice weighing approximately 15-20 g.

Mouse (B16F10), and human (BxPC3, NCI N87 and CHL-1) tumor cell lines were obtained from a cell repository.

3.2. Experimental Protocol(s)

3.2.1. Mouse B16F10 Melanoma Syngeneic Model

C57BL/6 female mice were injected i.v. with $2 \times 10^5$ B16F10 cells. Mouse anti-HER3 antibodies or isotype controls were administered i.p. at 50 or 25 mg/kg on Day 3, and subsequently at 25 or 5 mg/kg i.p. on Days 7 and 11 post tumor cell injection. GEMZAR™ (NDC 0002-7502-01; gemcitabine) was administered i.v. on Day 3 post injection Animals were euthanized on Day 20 and lungs harvested for wet weight measurements.

3.2.2. Human CHL-1 Melanoma Xenograft Model

CHL-1 cells ($5 \times 10^5$ to $5 \times 10^6$) in MATRIGEL™ were injected subcutaneously (s.c.) into the flanks of CB-17 SCID mice. Once tumor xenografts reached mean volume of 80-120 mm³, mice were randomized into therapeutic groups (n=6 mice per group) and administered anti-HER3 mAbs or isotype controls. Doses of 0.5 to 100 mg/kg were given twice weekly, i.p. Vehicle-treated mice served as the control group for tumor growth.

Tumor width (W) and length (L) were measured weekly with manual callipers, and tumor volumes (V) were calculated using the following formula: $V=\frac{1}{2}(L \times W^2)$. The study was terminated when mean tumor volume of isotype control exceeded 1000 mm³

3.2.3. Human BxPC3 Pancreatic Xenograft Model: Subcutaneous and Orthotopic Implantation BxPC3 cells ($5 \times 10^6$/mouse) were injected s.c. into CB-17 SCID mice that served as donors. BxPC3 tumor bearing donor mice were euthanized when tumors reached volumes of 800-1000 mm³; tumors were then harvested and divided into 3 mm³ tumor fragments. Freshly harvested BxPC3 tumor fragments were implanted s.c. into the flank of recipient mice. In the orthotopic model, fragments were surgically implanted into the pancreas of recipient mice.

Once tumor xenografts of recipient mice reached mean volume of 80-120 mm³, mice were randomized into therapeutic groups (n=6 mice per group) and treated with anti-HER3 mAbs or isotype controls. Doses of 0.5 to 100 mg/kg were given twice weekly, i.p. (subcutaneous implant model) or i.v. (orthotopic implant model). Vehicle-treated mice served as the control group for tumor growth.

Tumor volume was measured weekly with manual callipers as described above. In the orthotopic model, tumors were measured by ultrasound, and the volume determined using a VISUAL SONICS VEVO™ 770 image analysis system.

3.2.4. Human NCI-N87 Gastric Xenograft Model

NCI-N87 cells were implanted into the right flank of donor mice at $\sim 1 \times 10^6$ cells per animal. Tumor fragments were collected from donor mice and implanted s.c. into the flank of 10-12 week old recipient mice. Treatment with mouse anti-HER3 mAbs was initiated when tumor xenografts reached a mean volume of 50-80 mm³, or on Day 29 post fragment implantation. Treatment with the genetically engineered anti-HER3 mAbs was initiated when tumor xenografts reached mean volume of 80-100³ mm, or Day 15 post transplantation.

Tumor volume was measured with manual callipers as described above.

3.3. Drugs and Materials

Anti-HER3 antibodies and isotype controls used in this study are listed in the table below. Also included is the abbreviated nomenclature contained herein. All antibodies were formulated and prepared in phosphate buffered saline, pH 7.0, for dosing.

TABLE 16

| Anti-HER3 mAb (alternative designation; Isotype) | Nomenclature in Example 8 and other selected examples |
|---|---|
| Murine 1D9 antibody (M5.1D9.1F5; IgG2b) | m1D9 |
| Murine 15D5 antibody (M5.15D5.2A1; IgG1) | m15D5 |
| Chimeric 1D9 antibody (IgG1) | Ch1D9 |
| Humanized 15D5 antibody (IgG1) | h15D5 |
| Humanized 1D9 RR antibody (H6L2; IgG1) | h1D9 RR wt |

TABLE 16-continued

| Anti-HER3 mAb (alternative designation; Isotype) | Nomenclature in Example 8 and other selected examples |
|---|---|
| Humanized 1D9 RR POTELLIGENT ™ antibody (H6L2; IgG1) | h1D9 RR Potelligent |
| Humanized 1D9 RR ACCRETAMAB ™ (H6L2; IgG1) | H1D9 RR Accretamab |
| Isotype Controls | |
| Mouse IgG1; MOPC21 | N/A |
| Mouse IgG1; TIB-9 | N/A |
| Mouse IgG2b; 6x His | N/A |
| Human IgG1; α-malaria | N/A |
| Human IgG1; α-factor X | N/A |

3.4. Data Analysis

Group mean and standard error of mean were determined for the control and treatment groups. Data were graphed and analyzed using 2-Way ANOVA with Bonferroni post test for human xenograft models or 1-Way Anova with Dunnett's post test for the mouse syngeneic model (GRAPHPAD™ PRISM™ software, v.5).

4. Results 4.1. In Vivo Efficacy of Mouse Anti-HER3 mAbs

The murine 1D9 antibody and the murine 15D5 antibody, were evaluated in a mouse syngeneic model, and in several human xenograft models to demonstrate efficacy against tumor cell growth.

4.1.1. Mouse B16F10 Melanoma Syngeneic Model

Treatment with anti-HER3 murine 1D9 antibody decreased B16F10 tumor colonization in the lung of C57BL/6 mice. The 50/25 mg/kg group had a significant decrease in lung weight compared to the isotype control group ($p<0.01$) (FIG. 30). Treatment with the murine 15D5 antibody also demonstrated reduced tumor colonization in the lung in the 25/5 mg/kg group as compared to the isotype control ($p<0.05$; FIG. 31).

4.1.2. Human CHL-1 Melanoma Xenograft Model

CB-17 SCID mice administered the anti-HER3 murine 1D9 antibody or the murine 15D5 antibody at doses ranging from 5 to 100 mg/kg i.p., twice weekly, had dose-dependent and statistically significant decreases ($p<0.001$) in human CHL-1 tumor growth compared to their respective isotype control groups (FIG. 32 and FIG. 33).

4.1.3. Human BxPC3 Pancreatic Xenograft Model

CB-17 SCID mice administered the murine 1D9 antibody at doses of 0.5 to 50 mg/kg i.p., twice weekly, had significant decreases in BxPC3 tumor growth compared to the isotype control group ($p<0.001$ at >5 mg/kg) (FIG. 36). Similarly, treatment with the murine 15D5 antibody resulted in decreased BxPC3 tumor growth in the 5 to 50 mg/kg groups compared to the isotype control group ($p<0.001$) (FIG. 35).

4.1.4. Human NCI-N87 Gastric Xenograft Model

CB-17 SCID mice administered murine 1D9 antibody at doses of 75 or 100 mg/kg, i.p., twice weekly, had a significant decrease in tumor volume compared to the vehicle control group ($p<0.001$) (FIG. 36). The effect of the murine 15D5 antibody on NCI-N87 tumor growth as compared to the vehicle and isotype control groups is shown in FIG. 37.

4.2. In vivo Efficacy of Chimeric and Humanized Anti-HER3 mAbs

The humanized 15D5 antibody, the chimeric 1D9 antibody, and humanized 1D9 RR antibody were generated and assessed. Based on the activity of the humanized 1D9 RR antibody in various in vitro and in vivo models, further engineering was employed to enhance antibody dependent cellular cytotoxicity (ADCC) and complement dependent cytotoxicity (CDC) attributes of the IgG1 mAb (humanized 1D9 RR ACCRETAMAB™ antibody), or CDC only (humanized 1D9 RR POTELLIGENT™ antibody). Below is a summary of the activity of the various antibodies in the human xenograft models.

4.2.1. Human CHL-1 Xenograft Model

CB-17 SCID mice administered chimeric 1D9 antibody at 5 to 50 mg/kg i.p., twice weekly, had dose-dependent decreases in CHL-1 tumor growth compared to the isotype control group. On Day 24 post implantation, the decrease was statistically significant in the and 50 mg/kg groups ($p<0.05$) and on Day 27 post implantation significant decreases were observed in all treatment groups ($p<0.001$) (FIG. 38). Similar findings were observed in the humanized 15D5 antibody treatment groups (FIG. 39).

The humanized H1D9 RR antibody, humanized H1D9 RR ACCRETAMAB™ antibody and humanized H1D9 RR POTELLIGENT™ antibody were evaluated in the CHL-1 xenograft model at doses of 5 to 50 mg/kg. The humanized H1D9 RR antibody, humanized H1D9 RR ACCRETAMAB™ antibody and humanized H1D9 RR POTELLIGENT™ antibody had similar profiles of activity. Significant decreases in tumor growth were observed at all dose levels beginning on Day 29 post implantation until study termination on Day 34 ($p<0.001$) (FIG. 40, FIG. 41 and FIG. 42).

4.2.2. Human BxPC3 Xenograft Models (Subcutaneous and Orthotopic Implant)

CB-17 SCID mice administered ch1D9 at 0.5 to 50 mg/kg i.p., twice weekly, post subcutaneous BxPC3 implantation had statistically significant, dose-dependent decreases in tumor growth beginning on Day 33 in the 50 mg/kg group ($p<0.001$) and in the 5 and 0.5 mg/kg groups ($p<0.01$). Significantly lower tumor volume was sustained until Day 36 in the 50 mg/kg group ($p<0.001$) (FIG. 43). Treatment with h15D5 at 0.5 to 50 mg/kg resulted in tumor growth delay in the 50 mg/kg group, detectable on Days 33 and 36 post implantation ($p<0.01$) (FIG. 44). Characteristics of the observed decrease in BxPC3 tumor growth following twice weekly treatment with humanized 1D9 RR antibody at 0.5 to 50 mg/kg are shown in (FIG. 45).

The chimeric 1D9 antibody and humanized 15D5 antibody were evaluated in the BxPC3 surgical orthotopic implantation model which is considered to be more predictive of clinical outcome relative to subcutaneous implantation. Treatment with 50 mg/kg chimeric 1D9 antibody or humanized 15D5 antibody twice weekly by the i.v. route resulted in significant tumor growth delay compared to the isotype control from weeks 5 through 7 post implantation ($p<0.01$) (FIG. 46).

4.2.3. Human NCI-N87 Gastric Xenograft Model

The anti-tumor activity of the humanized H1D9 RR antibody, humanized H1D9 RR ACCRETAMAB™ antibody and humanized H1D9 RR POTELLIGENT™ antibody was assessed in the human NCI-N87 gastric model. CB-17 SCID mice were administered 50 mg/kg i.p., twice weekly. Humanized H1D9 RR ACCRETAMAB™ antibody administered at 50 mg/kg resulted in decreased tumor volume that reached statistical significance on Day 44 post implantation ($p<0.05$) (FIG. 47).

5. Discussion

Mouse models of human cancer have been extensively utilized in the preclinical setting to demonstrate the in vivo activity of new anti-cancer drugs. In the present study, mouse anti-HER3 monoclonal mAbs were evaluated in a mouse syngeneic pulmonary colonization model and in several human xenograft models to establish activity and prioritize lead candidates for further development applicable to human clinical trials.

Mouse anti-HER3 mAbs caused a significant reduction in mouse B16F10 tumor cell colonization in the lungs of C57BL/6 mice. The effective dose regimen of murine 1D9 antibody was 50/25 mg/kg, i.p., whilst the 25/5 mg/kg, i.p. regimen with murine 15D5 antibody had greater efficacy compared to the higher dose level. Both mouse anti-HER3 mAbs were subsequently evaluated in xenograft models to assess activity against human tumors.

Mouse anti-HER3 mAbs delayed growth of established tumors in advanced HER3+ human xenografts. Treatment with either murine 1D9 antibody or murine 15D5 antibody at doses >5 mg/kg, twice weekly post CHL-1 melanoma cell implantation, resulted in significant and dose-dependent decreases in tumor growth. Similar activity was observed in the subcutaneous BxPC3 pancreatic xenograft model.

The 1D9 antibodies and 15D5 antibodies retained dose-dependent, anti-tumor activity at ≥5 mg/kg in the CHL-1 melanoma xenograft model. Moreover, treatment with the humanized 1D9 RR antibody or the humanized 1D9 RR ACCRETAMAB™ antibody at 5 mg/kg resulted in tumor growth delay comparable to doses ≥25 mg/kg.

In the subcutaneous and orthotopic BxPC3 xenograft models, 50 mg/kg chimeric 1D9 antibody or humanized 15D5 antibody caused significant inhibition of tumor growth up until study termination, while 20 mg/kg humanized 1D9 RR antibody showed a significant effect on tumor growth in the subcutaneous BxPC3 model. Efficacy of the antibodies against tumor growth was demonstrated.

Finally, evaluation of the humanized 1D9 RR antibody, the humanized 1D9 RR ACCRETAMAB™ antibody and the humanized 1D9 RR POTELLIGENT™ antibody in the NCI-N87 gastric model indicated some activity of the enhanced mAbs compared to activity against CHL-1 melanoma xenografts.

6. Conclusion

Therapy with murine parental and/or humanized HER3 monoclonal antibodies, dosed twice weekly at concentrations ranging from 0.5 to 100 mg/kg, was able to delay growth of established HER3+ human tumors in CHL-1 melanoma and BxPC3 pancreatic human xenograft models.

Example 9

1. Summary

Both antibody dependent cell-mediated cytotoxicity (ADCC) assays as well as complement-mediated cytotoxicity (CDC) assays were used to evaluate the functionality of the wild-type anti-HER3 antibodies as well as the enhanced versions of these antibodies.

This example describes the in-vitro assays used to access the functionality of the wild-type and enhanced versions of the antibodies. These assays used a variety of HER3 expressing "target" cells to evaluate the ability of the antibody to bind its target and then follow with the addition of complement or "effector" cells to evaluate the functional Fc region of the antibody.

2. Introduction

These examples show the increased functionality/potency of the anti-HER3 "enhanced antibodies" over the non-enhanced "wild-type" antibody.

3. Methods 3.1. Experimental Preparation(s)
3.2. Experimental Protocol(s)
3.2.1 Antibody Dependent Cell-Mediated Cytotoxicity Purified human peripheral blood mononuclear cells were profiled as effector cells in these ADCC assays. Briefly, human whole blood, collected with sodium heparin, was purified using density gradient separation centrifuge tubes (UNI-SEPMAXT™ from Accurate Surgical and Scientific). These purified peripheral blood mononuclear cells were then washed and re-suspended in RMPI 1640 without Phenol Red+10% FBS ($1 \times 10^7$ cells/ml for T:E ratio of 1:50). The HER3 receptor positive cells (HER3BACMAM™ transduced HEK293 MSRII or CHL-1 cells) were then loaded with europium for use as target cells. The transduced cells served as a high HER3-expressing cell line, while the CHL-1 cells served as a low-expressing cell line. These loaded target cells were resuspended with RMPI 1640 without Phenol Red+10% FBS to $8 \times 10^5$ cells/ml.

Several anti-HER3 antibodies (25 ul/well) were loaded into a 96-well round-bottom plate. Europium loaded target cells (25 ul/well) were then added into the plate containing antibody, and incubated at 37° C. and 5% $CO_2$ for 30 minutes. Following this 30 minute incubation, 100 µl/well of effector cells were added to the plate and returned to the incubator for an additional 2 hours. The measurement of specific cell lysis was carried out by removing 25 ul/well of supernatant from this experimental plate and transferring it into a 96-well maxisorp plate containing 100 ul/well of DELFIA™ enhancement solution. Following a five minute incubation at room temperature, the plate was then read using time-resolved fluorescence on a Wallac VICTOR™ V plate reader. Any europium released from lysed target cells into the surrounding supernatant (cell cytotoxicity) was measured as fluorescent units. The values are converted into percent specific-lysis and plotted using GRAPHPAD™ PRISM™ software as percent lysis vs antibody concentration. The formula used for calculating percent specific cytotoxicity was:

$$\% \text{ Cytotoxicity} = \frac{(\text{Experimental Release}) - (\text{Spontaneous Release}) \times 100}{(\text{Maximum Release}) - (\text{Spontaneous Release})}$$

Control Wells:

A 1% solution of the detergent TRITON X™ was added to the "maximum release" wells to induce cell death and subsequent release of europium. Some additional control wells contained target cells without effector cells in order to measure the level of "spontaneous" europium release.

Transductions:

The appropriate BACMAM™ virus (human HER3, cynomologus monkey HER3, or rat HER3) was added to HEK293 MSRII cells at an moi of 100 which corresponds to 8-15% virus (v/v) for 24 hrs. The transduced cells were then removed from the tissue culture flask using TrypLE, washed several times, and loaded with europium prior to using as target cells in the ADCC assay.

Monkey Blood:

Density gradient separation buffer (FICOLL™) was diluted 10% (v/v) with PBS without $Ca_2$ and $Mg_2$ prior to performing the density centrifugation on the monkey peripheral blood lymphocytes (effector cells).

Human blood was used for these studies in conformity with established policies. The monkey blood was obtained under established protocols. The models used in these studies conform to US standards of animal care.

3.2.2 Complement Dependent Cytotoxicity

These experiments were performed with a hHER3BACMAM™ transduced HEK 293 MSR II cell line used as the target. Briefly, these cells were transduced (moi 100) for ~21 hours at 37° C. and 5% $CO_2$ in T175 culture flasks. The adherent cells were then removed from the flasks using TrypLE and washed several times before plating at $1 \times 10^5$ cells/50 ul/well into a 96-well plate. Immediately added 25 ul/well of anti-human HER3 mAbs and incubated at 37° C. and 5% $CO_2$ for 30 minutes. Following this incubation, 20 ul/well of rabbit complement from CALBIOCHEM™ (final 20%) was added to the experimental plate and incubated at 37° C. and 5% $CO_2$ for an additional 2 hours. An assessment of cell viability was carried out by adding 100 ul of CELLTITER-GLO™ to each well with gentle mixing using a multichannel pipet. The plate was then read for luminescence signal on a Wallac VICTOR™ V plate reader (viable cells have increased signal).

3.3. Drugs and Materials

Human HER3BACMAM™
Monkey (cynomolgus) HER3BACMAM™
FICOLL™ GE Healthcare #17-1440-02
TRITON X-100™ Sigma #T9284
Separation tubes Accurate Surgical & Scientific #UN-10
Europium Fluka #207128
96-well round-bottom plates Costar #3799)
96-well flat-bottom plates Thermo Scientific #436110
Humanized 1D9 Fc disabled antibody
Humanized 1D9 antibody
Humanized 1D9 ACCRETAMAB™ antibody
Humanized 1D9 1D9 POTELLIGENT™ antibody
Complement CALBIOCHEM™ #234400
CELLTITER GLO™ Promega #G7571
DELFIA™ enhancement solution #4001-0010

3.4. Data Analysis

GRAPHPAD™ PRISM™ software was used to plot the specific lysis versus antibody concentration and for calculating the EC50 values.

4. Results 4.1 ADCC Assay

The results obtained from a human PBL ADCC assay which evaluated the humanized 1D9 antibody (identified as HZ1D9 or H6L2 in some instances), the humanized 1D9 Fc disabled antibody, the humanized 1D9 POTELLIGENT™ antibody and humanized 1D9 ACCRETAMAB™ antibody are shown in FIG. 48 and FIG. 49. These results were obtained using HER3BACMAM™ transduced HEK293 cells as target cells and human peripheral blood lymphocytes as effector cells (FIG. 48). This experimental set-up was simultaneously conducted using CHL-1 cells as the target cell population with the same human PBL effector cells (FIG. 49). These results clearly showed both the increased potency and increased maximum lysis obtained with the enhanced antibodies as compared with the wild-type (non-enhanced) antibody.

The results obtained from a cynomolgus monkey PBL (peripheral blood lymphocyte) ADCC assay which evaluated the humanized 1D9 antibody (identified as HZ1D9 or H6L2 in some instances), the humanized 1D9 Fc disabled antibody, the humanized 1D9 POTELLIGENT™ antibody and humanized 1D9 ACCRETAMAB™ antibody are shown in FIG. 50 to FIG. 53. These results were obtained using HER3BACMAM™ transduced HEK293 cells as target cells and cynomolgus peripheral blood lymphocytes as effector cells (FIG. 50 and FIG. 51). This experimental set-up was simultaneously conducted using CHL-1 cells as the target cell population with the same cynomolgus PBL effector cells (FIG. 52 and FIG. 53). These results clearly showed both the increased potency and increased maximum lysis obtained with the enhanced antibodies as compared with the wild-type (non-enhanced) antibody.

4.2 CDC Assay

The results shown in FIG. 54 were obtained from CDC assays using human HER3 transduced HEK293 target cells and rabbit complement. The results showed the humanized 1D9 antibody (identified as HZ1D9 or H6L2 in some instances), and the humanized 1D9 POTELLIGENT™ antibody each gave similar levels of complement mediated target cell lysis. Whereas, the humanized 1D9 ACCRETAMAB™ antibody showed at least a 10-fold improvement in complement mediated lysis over and above that seen with these other antibodies. The humanized 1D9 Fc disabled antibody did not show any measureable complement mediated lysis.

5. Discussion

The results presented here demonstrated that the "Fc enhanced" versions of the humanized 1D9 antibody (e.g., the humanized 1D9 ACCRETAMAB™ antibody and the humanized 1D9 POTELLIGENT™ antibody) showed improved function in both antibody-dependent cell-mediated cytotoxicity assays as well as complement-dependent cytotoxicity assays. This was demonstrated in both high (ADCC and CDC) and low (ADCC) human HER3-expressing cell lines as well as in cynomolgus HER3 expressing cells (ADCC).

The human effector cell data is relevant for what may be seen in a human population since no selection criteria was used to ensure ADCC/CDC reactivity. Although differences were seen across individual human donors (high versus low specific lysis), the "Fc-enhanced" antibodies consistently showed higher potency than the parental wild-type antibody. The cynomolgus effector cell data allowed us to profile the effector cells from the actual monkeys being used in a gross toxicity study.

In summary, both the humanized 1D9 ACCRETAMAB™ antibody and the humanized 1D9 POTELLIGENT™ antibody showed improved ADCC and ADCC/CDC functionality (respectively).

Example 10

1. Summary

The murine 15D5 antibody (M5.15D5.2A1.1H10) is a murine anti-HER3 antibody which binds the Domain II extracellular region of the human HER3 receptor. This antibody has been shown to bind well with both frozen and formalin-fixed paraffin embedded (FFPE) cancerous human tissues via immunohistochemistry.

2. Introduction

The murine 15D5 antibody (M5.15D5.2A1.1H10) was validated for its potential use as a companion diagnostic for assessment of HER3 expression. This companion diagnostic would be used to help identify patients that may clinically benefit from an anti-HER3 monoclonal antibody therapy. The companion mAb may be used to classify tumors into catagories based on their HER3 expression level across their tumor tissue, and/or the intensity of their HER3 receptor expression.

This example will outline some of the key experiments used to help validate the specificity of the murine 15D5 antibody (M5.15D5.2A1.1H10). The experiments in this example will examine the immunoreactivity and specificity of the murine 15D5 antibody (M5.15D5.2A1.1H10) antibody to HER3 and other HER family members (e.g., HER1, HER2 and HER4). This example describes results from immunohistochemistry on frozen and formalin-fixed paraffin-embedded tissues; immunocytochemistry of the four HER family members (e.g., HER1, HER2, HER3 and HER4), immunoprecipitations; competition assays to confirm specificity and Western blotting of cell lysates and purified HER3 extracellular domain regions.

3. Methods 3.1. Experimental Preparation(s)
3.2. Experimental Protocol(s)
3.2.1. Western Blots of Her Family Members HEK 293 MSRII cells were transduced with HER1, HER2, HER3 or HER4 BACMAM™ at 100 multiplicity of infection (moi) for 22 hrs at 37° C. and 5% $CO_2$. Each cell line was harvested using versene and then cell counts were performed using trypan blue exclusion staining. After washing the cell suspensions with 10 mls of PBS, $3\times10^7$ cells were collected and placed into 1 ml of RIPA lysis solution (stock RIPA lysis solution: 10 ml 1×RIPA lysis buffer+1 tablet of mini halt protease inhibitor). This preparation was then vortexed for 2 minutes, centrifuged and the supernatants (cell lysates) were stored at 4° C.

The cell lysates were combined with LDS sample buffer and reducing agent and then heated to 70° C. for 10 minutes. After cooling to room temperature, the lysates were placed into a QIASHREDDER™ and spun for 2 minutes at 14,000 rpm. The lysates were then loaded into lanes of a 4-12% gradient Bis-Tris gel and electrophoresed to allow protein separation. The separated proteins were transferred to nitrocellulose and then incubated overnight with a block solution containing 0.1% Tween-20. Primary antibodies directed to either HER1, HER2, HER3 or HER4 family members were added for 5 hours at room temperature. This was followed by incubation with IR-conjugated secondary antibodies for 1 hour. The blots were then visualized using a L1-COR™ ODYSSEY™ image analyzer instrument.

3.2.2, Immunoprecipitation Using the Murine 15D5 Antibody

200 µl of a lysate prepared from a suspension of $3\times10^7$ cell/ml, as described above, was combined with 10 ug of the murine 15D5 antibody (M5.15D5.2A1.1H10) and incubated overnight at 4° C. on a rotating device. Then combined the antigen-antibody complex with 50 µl of settled immobilized Protein A/G resin (100 µl resin slurry) and incubated with gentle mixing for 2 hours at room temperature on a rotating device. Immune-precipitates were harvested by centrifugation at 5,000 rpm (~1,000×g) for 5 minutes at 4° C. The pellet was then washed four times with 1 ml RIPA buffer. Resuspended the washed pellet with 20 ul of 1×LDS loading buffer (100 ul of RIPA buffer, 33 ul of LDS sample buffer (4×), 13.3 ul of reducing agent (10×)), and boiled the samples at 100° C. for 5 minutes. After allowing the samples to cool on ice, they were centrifuged at 5,000 rpm (~1,000×g) for 1 minute.

These samples were then loaded into a gel (0.4 ug/lane of HER3 antigen, 10 ul/lane of HER family BACMAM™ transduced HEK293 MSRII lysates and 20 ul/lane of CHL-1 cell lysates), and run at 200V for approximately 50 minutes. After transfer of gel separated proteins to nitrocellulose, the resulting blot was incubated with a commercially available anti-HER3 primary mAb (R&D System MAB3482), followed by an IR-conjugated goat anti-mouse secondary antibody. The blots were then visualized using a L1-COR™ ODYSSEY™ image analyzer instrument.

3.2.3. Immunocytochemistry of Her Family Members

HEK293 MSRII cells were transduced with Her3 BACMAM™ at 100 moi for 24 hrs at 37° C. and 5% $CO_2$. Cells were then harvested using TrypLE, cells were counted and washed using PBS. A suspension of $0.5\times10^6$ cells/ml in PBS was then prepared and 100 ul of this suspension was added to cytospin funnels with attached microscope slides. These were spun for 5 minutes at 500 rpm to produce a cell spot containing 50,000 cells. Slides were dried in a biological hood overnight and fixed with room temperature acetone for 2 minutes the following day. After drying for 2 hours, the slides were wrapped in Saran wrap and stored at −20° C. until ready for immunostaining.

Six slides were removed from the −20° C. freezer, allowed to come to room temperature and air dried. Once dry, each cell spot was marked with a Pap pen to form a hydrophobic barrier for staining Slides were placed into TBST (Tris buffered saline+0.05% TWEEN-20™) to hydrate for 10 minutes and added to the protein block solution for 30 minutes. 1 ug/ml of murine 15D5 antibody—as the primary antibody—was applied directly to the slides for 2 hours at room temperature. Slides were washed three times with TBST and HRP-conjugated anti-mouse secondary was applied directly for 2 hours at room temperature. Slides were washed three times for 5 minutes each time using TBST and then DAB substrate was added for 2 minutes. Slides were then rinsed three times for 5 minutes each time with water and placed in hematoxylin for 2 minutes. Slides were then washed three times for 5 minutes each time with water, slides were allowed to dry thoroughly and then coverslipped for viewing.

3.2.4. Competition Assay Using the Extracellular Domain II Region of HER3

HEK293 MSRII cells were transduced with HER3BACMAM™ at 100 moi for 24 hrs at 37° C. and 5% $CO_2$. Following this incubation time, the cells were harvested using TrypLE, a cell count was performed, and the cells were washed using PBS. The cells were resuspended to $0.5\times10^6$ cells/ml in PBS and 100 ul was added to cytospin funnels with attached microscope slides. These were spun for 5 minutes at 500 rpm to produce a cell spot containing 50,000 cells. The slides were dried in a biological hood overnight and then fixed with room temperature acetone for 2 minutes the following day. After drying for 2 hours, the slides were wrapped in SARAN™ wrap and stored at −20° C. until ready for immunostaining.

Two slides were then removed from the freezer and allowed to warm to room temperature and air-dry. Once dry, the cell spot was circled with a Pap pen to form a hydrophobic barrier for staining Slides were placed into TBST (Tris buffered saline+0.05% TWEEN-20™) to hydrate for 10 minutes and added to the protein block solution for 30 minutes. 1 ug/ml of primary antibody, or a 1:1 molar ratio of primary antibody and human HER3Domain II was applied directly to the slides for 2 hours at room temperature. Slides were washed three times with TBST and HRP-conjugated anti-mouse secondary was applied directly for 1 hour at room temperature. Slides were washed three times for 5 minutes each time using TBST and then DAB substrate was added for 5 minutes. Slides were then washed three times for 5 minutes each time with water, slides were allowed to dry thoroughly and then coverslipped for viewing.

3.2.5. Western Blot of HER3Extracellular Domains

The four extracellular domains of HER3 were combined with LDS (lithium dodecyl sulphate) sample buffer with reducing agent and heated to 70° C. for 10 minutes. After cooling to room temperature, the lysates were loaded into the lanes of a 4-12% gradient Bis-Tris gel and electrophoresed to allow protein separation. The separated proteins were blotted by transferre to nitrocellulose to produce a blot and the blot was incubated overnight with a block solution containing 0.1% TWEEN-20™. The blot was then incubated with diluted murine 15D5 antibody (M5.15D5.2A1.1H10) for 2 hours at room temperature. This was followed by incubation of the blot with an IR-conjugated secondary antibody for 1 hour. Blots were then visualized using a L1-COR™ ODYS-SEY™ image analyzer instrument.

3.2.6. Immunohistochemistry of Frozen and FFPE Tissues

Human breast cancer tissues (16943ald, 16945alo, 22687alp, 23110alk) were preserved as both frozen and formalin-fixed paraffin embedded (FFPE) samples from the same excised tumor.

Preserved human breast cancer tissues were sectioned for immunohistochemical (IHC) evaluation of HER3 receptor expression. Briefly, FFPE tissues were sectioned at 6 um, deparafinized and rehydrated by going through series of xylene substitute and alcohol steps using the VARISTAINT™ Gemini ES Automated Slide Stainer. Several antigen recovery (epitope retrieval) methods were applied using a DECLOAKING CHAMBER™ to allow for comparison of various conditions. Following a wash step with Tris-0.05% TWEEN-20™ buffer, the tissues were incubated with peroxidase block for 5 min, and then blocked with a protein block solution. Primary antibody was applied to the tissue sections for 30-60 minutes. Following a wash step, secondary antibody was applied for 30-60 minutes. After an additional wash step, specific immunoreactivity was visualized following a 5 minute incubation with DAB (diaminobenzidine). Tissue sections were then rinsed with water and counterstained with hematoxylin for one minute. Monoclonal antibody staining was performed using a Dako Autostainer System.

Frozen tissues were sectioned at 6 microns onto microscope slides and allowed to dry for two hours at room temperature. Sections tissues on the slides were then fixed with acetone for two minutes at room temperature and allowed to dry. After washing with Tris-0.05% TWEEN-20™ buffer the tissues were incubated with peroxidase block for 5 min, and received a protein block solution. The staining continued as outlined above for the FFPE tissues.

3.2.7. Immunohistochemistry Assessment of Multi-Tumor TMA

Slides were stained using standard manual or automated staining protocols. Tumors were sectioned and deparafinized. Sections were incubated with endogenous peroxidase and non specific antibody binding blocking solutions, subjected to epitope retrieval, and then incubated with the primary antibody. Washing steps were performed between incubations. Standard blocking steps for non-specific binding were performed. Standard antigen retrieval techniques were performed. For manual binding was visualized using either a secondary biotinylated antibody in conjunction with an ABC™ HRP kit (Vector Laboratories, Inc.), or an ENVISION™ HRP conjugated polymer kit (Dako North America, Inc.) and diaminobenzidine substrate reaction product consistent with the manufacturer's instructions. For automated staining visualization was achieved using OMNIMAP™ HRP polymer chemistry (Ventana Medical Systems, Inc.). Sections were counterstained using standard hematoxylin or methyl green nuclear counterstaining techniques when appropriate.

3.3. Drugs and Materials

HER1BACMAM™ virons
Human HER2BACMAM™ virons
Human HER3BACMAM™ virons
Human HER4BACMAM™ virons
LDS sample buffer (Invitrogen NP0007)
QIASHREDDER™ (Qiagen 79656)
mini-HALTT™ protease inhibitor (Roche diagnostics 13535400)
Western block buffer (Rockland MB-070)
Nitrocellulose membrane (Invitrogen LC2000)
Rabbit anti-human ErbB2 (human HER2) (Dako A0485)
Mouse anti-human EGFR (human HER1) Dako M3563 Clone H11
Goat anti-mouse IR-DYE800™ antibody (Rockland 610-131-121)
Goat anti-rabbit IR-DYE680™ antibody (L1-Cor Odyssey 827-88367)
Anti-human HER3 monoclonal antibody (R&D System MAB3482)
Tris-buffered saline (Dako #S1968)
ENVISION™ System-HRP DAB kit (Dako #K4007)
murine 15D5 antibody (M5.15D5.2A1.1H10) (3.19 mg/ml)
Human HER3Domain II (used for competition) (1.66 mg/ml)
Protein block solution (Dako X0909 lot 10037797)
THERMO SHANDON EZ DOUBLE CYTOFUNNELT™ (#A78710005)
VWR SUPERFROST PLUS™ #48311-703
TRYPLE™ Select (Gibco 12563-011)
RIPA buffer (Sigma R0278)
Multi-tumor human Tissue Micro Array (TMA) Hu80357 (CAMB12-GSK-TMA—Origene)

4. Results 4.1.1.

Western blotting of cell lysates which expressed the four HER family members showed that murine 15D5 antibody (M5.15D5.2A1.1H10) selectively recognized human HER3 with little to no cross-reactivity to human HER1, human HER2 and human HER4. To confirm HER2 and HER1 expression and for comparison, commercial antibodies to HER2 (Dako) and HER1 (Dako) were also tested on these lysates. The results confirmed that human HER2 and human HER1 were expressed through the transductions performed with the HEK293 cells. The results also showed some cross-reactivity with the anti-HER2 antibody (Dako).

4.1.2.

Immunoprecipitation experiments using human HER3 transduced HEK293 cells and CHL-1 cells provided an opportunity to examine high and low HER3-expressing cell lines. These experiments showed a similar banding pattern of immunoreactivity using the murine 15D5 antibody (M5.15D5.2A1.1H10) or a commercial anti-HER3 antibody (R&D Systems) for detection of human HER3 in immunoprecipitates.

4.1.3.

Immunocytochemical analysis of human HER1, human HER2, human HER3 and human HER4BACMAM™ transduced cells using the murine 15D5 antibody (M5.15D5.2A1.1H10) showed strong immunoreactivity to human HER3 with little to no immunoreactivity to the other HER family members. The murine 15D5 antibody (M5.15D5.2A1.1H10) preferentially binds human HER3.

4.1.4.

A competition assay using the murine 15D5 antibody (M5.15D5.2A1.1H10) or the murine 15D5 antibody (M5.15D5.2A1.1H10) in combination with an equal molar concentration of human HER3 domain II ECD showed that murine 15D5 antibody (M5.15D5.2A1.1H10) immunoreactivity was completely blocked by pre-incubation with domain II of human HER3. These results confirm that the murine 15D5 antibody (M5.15D5.2A1.1H10) specifically binds the extracellular domain II region of the human HER3 receptor.

4.1.5.

Western blot analysis of the HER3 extracellular domains demonstrated the specificity of the murine 15D5 antibody (M5.15D5.2A1.1H10) for domain II of human HER3 and the lack of immunoreactivity for this antibody to domains I, III, and IV of human HER3.

4.1.6.

Figure 6:
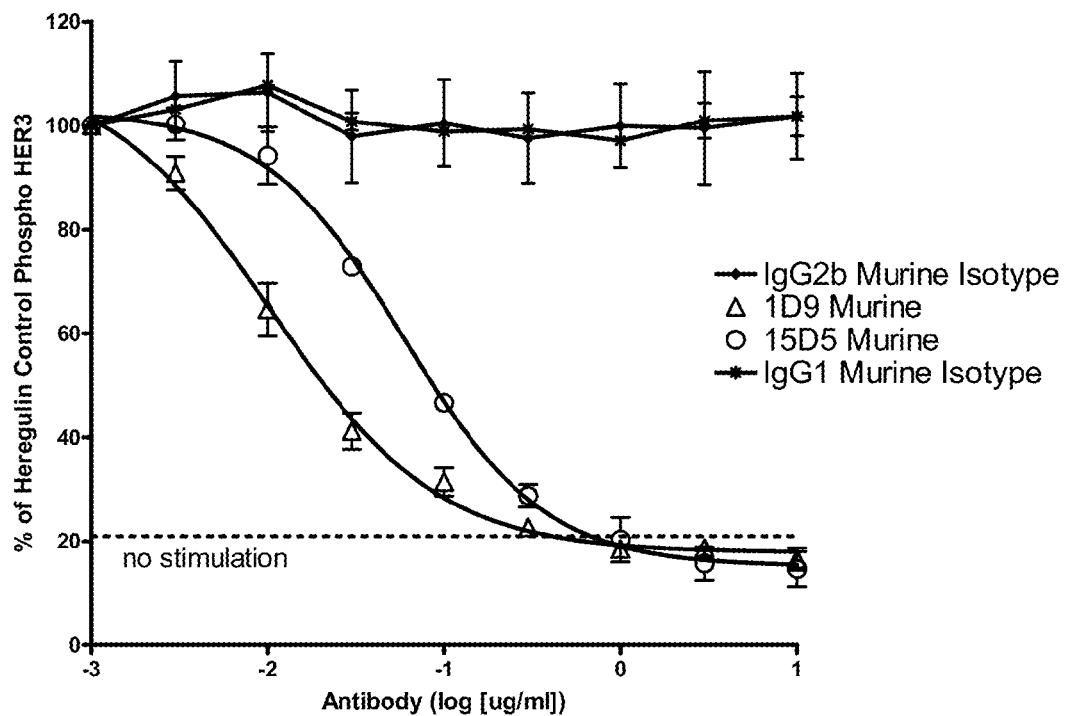
FIG. 6. Inhibition of heregulin induced human HER3 receptor phosphorylation with anti-HER3 antibodies in MCF-7 breast cancer cells.

Immunohistochemistry staining of frozen and FFPE matched cancerous breast tissues (n=4) showed concordant staining pattern. Although the structural integrity of the FFPE tissue is better preserved than the frozen sample, the membranous staining pattern was similar across these two preservation methods. FIG. 6 shows one representative photograph of the membranous staining seen across these frozen and fixed breast tissues.

4.1.7.

A multi-tumor array (Hu80357) containing tumor and representative normal tissue was evaluated for HER3 expression using the murine 15D5 antibody (M5.15D5.2A1.1H10). Qualitative assessment of indicated colon, prostate, breast, endometrial, brain and skin tumor cores all showed human HER3 expression. One kidney tumor sample and one lung cancer sample showed human HER3 expression. The most robust expression of human HER3 was seen in melanoma and prostate tumor samples. 7 melanoma and 7 prostate tumor samples demonstrated robust human HER3 expression. 8 breast cancer samples also showed human HER3 expression. Normal tissue samples showed considerably less signal relative to the tumor samples, however 3 normal colon sample and 1 normal breast sample showed moderate signal.

5. Discussion and Summary

The experiments described in this report demonstrate the sensitivity and specificity of the murine 15D5 antibody (M5.15D5.2A1.1H10). As described herein, the murine 15D5 antibody (M5.15D5.2A1.1H10) was initially selected from a panel of hybridomas for its specificity to the extracellular region of HER3 based on preliminary ELISA screens. Additional specificity for HER3 was carried out by Western blotting and immunocytochemistry using BACMAM™ transduced cells. In these experiments, human HER3 transduced cells showed specific immunoreactivity, whereas cells expressing other human HER family members showed little to no reactivity. The murine 15D5 antibody (M5.15D5.2A1.1H10) was also used in immunoprecipitation assays in combination with commercial antibodies showing specific "pull-down" of HER3. In addition, immunocytochemistry was performed on cytospin preparations of the human HER3 transduced cells as well as frozen preparations of these cells, confirming the murine 15D5 antibody (M5.15D5.2A1.1H10) recognizes HER3 across assays and can bind HER3 in immunocytochemical assays. The binding of the murine 15D5 antibody (M5.15D5.2A1.1H10) to the human HER3 receptor could be blocked by pre-incubation of the antibody with the extracellular domain II region of human HER3 confirming its specificity to this region of HER3.

Additional immunohistochemical protocols were developed for the murine 15D5 antibody (M5.15D5.2A1.1H10) on similar baculovirus transduced cells which were formalin fixed and processed to paraffin, further demonstrating the ability of the murine 15D5 antibody (M5.15D5.2A1.1H10) to detecting HER3 via IHC irrespective of the cellular preparation. Experiment described in this example rigorously confirm this cross platform consistency of the murine 15D5 antibody's (M5.15D5.2A1.1H10) behavior by demonstrating human HER3 immunoreactivity in matched pairs of frozen and FFPE samples of breast adenocarcinomas. The abundance and relative expression of the human HER3 signal detected by the murine 15D5 antibody (M5.15D5.2A1.1H10) was the same in both specimen preparations. Immunohistochemical target validation studies utilizing the murine 15D5 antibody (M5.15D5.2A1.1H10) on panels of different tumor types showed differences in expression, however the patterns and relative abundance of HER3 displayed consistency within particular tumor types (e.g., melanoma, prostate, breast). In addition, the murine 15D5 antibody (M5.15D5.2A1.1H10) has been successful at detecting HER3 in different protocols and staining systems. The findings demonstrate that the murine 15D5 antibody (M5.15D5.2A1.1H10) consistently and accurately can detect human HER3 by immunohistochemistry in tumor sections independent of protocols and specimen preservation.

The murine 15D5 antibody (M5.15D5.2A1.1H10) also specifically detects the extracellular domain of HER3 in a variety of assays. It has also been described in this example that the murine 15D5 antibody (M5.15D5.2A1.1H10) works consistently in these assays despite variations. In particular, the murine 15D5 antibody (M5.15D5.2A1.1H10) demonstrated a high degree of specificity and sensitivity to detect human HER3 in tissue sections via immunohistochemistry. In addition, the murine 15D5 antibody (M5.15D5.2A1.1H10) was able to detect equivalent levels of human HER3 in the same samples utilizing different assays (demonstrating a direct proportionality between the murine 15D5 antibody (M5.15D5.2A1.1H10) signal and the amount of human HER3 present). Collectively, the results described in this example demonstrate the performance, specificity and consistency of the murine 15D5 antibody (M5.15D5.2A1.1H10) and support its suitability as an antibody reagent in a human HER3 diagnostic assay (e.g., IHC assays).

Example 11

Informal Sequence Listing

Underlining below identifies CDR sequences in the variable heavy and variable light chain portions of the antibodies or the nucleic acid sequences encoding these CDR sequences. For example, in SEQ ID NO: 1 the frameworks and CDRS are presented as plaintext framework1, underlined CDR1, plaintext framework2, underlined CDR2, plaintext framework3, underlined CDR3 and plaintext framework4 in order from the amino proximal portion to the carboxy terminal portion of the sequences presented. Italics below indentify signal sequences. Asterisks to the right of a character for a single letter amino acid code indicates the amino acid residue to the left is a potential N-glycosylation site. This scheme is used in SEQ ID NO:s 5, 9, 13, 17, 22, 26, 30, 34, 38-43, 44, 48, 57, etc. for example. A table providing details concerning the various antibodies disclosed herein is also provided. See Table 17 below.

M5_15D5_2A1_1H10_VH
SEQ ID NO: 1
EFQLQQSGPELVKPGASVKISCKASGYSFTDYNMNWVKQNNGKSLEWIGGINPNYG

TTVYNQKFKGKATLTVDQSSSTAYMQLVSLTSEDSAVYYCARMTTIVPFDYWGQGT

TLTVSS

M5_15D5_2A1_1H10_CDRH1
SEQ ID NO: 2
DYNMN

M5_15D5_2A1_1H10_CDRH2
SEQ ID NO: 3
GINPNYGTTVYNQKFKG

M5_15D5_2A1_1H10_CDRH3
SEQ ID NO: 4
MTTIVPFDY

M5_15D5_2A1_1H10_VL
SEQ ID NO: 5
DIQMTQTTFSLSASLGDRVTISCRASQDISNYLNWYQQKPDGTVKLLIYYTSTLHSGV

PSRFSGSGSGTDYFLTIRNLEEEDIATYFCQQGYTLPWTFGGGTKLDIK

M5_15D5_2A1_1H10_CDRL1
SEQ ID NO: 6
RASQDISNYLN

M5_15D5_2A1_1H10_CDRL2
SEQ ID NO: 7
YTSTLHS

M5_15D5_2A1_1H10_CDRL3
SEQ ID NO: 8
QQGYTLPWT

M5_22A5_1G6_1C10_VH
SEQ ID NO: 9
EVQLVESGGGLVKPGGSLKLSCAASGFTFSDYGMHWLRQAPEKGLEWVAYITSGSS

EIYYVDTVKGRFTISRDNAKNTLCLQMTSLRSEDTAMYHCARGYGYREGYFDVWGT

GTTVTVSS

M5_22A5_1G6_1C10_CDRH1
SEQ ID NO: 10
DYGMH

M5_22A5_1G6_1C10_CDRH2
SEQ ID NO: 11
YITSGSSEIYYVDTVKG

M5_22A5_1G6_1C10_CDRH3
SEQ ID NO: 12
GYGYREGYFDV

M5_22A5_1G6_1C10_VL_LC1
SEQ ID NO: 13
DVVMTQTPLTLSVTIGQPASISCKSSQSLLDSDGKTYLNWLLQRPGQSPKRLIYLVSK

LDSGVPDRFTGSGSGTDFTLKISRVEAEDLGVYYCWQGTHFPQTFGGGTKLEIK

M5_22A5_1G6_1C10_CDRL1_LC1
SEQ ID NO: 14
KSSQSLLDSDGKTYLN

M5_22A5_1G6_1C10_CDRL2_LC1
SEQ ID NO: 15
LVSKLDS

M5_22A5_1G6_1C10_CDRL3_LC1
SEQ ID NO: 16
WQGTHFPQT

-continued

>M5_22A5_1G6_1C10_VL_LC2
SEQ ID NO: 17
DIQMTQSPASLSVSVGETVTITC<u>RTSENVYSNLA</u>WYQQKQGRSPQLLVY<u>GATRLPDG</u>

VPARFSGSGSTQYSLKINSLQSEDFGTYYC<u>QLFWGIPLT</u>FGAGTKLELK

M5_22A5_1G6_1C10_CDRL1_LC2
SEQ ID NO: 18
<u>RTSENVYSNLA</u>

M5_22A5_1G6_1C10_CDRL2_LC2
SEQ ID NO: 19
<u>GATRLPD</u>

M5_22A5_1G6_1C10_CDRL3_LC2
SEQ ID NO: 20
<u>QLFWGIPLT</u>

HUMAN HER3 amino acid sequence
SEQ ID NO: 21
MRANDALQVLGLLFSLARGSEVGNSQAVCPGTLNGLSVTGDAENQYQTLYKLYERC

EVVMGNLEIVLTGHNADLSFLQWIREVTGYVLVAMNEFSTLPLPNLRVVRGTQVYD

GKFAIFVMLNYNTNSSHALRQLRLTQLTEILSGGVYIEKNDKLCHMDTIDWRDIVRD

RDAEIVVKDNGRSCPPCHEVCKGRCWGPGSEDCQTLTKTICAPQCNGHCFGPNPNQC

CHDECAGGCSGPQDTDCFACRHFNDSGACVPRCPQPLVYNKLTFQLEPNPHTKYQY

GGVCVASCPHNFVVDQTSCVRACPPDKMEVDKNGLKMCEPCGGLCPKACEGTGSG

SRFQTVDSSNIDGFVNCTKILGNLDFLITGLNGDPWHKIPALDPEKLNVFRTVREITGY

LNIQSWPPHMHNFSVFSNLTTIGGRSLYNRGFSLLIMKNLNVTSLGFRSLKEISAGRIYI

SANRQLCYHHSLNWTKVLRGPTEERLDIKHNRPRRDCVAEGKVCDPLCSSGGCWGP

GPGQCLSCRNYSRGGVCVTHCNFLNGEPREFAHEAECFSCHPECQPMEGTATCNGSG

SDTCAQCAHFRDGPHCVSSCPHGVLGAKGPIYKYPDVQNECRPCHENCTQGCKGPE

LQDCLGQTLVLIGKTHLTMALTVIAGLVVIFMMLGGTFLYWRGRRIQNKRAMRRYL

ERGESIEPLDPSEKANKVLARIFKETELRKLKVLGSGVFGTVHKGVWIPEGESIKIPVCI

KVIEDKSGRQSFQAVTDHMLAIGSLDHAHIVRLLGLCPGSSLQLVTQYLPLGSLLDHV

RQHRGALGPQLLLNWGVQIAKGMYYLEEHGMVHRNLAARNVLLKSPSQVQVADFG

VADLLPPDDKQLLYSEAKTPIKWMALESIHFGKYTHQSDVWSYGVTVWELMTFGAE

PYAGLRLAEVPDLLEKGERLAQPQICTIDVYMVMVKCWMIDENIRPTFKELANEFTR

MARDPPRYLVIKRESGPGIAPGPEPHGLTNKKLEEVELEPELDLDLDLEAEEDNLATT

TLGSALSLPVGTLNRPRGSQSLLSPSSGYMPMNQGNLGESCQESAVSGSSERCPRPVS

LHPMPRGCLASESSEGHVTGSEAELQEKVSMCRSRSRSPRPRGDSAYHSQRHSLLT

PVTPLSPPGLEEEDVNGYVMPDTHLKGTPSSREGTLSSVGLSSVLGTEEEDEDEEYEY

MNRRRRHSPPHPPRPSSLEELGYEYMDVGSDLSASLGSTQSCPLHPVPIMPTAGTTPD

EDYEYMNRQRDGGGPGGDYAAMGACPASEQGYEEMRAFQGPGHQAPHVHYARLK

TLRSLEATDSAFDNPDYWHSRLFPKANAQRT

HUMANIZED_15D5_VH amino acid sequence
Humanized 15D5 H4
SEQ ID NO: 22
QVQLVQSGAEVKKPGASVKVSCKASGYTFT<u>DYNMN</u>WVRQAPGQGLEWMG<u>GINPN</u>

<u>YGTTVYNQKFKG</u>KVTLTVDTSISTAYMELSRLRSDDTAVYYCAR<u>MTTIVPFDY</u>WGQ

GTTVTVSS

-continued

HUMANIZED_15D5_CDRH1 amino acid sequence
SEQ ID NO: 23
DYNMN

HUMANIZED_15D5_CDRH2 amino acid sequence
SEQ ID NO: 24
GINPNYGTTVYNQKFKG

HUMANIZED_15D5_CDRH3 amino acid sequence
SEQ ID NO: 25
MTTIVPFDY

HUMANIZED_15D5_VL amino acid sequence
Humanized 15D5 L1
SEQ ID NO: 26
DIQMTQSPSSLSASVGDRVTITCRASQDISNYLNWYQQKPGKAPKLLIYYTSTLHSGV

PSRFSGSGSGTDYTFTISSLQPEDIATYYCQQGYTLPWTFGGGTKVEIKR

HUMANIZED_15D5_CDRL1 amino acid sequence
SEQ ID NO: 27
RASQDISNYLN

HUMANIZED_15D5_CDRL2 amino acid sequence
SEQ ID NO: 28
YTSTLHS

HUMANIZED_15D5_CDRL3 amino acid sequence
SEQ ID NO: 29
QQGYTLPWT

HUMANIZED_1D9_VH amino acid sequence
SEQ ID NO: 30
Humanized 1D9 H6
QVQLVQSGAEVKKPGASVKVSCKASGYTFTSYWMHWVRQAPGQGLEWMGVIDPS

DGYSHYNQKFKGKVTLTVDTSISTAYMELSRLRSDDTAVYYCAGGLAGTLDYWGQ

GTTVTVSS

HUMANIZED_1D9_CDRH1 amino acid sequence
SEQ ID NO: 31
SYWMH

HUMANIZED_1D9_CDRH2 amino acid sequence
SEQ ID NO: 32
VIDPSDGYSHYNQKFKG

HUMANIZED_1D9_CDRH3 amino acid sequence
SEQ ID NO: 33
GLAGTLDY

HUMANIZED_1D9_VL amino acid sequence
SEQ ID NO: 34
Humanized 1D9 L2
DIQMTQSPSSLSASVGDRVTITCRSSQSIVHSSGNTYLQWFQQKPGKAPKLLIYKVSN

RFSGVPSRFSGSGSGTDFTLTISSLQPEDFAVYYCFQGSHVPWTFGQGTKLEIKR

HUMANIZED_1D9_CDRL1 amino acid sequence
SEQ ID NO: 35
RSSQSIVHSSGNTYLQ

HUMANIZED_1D9_CDRL2 amino acid sequence
SEQ ID NO: 36
KVSNRFS

HUMANIZED_1D9_CDRL3 amino acid sequence
SEQ ID NO: 37
FQGSHVPWT

MURINE 15D5_VH nucleic acid sequence
SEQ ID NO: 38
GAGTTCCAGCTGCAGCAGAGCGGCCCCGAGCTGGTGAAGCCCGGCGCCAGCGTG

AAGATCAGCTGCAAGGCCAGCGGCTACAGCTTCACCGACTACAACATGAACTGG

GTGAAGCAGAACAACGGCAAGAGCCTGGAGTGGATCGGCGGCATCAACCCCAAC

TACGGCACCACCGTGTACAACCAGAAGTTCAAGGGCAAGGCCACCCTGACCGTG

```
GACCAGAGCAGCAGCACCGCCTACATGCAGCTGGTGAGCCTGACCAGCGAGGAC

AGCGCCGTGTACTACTGCGCCAGGATGACCACCATCGTGCCCTTCGACTACTGGG

GCCAGGGCACCACCCTGACCGTGAGCAGC
```

MURINE 15D5_VL nucleic acid sequence
SEQ ID NO: 39
```
GACATCCAGATGACCCAGACCACCTTCAGCCTGAGCGCCAGCCTGGGCGACAGG

GTGACCATCAGCTGCAGGGCCAGCCAGGACATCAGCAACTACCTGAACTGGTAC

CAGCAGAAGCCCGACGGCACCGTGAAGCTGCTGATCTACTACACCAGCACCCTG

CACAGCGGCGTGCCCAGCAGGTTCAGCGGCAGCGGCAGCGGCACCGACTACTTC

CTGACCATCAGGAACCTGGAGGAGGAGGACATCGCCACCTACTTCTGCCAGCAG

GGCTACACCCTGCCCTGGACCTTCGGCGGCGGCACCAAGCTGGACATCAAG
```

HUMANIZED_15D5_VH nucleic acid sequence (cells)
Humanized 15D5 H4
SEQ ID NO: 40
```
CAGGTCCAGCTCGTGCAGTCTGGGGCCGAGGTGAAGAAACCCGGCGCTAGCGTG

AAGGTGAGCTGCAAGGCCAGCGGCTACACCTTCACCGACTACAACATGAACTGG

GTGAGGCAGGCCCCCGGCCAGGGCCTGGAGTGGATGGGCGGCATCAACCCCAAC

TACGGCACCACCGTGTACAACCAGAAGTTCAAGGGCAAGGTGACCCTGACCGTG

GACACCAGCATCAGCACCGCCTACATGGAACTGAGCAGGCTGAGGAGCGACGAT

ACCGCCGTGTACTATTGCGCCAGGATGACCACCATCGTGCCCTTCGACTACTGGG

GACAGGGCACCACTGTGACAGTGTCAAGC
```

HUMANIZED_15D5_VL nucleic acid sequence (cells)
Humanized 15D5 L1
SEQ ID NO: 41
```
GACATCCAGATGACCCAGTCACCCAGCAGCCTGAGCGCCAGCGTGGGCGACAGG

GTGACCATTACCTGCAGGGCCAGCCAGGACATCAGCAACTACCTGAACTGGTACC

AGCAGAAGCCCGGCAAGGCCCCCAAGCTGCTGATCTACTACACCTCCACCCTGCA

CAGCGGCGTGCCCTCTAGGTTCTCCGGCAGCGGCAGCGGCACCGACTACACCTTC

ACCATCAGCAGCCTGCAGCCCGAGGACATCGCCACCTACTATTGCCAGCAGGGCT

ACACCCTCCCCTGGACTTTCGGAGGCGGCACCAAGGTGGAGATCAAGCGU
```

HUMANIZED_1D9_VH nucleic acid sequence (cells)
Humanized 1D9 H6
SEQ ID NO: 42
```
CAGGTGCAGCTGGTGCAGTCCGGCGCAGAGGTGAAGAAGCCCGGAGCCTCTGTG

AAGGTGAGCTGCAAGGCCAGCGGCTACACCTTCACCAGCTACTGGATGCACTGG

GTGAGGCAGGCCCCTGGCCAGGGCCTGGAGTGGATGGGCGTGATCGACCCCAGC

GACGGGTACAGCCACTACAACCAGAAGTTCAAGGGCAAGGTCACCCTGACCGTG

GACACCAGCATCAGCACCGCCTACATGGAACTCAGCAGGCTGAGGAGCGACGAC

ACCGCCGTGTACTATTGCGCCGGAGGCCTGGCTGGCACCCTGGATTACTGGGGCC

AGGGCACCACAGTGACCGTGAGCAGC
```

HUMANIZED_1D9_VL nucleic acid sequence (cells)
Humanized 1D9 L2
SEQ ID NO: 43
```
GACATCCAGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTtCCAGCAGAAACCCGGCAAGGCTCCCAAGCTGCTGATCTACA

AGGTGAGCAACAGGTTCAGCGGCGTGCCCTCTCGCTTCTCAGGCAGCGGCTCCGG
```

```
CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGG
```

MURINE_1D9_VH amino acid sequence
                                                    SEQ ID NO: 44
```
M5.1D9.1F5 VH
QVQLQQPGAELVRPGTSVKLSCKASGYTFTSYWMHWVKQRPGQGLEWIGVIDPSDG

YSHYNQKFKGKATLTVDTSSSTAYMQLSSLTSEDSAVYYCAGGLAGTLDYWGQGTT

LTVSS
```

MURINE_1D9_CDRH1 amino acid sequence
                                                    SEQ ID NO: 45
```
SYWMH
```

MURINE_1D9_CDRH2 amino acid sequence
                                                    SEQ ID NO: 46
```
VIDPSDGYSHYNQKFKG
```

MURINE_1D9_CDRH3 amino acid sequence
                                                    SEQ ID NO: 47
```
GLAGTLDY
```

MURINE_1D9_VL amino acid sequence
                                                    SEQ ID NO: 48
```
M5.1D9.1F5 VL
DVLMTQTPLSLPVSLGDQASISCRSSQSIVHSSGNTYLQWFLQKPGQSPKLLISKVSNR

FSGVPDRFSGSGSGTDFTLRISRVEAEDLGLYYCFQGSHVPWTFGGGTKLEIK
```

MURINE_1D9_CDRL1 amino acid sequence
                                                    SEQ ID NO: 49
```
RSSQSIVHSSGNTYLQ
```

MURINE_1D9_CDRL2 amino acid sequence
                                                    SEQ ID NO: 50
```
KVSNRFS
```

MURINE_1D9_CDRL3 amino acid sequence
                                                    SEQ ID NO: 51
```
FQGSHVPWT
```

MURINE_1D9_VH nucleic acid sequence
                                                    SEQ ID NO: 52
```
CAGGTGCAGCTGCAGCAGCCCGGCGCCGAGCTGGTGAGGCCCGGCACCAGCGTG

AAGCTGAGCTGCAAGGCCAGCGGCTACACCTTCACCAGCTACTGGATGCACTGG

GTGAAGCAGAGGCCCGGCCAGGGCCTGGAGTGGATCGGCGTGATCGACCCCAGC

GACGGCTACAGCCACTACAACCAGAAGTTCAAGGGCAAGGCCACCCTGACCGTG

GACACCAGCAGCAGCACCGCCTACATGCAGCTGAGCAGCCTGACCAGCGAGGAC

AGCGCCGTGTACTACTGCGCCGGCGGCCTGGCCGGCACCCTGGACTACTGGGGCC

AGGGCACCACCCTGACCGTGAGCAGC
```

MURINE_1D9_VL nucleic acid sequence
                                                    SEQ ID NO: 53
```
GACGTGCTGATGACCCAGACCCCCCTGAGCCTGCCCGTGAGCCTGGGCGACCAG

GCCAGCATCAGCTGCAGGAGCAGCCAGAGCATCGTGCACAGCAGCGGCAACACC

TACCTGCAGTGGTTCCTGCAGAAGCCCGGCCAGAGCCCCAAGCTGCTGATCAGCA

AGGTGAGCAACAGGTTCAGCGGCGTGCCCGACAGGTTCAGCGGCAGCGGCAGCG

GCACCGACTTCACCCTGAGGATCAGCAGGGTGGAGGCCGAGGACCTGGGCCTGT

ACTACTGCTTCCAGGGCAGCCACGTGCCCTGGACCTTCGGCGGCGGCACCAAGCT

GGAGATCAAG
```

-continued

MURINE_22A5_VH nucleic acid sequence
SEQ ID NO: 54
GAGGTGCAGCTGGTGGAGAGCGGCGGCGGCCTGGTGAAGCCCGGCGGCAGCCTG

AAGCTGAGCTGCGCCGCCAGCGGCTTCACCTTCAGCGACTACGGCATGCACTGGC

TGAGGCAGGCCCCCGAGAAGGGCCTGGAGTGGGTGGCCTACATCACCAGCGGCA

GCAGCGAGATCTACTACGTGGACACCGTGAAGGGCAGGTTCACCATCAGCAGGG

ACAACGCCAAGAACACCCTGTGCCTGCAGATGACCAGCCTGAGGAGCGAGGACA

CCGCCATGTACCACTGCGCCAGGGGCTACGGCTACAGGGAGGGCTACTTCGACGT

GTGGGGCACCGGCACCACCGTGACCGTGAGCAGC

MURINE_22A5_VL nucleic acid sequence
SEQ ID NO: 55
GACGTGGTGATGACCCAGACCCCCCTGACCCTGAGCGTGACCATCGGCCAGCCCG

CCAGCATCAGCTGCAAGAGCAGCCAGAGCCTGCTGGACAGCGACGGCAAGACCT

ACCTGAACTGGCTGCTGCAGAGGCCCGGCCAGAGCCCCAAGAGGCTGATCTACC

TGGTGAGCAAGCTGGACAGCGGCGTGCCCGACAGGTTCACCGGCAGCGGCAGCG

GCACCGACTTCACCCTGAAGATCAGCAGGGTGGAGGCCGAGGACCTGGGCGTGT

ACTACTGCTGGCAGGGCACCCACTTCCCCCAGACCTTCGGCGGCGGCACCAAGCT

GGAGATCAAG

MURINE_22A5_VL nucleic acid sequence
SEQ ID NO: 56
GACATCCAGATGACCCAGAGCCCCGCCAGCCTGAGCGTGAGCGTGGGCGAGACC

GTGACCATCACCTGCAGGACCAGCGAGAACGTGTACAGCAACCTGGCCTGGTAC

CAGCAGAAGCAGGGCAGGAGCCCCCAGCTGCTGGTGTACGGCGCCACCAGGCTG

CCCGACGGCGTGCCCGCCAGGTTCAGCGGCAGCGGCAGCGGCACCCAGTACAGC

CTGAAGATCAACAGCCTGCAGAGCGAGGACTTCGGCACCTACTACTGCCAGCTGT

TCTGGGGCATCCCCCTGACCTTCGGCGCCGGCACCAAGCTGGAGCTGAAG

HUMANIZED_1D9_E_VL amino acid sequence
SEQ ID NO: 57
Humanized 1D9 E L2
DIQMTQSPSSLSASVGDRVTITC<u>RSSQSIVHSSGNTYLQ</u>WFQQKPGKAPKLLIY<u>KVSN</u>

<u>RFS</u>GVPSRFSGSGSGTDFTLTISSLQPEDFAVYYC<u>FQGSHVPWT</u>FGQGTKLEIKRR

HUMANIZED_1D9_E_VL nucleic acid sequence (cells)
SEQ ID NO: 58
GACATCCAGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTtCCAGCAGAAACCCGGCAAGGCTCCCAAGCTGCTGATCTACA

AGGTGAGCAACAGGTTCAGCGGCGTGCCCTCTCGCTTCTCAGGCAGCGGCTCCGG

CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGGCGT

MURINE 15D5_VH nucleic acid sequence (cells)
SEQ ID NO: 59
GAGTTCCAGCTGCAGCAGTCTGGACCTGAGCTGGTGAAGCCTGGCGCTTCAGTGA

AGATATCCTGCAAGGCCTCTGGTTACTCATTTACTGACTACAATATGAACTGGGT

GAAACAGAACAATGGAAAGAGCCTTGAGTGGATTGGAGGAATTAATCCTAACTA

TGGTACTACTGTTTACAATCAGAAGTTCAAGGGCAAGGCCACATTGACTGTAGAC

CAATCTTCCAGCACAGCCTACATGCAGCTCGTTAGTCTGACATCTGAGGACTCTG

-continued

CAGTCTATTATTGTGCAAGAATGACCACGATAGTTCCCTTTGACTACTGGGGCCA

AGGCACCACTCTCACAGTCTCCTCA

MURINE 15D5_VL nucleic acid sequence (cells)
SEQ ID NO: 60
GATATCCAGATGACACAGACTACATTCTCCCTGTCTGCCTCTCTGGGAGACAGAG

TCACCATCAGTTGCAGGGCAAGTCAGGACATTAGTAATTATTTAAACTGGTATCA

GCAGAAACCAGATGGAACTGTTAAACTCCTGATCTATTACACATCAACATTACAC

TCAGGAGTCCCATCAAGATTCAGTGGCAGTGGGTCTGGAACAGATTATTTTCTCA

CCATTAGGAACCTGGAGGAAGAAGATATTGCCACTTACTTTTGCCAACAGGGTTA

TACGCTTCCGTGGACGTTCGGTGGAGGCACCAAGTTGGACATCAAA

MURINE_1D9_VH nucleic acid sequence (cells)
SEQ ID NO: 61
CAGGTCCAACTGCAGCAGCCTGGGGCTGAGCTGGTGAGGCCTGGGACTTCAGTG

AAGTTGTCCTGCAAGGCCTCTGGCTACACCTTCACCAGCTACTGGATGCACTGGG

TAAAGCAGAGGCCTGGACAAGGCCTTGAGTGGATCGGAGTGATTGATCCTTCTGA

TGGTTATAGTCACTACAATCAAAAGTTCAAGGGCAAGGCCACTTTGACTGTAGAC

ACATCCTCCAGTACAGCCTACATGCAGCTCAGCAGCCTGACCTCTGAGGACTCTG

CGGTCTATTACTGTGCAGGAGGCTTAGCTGGGACGCTTGACTACTGGGGCCAGGG

CACCACTCTCACAGTCTCCTCA

MURINE_1D9_VL nucleic acid sequence (cells)
SEQ ID NO: 62
GATGTTTTGATGACCCAAACTCCACTCTCCCTGCCTGTCAGTCTTGGAGATCAAGC

CTCCATCTCTTGCAGATCTAGTCAGAGCATTGTACATAGTTCTGGAAACACCTATT

TACAATGGTTCCTGCAGAAACCAGGCCAGTCTCCAAAGCTCCTGATCTCCAAAGT

TTCCAACCGATTTTCTGGGGTCCCAGACAGGTTCAGTGGCAGTGGATCAGGGACA

GATTTCACACTCAGGATCAGCAGAGTGGAGGCTGAGGATCTGGGACTTTATTACT

GCTTTCAAGGTTCACATGTTCCGTGGACGTTCGGTGGAGGCACCAAGTTGGAAAT

CAAA

MURINE_22A5_VH nucleic acid sequence (cells)
SEQ ID NO: 63
GAGGTGCAGCTGGTGGAGTCTGGGGGAGGCTTAGTGAAGCCCGGAGGGTCCCTG

AAACTCTCCTGTGCAGCCTCTGGATTCACTTTCAGTGACTATGGAATGCACTGGCT

TCGTCAGGCTCCAGAGAAGGGGCTGGAGTGGGTTGCATACATTACTAGTGGCAGT

AGTGAAATCTACTATGTAGACACAGTGAAGGGCCGATTCACCATCTCCAGAGAC

AATGCCAAGAACACCCTGTGCCTGCAAATGACCAGTCTGAGGTCTGAGGACACG

GCCATGTATCACTGTGCAAGGGGCTACGGTTATAGAGAGGGGTACTTCGATGTCT

GGGGCACAGGGACCACGGTCACCGTCTCCTCA

MURINE_22A5_VL nucleic acid sequence (cells)
SEQ ID NO: 64
GATGTTGTGATGACCCAGACTCCACTCACTTTGTCGGTTACCATTGGACAACCAG

CCTCCATCTCTTGCAAGTCAAGTCAGAGCCTCTTAGATAGTGATGGAAAGACATA

TTTGAATTGGTTGTTACAGAGGCCAGGCCAGTCTCCAAAGCGCCTAATCTATCTG

GTGTCTAAACTGGACTCTGGAGTCCCTGACAGGTTCACTGGCAGTGGATCAGGGA

CAGATTTCACACTGAAAATCAGCAGAGTGGAGGCTGAGGATTTGGGAGTTTATTA

TTGCTGGCAAGGTACACATTTTCCTCAGACGTTCGGTGGAGGCACCAAGCTGGAA

ATCAAA

-continued

MURINE_22A5_VL nucleic acid sequence (cells)
SEQ ID NO: 65
GACATCCAGATGACTCAGTCTCCAGCCTCCCTATCTGTATCTGTGGGAGAAACTG

TCACCATCACATGTCGAACAAGTGAGAATGTTTACAGTAATTTAGCATGGTATCA

GCAGAAACAGGGAAGATCTCCTCAGCTCCTGGTCTATGGTGCAACAAGGTTACCA

GATGGTGTGCCAGCAAGGTTCAGTGGCAGTGGATCAGGCACACAGTATTCCCTCA

AGATCAACAGCCTGCAGTCTGAAGATTTTGGGACTTATTACTGTCAACTTTTTGG

GGTATCCCGCTCACGTTCGGTGCTGGGACCAAGCTGGAGCTGAAA

HUMAN HER3 EXTRACELLULAR DOMAIN w/o signal sequence
(corresponds to crystal structure)
SEQ ID NO: 66
SEVGNSQAVCPGTLNGLSVTGDAENQYQTLYKLYERCEVVMGNLEIVLTGH

NADLSFLQWIREVTGYVLVAMNEFSTLPLPNLRVVRGTQVYDGKFAIFVMLN

YNTNSSHALRQLRLTQLTEILSGGVYIEKNDKLCHMDTIDWRDIVRDRDAEIV

VKDNGRSCPPCHEVCKGRCWGPGSEDCQTLTKTICAPQCNGHCFGPNPNQCC

HDECAGGCSGPQDTDCFACRHFNDSGACVPRCPQPLVYNKLTFQLEPNPHTK

YQYGGVCVASCPHNFVVDQTSCVRACPPDKMEVDKNGLKMCEPCGGLCPK

ACEGTGSGSRFQTVDSSNIDGFVNCTKILGNLDFLITGLNGDPWHKIPALDPE

KLNVFRTVREITGYLNIQSWPPHMHNFSVFSNLTTIGGRSLYNRGFSLLIMKN

LNVTSLGFRSLKEISAGRIYISANRQLCYHHSLNWTKVLRGPTEERLDIKHNRP

RRDCVAEGKVCDPLCSSGGCWGPGPGQCLSCRNYSRGGVCVTHCNFLNGEP

REFAHEAECFSCHPECQPMEGTATCNGSGSDTCAQCAHFRDGPHCVSSCPHG

VLGAKGPIYKYPDVQNECRPCHENCTQGCKGPELQDCLGQTLVLIGKTHLT

HUMANIZED 1D9 H0 VH amino acid sequence
SEQ ID NO: 67
QVQLVQSGAEVKKPGASVKVSCKASGYTFT<u>SYWMH</u>WVRQAPGQGLEWMG<u>VIDPS</u>

<u>DGYSHYNQKFKG</u>RVTMTRDTSISTAYMELSRLRSDDTAVYYCAR<u>GLAGTLDY</u>WGQ

GTTVTVSS

HUMANIZED 1D9 H0 VH nucleic acid sequence
SEQ ID NO: 68
CAGGTGCAGCTGGTGCAGTCCGGCGCAGAGGTGAAGAAGCCCGGAGCCTCTGTG

AAGGTGAGCTGCAAGGCCAGCGGCTACACCTTCACCAGCTACTGGATGCACTGG

GTGAGGCAGGCCCCTGGCCAGGGCCTGGAGTGGATGGGCGTGATCGACCCCAGC

GACGGGTACAGCCACTACAACCAGAAGTTCAAGGGCAGGGTCACCATGACCAGG

GACACCAGCATCAGCACCGCCTACATGGAACTCAGCAGGCTGAGGAGCGACGAC

ACCGCCGTGTACTATTGCGCCAGGGGCCTGGCTGGCACCCTGGATTACTGGGCC

AGGGCACCACAGTGACCGTGAGCAGC

HUMANIZED 1D9 H1 VH amino acid sequence
SEQ ID NO: 69
QVQLVQSGAEVKKPGASVKVSCKASGYTFT<u>SYWMH</u>WVRQAPGQGLEWMG<u>VIDPS</u>

<u>DGYSHYNQKFKG</u>RVTMTVDTSISTAYMELSRLRSDDTAVYYCARGLAGTLDYWGQ

GTTVTVSS

HUMANIZED 1D9 H1 VH nucleic acid sequence
SEQ ID NO: 70
CAGGTGCAGCTGGTGCAGTCCGGCGCAGAGGTGAAGAAGCCCGGAGCCTCTGTG

AAGGTGAGCTGCAAGGCCAGCGGCTACACCTTCACCAGCTACTGGATGCACTGG

GTGAGGCAGGCCCCTGGCCAGGGCCTGGAGTGGATGGGCGTGATCGACCCCAGC

```
GACGGGTACAGCCACTACAACCAGAAGTTCAAGGGCAGGGTCACCATGACCGTG

GACACCAGCATCAGCACCGCCTACATGGAACTCAGCAGGCTGAGGAGCGACGAC

ACCGCCGTGTACTATTGCGCCAGGGGCCTGGCTGGCACCCTGGATTACTGGGCC

AGGGCACCACAGTGACCGTGAGCAGC
```

HUMANIZED 1D9 H2 VH amino acid sequence
SEQ ID NO: 71
```
QVQLVQSGAEVKKPGASVKVSCKASGYTFTSYWMHWVRQAPGQGLEWMGVIDPS

DGYSHYNQKFKGRVTMTRDTSISTAYMELSRLRSDDTAVYYCAGGLAGTLDYWGQ

GTTVTVSS
```

HUMANIZED 1D9 H2 VH nucleic acid sequence
SEQ ID NO: 72
```
CAGGTGCAGCTGGTGCAGTCCGGCGCAGAGGTGAAGAAGCCCGGAGCCTCTGTG

AAGGTGAGCTGCAAGGCCAGCGGCTACACCTTCACCAGCTACTGGATGCACTGG

GTGAGGCAGGCCCCTGGCCAGGGCCTGGAGTGGATGGGCGTGATCGACCCCAGC

GACGGGTACAGCCACTACAACCAGAAGTTCAAGGGCAGGGTCACCATGACCAGG

GACACCAGCATCAGCACCGCCTACATGGAACTCAGCAGGCTGAGGAGCGACGAC

ACCGCCGTGTACTATTGCGCCGGAGGCCTGGCTGGCACCCTGGATTACTGGGCC

AGGGCACCACAGTGACCGTGAGCAGC
```

HUMANIZED 1D9 H3 VH amino acid sequence
SEQ ID NO: 73
```
QVQLVQSGAEVKKPGASVKVSCKASGYTFTSYWMHWVRQAPGQGLEWMGVIDPS

DGYSHYNQKFKGKVTMTRDTSISTAYMELSRLRSDDTAVYYCARGLAGTLDYWGQ

GTTVTVSS
```

HUMANIZED 1D9 H3 VH nucleic acid sequence
SEQ ID NO: 74
```
CAGGTGCAGCTGGTGCAGTCCGGCGCAGAGGTGAAGAAGCCCGGAGCCTCTGTG

AAGGTGAGCTGCAAGGCCAGCGGCTACACCTTCACCAGCTACTGGATGCACTGG

GTGAGGCAGGCCCCTGGCCAGGGCCTGGAGTGGATGGGCGTGATCGACCCCAGC

GACGGGTACAGCCACTACAACCAGAAGTTCAAGGGCAAGGTCACCATGACCAGG

GACACCAGCATCAGCACCGCCTACATGGAACTCAGCAGGCTGAGGAGCGACGAC

ACCGCCGTGTACTATTGCGCCAGGGGCCTGGCTGGCACCCTGGATTACTGGGCC

AGGGCACCACAGTGACCGTGAGCAGC
```

HUMANIZED 1D9 L0 VL amino acid sequence
SEQ ID NO: 75
```
DIQMTQSPSSLSASVGDRVTITCRSSQSIVHSSGNTYLQWYQQKPGKAPKLLIYKVSN

RFSGVPSRFSGSGSGTDFTLTISSLQPEDFAVYYCFQGSHVPWTFGQGTKLEIKR
```

HUMANIZED 1D9 L0 VL nucleic acid sequence
SEQ ID NO: 76
```
GACATCCAGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTACCAGCAGAAACCCGGCAAGGCTCCCAAGCTGCTGATCTACA

AGGTGAGCAACAGGTTCAGCGGCGTGCCCTCTCGCTTCTCAGGCAGCGGCTCCGG

CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGG
```

-continued

HUMANIZED 1D9 L3 VL amino acid sequence
SEQ ID NO: 77
DVQMTQSPSSLSASVGDRVTITC<u>RSSQSIVHSSGNTYLQ</u>WYQQKPGKAPKLLIY<u>KVSN</u>
<u>RFS</u>GVPSRFSGSGSGTDFTLTISSLQPEDFAVYYC<u>FQGSHVPWT</u>FGQGTKLEIKR HUMANIZED 1D9 L3 VL nucleic acid sequence
SEQ ID NO: 78
GACGTGCAGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTACCAGCAGAAACCCGGCAAGGCTCCCAAGCTGCTGATCTACA

AGGTGAGCAACAGGTTCAGCGGCGTGCCCTCTCGCTTCTCAGGCAGCGGCTCCGG

CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGG

HUMANIZED 1D9 L4 VL amino acid sequence
SEQ ID NO: 79
DILMTQSPSSLSASVGDRVTITC<u>RSSQSIVHSSGNTYLQ</u>WYQQKPGKAPKLLIY<u>KVSN</u>
<u>RFS</u>GVPSRFSGSGSGTDFTLTISSLQPEDFAVYYC<u>FQGSHVPWT</u>FGQGTKLEIKR HUMANIZED 1D9 L4 VL nucleic acid sequence
SEQ ID NO: 80
GACATCCTGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTACCAGCAGAAACCCGGCAAGGCTCCCAAGCTGCTGATCTACA

AGGTGAGCAACAGGTTCAGCGGCGTGCCCTCTCGCTTCTCAGGCAGCGGCTCCGG

CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGG

HUMANIZED 1D9 L5 VL amino acid sequence
SEQ ID NO: 81
DVLMTQSPSSLSASVGDRVTITC<u>RSSQSIVHSSGNTYLQ</u>WFQQKPGKAPKLLIS<u>KVSN</u>
<u>RFS</u>GVPSRFSGSGSGTDFTLTISSLQPEDFAVYYC<u>FQGSHVPWT</u>FGQGTKLEIKR HUMANIZED 1D9 L5 VL nucleic acid sequence
SEQ ID NO: 82
GACGTGCTGATGACCCAGAGCCCCTCTAGCCTGAGCGCCAGCGTGGGCGACAGG

GTGACCATTACCTGCAGGAGCAGCCAGAGCATCGTGCACAGCAGCGGCAACACC

TACCTGCAGTGGTTCCAGCAGAAACCCGGCAAGGCTCCCAAGCTGCTGATCAGCA

AGGTGAGCAACAGGTTCAGCGGCGTGCCCTCTCGCTTCTCAGGCAGCGGCTCCGG

CACCGATTTCACCCTGACCATCAGCTCACTGCAGCCCGAGGACTTCGCCGTCTAC

TACTGCTTCCAGGGAAGCCACGTGCCCTGGACTTTTGGCCAGGGCACCAAGCTCG

AGATCAAGAGG

HUMANIZED 1D9 L6 VL amino acid sequence
SEQ ID NO: 83
DVVMTQSPLSLPVTLGQPASISC<u>RSSQSIVHSSGNTYLQ</u>WFQQRPGQSPRRLIY<u>KVSN</u>
<u>RFS</u>GVPDRFSGSGSGTDFTLKISRVEAEDVGVYYC<u>FQGSHVPWT</u>FGQGTLKEIKR HUMANIZED 1D9 L6 VL nucleic acid sequence
SEQ ID NO: 84
GACGTGGTGATGACACAGAGCCCTCTGAGCCTGCCTGTGACCCTGGGCCAGCCCG

CCAGCATTAGCTGCAGGAGCAGCCAGTCCATCGTGCACAGCAGCGGCAACACCT

ACCTGCAGTGGTTCCAGCAGAGGCCCGGCCAGAGCCCCAGGAGGCTGATCTACA

AGGTGAGCAACAGGTTCAGCGGCGTGCCCGACAGATTCAGCGGCTCAGGCAGCG

```
GCACCGACTTCACCCTCAAGATCAGCAGGGTGGAGGCCGAGGACGTGGGCGTCT

ACTACTGCTTCCAGGGGAGCCACGTGCCCTGGACCTTTGGACAGGGCACCAAGCT

GGAGATCAAGAGG
```

HUMANIZED 1D9 L7 VL amino acid sequence
SEQ ID NO: 85
```
DVVMTQSPLSLPVTLGQPASISCRSSQSIVHSSGNTYLQWFQQRPGQSPRRLISKVSNR

FSGVPDRFSGSGSGTDFTLKISRVEAEDVGVYYCFQGSHVPWTFGQGTKLEIKR
```

HUMANIZED 1D9 L7 VL nucleic acid sequence
SEQ ID NO: 86
```
GACGTGGTGATGACACAGAGCCCTCTGAGCCTGCCTGTGACCCTGGGCCAGCCCG

CCAGCATTAGCTGCAGGAGCAGCCAGTCCATCGTGCACAGCAGCGGCAACACCT

ACCTGCAGTGGTTCCAGCAGAGGCCCGGCCAGAGCCCCAGGAGGCTGATCAGCA

AGGTGAGCAACAGGTTCAGCGGCGTGCCCGACAGATTCAGCGGCTCAGGCAGCG

GCACCGACTTCACCCTCAAGATCAGCAGGGTGGAGGCCGAGGACGTGGGCGTCT

ACTACTGCTTCCAGGGGAGCCACGTGCCCTGGACCTTTGGACAGGGCACCAAGCT

CGAGATCAAGAGG
```

HUMANIZED 1D9 L9 VL amino acid sequence
SEQ ID NO: 87
```
DVVMTQSPLSLPVTLGQPASISCRSSQSIVHSSGNTYLQWFQQRPGQSPKLLISKVSNR

FSGVPDRFSGSGSGTDFTLKISRVEAEDVGVYYCFQGSHVPWTFGQGTKLEIKR
```

HUMANIZED 1D9 L9 VL nucleic acid sequence
SEQ ID NO: 89
```
GACGTGGTGATGACACAGAGCCCTCTGAGCCTGCCTGTGACCCTGGGCCAGCCCG

CCAGCATTAGCTGCAGGAGCAGCCAGTCCATCGTGCACAGCAGCGGCAACACCT

ACCTGCAGTGGTTCCAGCAGAGGCCCGGCCAGAGCCCCAAGCTGCTGATCAGCA

AGGTGAGCAACAGGTTCAGCGGCGTGCCCGACAGATTCAGCGGCTCAGGCAGCG

GCACCGACTTCACCCTCAAGATCAGCAGGGTGGAGGCCGAGGACGTGGGCGTCT

ACTACTGCTTCCAGGGGAGCCACGTGCCCTGGACCTTTGGACAGGGCACCAAGCT

CGAGATCAAGAGG
```

HUMANIZED 15D5 H1 VH amino acid sequence
SEQ ID NO: 90
```
QFQLVQSGAEVKKPGASVKVSCKASGYSFTDYNMNWVKQAPGQGLEWIGGINPNY

GTTVYNQKFKGKATLTVDQSISTAYMELSRLRSDDTAVYYCARMTTIVPFDYWGQG

TTVTVSS
```

HUMANIZED 15D5 H1 VH nucleic acid sequence
SEQ ID NO: 91
```
CAGTTCCAGCTGGTGCAGAGCGGAGCCGAGGTGAAGAAGCCCGGAGCCAGCGTC

AAAGTGAGCTGCAAGGCCTCCGGCTACAGCTTCACCGACTACAACATGAACTGG

GTGAAGCAGGCCCCCGGGCAGGGCCTGGAGTGGATCGGCGGCATCAATCCCAAC

TACGGCACCACCGTGTACAACCAGAAGTTCAAGGGCAAGGCCACCCTGACCGTG

GACCAGAGCATCAGCACCGCCTACATGGAACTCAGCAGGCTGAGGAGCGACGAT

ACCGCCGTGTACTACTGCGCTAGGATGACCACCATCGTGCCCTTCGACTATTGGG

GCCAGGGCACAACCGTGACTGTGAGCAGC
```

-continued

HUMANIZED 15D5 H2 VH amino acid sequence
SEQ ID NO: 92
QVQLVQSGAEVKKPGASVKVSCKASGYTFT<u>DYNMN</u>WVKQAPGQGLEWIG<u>GINPNY</u>

<u>GTTVYNQKFKG</u>KATLTVDQSISTAYMELSRLRSDDTAVYYCAR<u>MTTIVPFDYW</u>

GQGTTVTVSS

HUMANIZED 15D5 H2 VH nucleic acid sequence
SEQ ID NO: 93
CAGGTGCAGCTCGTGCAGAGCGGAGCCGAGGTGAAAAAGCCCGGCGCTAGCGTG

AAGGTGAGCTGCAAGGCCAGCGGCTACACCTTCACCGACTACAACATGAACTGG

GTGAAGCAGGCACCCGGCCAGGGCCTGGAGTGGATCGGCGGCATCAACCCCAAC

TACGGCACTACCGTCTACAACCAGAAGTTCAAGGGCAAGGCCACCCTGACCGTG

GATCAGAGCATCAGCACCGCCTACATGGAACTGTCTAGGCTGAGGAGCGACGAC

ACCGCCGTGTACTATTGCGCCAGGATGACCACCATCGTGCCCTTCGACTACTGGG

GCCAGGGAACCACAGTCACCGTGAGCAGC

HUMANIZED 15D5 H3 VH amino acid sequence
SEQ ID NO: 94
QVQLVQSGAEVKKPGASVKVSCKASGYTFT<u>DYNMN</u>WVRQAPGQGLEWMG<u>GINPN</u>

<u>YGTTVYNQKFKG</u>KATLTVDQSISTAYMELSRLRSDDTAVYYCAR<u>MTTIVPFDYW</u>GQ

GTTVTVSS

HUMANIZED 15D5 H3 VH nucleic acid sequence
SEQ ID NO: 95
CAGGTGCAGCTGGTCCAGAGCGGAGCCGAGGTGAAAAAGCCCGGCGCAAGCGTG

AAGGTGAGCTGCAAGGCCAGCGGCTACACCTTCACCGACTACAACATGAACTGG

GTGAGGCAGGCCCCCGGCCAGGGCCTCGAGTGGATGGGAGGCATCAACCCCAAC

TACGGCACCACCGTGTACAACCAGAAGTTCAAGGGCAAGGCCACCCTGACCGTG

GACCAGAGCATCAGCACCGCCTACATGGAACTGAGCAGGCTGAGGAGCGACGAC

ACCGCCGTGTACTATTGCGCCAGGATGACCACCATCGTGCCCTTCGACTACTGGG

GCCAGGGCACAACCGTGACCGTGTCTAGC

HUMANIZED 15D5 L2 VL amino acid sequence
SEQ ID NO: 96
DIQMTQSPSSLSASVGDRVTITC<u>RASQDISNYLN</u>WYQQKPGKAPKLLIY<u>YTSTLHS</u>GV PSRFSGSGSGTDYTLTISSLQPEDFATYYC<u>QQGYTLPWT</u>FGQGTKLEIKR HUMANIZED 15D5 L2 VL nucleic acid sequence
SEQ ID NO: 97
GACATCCAGATGACCCAGAGCCCTAGCAGCCTGAGCGCCTCAGTGGGCGATAGG

GTGACCATCACCTGCAGGGCCAGCCAGGACATCAGCAACTACCTGAACTGGTAC

CAGCAGAAGCCCGGGAAGGCCCCCAAGCTGCTGATCTACTACACCTCCACCCTGC

ACAGCGGCGTGCCCTCAAGGTTCTCCGGCAGCGGCAGCGGCACCGACTACACTCT

GACCATCAGCAGCCTCCAGCCCGAGGACTTCGCCACCTACTACTGCCAGCAGGGC

TATACCCTGCCCTGGACCTTCGGCCAGGGCACCAAGCTGGAGATTAAGAGG

HUMANIZED 15D5 L3 VL amino acid sequence
SEQ ID NO: 98
DIQMTQSPSSLSASVGDRVTITC<u>RASQDISNYLN</u>WYQQKPGKAPKLLIY<u>YTSTLHS</u>GV PSRFSGSGSGTDFTLTISSLQPEDFATYYC<u>QQGYTLPWT</u>FGQGTKLEIKR HUMANIZED 15D5 L3 VL nucleic acid sequence
SEQ ID NO: 99
GACATCCAGATGACCCAGAGCCCCAGCAGCCTGAGCGCCAGCGTGGGCGATAGG

GTGACCATTACCTGCAGGGCCAGCCAGGACATCAGCAACTACCTGAACTGGTACC

AGCAGAAGCCCGGCAAGGCCCCCAAGCTGCTGATCTACTACACCTCCACTCTGCA

```
CAGCGGCGTGCCCTCTAGGTTCTCCGGCTCAGGCAGCGGAACCGACTTCACCCTG

ACCATCAGCAGCCTCCAGCCCGAGGACTTCGCCACCTACTACTGCCAGCAGGGCT

ATACCCTGCCTTGGACCTTCGGCCAGGGCACCAAACTGGAGATCAAGAGG
```

HUMANIZED 1D9 H6 FULL-LENGTH HEAVY CHAIN amino acid
sequence (used for expression of the humanized 1D9 H6L2
antibody in non-POTELLIGENT ™ system cells having a
functional copy of the FUT8 gene and used for expression
of the humanized 1D9 H6L2 POTELLIGENT ™ antibody in
POTELLIGENT ™ system CHOK1SV cells lacking a functional
copy of the FUT8 gene)
SEQ ID NO: 100

```
MGWSCIILFLVATATGVHSQVQLVQSGAEVKKPGASVKVSCKASGYTFTSYWMHWV

RQAPGQGLEWMGVIDPSDGYSHYNQKFKGKVTLTVDTSISTAYMELSRLRSDDTAV

YYCAGGLAGTLDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVD

VSHEDPEVKFNWYVDGVEVHNAKTKPREEQYN*STYRVVSVLTVLHQDWLNGKEY

KCKVSNKALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVMHEALHN

HYTQKSLSLSPGK
```

HUMANIZED 1D9 H6 FULL-LENGTH HEAVY CHAIN nucleic acid
sequence (used for expression of the humanized 1D9 H6L2
antibody in non-POTELLIGENT ™ system cells having a
functional copy of the FUT8 gene and used for expression
of the humanized 1D9 H6L2 POTELLIGENT ™ antibody in
POTELLIGENT ™ system CHOK1SV cells lacking a functional
copy of the FUT8 gene). Portion encoding
MGWSCIILFLVATATGVHS signal sequence can be omitted.
SEQ ID NO: 101

```
ATGGGCTGGTCCTGCATCATCCTGTTTCTGGTGGCCACCGCCACCGGTGTGCACA

GCCAGGTGCAGCTGGTGCAGTCCGGCGCAGAGGTGAAGAAGCCCGGAGCCTCTG

TGAAGGTGAGCTGCAAGGCCAGCGGCTACACCTTCACCAGCTACTGGATGCACTG

GGTGAGGCAGGCCCCTGGCCAGGGCCTGGAGTGGATGGGCGTGATCGACCCCAG

CGACGGGTACAGCCACTACAACCAGAAGTTCAAGGGCAAGGTCACCCTGACCGT

GGACACCAGCATCAGCACCGCCTACATGGAACTCAGCAGGCTGAGGAGCGACGA

CACCGCCGTGTACTATTGCGCCGGAGGCCTGGCTGGCACCCTGGATTACTGGGGC

CAGGGCACCACAGTGACCGTGAGCAGCGCCAGCACCAAGGGCCCCAGCGTGTTC

CCCCTGGCGCCCAGCAGCAAGAGCACCAGCGGCGGCACAGCCGCCCTGGGCTGC

CTGGTGAAGGACTACTTCCCCGAGCCAGTGACCGTGTCCTGGAACAGCGGAGCCC

TGACCAGCGGCGTGCACACCTTCCCAGCTGTCCTGCAGAGCAGCGGCCTGTACAG

CCTGAGCAGCGTGGTGACCGTGCCCAGCAGCAGCCTGGGCACCCAGACCTACAT

CTGTAACGTGAACCACAAGCCCAGCAACACCAAGGTGGACAAGAAGGTGGAGCC

CAAGAGCTGTGACAAGACCCACACCTGCCCCCCCTGCCCTGCCCCCGAGCTGCTG

GGAGGCCCCAGCGTGTTCCTGTTCCCCCCCAAGCCTAAGGACACCCTGATGATCA

GCAGAACCCCCGAGGTGACCTGTGTGGTGGTGGATGTGAGCCACGAGGACCCTG

AGGTGAAGTTCAACTGGTACGTGGACGGCGTGGAGGTGCACAATGCCAAGACCA

AGCCCAGGGAGGAGCAGTACAACAGCACCTACCGGGTGGTGTCCGTGCTGACCG

TGCTGCACCAGGATTGGCTGAACGGCAAGGAGTACAAGTGTAAGGTGTCCAACA

AGGCCCTGCCTGCCCCTATCGAGAAAACCATCAGCAAGGCCAAGGGCCAGCCCA
```

-continued

GAGAGCCCCAGGTGTACACCCTGCCCCCTAGCAGAGATGAGCTGACCAAGAACC

AGGTGTCCCTGACCTGCCTGGTGAAGGGCTTCTACCCCAGCGACATCGCCGTGGA

GTGGGAGAGCAACGGCCAGCCCGAGAACAACTACAAGACCACCCCCCCTGTGCT

GGACAGCGATGGCAGCTTCTTCCTGTACAGCAAGCTGACCGTGGACAAGAGCAG

ATGGCAGCAGGGCAACGTGTTCAGCTGCTCCGTGATGCACGAGGCCCTGCACAAT

CACTACACCCAGAAGAGCCTGAGCCTGTCCCCTGGCAAG

HUMANIZED 1D9 H6 COMPLEGENT ™ (when used for expression
of THE humanized 1D9 H6L2 COMPLEGENT ™ antibody in
non-POTELLIGENT ™ system cells having a functional copy
of the FUT8 gene) or ACCRETAMAB ™ (when used for
expression of the humanized 1D9 H6L2 ACCRETAMAB ™
antibody when expressed in POTELLIGENT ™ system CHOK1SV
cells lacking a functional copy of the FUT8 gene) IgG1/
IgG3 isotype chimera FULL-LENGTH HEAVY CHAIN amino
acid sequence
SEQ ID NO: 102

*MGWSCIILFLVATATGVHS*QVQLVQSGAEVKKPGASVKVSCKASGYTFT<u>SYWMH</u>WV

RQAPGQGLEWMG<u>VIDPSDGYSHYNQKFK</u>GKVTLTVDTSISTAYMELSRLRSDDTAV

YYCAG<u>GLAGTLDY</u>WGQGTTVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPS

NTKVDKKVEPKSCDKTHTCPPCPAPELLGGPSVFLFPPKPKDTLMISRTPEVTCVVVD

VSHEDPEVQFKWYVDGVEVHNAKTKPREEQFN*STFRVVSVLTVLHQDWLNGKEY

KCKVSNKALPAPIEKTISKTKGQPREPQVYTLPPSREEMTKNQVSLTCLVKGFYPSDI

AVEWESSGQPENNYKTTPPMLDSDGSFFLYSKLTVDKSRWQQGNIFSCSVMHEALH

NHYTQKSLSLSPGK

HUMANIZED 1D9 H6 COMPLEGENT ™ (when used for expression
of THE humanized 1D9 H6L2 COMPLEGENT ™ antibody in
non-POTELLIGENT ™ system cells having a functional copy
of the FUT8 gene) or ACCRETAMAB ™ (when used for
expression of the humanized 1D9 H6L2 ACCRETAMAB ™
antibody when expressed in POTELLIGENT ™ system CHOK1SV
cells lacking a functional copy of the FUT8 gene) IgG1/
IgG3 isotype chimera FULL-LENGTH HEAVY CHAIN nucleic
acid sequence. Portion encoding *MGWSCIILFLVATATGVHS*
signal sequence can be omitted.
SEQ ID NO: 103
ATGGGCTGGTCCTGCATCATCCTGTTTCTGGTGGCCACCGCCACCGGTGTGCACA

GCCAGGTGCAGCTGGTGCAGTCCGGCGCAGAGGTGAAGAAGCCCGGAGCCTCTG

TGAAGGTGAGCTGCAAGGCCAGCGGCTACACCTTCACCAGCTACTGGATGCACTG

GGTGAGGCAGGCCCCTGGCCAGGGCCTGGAGTGGATGGGCGTGATCGACCCCAG

CGACGGGTACAGCCACTACAACCAGAAGTTCAAGGGCAAGGTCACCCTGACCGT

GGACACCAGCATCAGCACCGCCTACATGGAACTCAGCAGGCTGAGGAGCGACGA

CACCGCCGTGTACTATTGCGCCGGAGGCCTGGCTGGCACCCTGGATTACTGGGGC

CAGGGCACCACAGTGACCGTGAGCAGCGCCAGCACCAAGGGCCCAAGCGTGTTT

CCCCTGGCCCCCAGCAGCAAGTCTACCAGCGGCGGCACAGCCGCCCTGGGCTGCC

TGGTCAAAGACTACTTCCCCGAGCCCGTCACCGTGAGCTGGAATAGCGGCGCACT

GACCAGCGGCGTGCACACCTTTCCCGCCGTGCTGCAGAGCTCAGGCCTGTATAGC

CTGAGCAGCGTGGTGACCGTGCCTTCTAGCAGCCTGGGCACCCAGACCTACATCT

GCAACGTCAACCACAAGCCCAGCAACACCAAGGTGGACAAGAAAGTGGAGCCCA

AGAGCTGCGACAAGACCCACACCTGCCCCCCCTGTCCAGCTCCGGAGCTGCTGGG

CGGCCCCAGCGTGTTCCTCTTCCCCCCCAAGCCCAAGGACACCCTGATGATCTCT

```
AGAACCCCCGAGGTGACCTGCGTGGTGGTGGACGTCAGCCACGAAGACCCCGAG

GTGCAGTTCAAGTGGTACGTGGACGGGGTGGAGGTGCACAACGCCAAGACTAAG

CCCAGGGAGGAGCAGTTCAACTCCACCTTCAGGGTGGTGAGCGTCCTGACCGTGC

TGCATCAGGACTGGCTGAACGGCAAGGAGTACAAGTGCAAGGTGAGCAACAAGG

CCCTGCCCGCCCCCATCGAGAAGACCATCAGCAAAACCAAGGGCCAGCCTAGGG

AACCCCAGGTGTACACCCTGCCCCCCTCCAGGGAGGAGATGACCAAGAACCAGG

TGAGCCTCACCTGCCTGGTGAAGGGCTTCTACCCCAGCGACATTGCCGTGGAGTG

GGAGTCAAGCGGCCAGCCCGAGAACAACTACAAGACCACCCCCCCCATGCTCGA

TAGCGACGGCAGCTTCTTCCTGTACAGCAAGCTGACCGTGGACAAGAGCCGGTG

GCAGCAGGGCAACATCTTCAGCTGCAGCGTGATGCACGAGGCCCTGCACAACCA

CTACACCCAGAAGAGCCTGAGCCTGAGCCCCGGAAAG
```

HUMANIZED 1D9 L2 FULL-LENGTH LIGHT CHAIN amino acid
sequence (used for co-expression with SEQ ID NO: 100
in non-POTELLIGENT ™ system cells having a functional
copy of the FUT8 gene to produce the humanized 1D9
H6L2 antibody, used for co-expression with SEQ ID
NO: 100 in POTELLIGENT ™ system CHOK1SV cells lacking
a functional copy of the FUT8 gene to produce the
humanized 1D9 H6L2 POTELLIGENT ™ antibody, used for
co-expression with SEQ ID NO: 102 in non-POTELLIGENT ™
system cells with a functional copy of the FUT8 gene
to produce the humanized 1D9 H6L2 COMPLEGENT ™
antibody, and used for co-expression with SEQ ID
NO: 102 in POTELLIGENT ™ system cells lacking a
functional copy of the FUT8 gene to produce the
humanized 1D9 H6L2 ACCRETAMAB ™ antibody)
SEQ ID NO: 104

```
MGWSCIILFLVATATGVHSDIQMTQSPSSLSASVGDRVTITCRSSQSIVHSSGNTYLQWF

QQKPGKAPKLLIYKVSNRFSGVPSRFSGSGSGTDFTLTISSLQPEDFAVYYCFQGSHVP

WTFGQGTKLEIKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSF

NRGEC
```

HUMANIZED 1D9 L2 FULL-LENGTH LIGHT CHAIN nucleic acid
sequence (used for co-expression with SEQ ID NO: 100
in non-POTELLIGENT ™ system cells having a functional
copy of the FUT8 gene to produce the humanized 1D9
H6L2 antibody, used for co-expression with SEQ ID
NO: 100 in POTELLIGENT ™ system CHOK1SV cells lacking
a functional copy of the FUT8 gene to produce the
humanized 1D9 H6L2 POTELLIGENT ™ antibody, used for
co-expression with SEQ ID NO: 102 in non-POTELLIGENT ™
system cells with a functional copy of the FUT8 gene
to produce the humanized 1D9 H6L2 COMPLEGENT ™
antibody, and used for co-expression with SEQ ID
NO: 102 in POTELLIGENT ™ system cells lacking a
functional copy of the FUT8 gene to produce the
humanized 1D9 H6L2 ACCRETAMAB ™ antibody). Portion
encoding MGWSCIILFLVATATGVHS signal sequence can
be omitted.
SEQ ID NO: 105

```
ATGGGATGGAGCTGTATCATCCTCTTCTTGGTAGCAACAGCTACAGGTGTCCACT

CCGACATCCAGATGACCCAGAGCCCCTCTAGCCTGAGCGCCAGCGTGGGCGACA

GGGTGACCATTACCTGCAGGAGCAGCCAGAGCATCGTGCACAGCAGCGGCAACA

CCTACCTGCAGTGGTTCCAGCAGAAACCCGGCAAGGCTCCCAAGCTGCTGATCTA

CAAGGTGAGCAACAGGTTCAGCGGCGTGCCCTCTCGCTTCTCAGGCAGCGGCTCC

GGCACCGATTTCACCCTGACCATCAGCTCACTGCAGCCCGAGGACTTCGCCGTCT

ACTACTGCTTCCAGGGAAGCCACGTGCCCTGGACTTTTGGCCAGGGCACCAAGCT
```

-continued

```
CGAGATCAAGCGTACGGTGGCCGCCCCCAGCGTGTTCATCTTCCCCCCCAGCGAT

GAGCAGCTGAAGAGCGGCACCGCCAGCGTGGTGTGTCTGCTGAACAACTTCTACC

CCCGGGAGGCCAAGGTGCAGTGGAAGGTGGACAATGCCCTGCAGAGCGGCAACA

GCCAGGAGAGCGTGACCGAGCAGGACAGCAAGGACTCCACCTACAGCCTGAGCA

GCACCCTGACCCTGAGCAAGGCCGACTACGAGAAGCACAAGGTGTACGCCTGTG

AGGTGACCCACCAGGGCCTGTCCAGCCCCGTGACCAAGAGCTTCAACCGGGGCG

AGTGC
```

TABLE 17

Antibody details.

| Antibody | SEQ ID NO:s for Associated VH/VL Pairs | Details |
| --- | --- | --- |
| Murine 1D9 antibody | Comprises SEQ ID NO: 44 (VH) and SEQ ID NO: 48 (VL). | |
| Murine 15D5 antibody | Comprises SEQ ID NO: 1 (VH) and SEQ ID NO: 5 (VH). | |
| Chimeric 1D9 antibody | Comprises SEQ ID NO: 44 (VH) and SEQ ID NO: 48 (VL). | Comprises murine VH fused to human IgG1 CH1-Fc domains. Comprises murine VL fused to human IgG1 CK domain. |
| Chimeric 15D5 antibody | Comprises SEQ ID NO: 44 (VH) and SEQ ID NO: 48 (VL). | Comprises murine VH fused to human IgG1 CH1-Fc domains. Comprises murine VL fused to human IgG1 CK domain. |
| Humanized 1D9 antibody | Comprises SEQ ID NO: 30 (VH) and SEQ ID NO: 34 (VL) expressed in FUT8+ cells. Comprises SEQ ID NO: 100 (VH) and SEQ ID NO: 104 (VL) expressed in FUT8+ cells. | Fucosylated glycans may be present. G0, G2, G0F, G2F, G1, Man5, G1F and G1F' glycans may be present on N* residue marked in heavy chain sequence shown in SEQ ID: 100 of Example 11. VH and VL signal sequences are absent in mature form antibodies. |
| Humanized 1D9 Fc disabled antibody | Comprises SEQ ID NO: 30 (VH) and SEQ ID NO: 34 (VL). | Comprises a humanized VH fused to a modified Fc domain incapable of mediating CDC/ADCC. |
| Humanized 1D9 POTELLIGENT ™ antibody | Comprises SEQ ID NO: 30 (VH) and SEQ ID NO: 34 (VL) expressed in FUT8− cells. Comprises SEQ ID NO: 100 (VH) and SEQ ID NO: 104 (VL) expressed in FUT8− cells. | Fucosylated glycans are absent. G0, G2, G1 and Man5 glycans may be present on N* residue marked in heavy chain sequence shown in SEQ ID: 100 of Example 11. VH and VL signal sequences are absent in mature form antibodies. |
| Humanized 1D9 COMPLEGENT ™ antibody | SEQ ID NO: 30 (VH) and SEQ ID NO: 34 (VL) expressed in FUT8+ cells. SEQ ID NO: 102 (VH) and SEQ ID NO: 104 (VL) expressed in FUT8+ cells. | Fucosylated glycans may be present. G0, G2, G0F, G2F, G1, Man5, G1F and G1F' glycans may be present on N* residue marked in heavy chain sequence shown in SEQ ID: 102 of Example 11. Comprises a chimeric IgG1/IgG3 isotype Fc domain. VH and VL signal sequences are absent in mature form antibodies. |

TABLE 17-continued

Antibody details.

| Antibody | SEQ ID NO:s for Associated VH/VL Pairs | Details |
|---|---|---|
| Humanized 1D9 ACCRETAMAB ™ antibody | SEQ ID NO: 30 (VH) and SEQ ID NO: 34 (VL) expressed in FUT8⁻ cells. SEQ ID NO: 102 (VH) and SEQ ID NO: 104 (VL) expressed in FUT8⁻ cells. | Fucosylated glycans are absent. G0, G2, G1 and Man5 glycans may be present on N* residue marked in heavy chain sequence shown in SEQ ID: 104 of Example 11. Comprises a chimeric IgG1/IgG3 isotype Fc. VH and VL signal sequences are absent in mature form antibodies. |
| Humanized 1D9 RR antibody | Comprises SEQ ID NO: 30 (VH) and SEQ ID NO: 34 (VL) expressed in FUT8+ cells. Comprises SEQ ID NO: 100 (VH) and SEQ ID NO: 104 (VL) expressed in FUT8⁺ cells. | Fucosylated glycans may be present. G0, G2, G0F, G2F, G1, Man5, G1F and G1F' glycans may be present on N* residue marked in heavy chain sequence shown in SEQ ID: 100 of Example 11. VH and VL signal sequences are absent in mature form antibodies. Additional R amino acid residue is inserted on carboxy terminal side of EIK at terminus of Framework 4 in the VL chain. |
| Humanized 1D9 RR POTELLIGENT ™ antibody | Comprises SEQ ID NO: 30 (VH) and SEQ ID NO: 34 (VL) expressed in FUT8⁻ cells; or Comprises SEQ ID NO: 100 (VH) and SEQ ID NO: 104 (VL) expressed in FUT8⁻ cells. | Fucosylated glycans are absent. G0, G2, G1 and Man5 glycans may be present on N* residue marked in heavy chain sequence shown in SEQ ID: 100 of Example 11. VH and VL signal sequences are absent in mature form antibodies. Additional R amino acid residue is inserted on carboxy terminal side of EIK at terminus of Framework 4 in the VL chain. |
| Humanized 1D9 RR COMPLEGENT ™ antibody | Comprises SEQ ID NO: 30 (VH) and SEQ ID NO: 34 (VL) expressed in FUT8⁺ cells; or Comprises SEQ ID NO: 102 (VH) and SEQ ID NO: 104 (VL) expressed in FUT8⁺ cells. | Fucosylated glycans may be present. G0, G2, G0F, G2F, G1, Man5, G1F and G1F' glycans may be present on N* residue marked in heavy chain sequence shown in SEQ ID: 102 of Example 11. Comprises a chimeric IgG1/IgG3 isotype Fc domain. VH and VL signal sequences are absent in mature form antibodies. Additional R amino acid residue is inserted on carboxy terminal side of EIK at terminus of Framework 4 in the VL chain. |
| Humanized 1D9 RR ACCRETAMAB ™ antibody | Comprises SEQ ID NO: 30 (VH) and SEQ ID NO: 34 (VL) expressed in FUT8⁻ cells; or Comprises SEQ ID NO: 102 (VH) and SEQ ID NO: 104 (VL) expressed in FUT8⁻ cells. | Fucosylated glycans are absent. G0, G2, G1 and Man5 glycans may be present on N* residue marked in heavy chain sequence shown in SEQ ID: 104 of Example 11. Comprises a chimeric IgG1/IgG3 isotype Fc. VH and VL signal sequences are absent in mature form antibodies. Additional R amino acid |

TABLE 17-continued

Antibody details.

| Antibody | SEQ ID NO:s for Associated VH/VL Pairs | Details |
|---|---|---|
| Humanized 15D5 antibody | Comprises SEQ ID NO:s 22 (VH) and SEQ ID NO: 26 (VL). May be expressed in FUT8$^+$ cells. or May be expressed in FUT8$^-$ cells | residue is inserted on carboxy terminal side of EIK at terminus of Framework 4 in the VL chain. Fucosylated glycans may be present on expression in FUT8$^+$ cells. G0, G2, G0F, G2F, G1, Man5, G1F and G1F' glycans may be present on N-glycosylation sites on expression in FUT8$^+$ cells. or Fucosylated glycans are absent on expression in FUT8$^-$ cells. G0, G2, G1 and Man5 glycans may be present on N-glycoslation sites on expression in FUT8$^-$ cells. also some embodiments may comprise a chimeric IgG1/IgG3 isotype Fc identical to that in the humanized 1D9 COMPLEGENT ™ antibody and humanized 1D9 ACCRETAMAB ™ antibody, fused to the VH domain shown in SEQ ID NO: 22 (e.g., at the carboxy terminus of this VH domain). |

The present invention now being fully described, it will be apparent to one of ordinary skill in the art that many changes and modifications can be made thereto without departing from the spirit or scope of the appended claims.

The material in the ASCII text file named "PU64334USNatlSeqList.txt," created on Aug. 29, 2012 and having a size of 91,492 bytes is incorporated herein by reference in its entirety.

What is claimed is:

1. An anti-HER3 antibody comprising a heavy chain variable region having the CDRH1 amino acid sequence shown in SEQ ID NO: 31, the CDRH2 amino acid sequence shown in SEQ ID NO: 32, and the CDRH3 amino acid sequence shown in SEQ ID NO: 33; and a light chain variable region having the CDRL1 amino acid sequence shown in SEQ ID NO: 35, the CDRL2 amino acid sequence shown in SEQ ID NO: 36, and the CDRL3 amino acid sequence shown in SEQ ID NO: 37.

2. The antibody of claim 1 wherein the antibody is selected from the group consisting of a chimeric antibody and a humanized antibody.

3. The antibody of claim 1 which specifically binds to a peptide chain domain comprising amino acid residues 330 to 495 of SEQ ID NO: 21.

4. An anti-HER3 antibody comprising a heavy chain variable region sequence having the amino acid sequence shown in SEQ ID NO: 30 and a light chain variable region sequence having the amino acid sequence shown in SEQ ID NO: 34.

5. An isolated nucleic acid encoding the antibody of claim 1.

6. The isolated nucleic acid of claim 5 comprising at least one nucleic acid selected from the group consisting of the nucleic acid sequence shown in SEQ ID NO: 42 and the nucleic acid sequence shown in SEQ ID NO: 43.

7. An expression vector comprising the isolated nucleic acid of claim 5.

8. A recombinant host cell comprising an expression vector comprising the isolated nucleic acid of claim 5.

9. A method for the production of an antibody comprising the step of culturing a recombinant host cell comprising an expression vector comprising the isolated nucleic acid of claim 5; and recovering the antibody.

10. A pharmaceutical composition comprising the antibody of claim 1; and a pharmaceutically acceptable carrier.

11. A method of treating cancer expressing HER3 in a subject comprising the step of administering a therapeutically effective amount of the antibody of claim 1 to the subject, whereby the cancer in the subject is treated.

12. A method of treating cancer expressing HER3 in a subject comprising the steps of:
   a) identifying a subject with a cancer selected from the group consisting of breast cancer, ovarian cancer, prostate cancer, bladder cancer, pancreatic cancer, skin cancer, gastric cancer and melanoma; and
   b) administering a therapeutically effective amount of the antibody of claim 4 to the subject, whereby the cancer in the subject is treated.

13. The method of claim 12 further comprising the step of:
   c) determining the cancer expresses a protein comprising amino acid residues 330 to 495 of SEQ ID NO: 21.

14. The method of claim 13 wherein the protein comprises the amino acid sequence shown in SEQ ID NO: 21.

15. A method for the production of an antibody comprising the steps of:
   a) culturing a recombinant host cell comprising an expression vector comprising the isolated nucleic acid of claim 5, wherein the FUT8 gene encoding alpha-1,6-fucosyltransferase has been inactivated in the recombinant host cell; and
   b) recovering the antibody;
whereby the antibody is produced.

16. An antibody produced by the method of claim 15.

17. A method for the production of an antibody comprising the steps of:
   a) culturing a recombinant host cell comprising an expression vector comprising the isolated nucleic acid of claim 5, wherein the expression vector comprises a Fc nucleic acid sequence encoding a chimeric Fc domain having both IgG1 and IgG3 Fc domain amino acid residues; and
   b) recovering the antibody;
whereby the antibody is produced.

18. The method of claim 17 wherein the Fc nucleic acid sequence is fused in frame to a nucleic acid selected from the group consisting of the nucleic acid sequence shown in SEQ ID NO: 43 and the nucleic acid sequence shown in SEQ ID NO: 42.

19. An antibody produced by the method of claim 18.

20. A method for the production of an antibody comprising the steps of:
   a) culturing a recombinant host cell containing an expression vector containing an isolated nucleic acid of claim 5, said expression vector further comprising a Fc nucleic acid sequence encoding a chimeric Fc domain having both IgG1 and IgG3 Fc domain amino acid residues, and wherein the FUT8 gene encoding alpha-1,6-fucosyltransferase has been inactivated in the recombinant host cell; and b) recovering the antibody;

whereby the antibody is produced.

21. The method of claim 20 wherein the Fc nucleic acid sequence is fused in frame to a nucleic acid selected from the group consisting of the nucleic acid sequence shown in SEQ ID NO: 43 and the nucleic acid sequence shown in SEQ ID NO: 42.

22. An antibody produced by the method of claim 20.

23. An antibody which specifically binds a HER3 receptor and comprises CDRH1 having the amino acid sequence shown in SEQ ID NO: 31, CDRH2 having the amino acid sequence shown in SEQ ID NO: 32, CDRH3 having the amino acid sequence shown in SEQ ID NO: 33, CDRL1 having the amino acid sequence shown in SEQ ID NO: 35, CDRL2 having the amino acid sequence shown in SEQ ID NO: 36, and CDRL3 having the amino acid sequence shown in SEQ ID NO: 37.

24. A method of treating cancer expressing HER3 in a mammal comprising administering a therapeutically effective amount of an antibody of claim 1; whereby the cancer is treated.

25. The method of claim 24 wherein the mammal is a human.

26. The method of claim 25 wherein the cancer is selected from breast cancer, ovarian cancer, prostate cancer, bladder cancer, pancreatic cancer, skin cancer, gastric cancer and melanoma.

27. An antibody comprising a heavy chain sequence having amino acid residues 20 to 466 of the amino acid sequence shown in SEQ ID NO: 102 and a light chain sequence having amino acid residues 20 to 238 of the amino acid sequence shown in SEQ ID NO: 104.

28. The antibody of claim 27 comprising non-fucosylated glycans.

29. The antibody of claim 28 wherein the non-fucosylated glycans are selected from the group consisting of G0, G2, G1 and Man5.

30. An isolated nucleic acid encoding amino acid residues 20 to 238 of the amino acid sequence shown in SEQ ID NO: 104.

31. The isolated nucleic acid of claim 30 comprising nucleic acid residues 58 to 714 of the nucleic acid sequence shown in SEQ ID NO: 105.

32. An isolated nucleic acid encoding amino acid residues 20 to 466 of the amino acid sequence shown in SEQ ID NO: 102.

33. The isolated nucleic acid of claim 32 comprising nucleic acid residues 58 to 1398 of the nucleic acid sequence shown in SEQ ID NO: 103.

34. An expression vector comprising the isolated nucleic acid of claim 32.

35. A recombinant host cell comprising an expression vector comprising the isolated nucleic acid of claim 32.

36. The recombinant host cell of claim 35 wherein the FUT8 gene encoding alpha-1,6-fucosyltransferase has been inactivated.

37. A pharmaceutical composition comprising the antibody of claim 27; and a pharmaceutically acceptable carrier.

38. A method of treating cancer expressing HER3 in a subject comprising the step of administering a therapeutically effective amount of the antibody of claim 27 to the subject, whereby the cancer in the subject is treated.

39. A method of treating cancer expressing HER3 in a subject comprising the steps of:
a) identifying a subject with a cancer selected from the group consisting of breast cancer, ovarian cancer, prostate cancer, bladder cancer, pancreatic cancer, skin cancer, gastric cancer and melanoma; and
b) administering a therapeutically effective amount of the antibody of claim 27 to the subject, whereby the cancer in a subject is treated.

40. The method of claim 39 further comprising the step of:
c) determining the cancer expresses a protein comprising amino acid residues 330 to 495 of SEQ ID NO: 21.

41. The method of claim 40 wherein the protein comprises the amino acid sequence shown in SEQ ID NO: 21.

42. A method for the production of an antibody comprising the steps of:
a) culturing a recombinant host cell comprising an expression vector comprising an isolated nucleic acid encoding amino acid residues 20 to 238 of the amino acid sequence shown in SEQ ID NO: 104 and comprising an isolated nucleic acid encoding amino acid residues 20 to 466 of the amino acid sequence shown in SEQ ID NO: 102, wherein the FUT8 gene encoding alpha-1,6-fucosyltransferase has been inactivated in the recombinant host cell; and
b) recovering the antibody;

whereby the antibody is produced.

43. An antibody produced by the method of claim 42.

44. A pharmaceutical composition comprising the antibody of claim 4; and a pharmaceutically acceptable carrier.

45. A method of treating cancer expressing HER3 in a subject comprising the step of administering a therapeutically effective amount of the antibody of claim 4 to the subject, whereby the cancer in the subject is treated.

46. A method of treating cancer expressing HER3 in a mammal comprising administering a therapeutically effective amount of an antibody of claim 4; whereby the cancer is treated.

47. The method of claim 46 wherein the mammal is a human.

48. The method of claim 47 wherein the cancer is selected from breast cancer, ovarian cancer, prostate cancer, bladder cancer, pancreatic cancer, skin cancer, gastric cancer and melanoma.

49. An expression vector comprising the isolated nucleic acid of claim 33.

50. A recombinant host cell comprising an expression vector comprising the isolated nucleic acid of claim 33.

51. The recombinant host cell of claim 50 wherein the FUT8 gene encoding alpha-1,6-fucosyltransferase has been inactivated.

52. An isolated nucleic acid comprising the nucleic acid sequence shown in SEQ ID NO: 105.

53. An isolated nucleic acid comprising the nucleic acid sequence shown in SEQ ID NO: 103.

54. A pharmaceutical composition comprising the antibody of claim 28; and a pharmaceutically acceptable carrier.

55. A method of treating cancer expressing HER3 in a subject comprising the step of administering a therapeutically effective amount of the antibody of claim 28 to the subject, whereby the cancer in the subject is treated.

56. A method of treating cancer expressing HER3 in a subject comprising the steps of:
a) identifying a subject with a cancer selected from the group consisting of breast cancer, ovarian cancer, prostate cancer, bladder cancer, pancreatic cancer, skin cancer, gastric cancer and melanoma; and b) administering a therapeutically effective amount of the antibody of claim 28 to the subject, whereby the cancer in a subject is treated.

57. The method of claim 56 further comprising the step of:
c) determining the cancer expresses a protein comprising amino acid residues 330 to 495 of SEQ ID NO: 21.

58. The method of claim 57 wherein the protein comprises the amino acid sequence shown in SEQ ID NO: 21.

59. A method of treating cancer expressing HER3 in a subject comprising the steps of:
a) identifying a subject with a cancer selected from the group consisting of breast cancer, ovarian cancer, prostate cancer, bladder cancer, pancreatic cancer, skin cancer, gastric cancer and melanoma; and
b) administering a therapeutically effective amount of the antibody of claim 29 to the subject, whereby the cancer in a subject is treated.

60. The method of claim 59 further comprising the step of:
c) determining the cancer expresses a protein comprising amino acid residues 330 to 495 of SEQ ID NO: 21.

61. The method of claim 60 wherein the protein comprises the amino acid sequence shown in SEQ ID NO: 21.

62. A method for the production of an antibody comprising the steps of:
a) culturing a recombinant host cell comprising an expression vector comprising an isolated nucleic acid having the nucleic acid sequence shown in SEQ ID NO: 105 and comprising an isolated nucleic acid having the nucleic acid sequence shown in SEQ ID NO: 103, wherein the FUT8 gene encoding alpha-1,6-fucosyltransferase has been inactivated in the recombinant host cell; and
b) recovering the antibody;
whereby the antibody is produced.

63. An antibody produced by the method of claim 62.

64. An expression vector comprising the isolated nucleic acid of claim 30.

65. A recombinant host cell comprising an expression vector comprising the isolated nucleic acid of claim 30.

66. The recombinant host cell of claim 65 wherein the FUT8 gene encoding alpha-1,6-fucosyltransferase has been inactivated.

67. An expression vector comprising the isolated nucleic acid of claim 31.

68. A recombinant host cell comprising an expression vector comprising the isolated nucleic acid of claim 31.

69. The recombinant host cell of claim 68 wherein the FUT8 gene encoding alpha-1,6-fucosyltransferase has been inactivated.

\* \* \* \* \*

```
                         SEQUENCE LISTING

<160> NUMBER OF SEQ ID NOS: 105

<210> SEQ ID NO 1
<211> LENGTH: 118
<212> TYPE: PRT
<213> ORGANISM: Mus musculus

<400> SEQUENCE: 1

Glu Phe Gln Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Asp Tyr
             20                  25                  30

Asn Met Asn Trp Val Lys Gln Asn Gly Lys Ser Leu Glu Trp Ile
         35                  40                  45

Gly Gly Ile Asn Pro Asn Tyr Gly Thr Thr Val Tyr Asn Gln Lys Phe
     50                  55                  60

Lys Gly Lys Ala Thr Leu Thr Val Asp Gln Ser Ser Ser Thr Ala Tyr
 65                  70                  75                  80

Met Gln Leu Val Ser Leu Thr Ser Glu Asp Ser Ala Val Tyr Tyr Cys
                 85                  90                  95

Ala Arg Met Thr Thr Ile Val Pro Phe Asp Tyr Trp Gly Gln Gly Thr
             100                 105                 110
```

```
Thr Leu Thr Val Ser Ser
        115

<210> SEQ ID NO 2
<211> LENGTH: 5
<212> TYPE: PRT
<213> ORGANISM: Mus musculus

<400> SEQUENCE: 2

Asp Tyr Asn Met Asn
1               5

<210> SEQ ID NO 3
<211> LENGTH: 17
<212> TYPE: PRT
<213> ORGANISM: Mus musculus

<400> SEQUENCE: 3

Gly Ile Asn Pro Asn Tyr Gly Thr Thr Val Tyr Asn Gln Lys Phe Lys
1               5                   10                  15

Gly

<210> SEQ ID NO 4
<211> LENGTH: 9
<212> TYPE: PRT
<213> ORGANISM: Mus musculus

<400> SEQUENCE: 4

Met Thr Thr Ile Val Pro Phe Asp Tyr
1               5

<210> SEQ ID NO 5
<211> LENGTH: 107
<212> TYPE: PRT
<213> ORGANISM: Mus musculus

<400> SEQUENCE: 5

Asp Ile Gln Met Thr Gln Thr Thr Phe Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Thr Leu His Ser Gly Val Pro Ser Arg Phe Ser Gly
        50                  55                  60

Ser Gly Ser Gly Thr Asp Tyr Phe Leu Thr Ile Arg Asn Leu Glu Glu
65                  70                  75                  80

Glu Asp Ile Ala Thr Tyr Phe Cys Gln Gln Gly Tyr Thr Leu Pro Trp
                85                  90                  95

Thr Phe Gly Gly Gly Thr Lys Leu Asp Ile Lys
            100                 105

<210> SEQ ID NO 6
<211> LENGTH: 11
<212> TYPE: PRT
<213> ORGANISM: Mus musculus

<400> SEQUENCE: 6

Arg Ala Ser Gln Asp Ile Ser Asn Tyr Leu Asn
1               5                   10
```

```
<210> SEQ ID NO 7
<211> LENGTH: 7
<212> TYPE: PRT
<213> ORGANISM: Mus musculus

<400> SEQUENCE: 7

Tyr Thr Ser Thr Leu His Ser
1               5

<210> SEQ ID NO 8
<211> LENGTH: 9
<212> TYPE: PRT
<213> ORGANISM: Mus musculus

<400> SEQUENCE: 8

Gln Gln Gly Tyr Thr Leu Pro Trp Thr
1               5

<210> SEQ ID NO 9
<211> LENGTH: 120
<212> TYPE: PRT
<213> ORGANISM: Mus musculus

<400> SEQUENCE: 9

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Leu Arg Gln Ala Pro Glu Lys Gly Leu Glu Trp Val
        35                  40                  45

Ala Tyr Ile Thr Ser Gly Ser Ser Glu Ile Tyr Tyr Val Asp Thr Val
    50                  55                  60

Lys Gly Arg Phe Thr Ile Ser Arg Asp Asn Ala Lys Asn Thr Leu Cys
65                  70                  75                  80

Leu Gln Met Thr Ser Leu Arg Ser Glu Asp Thr Ala Met Tyr His Cys
                85                  90                  95

Ala Arg Gly Tyr Gly Tyr Arg Glu Gly Tyr Phe Asp Val Trp Gly Thr
            100                 105                 110

Gly Thr Thr Val Thr Val Ser Ser
        115                 120

<210> SEQ ID NO 10
<211> LENGTH: 5
<212> TYPE: PRT
<213> ORGANISM: Mus musculus

<400> SEQUENCE: 10

Asp Tyr Gly Met His
1               5

<210> SEQ ID NO 11
<211> LENGTH: 17
<212> TYPE: PRT
<213> ORGANISM: Mus musculus

<400> SEQUENCE: 11

Tyr Ile Thr Ser Gly Ser Ser Glu Ile Tyr Tyr Val Asp Thr Val Lys
1               5                   10                  15

Gly
```

<210> SEQ ID NO 12
<211> LENGTH: 11
<212> TYPE: PRT
<213> ORGANISM: Mus musculus

<400> SEQUENCE: 12

Gly Tyr Gly Tyr Arg Glu Gly Tyr Phe Asp Val
1               5                   10

<210> SEQ ID NO 13
<211> LENGTH: 112
<212> TYPE: PRT
<213> ORGANISM: Mus musculus

<400> SEQUENCE: 13

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 14
<211> LENGTH: 16
<212> TYPE: PRT
<213> ORGANISM: Mus musculus

<400> SEQUENCE: 14

Lys Ser Ser Gln Ser Leu Leu Asp Ser Asp Gly Lys Thr Tyr Leu Asn
1               5                   10                  15

<210> SEQ ID NO 15
<211> LENGTH: 7
<212> TYPE: PRT
<213> ORGANISM: Mus musculus

<400> SEQUENCE: 15

Leu Val Ser Lys Leu Asp Ser
1               5

<210> SEQ ID NO 16
<211> LENGTH: 9
<212> TYPE: PRT
<213> ORGANISM: Mus musculus

<400> SEQUENCE: 16

Trp Gln Gly Thr His Phe Pro Gln Thr
1               5

<210> SEQ ID NO 17
<211> LENGTH: 107
<212> TYPE: PRT
<213> ORGANISM: Mus musculus

<400> SEQUENCE: 17

```
Asp Ile Gln Met Thr Gln Ser Pro Ala Ser Leu Ser Val Ser Val Gly
  1               5                  10                  15

Glu Thr Val Thr Ile Thr Cys Arg Thr Ser Glu Asn Val Tyr Ser Asn
             20                  25                  30

Leu Ala Trp Tyr Gln Lys Gln Gly Arg Ser Pro Gln Leu Leu Val
         35                  40                  45

Tyr Gly Ala Thr Arg Leu Pro Asp Gly Val Pro Ala Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln Leu Phe Trp Gly Ile Pro Leu
             85                  90                  95

Thr Phe Gly Ala Gly Thr Lys Leu Glu Leu Lys
            100                 105
```

```
<210> SEQ ID NO 18
<211> LENGTH: 11
<212> TYPE: PRT
<213> ORGANISM: Mus musculus

<400> SEQUENCE: 18

Arg Thr Ser Glu Asn Val Tyr Ser Asn Leu Ala
 1               5                  10

<210> SEQ ID NO 19
<211> LENGTH: 7
<212> TYPE: PRT
<213> ORGANISM: Mus musculus

<400> SEQUENCE: 19

Gly Ala Thr Arg Leu Pro Asp
 1               5

<210> SEQ ID NO 20
<211> LENGTH: 9
<212> TYPE: PRT
<213> ORGANISM: Mus musculus

<400> SEQUENCE: 20

Gln Leu Phe Trp Gly Ile Pro Leu Thr
 1               5

<210> SEQ ID NO 21
<211> LENGTH: 1342
<212> TYPE: PRT
<213> ORGANISM: Homo sapien

<400> SEQUENCE: 21
```

```
Met Arg Ala Asn Asp Ala Leu Gln Val Leu Gly Leu Leu Phe Ser Leu
 1               5                  10                  15

Ala Arg Gly Ser Glu Val Gly Asn Ser Gln Ala Val Cys Pro Gly Thr
             20                  25                  30

Leu Asn Gly Leu Ser Val Thr Gly Asp Ala Glu Asn Gln Tyr Gln Thr
         35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
```

```
                85                  90                  95
Leu Pro Leu Pro Asn Leu Arg Val Val Arg Gly Thr Gln Val Tyr Asp
            100                 105                 110
Gly Lys Phe Ala Ile Phe Val Met Leu Asn Tyr Asn Thr Asn Ser Ser
            115                 120                 125
His Ala Leu Arg Gln Leu Arg Leu Thr Gln Leu Thr Glu Ile Leu Ser
            130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                165                 170                 175
Lys Asp Asn Gly Arg Ser Cys Pro Pro Cys His Glu Val Cys Lys Gly
            180                 185                 190
Arg Cys Trp Gly Pro Gly Ser Glu Asp Cys Gln Thr Leu Thr Lys Thr
                195                 200                 205
Ile Cys Ala Pro Gln Cys Asn Gly His Cys Phe Gly Pro Asn Pro Asn
210                 215                 220
Gln Cys Cys His Asp Glu Cys Ala Gly Gly Cys Ser Gly Pro Gln Asp
225                 230                 235                 240
Thr Asp Cys Phe Ala Cys Arg His Phe Asn Asp Ser Gly Ala Cys Val
                245                 250                 255
Pro Arg Cys Pro Gln Pro Leu Val Tyr Asn Lys Leu Thr Phe Gln Leu
            260                 265                 270
Glu Pro Asn Pro His Thr Lys Tyr Gln Tyr Gly Gly Val Cys Val Ala
            275                 280                 285
Ser Cys Pro His Asn Phe Val Val Asp Gln Thr Ser Cys Val Arg Ala
            290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                325                 330                 335
Gly Ser Arg Phe Gln Thr Val Asp Ser Ser Asn Ile Asp Gly Phe Val
            340                 345                 350
Asn Cys Thr Lys Ile Leu Gly Asn Leu Asp Phe Leu Ile Thr Gly Leu
            355                 360                 365
Asn Gly Asp Pro Trp His Lys Ile Pro Ala Leu Asp Pro Glu Lys Leu
            370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
            420                 425                 430
Met Lys Asn Leu Asn Val Thr Ser Leu Gly Phe Arg Ser Leu Lys Glu
            435                 440                 445
Ile Ser Ala Gly Arg Ile Tyr Ile Ser Ala Asn Arg Gln Leu Cys Tyr
            450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
            500                 505                 510
```

```
Gly Pro Gly Gln Cys Leu Ser Cys Arg Asn Tyr Ser Arg Gly Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
            770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
            885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
            915                 920                 925
```

-continued

```
Arg Leu Ala Gln Pro Gln Ile Cys Thr Ile Asp Val Tyr Met Val Met
    930                 935                 940
Val Lys Cys Trp Met Ile Asp Glu Asn Ile Arg Pro Thr Phe Lys Glu
945                 950                 955                 960
Leu Ala Asn Glu Phe Thr Arg Met Ala Arg Asp Pro Arg Tyr Leu
                965                 970                 975
Val Ile Lys Arg Glu Ser Gly Pro Gly Ile Ala Pro Gly Pro Glu Pro
            980                 985                 990
His Gly Leu Thr Asn Lys Lys Leu Glu Glu Val Glu Leu Glu Pro Glu
            995                 1000                1005
Leu Asp Leu Asp Leu Asp Leu Glu Ala Glu Asp Asn Leu Ala Thr
    1010                1015                1020
Thr Thr Leu Gly Ser Ala Leu Ser Leu Pro Val Gly Thr Leu Asn Arg
1025                1030                1035                1040
Pro Arg Gly Ser Gln Ser Leu Leu Ser Pro Ser Ser Gly Tyr Met Pro
                1045                1050                1055
Met Asn Gln Gly Asn Leu Gly Glu Ser Cys Gln Glu Ser Ala Val Ser
                1060                1065                1070
Gly Ser Ser Glu Arg Cys Pro Arg Pro Val Ser Leu His Pro Met Pro
        1075                1080                1085
Arg Gly Cys Leu Ala Ser Glu Ser Ser Glu Gly His Val Thr Gly Ser
    1090                1095                1100
Glu Ala Glu Leu Gln Glu Lys Val Ser Met Cys Arg Ser Arg Ser Arg
1105                1110                1115                1120
Ser Arg Ser Pro Arg Pro Arg Gly Asp Ser Ala Tyr His Ser Gln Arg
                1125                1130                1135
His Ser Leu Leu Thr Pro Val Thr Pro Leu Ser Pro Pro Gly Leu Glu
                1140                1145                1150
Glu Glu Asp Val Asn Gly Tyr Val Met Pro Asp Thr His Leu Lys Gly
            1155                1160                1165
Thr Pro Ser Ser Arg Glu Gly Thr Leu Ser Ser Val Gly Leu Ser Ser
    1170                1175                1180
Val Leu Gly Thr Glu Glu Glu Asp Glu Asp Glu Glu Tyr Glu Tyr Met
1185                1190                1195                1200
Asn Arg Arg Arg Arg His Ser Pro Pro His Pro Pro Arg Pro Ser Ser
                1205                1210                1215
Leu Glu Glu Leu Gly Tyr Glu Tyr Met Asp Val Gly Ser Asp Leu Ser
                1220                1225                1230
Ala Ser Leu Gly Ser Thr Gln Ser Cys Pro Leu His Pro Val Pro Ile
            1235                1240                1245
Met Pro Thr Ala Gly Thr Thr Pro Asp Glu Asp Tyr Glu Tyr Met Asn
    1250                1255                1260
Arg Gln Arg Asp Gly Gly Gly Pro Gly Gly Asp Tyr Ala Ala Met Gly
1265                1270                1275                1280
Ala Cys Pro Ala Ser Glu Gln Gly Tyr Glu Glu Met Arg Ala Phe Gln
                1285                1290                1295
Gly Pro Gly His Gln Ala Pro His Val His Tyr Ala Arg Leu Lys Thr
            1300                1305                1310
Leu Arg Ser Leu Glu Ala Thr Asp Ser Ala Phe Asp Asn Pro Asp Tyr
    1315                1320                1325
Trp His Ser Arg Leu Phe Pro Lys Ala Asn Ala Gln Arg Thr
1330                1335                1340
```

```
<210> SEQ ID NO 22
<211> LENGTH: 118
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asn Trp Val Arg Gln Ala Pro Gly Gln Gly Leu Glu Trp Met
            35                  40                  45

Gly Gly Ile Asn Pro Asn Tyr Gly Thr Thr Val Tyr Asn Gln Lys Phe
    50                  55                  60

Lys Gly Lys Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Met Thr Thr Ile Val Pro Phe Asp Tyr Trp Gly Gln Gly Thr
                100                 105                 110

Thr Val Thr Val Ser Ser
            115

<210> SEQ ID NO 23
<211> LENGTH: 5
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 23

Asp Tyr Asn Met Asn
1               5

<210> SEQ ID NO 24
<211> LENGTH: 17
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 24

Gly Ile Asn Pro Asn Tyr Gly Thr Thr Val Tyr Asn Gln Lys Phe Lys
1               5                   10                  15

Gly

<210> SEQ ID NO 25
<211> LENGTH: 9
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 25

Met Thr Thr Ile Val Pro Phe Asp Tyr
1               5
```

```
<210> SEQ ID NO 26
<211> LENGTH: 108
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Tyr Thr Leu Pro Trp
                85                  90                  95

Thr Phe Gly Gly Gly Thr Lys Val Glu Ile Lys Arg
            100                 105

<210> SEQ ID NO 27
<211> LENGTH: 11
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 27

Arg Ala Ser Gln Asp Ile Ser Asn Tyr Leu Asn
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 28

Tyr Thr Ser Thr Leu His Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 29

Gln Gln Gly Tyr Thr Leu Pro Trp Thr
1               5

<210> SEQ ID NO 30
<211> LENGTH: 117
<212> TYPE: PRT
<213> ORGANISM: Artificial Sequence
<220> FEATURE:
```

<223> OTHER INFORMATION: Humanized antibody amino acid sequence designed
     in silico and made using molecular biology synthetic techniques.

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Val Ile Asp Pro Ser Asp Gly Tyr Ser His Tyr Asn Gln Lys Phe
    50                  55                  60

Lys Gly Lys Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Gly Gly Leu Ala Gly Thr Leu Asp Tyr Trp Gly Gln Gly Thr Thr
            100                 105                 110

Val Thr Val Ser Ser
        115

<210> SEQ ID NO 31
<211> LENGTH: 5
<212> TYPE: PRT
<213> ORGANISM: Artificial Sequence
<220> FEATURE:
<223> OTHER INFORMATION: Humanized antibody amino acid sequence designed
     in silico and made using molecular biology synthetic techniques.

<400> SEQUENCE: 31

Ser Tyr Trp Met His
1               5

<210> SEQ ID NO 32
<211> LENGTH: 17
<212> TYPE: PRT
<213> ORGANISM: Artificial Sequence
<220> FEATURE:
<223> OTHER INFORMATION: Humanized antibody amino acid sequence designed
     in silico and made using molecular biology synthetic techniques.

<400> SEQUENCE: 32

Val Ile Asp Pro Ser Asp Gly Tyr Ser His Tyr Asn Gln Lys Phe Lys
1               5                   10                  15

Gly

<210> SEQ ID NO 33
<211> LENGTH: 8
<212> TYPE: PRT
<213> ORGANISM: Artificial Sequence
<220> FEATURE:
<223> OTHER INFORMATION: Humanized antibody amino acid sequence designed
     in silico and made using molecular biology synthetic techniques.

<400> SEQUENCE: 33

Gly Leu Ala Gly Thr Leu Asp Tyr
1               5

<210> SEQ ID NO 34
<211> LENGTH: 113
<212> TYPE: PRT
<213> ORGANISM: Artificial Sequence
<220> FEATURE:

<223> OTHER INFORMATION: Humanized antibody amino acid sequence designed
      in silico and made using molecular biology synthetic techniques.

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Ser Gly Asn Thr Tyr Leu Gln Trp Phe Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg

<210> SEQ ID NO 35
<211> LENGTH: 16
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 35

Arg Ser Ser Gln Ser Ile Val His Ser Ser Gly Asn Thr Tyr Leu Gln
1               5                   10                  15

<210> SEQ ID NO 36
<211> LENGTH: 7
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 36

Lys Val Ser Asn Arg Phe Ser
1               5

<210> SEQ ID NO 37
<211> LENGTH: 9
<212> TYPE: PRT
<213> ORGANISM: Artificial Sequence
<220> FEATURE:
<223> OTHER INFORMATION: Humanized antibody amino acid sequence designed
      in silico and made using molecular biology synthetic techniques.

<400> SEQUENCE: 37

Phe Gln Gly Ser His Val Pro Trp Thr
1               5

<210> SEQ ID NO 38
<211> LENGTH: 354
<212> TYPE: DNA
<213> ORGANISM: Mus musculus

<400> SEQUENCE: 38
gagttccagc tgcagcagag cggccccgag ctggtgaagc ccggcgccag cgtgaagatc      60

```
agctgcaagg ccagcggcta cagcttcacc gactacaaca tgaactgggt gaagcagaac    120
aacggcaaga gcctggagtg gatcggcggc atcaaccccca actacggcac caccgtgtac    180
aaccagaagt tcaagggcaa ggccaccctg accgtggacc agagcagcag caccgcctac    240
atgcagctgg tgagcctgac cagcgaggac agcgccgtgt actactgcgc caggatgacc    300
accatcgtgc ccttcgacta ctggggccag ggcaccaccc tgaccgtgag cagc          354
```

<210> SEQ ID NO 39
<211> LENGTH: 321
<212> TYPE: DNA
<213> ORGANISM: Mus musculus

<400> SEQUENCE: 39

```
gacatccaga tgacccagac caccttcagc ctgagcgcca gcctgggcga cagggtgacc     60
atcagctgca gggccagcca ggacatcagc aactacctga actggtacca gcagaagccc    120
gacggcaccg tgaagctgct gatctactac accagcaccc tgcacagcgg cgtgcccagc    180
aggttcagcg gcagcggcag cggcaccgac tacttcctga ccatcaggaa cctggaggag    240
gaggacatcg ccacctactt ctgccagcag ggctacaccc tgccctggac cttcggcggc    300
ggcaccaagc tggacatcaa g                                              321
```

<210> SEQ ID NO 40
<211> LENGTH: 357
<212> TYPE: DNA
<213> ORGANISM: Artificial Sequence
<220> FEATURE:
<223> OTHER INFORMATION: Humanized antibody nucleic acid sequene
      designed in silico and made using molecular biology synthetic
      techniques.

<400> SEQUENCE: 40

```
caggtccagc tcgtgcagtc tggggccgag gtgaagaaac ccggcgctag cgtgaaggtg     60
agctgcaagg ccagcggcta caccttcacc gactacaaca tgaactgggt gaggcaggcc    120
cccggccagg gcctggagtg gatgggcggc atcaaccccca actacggcac caccgtgtac    180
aaccagaagt tcaagggcaa ggtgaccctg accgtggaca ccagcatcag caccgcctac    240
atggaactga gcaggctgag gagcgacgat accgccgtgt actattgcgc caggatgacc    300
accatcgtgc ccttcgacta ctggggacag ggcaccactg tgacagtgtc aagccgu       357
```

<210> SEQ ID NO 41
<211> LENGTH: 321
<212> TYPE: DNA
<213> ORGANISM: Artificial Sequence
<220> FEATURE:
<223> OTHER INFORMATION: Humanized antibody nucleic acid sequene
      designed in silico and made using molecular biology synthetic
      techniques.

<400> SEQUENCE: 41

```
gacatccaga tgacccagtc acccagcagc ctgagcgcca gcgtgggcga cagggtgacc     60
attacctgca gggccagcca ggacatcagc aactacctga actggtacca gcagaagccc    120
ggcaaggccc ccaagctgct gatctactac acctccaccc tgcacagcgg cgtgccctct    180
aggttctccg gcagcggcag cggcaccgac tacaccttca ccatcagcag cctgcagccc    240
gaggacatcg ccacctacta ttgccagcag ggctacaccc tccccctggac tttcggaggc    300 ggcaccaagg tggagatcaa g                                              321
```

<210> SEQ ID NO 42
<211> LENGTH: 351
<212> TYPE: DNA
<213> ORGANISM: Artificial Sequence
<220> FEATURE:
<223> OTHER INFORMATION: Humanized antibody nucleic acid sequene designed in silico and made using molecular biology synthetic techniques.

<400> SEQUENCE: 42

```
caggtgcagc tggtgcagtc cggcgcagag gtgaagaagc ccggagcctc tgtgaaggtg      60
agctgcaagg ccagcggcta caccttcacc agctactgga tgcactgggt gaggcaggcc     120
cctggccagg gcctggagtg gatgggcgtg atcgacccca gcgacgggta cagccactac     180
aaccagaagt tcaagggcaa ggtcaccctg accgtggaca ccagcatcag caccgcctac     240
atggaactca gcaggctgag gagcgacgac accgccgtgt actattgcgc cggaggcctg     300
gctggcaccc tggattactg gggccagggc accacagtga ccgtgagcag c              351
```

<210> SEQ ID NO 43
<211> LENGTH: 339
<212> TYPE: DNA
<213> ORGANISM: Artificial Sequence
<220> FEATURE:
<223> OTHER INFORMATION: Humanized antibody nucleic acid sequene designed in silico and made using molecular biology synthetic techniques.

<400> SEQUENCE: 43

```
gacatccaga tgacccagag ccccctctagc ctgagcgcca gcgtgggcga cagggtgacc    60
attacctgca ggagcagcca gagcatcgtg cacagcagcg gcaacaccta cctgcagtgg    120
ttccagcaga aacccggcaa ggctcccaag ctgctgatct acaaggtgag caacaggttc    180
agcggcgtgc cctctcgctt ctcaggcagc ggctccggca ccgatttcac cctgaccatc    240
agctcactgc agcccgagga cttcgccgtc tactactgct tccagggaag ccacgtgccc    300
tggactttg gccagggcac caagctcgag atcaagagg                            339
```

<210> SEQ ID NO 44
<211> LENGTH: 117
<212> TYPE: PRT
<213> ORGANISM: Mus musculus

<400> SEQUENCE: 44

```
Gln Val Gln Leu Gln Gln Pro Gly Ala Glu Leu Val Arg Pro Gly Thr
  1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Val Ile Asp Pro Ser Asp Gly Tyr Ser His Tyr Asn Gln Lys Phe
     50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Gly Gly Leu Ala Gly Thr Leu Asp Tyr Trp Gly Gln Gly Thr Thr
            100                 105                 110

Leu Thr Val Ser Ser
            115
```

<210> SEQ ID NO 45
<211> LENGTH: 5
<212> TYPE: PRT
<213> ORGANISM: Mus musculus

<400> SEQUENCE: 45

Ser Tyr Trp Met His
1               5

<210> SEQ ID NO 46
<211> LENGTH: 17
<212> TYPE: PRT
<213> ORGANISM: Mus musculus

<400> SEQUENCE: 46

Val Ile Asp Pro Ser Asp Gly Tyr Ser His Tyr Asn Gln Lys Phe Lys
1               5                   10                  15

Gly

<210> SEQ ID NO 47
<211> LENGTH: 8
<212> TYPE: PRT
<213> ORGANISM: Mus musculus

<400> SEQUENCE: 47

Gly Leu Ala Gly Thr Leu Asp Tyr
1               5

<210> SEQ ID NO 48
<211> LENGTH: 112
<212> TYPE: PRT
<213> ORGANISM: Mus musculus

<400> SEQUENCE: 48

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Ser Gly Asn Thr Tyr Leu Gln Trp Phe Leu Gln Lys Pro Gly Gln Ser
        35                  40                  45

Pro Lys Leu Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Leu Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 49
<211> LENGTH: 16
<212> TYPE: PRT
<213> ORGANISM: Mus musculus

<400> SEQUENCE: 49

Arg Ser Ser Gln Ser Ile Val His Ser Gly Asn Thr Tyr Leu Gln
1               5                   10                  15

<210> SEQ ID NO 50
<211> LENGTH: 7

<212> TYPE: PRT
<213> ORGANISM: Mus musculus

<400> SEQUENCE: 50

Lys Val Ser Asn Arg Phe Ser
 1               5

<210> SEQ ID NO 51
<211> LENGTH: 9
<212> TYPE: PRT
<213> ORGANISM: Mus musculus

<400> SEQUENCE: 51

Phe Gln Gly Ser His Val Pro Trp Thr
 1               5

<210> SEQ ID NO 52
<211> LENGTH: 351
<212> TYPE: DNA
<213> ORGANISM: Mus musculus

<400> SEQUENCE: 52

```
caggtgcagc tgcagcagcc cggcgccgag ctggtgaggc ccggcaccag cgtgaagctg       60
agctgcaagg ccagcggcta caccttcacc agctactgga tgcactgggt gaagcagagg     120
cccggccagg gcctggagtg gatcggcgtg atcgacccca cgacggcta cagccactac      180
aaccagaagt tcaagggcaa ggccaccctg accgtggaca ccagcagcag caccgcctac     240
atgcagctga gcagcctgac cagcgaggac agcgccgtgt actactgcgc cggcggcctg     300
gccggcaccc tggactactg gggccagggc accaccctga ccgtgagcag c             351
```

<210> SEQ ID NO 53
<211> LENGTH: 336
<212> TYPE: DNA
<213> ORGANISM: Mus musculus

<400> SEQUENCE: 53

```
gacgtgctga tgacccagac cccctgagc ctgcccgtga gcctgggcga ccaggccagc       60
atcagctgca ggagcagcca gagcatcgtg cacagcagcg gcaacaccta cctgcagtgg     120
ttcctgcaga agcccggcca gagccccaag ctgctgatca gcaaggtgag caacaggttc     180
agcggcgtgc ccgacaggtt cagcggcagc ggcagcggca ccgacttcac cctgaggatc     240
agcagggtgg aggccgagga cctgggcctg tactactgct tccagggcag ccacgtgccc     300
tggaccttcg gcggcggcac caagctggag atcaag                              336
```

<210> SEQ ID NO 54
<211> LENGTH: 360
<212> TYPE: DNA
<213> ORGANISM: Mus musculus

<400> SEQUENCE: 54

```
gaggtgcagc tggtggagag cggcggcggc ctggtgaagc ccggcggcag cctgaagctg       60
agctgcgccg ccagcggctt caccttcagc gactacggca tgcactggct gaggcaggcc     120
cccgagaagg gcctggagtg ggtggcctac atcaccagcg gcagcagcga gatctactac     180
gtggacaccg tgaagggcag gttcaccatc agcagggaca acgccaagaa caccctgtgc     240
ctgcagatga ccagcctgag gagcgaggac accgccatgt accactgcgc caggggctac     300
ggctacaggg agggctactt cgacgtgtgg ggcaccggca ccaccgtgac cgtgagcagc     360
```

<210> SEQ ID NO 55
<211> LENGTH: 336
<212> TYPE: DNA
<213> ORGANISM: Mus musculus

<400> SEQUENCE: 55

```
gacgtggtga tgacccagac cccctgacc ctgagcgtga ccatcggcca gcccgccagc      60
atcagctgca agagcagcca gagcctgctg gacagcgacg gcaagaccta cctgaactgg     120
ctgctgcaga ggcccggcca gagccccaag aggctgatct acctggtgag caagctggac     180
agcggcgtgc ccgacaggtt caccggcagc ggcagcggca ccgacttcac cctgaagatc     240
agcagggtgg aggccgagga cctgggcgtg tactactgct ggcagggcac ccacttcccc     300
cagaccttcg gcggcggcac caagctggag atcaag                               336
```

<210> SEQ ID NO 56
<211> LENGTH: 321
<212> TYPE: DNA
<213> ORGANISM: Mus musculus

<400> SEQUENCE: 56

```
gacatccaga tgacccagag ccccgccagc ctgagcgtga gcgtgggcga ccgtgacc       60
atcacctgca ggaccagcga gaacgtgtac agcaacctgg cctggtacca gcagaagcag     120
ggcaggagcc cccagctgct ggtgtacggc gccaccaggc tgcccgacgg cgtgcccgcc     180
aggttcagcg gcagcggcag cggcacccag tacagcctga agatcaacag cctgcagagc     240
gaggacttcg gcacctacta ctgccagctg ttctggggca tccccctgac cttcggcgcc     300
ggcaccaagc tggagctgaa g                                               321
```

<210> SEQ ID NO 57
<211> LENGTH: 114
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 57

```
Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Val His Ser
             20                  25                  30

Ser Gly Asn Thr Tyr Leu Gln Trp Phe Gln Gln Lys Pro Gly Lys Ala
         35                  40                  45

Pro Lys Leu Leu Ile Tyr Lys Val Ser Asn Arg Phe Ser Gly Val Pro
     50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Val Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Arg
```

<210> SEQ ID NO 58
<211> LENGTH: 342
<212> TYPE: DNA

<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 58

```
gacatccaga tgacccagag cccctctagc ctgagcgcca gcgtgggcga cagggtgacc      60
attacctgca ggagcagcca gagcatcgtg cacagcagcg caacaccta cctgcagtgg     120
ttccagcaga aacccggcaa ggctcccaag ctgctgatct acaaggtgag caacaggttc     180
agcggcgtgc cctctcgctt ctcaggcagc ggctccggca ccgatttcac cctgaccatc     240
agctcactgc agcccgagga cttcgccgtc tactactgct ccagggaag ccacgtgccc      300
tggacttttg gccagggcac caagctcgag atcaagaggc gt                        342
```

<210> SEQ ID NO 59
<211> LENGTH: 354
<212> TYPE: DNA
<213> ORGANISM: Mus musculus

<400> SEQUENCE: 59

```
gagttccagc tgcagcagtc tggacctgag ctggtgaagc ctggcgcttc agtgaagata      60
tcctgcaagg cctctggtta ctcatttact gactacaata tgaactgggt gaaacagaac     120
aatgaaaga gccttgagtg gattggagga attaatccta actatggtac tactgtttac     180
aatcagaagt tcaagggcaa ggccacattg actgtagacc aatcttccag cacagcctac     240
atgcagctcg ttagtctgac atctgaggac tctgcagtct attattgtgc aagaatgacc     300
acgatagttc cctttgacta ctggggccaa ggcaccactc tcacagtctc ctca          354
```

<210> SEQ ID NO 60
<211> LENGTH: 321
<212> TYPE: DNA
<213> ORGANISM: Mus musculus

<400> SEQUENCE: 60

```
gatatccaga tgacacagac tacattctcc ctgtctgcct ctctgggaga cagagtcacc      60
atcagttgca gggcaagtca ggacattagt aattatttaa actggtatca gcagaaacca     120
gatggaactg ttaaactcct gatctattac acatcaacat tacactcagg agtcccatca     180
agattcagtg gcagtgggtc tggaacagat tattttctca ccattaggaa cctggaggaa     240
gaagatattg ccacttactt ttgccaacag ggttatacgc ttccgtggac gttcggtgga     300
ggcaccaagt tggacatcaa a                                              321
```

<210> SEQ ID NO 61
<211> LENGTH: 351
<212> TYPE: DNA
<213> ORGANISM: Mus musculus

<400> SEQUENCE: 61

```
caggtccaac tgcagcagcc tggggctgag ctggtgaggc ctgggacttc agtgaagttg      60
tcctgcaagg cctctggcta caccttcacc agctactgga tgcactgggt aaagcagagg     120
cctggacaag gccttgagtg gatcggagtg attgatcctt ctgatggtta tagtcactac     180
aatcaaaagt tcaagggcaa ggccacttttg actgtagaca catcctccag tacagcctac     240
atgcagctca gcagcctgac ctctgaggac tctgcggtct attactgtgc aggaggctta     300
gctgggacgc ttgactactg ggccagggc accactctca cagtctcctc a               351
```

```
<210> SEQ ID NO 62
<211> LENGTH: 336
<212> TYPE: DNA
<213> ORGANISM: Mus musculus

<400> SEQUENCE: 62
gatgttttga tgacccaaac tccactctcc ctgcctgtca gtcttggaga tcaagcctcc    60
atctcttgca gatctagtca gagcattgta catagttctg gaaacaccta tttacaatgg   120
ttcctgcaga aaccaggcca gtctccaaag ctcctgatct ccaaagtttc caaccgattt   180
tctggggtcc cagacaggtt cagtggcagt ggatcaggga cagatttcac actcaggatc   240
agcagagtgg aggctgagga tctggacttt attactgct ttcaaggttc acatgttccg   300
tggacgttcg gtggaggcac caagttggaa atcaaa                             336

<210> SEQ ID NO 63
<211> LENGTH: 360
<212> TYPE: DNA
<213> ORGANISM: Mus musculus

<400> SEQUENCE: 63
gaggtgcagc tggtggagtc tgggggaggc ttagtgaagc ccggagggtc cctgaaactc    60
tcctgtgcag cctctggatt cacttttcagt gactatggaa tgcactggct tcgtcaggct   120
ccagagaagg ggctggagtg ggttgcatac attactagtg gcagtagtga aatctactat   180
gtagacacag tgaagggccg attcaccatc tccagagaca tgccaagaa cccctgtgc    240 ctgcaaatga ccagtctgag gtctgaggac acggccatgt atcactgtgc aaggggctac   300
ggttatagag aggggtactt cgatgtctgg ggcacaggga ccacggtcac cgtctcctca   360

<210> SEQ ID NO 64
<211> LENGTH: 336
<212> TYPE: DNA
<213> ORGANISM: Mus musculus

<400> SEQUENCE: 64
gatgttgtga tgacccagac tccactcact ttgtcggtta ccattggaca accagcctcc    60
atctcttgca agtcaagtca gagcctctta gatagtgatg aaagacata tttgaattgg   120 ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acatttcct   300 cagacgttcg gtggaggcac caagctggaa atcaaa                             336

<210> SEQ ID NO 65
<211> LENGTH: 321
<212> TYPE: DNA
<213> ORGANISM: Mus musculus

<400> SEQUENCE: 65
gacatccaga tgactcagtc tccagcctcc ctatctgtat ctgtgggaga aactgtcacc    60
atcacatgtc gaacaagtga aatgttac agtaatttag catggtatca gcagaaacag   120
ggaagatctc ctcagctcct ggtctatggt gcaacaaggt taccagatgg tgtgccagca   180
aggttcagtg gcagtggatc aggcacacag tattccctca agatcaacag cctgcagtct   240
gaagattttg ggacttatta ctgtcaactt ttttggggta tcccgctcac gttcggtgct   300
```
gggaccaagc tggagctgaa a                                      321

<210> SEQ ID NO 66
<211> LENGTH: 624
<212> TYPE: PRT
<213> ORGANISM: Homo sapien

<400> SEQUENCE: 66

Ser Glu Val Gly Asn Ser Gln Ala Val Cys Pro Gly Thr Leu Asn Gly
 1               5                  10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

```
Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
                435                 440                 445

Leu Asn Trp Thr Lys Val Leu Arg Gly Pro Thr Glu Glu Arg Leu Asp
450                 455                 460

Ile Lys His Asn Arg Pro Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
                500                 505                 510

His Cys Asn Phe Leu Asn Gly Glu Pro Arg Glu Phe Ala His Glu Ala
                515                 520                 525

Glu Cys Phe Ser Cys His Pro Glu Cys Gln Pro Met Glu Gly Thr Ala
530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
                580                 585                 590

Pro Cys His Glu Asn Cys Thr Gln Gly Cys Lys Gly Pro Glu Leu Gln
                595                 600                 605

Asp Cys Leu Gly Gln Thr Leu Val Leu Ile Gly Lys Thr His Leu Thr
                610                 615                 620

<210> SEQ ID NO 67
<211> LENGTH: 117
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Val Ile Asp Pro Ser Asp Gly Tyr Ser His Tyr Asn Gln Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ala Gly Thr Leu Asp Tyr Trp Gly Gln Gly Thr Thr
```

Val Thr Val Ser Ser
        115

<210> SEQ ID NO 68
<211> LENGTH: 351
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 68
caggtgcagc tggtgcagtc cggcgcagag gtgaagaagc ccggagcctc tgtgaaggtg      60
agctgcaagg ccagcggcta caccttcacc agctactgga tgcactgggt gaggcaggcc     120
cctggccagg gcctggagtg gatgggcgtg atcgacccca gcgacgggta cagccactac     180
aaccagaagt tcaagggcag ggtcaccatg accaggaca ccagcatcag caccgcctac      240
atggaactca gcaggctgag gagcgacgac accgccgtgt actattgcgc caggggcctg     300
gctggcaccc tggattactg gggccagggc accacagtga ccgtgagcag c              351

<210> SEQ ID NO 69
<211> LENGTH: 117
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 69

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Val Ile Asp Pro Ser Asp Gly Tyr Ser His Tyr Asn Gln Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ala Gly Thr Leu Asp Tyr Trp Gly Gln Gly Thr Thr
            100                 105                 110

Val Thr Val Ser Ser
        115

<210> SEQ ID NO 70
<211> LENGTH: 351
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 70
caggtgcagc tggtgcagtc cggcgcagag gtgaagaagc ccggagcctc tgtgaaggtg      60

```
agctgcaagg ccagcggcta caccttcacc agctactgga tgcactgggt gaggcaggcc    120
cctggccagg gcctggagtg gatgggcgtg atcgacccca gcgacgggta cagccactac    180
aaccagaagt tcaagggcag ggtcaccatg accgtggaca ccagcatcag caccgcctac    240
atggaactca gcaggctgag gagcgacgac accgccgtgt actattgcgc caggggcctg    300
gctggcaccc tggattactg gggccagggc accacagtga ccgtgagcag c             351
```

<210> SEQ ID NO 71
<211> LENGTH: 117
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 71

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Val Ile Asp Pro Ser Asp Gly Tyr Ser His Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Gly Gly Leu Ala Gly Thr Leu Asp Tyr Trp Gly Gln Gly Thr Thr
            100                 105                 110

Val Thr Val Ser Ser
        115
```

<210> SEQ ID NO 72
<211> LENGTH: 351
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 72

```
caggtgcagc tggtgcagtc cggcgcagag gtgaagaagc ccggagcctc tgtgaaggtg    60
agctgcaagg ccagcggcta caccttcacc agctactgga tgcactgggt gaggcaggcc    120
cctggccagg gcctggagtg gatgggcgtg atcgacccca gcgacgggta cagccactac    180
aaccagaagt tcaagggcag ggtcaccatg accagggaca ccagcatcag caccgcctac    240
atggaactca gcaggctgag gagcgacgac accgccgtgt actattgcgc cggaggcctg    300
gctggcaccc tggattactg gggccagggc accacagtga ccgtgagcag c             351
```

<210> SEQ ID NO 73
<211> LENGTH: 117
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

-continued

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Val Ile Asp Pro Ser Asp Gly Tyr Ser His Tyr Asn Gln Lys Phe
    50                  55                  60

Lys Gly Lys Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Leu Ala Gly Thr Leu Asp Tyr Trp Gly Gln Gly Thr Thr
            100                 105                 110

Val Thr Val Ser Ser
        115

<210> SEQ ID NO 74
<211> LENGTH: 351
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 74
caggtgcagc tggtgcagtc cggcgcagag gtgaagaagc ccggagcctc tgtgaaggtg     60
agctgcaagg ccagcggcta caccttcacc agctactgga tgcactgggt gaggcaggcc    120
cctggccagg gcctggagtg gatgggcgtg atcgacccca gcgacgggta cagccactac    180
aaccagaagt tcaagggcaa ggtcaccatg accagggaca ccagcatcag caccgcctac    240
atggaactca gcaggctgag gagcgacgac accgccgtgt actattgcgc caggggcctg    300
gctggcaccc tggattactg gggccagggc accacagtga ccgtgagcag c             351

<210> SEQ ID NO 75
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Ser Gly Asn Thr Tyr Leu Gln Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Phe Gln Gly

Ser His Val Pro Trp Thr Phe Gly Gln Gly Thr Lys Leu Glu Ile Lys
            100                 105                 110
Arg

<210> SEQ ID NO 76
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 76
gacatccaga tgacccagag cccctctagc ctgagcgcca gcgtgggcga cagggtgacc      60
attacctgca ggagcagcca gagcatcgtg cacagcagcg gcaacaccta cctgcagtgg     120
taccagcaga aacccggcaa ggctcccaag ctgctgatct acaaggtgag caacaggttc     180
agcggcgtgc cctctcgctt ctcaggcagc ggctccggca ccgatttcac cctgaccatc     240
agctcactgc agcccgagga cttcgccgtc tactactgct tccagggaag ccacgtgccc     300 tggactttg gccagggcac caagctcgag atcaagagg                             339

<210> SEQ ID NO 77
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 77

Asp Val Gln Met Thr Gln Ser Pro Ser Ser Leu Ser Ala Ser Val Gly
 1               5                   10                  15

Asp Arg Val Thr Ile Thr Cys Arg Ser Ser Gln Ser Ile Val His Ser
                20                  25                  30

Ser Gly Asn Thr Tyr Leu Gln Trp Tyr Gln Gln Lys Pro Gly Lys Ala
            35                  40                  45

Pro Lys Leu Leu Ile Tyr Lys Val Ser Asn Arg Phe Ser Gly Val Pro
        50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg

<210> SEQ ID NO 78
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 78
gacgtgcaga tgacccagag cccctctagc ctgagcgcca gcgtgggcga cagggtgacc      60

```
attacctgca ggagcagcca gagcatcgtg cacagcagcg gcaacaccta cctgcagtgg      120
taccagcaga aacccggcaa ggctcccaag ctgctgatct acaaggtgag caacaggttc      180
agcggcgtgc cctctcgctt ctcaggcagc ggctccggca ccgatttcac cctgaccatc      240
agctcactgc agcccgagga cttcgccgtc tactactgct tccagggaag ccacgtgccc      300 tggactttg gccagggcac caagctcgag atcaagagg                              339
```

<210> SEQ ID NO 79
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 79

```
Asp Ile Leu Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Ser Gly Asn Thr Tyr Leu Gln Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg
```

<210> SEQ ID NO 80
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 80

```
gacatcctga tgacccagag cccctctagc ctgagcgcca gcgtgggcga cagggtgacc      60
attacctgca ggagcagcca gagcatcgtg cacagcagcg gcaacaccta cctgcagtgg      120
taccagcaga aacccggcaa ggctcccaag ctgctgatct acaaggtgag caacaggttc      180
agcggcgtgc cctctcgctt ctcaggcagc ggctccggca ccgatttcac cctgaccatc      240
agctcactgc agcccgagga cttcgccgtc tactactgct tccagggaag ccacgtgccc      300 tggactttg gccagggcac caagctcgag atcaagagg                              339
```

<210> SEQ ID NO 81
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 81

Asp Val Leu Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Ser Gly Asn Thr Tyr Leu Gln Trp Phe Gln Gln Lys Pro Gly Lys Ala
        35                  40                  45

Pro Lys Leu Leu Ile Ser Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg

<210> SEQ ID NO 82
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 82
gacgtgctga tgacccagag cccctctagc ctgagcgcca gcgtgggcga cagggtgacc      60
attacctgca ggagcagcca gagcatcgtg cacagcagcg gcaacaccta cctgcagtgg     120
ttccagcaga aacccggcaa ggctcccaag ctgctgatca gcaaggtgag caacaggttc     180
agcggcgtgc cctctcgctt ctcaggcagc ggctccggca ccgatttcac cctgaccatc     240
agctcactgc agcccgagga cttcgccgtc tactactgct tccagggaag ccacgtgccc     300 tggactttg gccagggcac caagctcgag atcaagagg                             339

<210> SEQ ID NO 83
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Ser Gly Asn Thr Tyr Leu Gln Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg

<210> SEQ ID NO 84
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 84
gacgtggtga tgacacagag ccctctgagc ctgcctgtga ccctgggcca gcccgccagc    60
attagctgca ggagcagcca gtccatcgtg cacagcagcg gcaacaccta cctgcagtgg   120
ttccagcaga ggcccggcca gagccccagg aggctgatct acaaggtgag caacaggttc   180
agcggcgtgc ccgacagatt cagcggctca ggcagcggca ccgacttcac cctcaagatc   240
agcagggtgg aggccgagga cgtgggcgtc tactactgct tccaggggag ccacgtgccc   300
tggacctttg gacagggcac caagctggag atcaagagg                         339

<210> SEQ ID NO 85
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 85

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val His Ser
            20                  25                  30

Ser Gly Asn Thr Tyr Leu Gln Trp Phe Gln Gln Arg Pro Gly Gln Ser
        35                  40                  45

Pro Arg Arg Leu Ile Ser Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gln Gly Thr Lys Leu Glu Ile Lys
            100                 105                 110

Arg

<210> SEQ ID NO 86
<211> LENGTH: 339
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 86
gacgtggtga tgacacagag ccctctgagc ctgcctgtga ccctgggcca gcccgccagc    60

```
attagctgca ggagcagcca gtccatcgtg cacagcagcg gcaacaccta cctgcagtgg    120
ttccagcaga ggcccggcca gagccccagg aggctgatca gcaaggtgag caacaggttc    180
agcggcgtgc ccgacagatt cagcggctca ggcagcggca ccgacttcac cctcaagatc    240
agcagggtgg aggccgagga cgtgggcgtc tactactgct tccaggggag ccacgtgccc    300 tggaccttg gacagggcac caagctcgag atcaagagg                            339
```

<210> SEQ ID NO 87
<211> LENGTH: 113
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 87

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
             20                  25                  30

Ser Gly Asn Thr Tyr Leu Gln Trp Phe Gln Gln Arg Pro Gly Gln Ser
         35                  40                  45

Pro Lys Leu Leu Ile Ser Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

Arg
```

<210> SEQ ID NO 88
<211> LENGTH: 113
<212> TYPE: PRT
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 88

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
             20                  25                  30

Ser Gly Asn Thr Tyr Leu Gln Trp Phe Gln Gln Arg Pro Gly Gln Ser
         35                  40                  45

Pro Lys Leu Leu Ile Ser Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Leu Glu Ile Lys
            100                 105                 110

Arg
```

<210> SEQ ID NO 89
<211> LENGTH: 339
<212> TYPE: DNA
<213> ORGANISM: Artificial Sequence
<220> FEATURE:
<223> OTHER INFORMATION: Humanized antibody nucleic acid sequence
designed in silico and made using molecular biology
synthetic techniques.

<400> SEQUENCE: 89

```
gacgtggtga tgacacagag ccctctgagc ctgcctgtga ccctgggcca gcccgccagc      60
attagctgca ggagcagcca gtccatcgtg cacagcagcg gcaacaccta cctgcagtgg     120
ttccagcaga ggcccggcca gagccccaag ctgctgatca gcaaggtgag caacaggttc     180
agcggcgtgc ccgacagatt cagcggctca ggcagcggca ccgacttcac cctcaagatc     240
agcagggtgg aggccgagga cgtgggcgtc tactactgct ccaggggag ccacgtgccc      300
tggacctttg gacagggcac caagctcgag atcaagagg                            339
```

<210> SEQ ID NO 90
<211> LENGTH: 118
<212> TYPE: PRT
<213> ORGANISM: Artificial Sequence
<220> FEATURE:
<223> OTHER INFORMATION: Humanized antibody amino acid sequence designed
in silico and made using molecular biology synthetic
techniques.

<400> SEQUENCE: 90

```
Gln Phe Gln Leu Val Gln Ser Gly Ala Glu Val Lys Lys Pro Gly Ala
  1               5                  10                  15

Ser Val Lys Val Ser Cys Lys Ala Ser Gly Tyr Ser Phe Thr Asp Tyr
             20                  25                  30

Asn Met Asn Trp Val Lys Gln Ala Pro Gly Gln Gly Leu Glu Trp Ile
         35                  40                  45

Gly Gly Ile Asn Pro Asn Tyr Gly Thr Thr Val Tyr Asn Gln Lys Phe
     50                  55                  60

Lys Gly Lys Ala Thr Leu Thr Val Asp Gln Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Met Thr Thr Ile Val Pro Phe Asp Tyr Trp Gly Gln Gly Thr
            100                 105                 110

Thr Val Thr Val Ser Ser
        115
```

<210> SEQ ID NO 91
<211> LENGTH: 354
<212> TYPE: DNA
<213> ORGANISM: Artificial Sequence
<220> FEATURE:
<223> OTHER INFORMATION: Humanized antibody nucleic acid sequence
designed in silico and made using molecular biology
synthetic techniques.

<400> SEQUENCE: 91

```
cagttccagc tggtgcagag cggagccgag gtgaagaagc ccggagccag cgtcaaagtg      60
agctgcaagg cctccggcta cagcttcacc gactacaaca tgaactgggt gaagcaggcc     120
cccgggcagg gcctggagtg gatcggcggc atcaatccca actacggcac caccgtgtac     180
```

```
aaccagaagt tcaagggcaa ggccaccctg accgtggacc agagcatcag caccgcctac    240
atggaactca gcaggctgag gagcgacgat accgccgtgt actactgcgc taggatgacc    300
accatcgtgc ccttcgacta ttggggccag ggcacaaccg tgactgtgag cagc          354
```

<210> SEQ ID NO 92
<211> LENGTH: 118
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 92

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                 20                  25                  30

Asn Met Asn Trp Val Lys Gln Ala Pro Gly Gln Gly Leu Glu Trp Ile
             35                  40                  45

Gly Gly Ile Asn Pro Asn Tyr Gly Thr Thr Val Tyr Asn Gln Lys Phe
 50                  55                  60

Lys Gly Lys Ala Thr Leu Thr Val Asp Gln Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Met Thr Thr Ile Val Pro Phe Asp Tyr Trp Gly Gln Gly Thr
                100                 105                 110

Thr Val Thr Val Ser Ser
        115
```

<210> SEQ ID NO 93
<211> LENGTH: 354
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 93

```
caggtgcagc tcgtgcagag cggagccgag gtgaaaaagc ccggcgctag cgtgaaggtg    60
agctgcaagg ccagcggcta caccttcacc gactacaaca tgaactgggt gaagcaggca    120
cccggccagg gcctggagtg gatcggcggc atcaaccccc actacggcac taccgtctac    180
aaccagaagt tcaagggcaa ggccaccctg accgtggatc agagcatcag caccgcctac    240
atggaactgt ctaggctgag gagcgacgac accgccgtgt actattgcgc caggatgacc    300
accatcgtgc ccttcgacta ctggggccag ggaaccacag tcaccgtgag cagc          354
```

<210> SEQ ID NO 94
<211> LENGTH: 118
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 94

```
Gln Val Gln Leu Val Gln Ser Gly Ala Glu Val Lys Lys Pro Gly Ala
```

```
                1               5                   10                  15
            Ser Val Lys Val Ser Cys Lys Ala Ser Gly Tyr Thr Phe Thr Asp Tyr
                        20                  25                  30

Asn Met Asn Trp Val Arg Gln Ala Pro Gly Gln Gly Leu Glu Trp Met
                        35                  40                  45

Gly Gly Ile Asn Pro Asn Tyr Gly Thr Thr Val Tyr Asn Gln Lys Phe
                        50                  55                  60

Lys Gly Lys Ala Thr Leu Thr Val Asp Gln Ser Ile Ser Thr Ala Tyr
            65                  70                  75                  80

Met Glu Leu Ser Arg Leu Arg Ser Asp Asp Thr Ala Val Tyr Tyr Cys
                        85                  90                  95

Ala Arg Met Thr Thr Ile Val Pro Phe Asp Tyr Trp Gly Gln Gly Thr
                        100                 105                 110

Thr Val Thr Val Ser Ser
                        115
```

<210> SEQ ID NO 95
<211> LENGTH: 354
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 95

```
caggtgcagc tggtccagag cggagccgag gtgaaaaagc ccggcgcaag cgtgaaggtg      60
agctgcaagg ccagcggcta caccttcacc gactacaaca tgaactgggt gaggcaggcc     120
cccggccagg gcctcgagtg gatgggaggc atcaacccca actacggcac caccgtgtac     180
aaccagaagt tcaagggcaa ggccaccctg accgtggacc agagcatcag caccgcctac     240
atggaactga gcaggctgag gagcgacgac accgccgtgt actattgcgc caggatgacc     300
accatcgtgc ccttcgacta ctggggccag ggcacaaccg tgaccgtgtc tagc           354
```

<210> SEQ ID NO 96
<211> LENGTH: 108
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 96

```
            Asp Ile Gln Met Thr Gln Ser Pro Ser Ser Leu Ser Ala Ser Val Gly
            1               5                   10                  15

Asp Arg Val Thr Ile Thr Cys Arg Ala Ser Gln Asp Ile Ser Asn Tyr
                        20                  25                  30

Leu Asn Trp Tyr Gln Gln Lys Pro Gly Lys Ala Pro Lys Leu Leu Ile
                        35                  40                  45

Tyr Tyr Thr Ser Thr Leu His Ser Gly Val Pro Ser Arg Phe Ser Gly
                        50                  55                  60

Ser Gly Ser Gly Thr Asp Tyr Thr Leu Thr Ile Ser Ser Leu Gln Pro
            65                  70                  75                  80

Glu Asp Phe Ala Thr Tyr Tyr Cys Gln Gln Gly Tyr Thr Leu Pro Trp
                        85                  90                  95

Thr Phe Gly Gln Gly Thr Lys Leu Glu Ile Lys Arg
                        100                 105
```

<210> SEQ ID NO 97
<211> LENGTH: 324
<212> TYPE: DNA
<213> ORGANISM: Artificial Sequence
<220> FEATURE:
<223> OTHER INFORMATION: Humanized antibody nucleic acid sequence
designed in silico and made using molecular biology
synthetic techniques.

<400> SEQUENCE: 97

```
gacatccaga tgacccagag ccctagcagc ctgagcgcct cagtgggcga tagggtgacc      60
atcacctgca gggccagcca ggacatcagc aactacctga actggtacca gcagaagccc     120
gggaaggccc ccaagctgct gatctactac acctccaccc tgcacagcgg cgtgccctca     180
aggttctccg gcagcggcag cggcaccgac tacactctga ccatcagcag cctccagccc     240
gaggacttcg ccacctacta ctgccagcag ggctataccc tgccctggac cttcggccag     300
ggcaccaagc tggagattaa gagg                                             324
```

<210> SEQ ID NO 98
<211> LENGTH: 108
<212> TYPE: PRT
<213> ORGANISM: Artificial Sequence
<220> FEATURE:
<223> OTHER INFORMATION: Humanized antibody amino acid sequence designed
in silico and made using molecular biology synthetic
techniques.

<400> SEQUENCE: 98

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Thr Leu His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Leu Pro Trp
                 85                  90                  95

Thr Phe Gly Gln Gly Thr Lys Leu Glu Ile Lys Arg
            100                 105
```

<210> SEQ ID NO 99
<211> LENGTH: 324
<212> TYPE: DNA
<213> ORGANISM: Artificial Sequence
<220> FEATURE:
<223> OTHER INFORMATION: Humanized antibody nucleic acid sequence
designed in silico and made using molecular biology
synthetic techniques.

<400> SEQUENCE: 99

```
gacatccaga tgacccagag ccccagcagc ctgagcgcca gcgtgggcga tagggtgacc      60
attacctgca gggccagcca ggacatcagc aactacctga actggtacca gcagaagccc     120
ggcaaggccc ccaagctgct gatctactac acctccactc tgcacagcgg cgtgccctct     180
aggttctccg gctcaggcag cggaaccgac ttcaccctga ccatcagcag cctccagccc     240
gaggacttcg ccacctacta ctgccagcag ggctataccc tgccttggac cttcggccag     300
```
ggcaccaaac tggagatcaa gagg 324

```
<210> SEQ ID NO 100
<211> LENGTH: 466
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 100
```

| Met | Gly | Trp | Ser | Cys | Ile | Ile | Leu | Phe | Leu | Val | Ala | Thr | Ala | Thr | Gly |
|---|---|---|---|---|---|---|---|---|---|---|---|---|---|---|---|
| 1 | | | | 5 | | | | | 10 | | | | | 15 | |

| Val | His | Ser | Gln | Val | Gln | Leu | Val | Gln | Ser | Gly | Ala | Glu | Val | Lys | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Val | Ser | Cys | Lys | Ala | Ser | Gly | Tyr | Thr | Phe |
|---|---|---|---|---|---|---|---|---|---|---|---|---|---|---|---|
| | | | 35 | | | | | 40 | | | | | 45 | | |

| Thr | Ser | Tyr | Trp | Met | His | Trp | Val | Arg | Gln | Ala | Pro | Gly | Gln | Gly | Leu |
|---|---|---|---|---|---|---|---|---|---|---|---|---|---|---|---|
| | 50 | | | | | 55 | | | | | 60 | | | | |

| Glu | Trp | Met | Gly | Val | Ile | Asp | Pro | Ser | Asp | Gly | Tyr | Ser | His | Tyr | Asn |
|---|---|---|---|---|---|---|---|---|---|---|---|---|---|---|---|
| 65 | | | | | 70 | | | | | 75 | | | | | 80 |

| Gln | Lys | Phe | Lys | Gly | Lys | Val | Thr | Leu | Thr | Val | Asp | Thr | Ser | Ile | Ser |
|---|---|---|---|---|---|---|---|---|---|---|---|---|---|---|---|
| | | | | 85 | | | | | 90 | | | | | 95 | |

| Thr | Ala | Tyr | Met | Glu | Leu | Ser | Arg | Leu | Arg | Ser | Asp | Asp | Thr | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Gly | Gly | Leu | Ala | Gly | Thr | Leu | Asp | Tyr | Trp | Gly | Gln |
|---|---|---|---|---|---|---|---|---|---|---|---|---|---|---|---|
| | | 115 | | | | | 120 | | | | | 125 | | | |

| Gly | Thr | Thr | Val | Thr | Val | Ser | Ser | Ala | Ser | Thr | Lys | Gly | Pro | Ser | Val |
|---|---|---|---|---|---|---|---|---|---|---|---|---|---|---|---|
| | 130 | | | | | 135 | | | | | 140 | | | | |

| Phe | Pro | Leu | Ala | Pro | Ser | Ser | Lys | Ser | Thr | Ser | Gly | Gly | Thr | Ala | Ala |
|---|---|---|---|---|---|---|---|---|---|---|---|---|---|---|---|
| 145 | | | | | 150 | | | | | 155 | | | | | 160 |

| Leu | Gly | Cys | Leu | Val | Lys | Asp | Tyr | Phe | Pro | Glu | Pro | Val | Thr | Val | Ser |
|---|---|---|---|---|---|---|---|---|---|---|---|---|---|---|---|
| | | | | 165 | | | | | 170 | | | | | 175 | |

| Trp | Asn | Ser | Gly | Ala | Leu | Thr | Ser | Gly | Val | His | Thr | Phe | Pro | Ala | Val |
|---|---|---|---|---|---|---|---|---|---|---|---|---|---|---|---|
| | | | 180 | | | | | 185 | | | | | 190 | | |

| Leu | Gln | Ser | Ser | Gly | Leu | Tyr | Ser | Leu | Ser | Ser | Val | Val | Thr | Val | Pro |
|---|---|---|---|---|---|---|---|---|---|---|---|---|---|---|---|
| | | 195 | | | | | 200 | | | | | 205 | | | |

| Ser | Ser | Ser | Leu | Gly | Thr | Gln | Thr | Tyr | Ile | Cys | Asn | Val | Asn | His | Lys |
|---|---|---|---|---|---|---|---|---|---|---|---|---|---|---|---|
| | 210 | | | | | 215 | | | | | 220 | | | | |

| Pro | Ser | Asn | Thr | Lys | Val | Asp | Lys | Lys | Val | Glu | Pro | Lys | Ser | Cys | Asp |
|---|---|---|---|---|---|---|---|---|---|---|---|---|---|---|---|
| 225 | | | | | 230 | | | | | 235 | | | | | 240 |

| Lys | Thr | His | Thr | Cys | Pro | Pro | Cys | Pro | Ala | Pro | Glu | Leu | Leu | Gly | Gly |
|---|---|---|---|---|---|---|---|---|---|---|---|---|---|---|---|
| | | | | 245 | | | | | 250 | | | | | 255 | |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | | 260 | | | | | 265 | | | | | 270 | | |

| Ser | Arg | Thr | Pro | Glu | Val | Thr | Cys | Val | Val | Val | Asp | Val | Ser | His | Glu |
|---|---|---|---|---|---|---|---|---|---|---|---|---|---|---|---|
| | | 275 | | | | | 280 | | | | | 285 | | | |

| Asp | Pro | Glu | Val | Lys | Phe | Asn | Trp | Tyr | Val | Asp | Gly | Val | Glu | Val | His |
|---|---|---|---|---|---|---|---|---|---|---|---|---|---|---|---|
| | 290 | | | | | 295 | | | | | 300 | | | | |

| Asn | Ala | Lys | Thr | Lys | Pro | Arg | Glu | Glu | Gln | Tyr | Asn | Ser | Thr | Tyr | Arg |
|---|---|---|---|---|---|---|---|---|---|---|---|---|---|---|---|
| 305 | | | | | 310 | | | | | 315 | | | | | 320 |

| Val | Val | Ser | Val | Leu | Thr | Val | Leu | His | Gln | Asp | Trp | Leu | Asn | Gly | Lys |
|---|---|---|---|---|---|---|---|---|---|---|---|---|---|---|---|
| | | | | 325 | | | | | 330 | | | | | 335 | |

| Glu | Tyr | Lys | Cys | Lys | Val | Ser | Asn | Lys | Ala | Leu | Pro | Ala | Pro | Ile | Glu |

```
                340             345             350
Lys Thr Ile Ser Lys Ala Lys Gly Gln Pro Arg Glu Pro Gln Val Tyr
            355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 101
<211> LENGTH: 1398
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 101
atgggctggt cctgcatcat cctgtttctg gtggccaccg ccaccggtgt gcacagccag      60
gtgcagctgg tgcagtccgg cgcagaggtg aagaagcccg agcctctgt gaaggtgagc     120 tgcaaggcca gcggctacac cttcaccagc tactggatgc actgggtgag gcaggcccct     180
ggccagggcc tggagtggat gggcgtgatc gaccccagcg acgggtacag ccactacaac     240
cagaagttca agggcaaggt caccctgacc gtggacacca gcatcagcac cgcctacatg     300
gaactcagca ggctgaggag cgacgacacc gccgtgtact attgcgccgg aggcctggct     360
ggcacccctg gattactggg gccagggcacc acagtgaccg tgagcagcgc cagcaccaag     420
ggccccagcg tgttcccccct ggcgcccagc agcaagagca ccagcggcgg cacagccgcc     480
ctgggctgcc tggtgaagga ctacttcccc gagccagtga ccgtgtcctg gaacagcgga     540
gccctgacca gcggcgtgca caccttccca gctgtcctgc agagcagcgg cctgtacagc     600
ctgagcagcg tggtgaccgt gcccagcagc agcctgggca cccagaccta catctgtaac     660
gtgaaccaca gcccagcaa caccaaggtg gacaagaagg tggagcccaa gagctgtgac     720
aagacccaca cctgcccccc ctgccctgcc ccgagctgc tgggaggccc cagcgtgttc     780 ctgttcccccc ccaagcctaa ggacaccctg atgatcagca accccccga ggtgacctgt     840 gtggtggtgg atgtgagcca cgaggaccct gaggtgaagt tcaactggta cgtggacggc     900
gtggaggtgc acaatgccaa gaccaagccc agggaggagc agtacaacag cacctaccgg     960
gtggtgtccg tgctgaccgt gctgcaccag gattggctga acggcaagga gtacaagtgt    1020
aaggtgtcca acaaggccct gcctgcccct atcgagaaaa ccatcagcaa ggccaagggc    1080
cagcccagag agccccaggt gtacaccctg cccctagca gagatgagct gaccaagaac    1140
caggtgtccc tgacctgcct ggtgaagggc ttctacccca cgacatcgc cgtggagtgg    1200 gagagcaacg gccagcccga gaacaactac aagaccaccc ccctgtgct ggacagcgat    1260
```

```
ggcagcttct tcctgtacag caagctgacc gtggacaaga gcagatggca gcagggcaac   1320
gtgttcagct gctccgtgat gcacgaggcc ctgcacaatc actacaccca gaagagcctg   1380
agcctgtccc ctggcaag                                                  1398
```

<210> SEQ ID NO 102
<211> LENGTH: 466
<212> TYPE: PRT
<213> ORGANISM: Artificial Sequence
<220> FEATURE:
<223> OTHER INFORMATION: Humanized antibody amino acid sequence designed
      in silico and made using molecular biology synthetic
      techniques.

<400> SEQUENCE: 102

```
Met Gly Trp Ser Cys Ile Ile Leu Phe Leu Val Ala Thr Ala Thr Gly
 1               5                  10                  15

Val His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Trp Met His Trp Val Arg Gln Ala Pro Gly Gln Gly Leu
     50                  55                  60

Glu Trp Met Gly Val Ile Asp Pro Ser Asp Gly Tyr Ser His Tyr Asn
 65                  70                  75                  80

Gln Lys Phe Lys Gly Lys Val Thr Leu Thr Val Asp Thr Ser Ile Ser
                 85                  90                  95

Thr Ala Tyr Met Glu Leu Ser Arg Leu Arg Ser Asp Asp Thr Ala Val
            100                 105                 110

Tyr Tyr Cys Ala Gly Gly Leu Ala Gly Thr Leu Asp Tyr Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Lys Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320
```

```
Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Ser Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Ile Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 103
<211> LENGTH: 1398
<212> TYPE: DNA
<213> ORGANISM: Artificial Sequence
<220> FEATURE:
<223> OTHER INFORMATION: Humanized antibody nucleic acid sequence
      designed in silico and made using molecular biology
      synthetic techniques.

<400> SEQUENCE: 103
atgggctggt cctgcatcat cctgtttctg gtggccaccg ccaccggtgt gcacagccag      60
gtgcagctgg tgcagtccgg cgcagaggtg aagaagcccg agcctctgt gaaggtgagc      120 tgcaaggcca gcggctacac cttcaccagc tactggatgc actgggtgag gcaggcccct     180
ggccagggcc tggagtggat gggcgtgatc gaccccagcg acgggtacag ccactacaac     240
cagaagttca agggcaaggt caccctgacc gtggacacca gcatcagcac cgcctacatg     300
gaactcagca ggctgaggag cgacgacacc gccgtgtact attgcgccgg aggcctggct     360 ggcacccctgg attactgggg ccagggcacc acagtgaccg tgagcagcgc cagcaccaag     420
ggcccaagcg tgtttcccct ggcccccagc agcaagtcta ccagcggcgg cacagccgcc     480
ctgggctgcc tggtcaaaga ctacttcccc gagcccgtca ccgtgagctg gaatagcggc     540
gcactgacca gcggcgtgca caccttttccc gccgtgctgc agagctcagg cctgtatagc     600
ctgagcagcg tggtgaccgt gccttctagc agcctgggca cccagaccta catctgcaac     660
gtcaaccaca gcccagcaa caccaaggtg gacaagaaag tggagcccaa gagctgcgac     720
aagacccaca cctgccccc ctgtccagct ccggagctgc tgggcggccc cagcgtgttc     780
ctcttccccc caagcccaa ggacaccctg atgatctcta gaacccccga ggtgacctgc     840
gtggtggtgg acgtcagcca cgaagacccc gaggtgcagt tcaagtggta cgtggacggg     900
gtggaggtgc acaacgccaa gactaagccc agggaggagc agttcaactc caccttcagg     960
gtggtgagcg tcctgaccgt gctgcatcag gactggctga acggcaagga gtacaagtgc    1020
aaggtgagca caaggccct gcccgccccc atcgagaaga ccatcagcaa aaccaagggc    1080
cagcctaggg aaccccaggt gtacaccctg cccccctcca gggaggagat gaccaagaac    1140
```

```
caggtgagcc tcacctgcct ggtgaagggc ttctacccca gcgacattgc cgtggagtgg    1200
gagtcaagcg gccagcccga gaacaactac aagaccaccc cccccatgct cgatagcgac    1260
ggcagcttct tcctgtacag caagctgacc gtggacaaga gccggtggca gagggcaac     1320 atcttcagct gcagcgtgat gcacgaggcc ctgcacaacc actacaccca gaagagcctg    1380
agcctgagcc ccggaaag                                                   1398
```

<210> SEQ ID NO 104
<211> LENGTH: 238
<212> TYPE: PRT
<213> ORGANISM: Artificial Sequence
<220> FEATURE:
<223> OTHER INFORMATION: Humanized antibody amino acid sequence designed
    in silico and made using molecular biology synthetic
    techniques.

<400> SEQUENCE: 104

```
Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ser Ser Gln Ser Ile
        35                  40                  45

Val His Ser Ser Gly Asn Thr Tyr Leu Gln Trp Phe Gln Gln Lys Pro
    50                  55                  60

Gly Lys Ala Pro Lys Leu Leu Ile Tyr Lys Val Ser Asn Arg Phe Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Val Tyr Tyr Cys
            100                 105                 110

Phe Gln Gly Ser His Val Pro Trp Thr Phe Gly Gln Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 105
<211> LENGTH: 714
<212> TYPE: DNA
<213> ORGANISM: Artificial Sequence
<220> FEATURE:
<223> OTHER INFORMATION: Humanized antibody nucleic acid sequence
    designed in silico and made using molecular biology
    synthetic techniques.

<400> SEQUENCE: 105

-continued

```
atgggatgga gctgtatcat cctcttcttg gtagcaacag ctacaggtgt ccactccgac      60
atccagatga cccagagccc ctctagcctg agcgccagcg tgggcgacag ggtgaccatt     120
acctgcagga gcagccagag catcgtgcac agcagcggca acacctacct gcagtggttc     180
cagcagaaac ccggcaaggc tcccaagctg ctgatctaca aggtgagcaa caggttcagc     240
ggcgtgccct ctcgcttctc aggcagcggc tccggcaccg atttcaccct gaccatcagc     300
tcactgcagc ccgaggactt cgccgtctac tactgcttcc agggaagcca cgtgccctgg     360
acttttggcc agggcaccaa gctcgagatc aagcgtacgg tggccgcccc cagcgtgttc     420
atcttccccc ccagcgatga gcagctgaag agcggcaccg ccagcgtggt gtgtctgctg     480
aacaacttct accccggga ggccaaggtg cagtggaagg tggacaatgc cctgcagagc     540
ggcaacagcc aggagagcgt gaccgagcag gacagcaagg actccaccta cagcctgagc     600
agcaccctga ccctgagcaa ggccgactac gagaagcaca aggtgtacgc ctgtgaggtg     660
acccaccagg gcctgtccag ccccgtgacc aagagcttca accggggcga gtgc           714
```